US012440584B2

(12) United States Patent
Tatum et al.

(10) Patent No.: US 12,440,584 B2
(45) **Date of Patent: *Oct. 14, 2025**

(54) MACROCYCLIC LIGANDS WITH PENDANT CHELATING MOIETIES AND COMPLEXES THEREOF

(71) Applicant: LUMIPHORE, INC., Berkeley, CA (US)

(72) Inventors: David Tatum, Berkeley, CA (US); Jide Xu, Richmond, CA (US); Darren Magda, San Leandro, CA (US); Nathaniel Butlin, Shawnigan Lake, CA (US)

(73) Assignee: LUMIPHORE, INC., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/629,717

(22) Filed: Apr. 8, 2024

(65) Prior Publication Data

US 2025/0090696 A1 Mar. 20, 2025

Related U.S. Application Data

(63) Continuation of application No. 16/979,017, filed as application No. PCT/US2019/021229 on Mar. 7, 2019, now Pat. No. 11,951,188.

(60) Provisional application No. 62/639,939, filed on Mar. 7, 2018.

(51) Int. Cl.

| | |
|---|---|
| ***A61K 51/04*** | (2006.01) |
| ***A61K 51/08*** | (2006.01) |
| ***C07D 471/18*** | (2006.01) |
| ***C07D 491/22*** | (2006.01) |
| ***C07F 5/00*** | (2006.01) |

(52) U.S. Cl.

CPC ........ *A61K 51/0482* (2013.01); *A61K 51/082* (2013.01); *C07D 471/18* (2013.01); *C07D 491/22* (2013.01); *C07F 5/003* (2013.01)

(58) Field of Classification Search

CPC .............. A61K 51/0482; A61K 51/082; A61K 49/0013; C07D 491/22; C07D 471/18; C07F 5/003

See application file for complete search history.

(56) References Cited

U.S. PATENT DOCUMENTS

| | | | | |
|---|---|---|---|---|
| 4,698,431 | A | 10/1987 | Raymond et al. | |
| 5,049,280 | A | 9/1991 | Raymond et al. | |
| 5,624,901 | A | 4/1997 | Raymond et al. | |
| 6,406,297 | B1 | 6/2002 | Raymond et al. | |
| 6,515,113 | B2 | 2/2003 | Raymond et al. | |
| 6,846,915 | B2 | 1/2005 | Raymond et al. | |
| 7,018,850 | B2 | 3/2006 | Raymond et al. | |
| 10,239,878 | B2 * | 3/2019 | Tatum .................. | C07D 471/18 |
| 11,603,371 | B2 * | 3/2023 | Tatum .................. | C07D 491/22 |
| 11,951,188 | B2 * | 4/2024 | Tatum .................. | C07D 471/18 |
| 2008/0213780 | A1 | 9/2008 | Butlin et al. | |
| 2008/0213917 | A1 | 9/2008 | Raymond et al. | |
| 2009/0023928 | A1 | 1/2009 | Raymond et al. | |
| 2010/0015725 | A1 | 1/2010 | Raymond et al. | |
| 2012/0214253 | A1 | 8/2012 | Butlin et al. | |
| 2014/0039169 | A1 | 2/2014 | Raymond et al. | |
| 2015/0157746 | A1 | 6/2015 | Raymond et al. | |
| 2018/0194766 | A1 | 7/2018 | Tatum et al. | |
| 2020/0062757 | A1 | 2/2020 | Tatum et al. | |
| 2020/0405887 | A1 | 12/2020 | Tatum et al. | |

FOREIGN PATENT DOCUMENTS

| | | |
|---|---|---|
| WO | WO 2008/008797 A1 | 1/2008 |
| WO | WO 2011/025790 A1 | 3/2011 |
| WO | WO 2014/078690 A1 | 5/2014 |
| WO | WO 2015/157057 A1 | 10/2015 |
| WO | WO 2016/106241 A1 | 6/2016 |
| WO | WO 2017/105565 A1 | 6/2017 |
| WO | WO 2018/045385 A1 | 3/2018 |
| WO | WO 2019/173639 A1 | 9/2019 |

OTHER PUBLICATIONS

Berge et al., "Pharmaceutical Salts." Journal of Pharmaceutical Sciences, vol. 66, No. 1 (1977).
Doble et al., "Toward Optimized High-Relaxivity MRI Agents: The Effect of Ligand Basicity on the Thermodynamic Stability of Hexadentate Hydroxypyridonate/Catecholate Gadolinium(III) Complexes." Inorganic Chemistry, vol. 42, No. 16 (2003).
Keana and Cai, "New reagents for photoaffinity labeling: Synthsis and photolysis of functionalized perfluorophenyl azides." The Journal of Organic Chemistry, vol. 55, pp. 3640-3647 (1990).
Moore et al., "Eu(III) Complexes of Functionalized Octadentate 1-Hydroxypyridin-2-ones: Stability, Bioconjugation, and Luminescence Resonance Energy Transfer Studies." Inorganic Chemistry, vol. 49, pp. 9928-9939 (2010).
Petoud et al., "Stable Lanthanide Luminescence Agents Highly Emissive in Aqueous Solution: Multidentate 2-Hydroxyisophthalamide Complexes of $Sm^{3+}$, $Eu^{3+}$, $Tb^{3+}$, $Dy^{3+}$." J. Am. Chem. Soc., vol. 125, pp. 13324-13325 (2003).
Samuel et al., "Water-Soluble 2-Hydroxyisophthalamides for Sensitization of Lanthanide Luminescence." Inorganic Chemistry, vol. 47, No. 17, pp. 7535-7544 (2008).
Xu et al., "Gadolinium(III) 1,2-Hydroxypyridonate-Based Complexes: Toward MRI Contrast Agents of High Relaxivity." Inorganic Chemistry. vol. 43, pp. 5492-5494 (2004).
Yamada et al., Biochemistry, 20: 4836-4842 (1981).
Ait-Mohand et al., "Development of Bifunctional Chelates Bearing Hydroxamate Arms for Highly Efficient $^{64}$Cu Radiolabeling." Org. Letters, vol. 16, No. 17 (2014).
Wei et al., "Synthesis, Orbinding ability and catalytic oxidation performance of cobalt(II) complexes with dihydroxamic acid functionalized N-pivot lariat ethers." Chinese Chemical Letters, Amsterdam, NL, vol. 26, No. 1 (2015).

* cited by examiner

*Primary Examiner* — Michael G. Hartley
*Assistant Examiner* — Leah H Schlientz
(74) *Attorney, Agent, or Firm* — Morgan, Lewis & Bockius LLP; Jeffry S. Mann

(57) ABSTRACT

The invention relates to ligands and complexes of metal ions with the ligands useful in various applications, including therapeutic and diagnostic applications.

20 Claims, 27 Drawing Sheets

MACROCYCLIC LIGANDS WITH PENDANT CHELATING MOIETIES AND COMPLEXES THEREOF

CROSS-REFERENCE TO RELATED APPLICATIONS

The present application is a Continuation of U.S. patent application Ser. No. 16/979,017 filed Sep. 8, 2020, now U.S. Pat. No. 11,951,188, which is a 371 of PCT/US19/21229 filed Mar. 7, 2019, which claims the benefit of U.S. Provisional Application No. 62/639,939, filed on Mar. 7, 2018, each of which is expressly incorporated by reference in its entirety for all purposes.

STATEMENT OF GOVERNMENT RIGHTS

This invention was made with Government support under Grant No. IIP-1353612 awarded by the Small Business Administration. The Government has certain rights in the invention.

FIELD OF THE INVENTION

The invention relates to chemical compounds and complexes that can be used in therapeutic and diagnostic applications.

BACKGROUND

Current radioimmunotherapy practice makes use of two classes of chelating agents: acyclic species based on diethylenetriamine pentaacetic acid (DTPA) or macrocyclic derivatives similar to 1,4,7,20-tetraazacyclododeccane N,N',N'',N'''-tetraacetic acid (DOTA). The former display more rapid association kinetics, while the DOTA-like compounds tend to produce a more stable complex, with the caveat that complexation typically requires harsher conditions such as high temperatures. A list of radiometals currently under clinical investigation (according to clinicaltrials.gov) includes actinium-225, bismuth-213, copper-64, gallium-67, gallium-68, holmium-166, indium-111, lutetium-177, rubidium-82, samarium-153, zirconium-89, strontium-89, technetium-99m, lead-212, and yttrium-90.

Lanthanide and actinide radiometal cations, in the absence of chelation, are largely deposited in bone, a significant concern given the potential for bone marrow suppression. Toxicity concerns that have arisen recently following the use of MRI contrast agents such as $Gd^{+3}$ DTPA, clearly underscore the insufficient control of the metal cation biodistribution by this chelating group. Similarly, radiometal loss can lead to a loss of signal specificity by targeted radiodiagnostics. Therefore, there is a recognized, compelling need for improved chelating agents for use in radioimmunotherapy. Such chelating agents and complexes and methods of their use are provided by the present invention.

SUMMARY OF INVENTION

The present invention provides a new class of ligands and metal complexes of these ligands which are particularly useful in therapeutic or diagnostic applications. The compounds (ligands) of this invention comprise a mixture of bridging chelating moieties and pendant chelating moieties that are linked together to have a structure of:

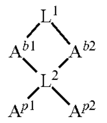

wherein $L^1$ and $L^2$ are independently selected scaffold moieties; $A^{b1}$ and $A^{b2}$ are independently selected bridging chelating moieties; and $A^{p1}$ and $A^{p2}$ are independently selected pendant chelating moieties.

The bridging chelating moieties and pendant chelating moieties of the present invention are independently selected from:

(I)

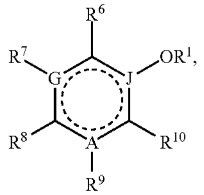

(II)

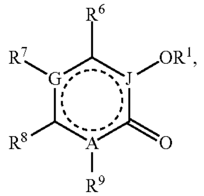

and (III)

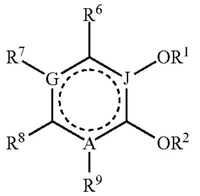

wherein A and G are independently selected from carbon, nitrogen and oxygen. J is selected from carbon and nitrogen. Each $R^1$ and $R^2$ is independently selected from H, an enzymatically labile group, a hydrolytically labile group, a metabolically labile group, a photolytically labile group and a single negative charge. Each $R^6$, $R^7$, $R^8$, $R^9$, and $R^{10}$ is independently selected from a bond to $L^1$ or $L^2$, alkanediyl attached to $L^1$ or $L^2$, H, substituted or unsubstituted alkyl, substituted or unsubstituted heteroalkyl, halogen, CN, $—CF_3$, $—C(O)R^{17}$, $—SO_2NR^{17}R^{18}$, $—NR^{17}R^{18}$, $—OR^{17}$, $—S(O)_2R^{17}$, $—COOR^{17}$, $—S(O)_2OR^{17}$, $—OC(O)R^{17}$, $—C(O)NR^{17}R^{18}$, $—NR^{17}C(O)R^{18}$, $—NR^{17}SO_2R^{18}$, and $—NO_2$, wherein at least two of $R^6$, $R^7$, $R^8$, $R^9$, and $R^{10}$ are optionally joined to form a ring system selected from substituted or unsubstituted cycloalkyl, substituted or unsubstituted heterocycloalkyl, substituted or unsubstituted aryl and substituted or unsubstituted heteroaryl. $R^{17}$ and $R^{18}$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl; and $R^{17}$ and $R^{18}$, together with the atoms to which they are attached, are optionally joined to form a 5-, 6- or 7-membered ring.

When A is oxygen, $R^9$ is not present; and when G is oxygen, $R^7$ is not present. $A^{b1}$ and $A^{b2}$ are attached to $L^1$ and $L^2$ through two members selected from $R^6$, $R^7$, $R^8$, $R^9$ and $R^{10}$; and $A^{p1}$ and $A^{p2}$ are attached to $L^2$ through a member selected from $R^6$, $R^7$, $R^8$, $R^9$ and $R^{10}$.

Advantages of the compounds of the present invention are that such chelating ligands bind the isotope rapidly, so that they are compatible with the practicalities of clinical laboratory preparation. Such compounds also bind the cation stably so that none is released in vivo, at least prior to its decay. These apparently contradictory properties of the compounds are in fact embodied by the pre-organized chelating groups that retain a sufficient degree of flexibility.

Exemplary compounds of the present invention also comprise a linker to a reactive functional group or a linker to a targeting moiety, therefore, the chelating ligands and their complexes provided herein can be directed to a site of interest for therapeutic or diagnostic purposes.

Compounds of the present invention and metal ion complexes thereof are particularly useful for targeted radioisotope applications and sensitized luminescence applications (such as Eu sensitized luminescence immunoassays). As shown in the Examples, compounds (ligands) of the present invention stably coordinate metal cations, display facile complexation kinetics, and possess an exceptionally high aqueous quantum yield with Eu(III).

DESCRIPTION OF EMBODIMENTS

Definitions

Figure 1:
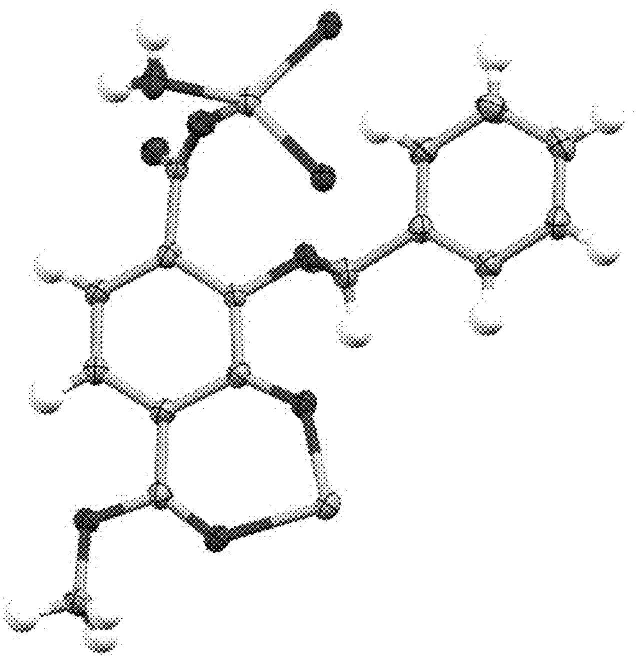
FIG. 1 shows the crystal structure ORTEP of compound 7, which confirms which one of the two methyl esters present in compound 6 is selectively hydrolyzed at low temperature by lithium hydroxide.

Where substituent groups are specified by their conventional chemical formulae, written from left to right, they optionally equally encompass the chemically identical substituents, which would result from writing the structure from right to left, e.g., $—CH_2O—$ is intended to also recite $—OCH_2—$.

The term "alkyl", by itself or as part of another substituent, means a straight or branched chain hydrocarbon, which may be fully saturated, mono- or polyunsaturated and includes mono-, di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl" can refer to "alkylene", which by itself or as part of another substituent means a divalent radical derived from an alkane, as exemplified, but not limited, by $—CH_2CH_2CH_2CH_2—$. Typically, an alkyl (or alkylene) group will have from 1 to 30 carbon atoms. A "lower alkyl" or "lower alkylene" is a shorter chain alkyl or alkylene group, generally having eight or fewer carbon atoms. In some embodiments, alkyl refers to an alkyl or combination of alkyls selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl.

The term "heteroalkyl," by itself or in combination with another term, means an alkyl in which one or more carbons are replaced with one or more heteroatoms selected from the group consisting of O, N, Si and S, (preferably O, N and S), wherein the nitrogen and sulfur atoms may optionally be oxidized and the nitrogen heteroatom may optionally be quaternized. The heteroatoms O, N, Si and S may be placed at any interior position of the heteroalkyl group or at the position at which the alkyl group is attached to the remainder of the molecule. In some embodiments, depending on whether a heteroatom terminates a chain or is in an interior position, the heteroatom may be bonded to one or more H or substituents such as ($C_1$, $C_2$, $C_3$, $C_4$, $C_5$ or $C_6$)alkyl according to the valence of the heteroatom. Examples of heteroalkyl groups include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH—CH—O—CH_3$, $—Si(CH_3)_3$, $—CH_2—CH{=}N—OCH_3$, and $—CH{=}CH—N(CH_3)—CH_3$. No more than two heteroatoms may be consecutive, as in, for example, $—CH_2—NH—OCH_3$ and $—CH_2—O—Si(CH_3)_3$, and in some instances, this may place a limit on the number of heteroatom substitutions. Similarly, the term "heteroalkylene, is sub-generic to "heteroalkyl" andby itself or as part of another substituent means a divalent radical derived from heteroalkyl, as exemplified, but not limited by, $—CH_2—CH_2—S—CH_2—CH_2—$ and $—CH_2—S—CH_2—CH_2—NH—CH_2—$. The designated number of carbons in hetero-forms of alkyl, alkenyl and alkynyl includes the heteroatom count. For example, a ($C_1$, $C_2$, $C_3$, $C_4$, $C_5$ or $C_6$) heteroalkyl will contain, respectively, 1, 2, 3, 4, 5 or 6 atoms selected from C, N, O, Si and S such that the heteroalkyl contains at least one C atom and at least one heteroatom, for example 1-5 C and 1 N or 1-4 C and 2 N. Further, a heteroalkyl may also contain one or more carbonyl groups. In some embodiments, a heteroalkyl is any $C_2$-$C_{30}$ alkyl, $C_2$-$C_{25}$ alkyl, $C_2$-$C_{20}$ alkyl, $C_2$-$C_{15}$ alkyl, $C_2$-$C_{10}$ alkyl or $C_2$-$C_6$ alkyl in any of which one or more carbons are replaced by one or more heteroatoms selected from O, N, Si and S (or from O, N and S). In some embodiments, each of 1, 2, 3, 4 or 5 carbons is replaced with a heteroatom. The terms "alkoxy," "alkylamino" and "alkylthio" (or thioalkoxy) are used in their conventional sense, and refer to those alkyl and heteroalkyl groups attached to the remainder of the molecule via an oxygen atom, a nitrogen atom (e.g., an amine group), or a sulfur atom, respectively.

The terms "cycloalkyl" and "heterocycloalkyl", by themselves or in combination with other terms, refer to cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means a polyunsaturated, aromatic substituent that can be a single ring or optionally multiple rings (preferably 1, 2 or 3 rings) that are fused together or linked covalently. In some embodiments, aryl is a 3, 4, 5, 6, 7 or 8 membered ring, which is optionally fused to one or two other 3, 4, 5, 6, 7 or 8 membered rings. The term "heteroaryl" refers to aryl groups (or rings) that contain 1, 2, 3 or 4 heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

In some embodiments, any of alkyl, heteroalkyl, cycloalkyl, heterocycloalkyl, aryl and heteroaryl is optionally substituted. That is, in some embodiments, any of these groups is substituted or unsubstituted. In some embodiments, substituents for each type of radical are selected from those provided below.

Substituents for the alkyl, heteroalkyl, cycloalkyl and heterocycloalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents". In some embodiments, an alkyl group substituent is selected from -halogen, —OR', =O, =NR', =N—OR', —NR'R", —SR', —SiR'R"R'", —OC(O)R', —C(O)R', $—CO_2R'$, —CONR'R", —OC(O)NR'R", —NR"C(O)R', —NR'—C(O)NR"R'", $—NR"C(O)_2R'$, —NR—C(NR'R"R'")=NR"", —NR—C(NR'R")=NR'", —S(O)R', $—S(O)_2R'$, $—S(O)_2NR'R"$, $—NRSO_2R'$, —CN and $—NO_2$ in a number ranging from zero to (2m'+1), where m' is the total number of carbon atoms in such radical. In one embodiment, R', R", R'" and R"" are each independently selected from hydrogen, alkyl (e.g., $C_1$, $C_2$, $C_3$, $C_4$, $C_5$ and $C_6$ alkyl). In one embodiment, R', R", R'" and R"" each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. In one embodiment, R', R", R'" and R"" are each independently selected from hydrogen, alkyl, heteroalkyl, cycloalkyl, heterocycloalkyl, aryl, heteroaryl, alkoxy, thioalkoxy groups, and arylalkyl. When R' and R" are attached to the same nitrogen atom, they can be combined with the nitrogen atom to form a 5-, 6-, or 7-membered ring. For example, —NR'R" can include 1-pyrrolidinyl and 4-morpholinyl. In some embodiments, an alkyl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Similar to the substituents described for the alkyl radical, substituents for the aryl and heteroaryl groups are generically referred to as "aryl group substituents". In some embodiments, an aryl group substituent is selected from -halogen, —OR', =O, =NR', =N—OR', —NR'R", —SR', —SiR'R"R'", —OC(O)R', —C(O)R', $—CO_2R'$, —CONR'R", —OC(O)NR'R", —NR"C(O)R', —NR'—C(O)NR"R'", $—NR"C(O)_2R'$, —NR—C(NR'R"R'")=NR"", —NR—C(NR'R")=NR", —S(O)R', $—S(O)_2R'$, $—S(O)_2$ NR'R", —$NRSO_2R'$, —CN and —$NO_2$, —R', —$N_3$, —CH$(Ph)_2$, fluoro ($C_1$-$C_4$)alkoxy, and fluoro ($C_1$-$C_4$)alkyl, in a number ranging from zero to the total number of open valences on the aromatic ring system. In some embodiments, R', R", R"' and R"" are independently selected from hydrogen and alkyl (e.g., $C_1$, $C_2$, $C_3$, $C_4$, $C_5$ and $C_6$ alkyl). In some embodiments, R', R", R"' and R"" are independently selected from hydrogen, substituted or unsubstituted alkyl, substituted or unsubstituted heteroalkyl, substituted or unsubstituted aryl and substituted or unsubstituted heteroaryl. In some embodiments, R', R", R"' and R"" are independently selected from hydrogen, alkyl, heteroalkyl, aryl and heteroaryl. In some embodiments, an aryl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Two of the substituents on adjacent atoms of the aryl or heteroaryl ring may optionally be replaced with a substituent of the formula -T-C(O)—$(CRR')_q$-U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2NR'$- or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X—$(CR"R"')_d$-, where s and d are independently integers of from 0 to 3, and X is —O—, —NR'—, —S—, —S(O)—, —$S(O)_2$—, or —$S(O)_2NR'$—. The substituents R, R', R" and R"' are preferably independently selected from hydrogen or substituted or unsubstituted ($C_1$-$C_6$)alkyl.

The term "acyl" refers to a species that includes the moiety —C(O)R, where R has the meaning defined herein. Exemplary species for R include H, halogen, substituted or unsubstituted alkyl, substituted or unsubstituted aryl, substituted or unsubstituted heteroaryl, and substituted or unsubstituted heterocycloalkyl. In some embodiments, R is selected from H and ($C_1$-$C_6$)alkyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. In some embodiments, halogen refers to an atom selected from F, Cl and Br.

The term "heteroatom" includes oxygen (O), nitrogen (N), sulfur(S) and silicon (Si). In some embodiments, a heteroatom is selected from N and S. In some embodiments, the heteroatom is O.

Unless otherwise specified, the symbol "R" is a general abbreviation that represents a substituent group that is selected from acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound includes more than one R, R', R", R"' and R"" group, they are each independently selected.

For groups with solvent exchangeable protons, the ionized form is equally contemplated. For example, —COOH also refers to —$COO^-$ and —OH also refers to —$O^-$.

Any of the compounds disclosed herein can be made into a pharmaceutically acceptable salt. The term "pharmaceutically acceptable salts" includes salts of compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science,* 66:1-19 (1977)). Certain specific compounds of the present invention contain both basic and acidic functionalities that allow the compounds to be converted into either base or acid addition salts. The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides any of the compounds disclosed herein in a prodrug form. Prodrugs of the compounds described herein are those compounds that readily undergo chemical changes under physiological conditions to provide the compounds of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may also contain unnatural proportions of atomic isotopes at one or more of the atoms that constitute such compounds. For example, the compounds may be labeled with deuterium ($^2H$) or radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The symbol, displayed perpendicular to a bond, indicates the point at which the displayed moiety is attached to the remainder of the molecule.

In some embodiments, the definition of terms used herein is according to IUPAC.

Compositions

The invention provides numerous compounds (ligands) and metal ion complexes thereof. Generally, a ligand comprises a plurality of chelating moieties that are linked together by way of a scaffold moiety.

Compounds (ligands) of the present invention and metal ion complexes thereof are particularly useful for targeted radioisotope applications and sensitized luminescence applications (such as Eu sensitized luminescence immunoassays). As shown in the Examples, compounds (ligands) of the present invention stably coordinate metal cations, display facile complexation kinetics, and possess an exceptionally high aqueous quantum yield with Eu(III).

There are several factors to be considered in the design for an alpha chelating agent for anticancer therapy. Some of the key issues apart from the kinetics will be the high affinity for the target metal (such as Th) which at the same time needs to have a low exchange rate for other biologically significant metal ions. So, in our ligand design, the electronic properties of the target metal and ligand are considered and matched. The chelate should also be able to assume the appropriate coordination cavity size and geometry for the desired metal. In this case, Th, an actinide ion, is a "hard" cation and has a large charge-to-radius ratio. Hence, Th prefers "hard" electron donors and negatively charged oxygen donors. A coordination number of 8 or greater is generally preferred by actinide ions as they have a tendency to form stable complexes with ligands of high denticity; however, the selectivity towards the binding of the thorium will be determined by our design of the chelating unit. The effective but nonselective amino-carboxylic acid ligands such as DTPA can deplete essential biological metal ions from patients, thus causing serious health problems. Selecting the correct type of chelating unit, therefore, is an important factor in achieving high selectivity toward the specific metal ion.

A ligand can comprise numerous chelating moieties. Particularly useful ligands contain a number of chelating moieties sufficient to provide, for example, 6, 8 or 10 heteroatoms such as oxygen that coordinate with a metal ion to form a complex. The heteroatoms such as oxygen provide electron density for forming coordinate bonds with a positively charged ion, and such heteroatoms can thus be considered "donors". In some embodiments, the plurality of chelating moieties of a ligand comprises a plurality of oxygen donors and a metal ion (such as a radionuclide) is chelated to the ligand via at least one of the oxygen donors. In some embodiments, a ligand comprises a plurality of oxygen donors and a metal ion (such as a radionuclide) is chelated to the ligand via a plurality or all of the oxygen donors.

Ligands

In one aspect, the invention provides a compound (ligand) having the structure:

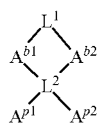

wherein $L^1$ and $L^2$ are independently selected scaffold moieties; $A^{b1}$ and $A^{b2}$ are independently selected bridging chelating moieties; and $A^{p1}$ and $A^{p2}$ are independently selected pendant chelating moieties. Scaffold moieties, bridging chelating moieties and pendant chelating moieties are as defined herein.

Any of the combinations of $L^1$, $L^2$, $A^{b1}$, $A^{b2}$, $A^{p1}$, and $A^{p2}$ are encompassed by this disclosure and specifically provided by the invention.

In some embodiments, the compound (ligand) comprises a linker to a reactive functional group, or a linker to a targeting moiety. In some embodiments, at least one of $L^1$, $L^2$, $A^{p1}$ and $A^{p2}$ is substituted with a linker to a reactive functional group, or a linker to a targeting moiety. The linker to a reactive functional group and the linker to a targeting moiety are as defined herein. In some embodiments, the functional moiety is a reactive functional group or a protected functional group.

In some embodiments, the compound (ligand) comprises one or more modifying moieties. The modifying moieties can be the same or different.

In some embodiments, when $A^{b1}$ and $A^{b2}$ are each:

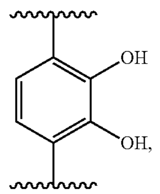 [SMILES: *c1ccc(*)c(O)c1O]

the compound comprises a linker to a reactive functional group, or a linker to a targeting moiety.

In some embodiments, when $A^{b1}$ and $A^{b2}$ are each:

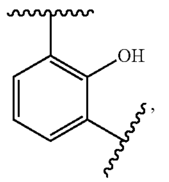 [SMILES: *c1cccc(*)c1O]

the compound comprises a linker to a reactive functional group, or a linker to a targeting moiety.

In some embodiments, the compounds (ligands) disclosed in WO 2013/187971 A2 are excluded.

In some embodiments, the compound (ligand) does not have the structure:

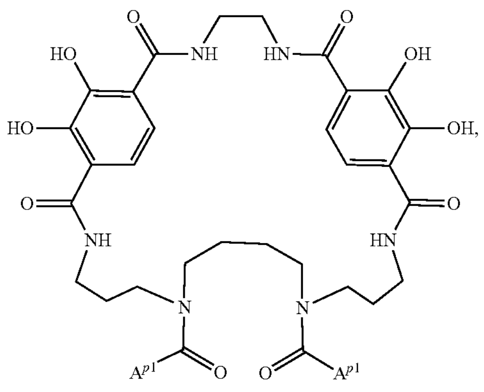

wherein each $A^{p1}$ is as defined in WO 2013/187971 A2, paragraph [0078]; i.e., wherein each $A^{p1}$ is independently selected from

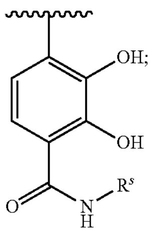
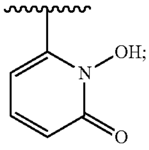
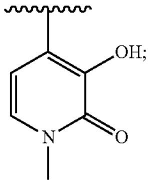
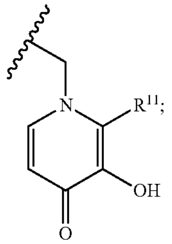
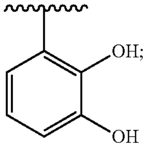
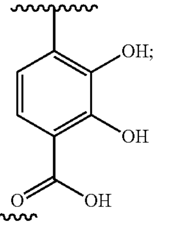
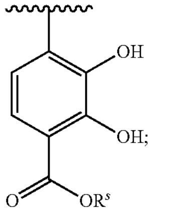
and
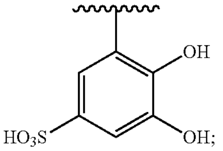

wherein $R^s$ comprises a solubilizing group; and $R^{11}$ is unsubstituted $C_1$, $C_2$, $C_3$, $C_4$, $C_5$ or $C_6$ alkyl.

In some embodiments, the compound (ligand) does not have the structure:

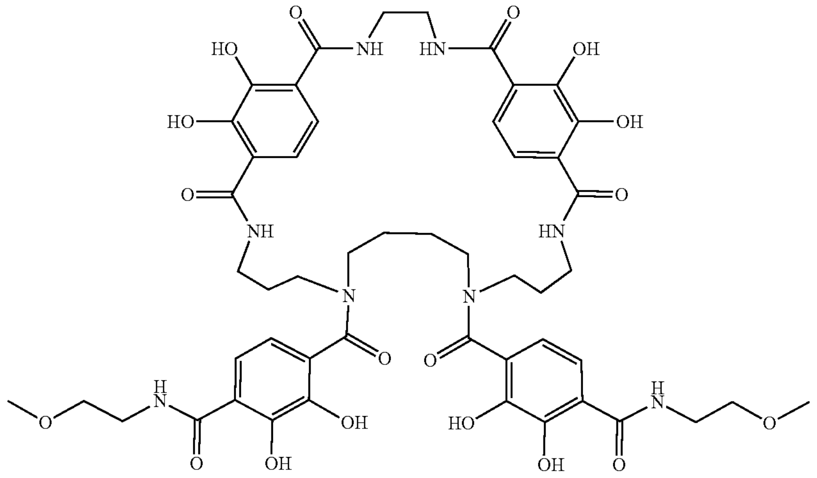

(cf. WO 2013/187971 A2, paragraph [0080]).

Scaffold Moieties

In some embodiments, $L^1$ has the structure:

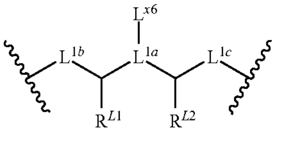

wherein $L^{1a}$, $L^{1b}$, $L^{1c}$, $L^{x6}$, $R^{L1}$, and $R^{L2}$ are as defined herein. Any of the combinations of $L^{1a}$, $L^{1b}$, $L^{1c}$, $L^{x6}$, $R^{L1}$, and $R^{L2}$ are encompassed by this disclosure and specifically provided by the invention.

In some embodiments, $L^1$ is substituted with a linker to a reactive functional group, or a linker to a targeting moiety.

In some embodiments, $L^1$ has the structure:

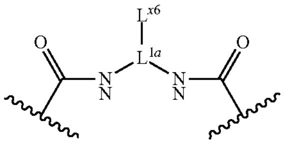

wherein $L^{1a}$ is as defined herein.

In some embodiments, $L^{1a}$ is selected from substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted heteroalkyl, substituted or unsubstituted heterocycloalkyl, substituted or unsubstituted aryl, substituted or unsubstituted arylalkyl, substituted or unsubstituted biaryl, substituted or unsubstituted heteroaryl, and a substituted or unsubstituted polycyclic ring system.

In some embodiments, $L^{1a}$ has the structure:

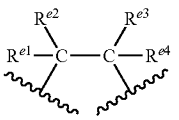
or
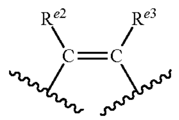

wherein $R^{e1}$, $R^{e2}$, $R^{e3}$, and $R^{e4}$ are independently selected from H, cyano, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted heteroalkyl, substituted or unsubstituted heterocycloalkyl, substituted or unsubstituted aryl, and substituted or unsubstituted heteroaryl; and two members selected from $R^{e1}$, $R^{e2}$, $R^{e3}$, and $R^{e4}$, together with the atom to which they are attached, are optionally joined, to form a substituted or unsubstituted ring (or ring system) selected from substituted or unsubstituted cycloalkyl, substituted or unsubstituted cycloalkenyl, substituted or unsubstituted heterocycloalkyl, substituted or unsubstituted aryl, substituted or unsubstituted heteroaryl. In some embodiments, $R^{e1}$ or $R^{e2}$ and $R^{e3}$ or $R^{e4}$ are hydrogen.

In a preferred embodiment, $L^{1a}$ has the structure:

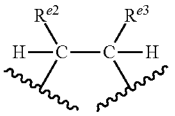

wherein $R^{e2}$ and $R^{e3}$ are as defined herein.

In some embodiments, $L^{1a}$ is selected from:

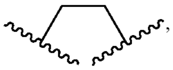, 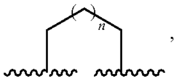, 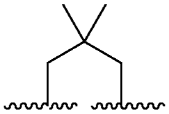, 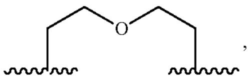, 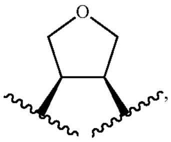, 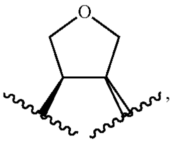, 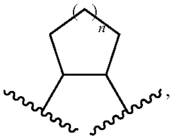, 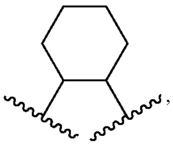, 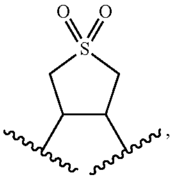, 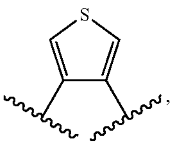, 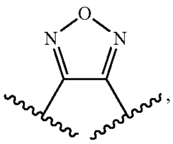, 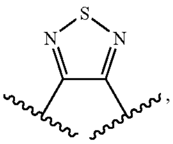, 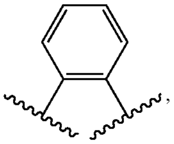, 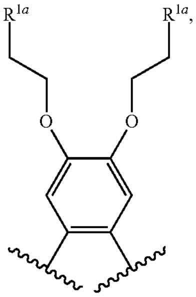, 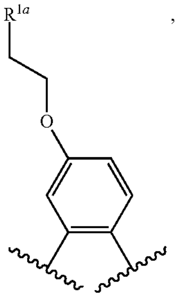, 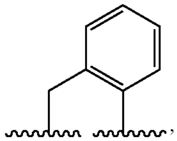, 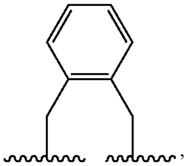, -continued

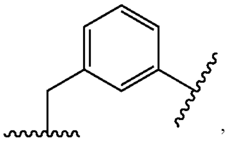, 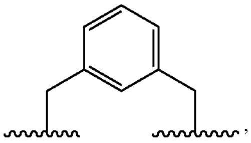, 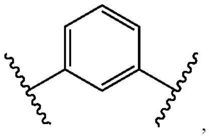, 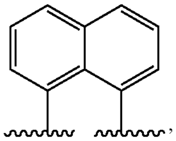, 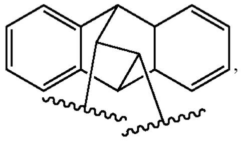, 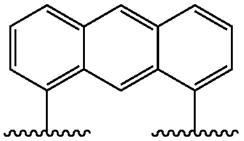, 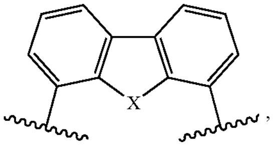, 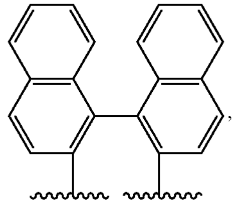, 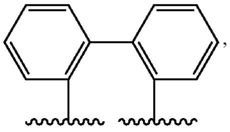, 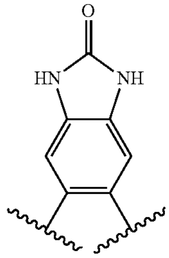, 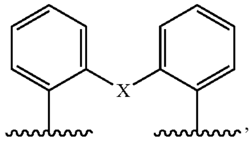, 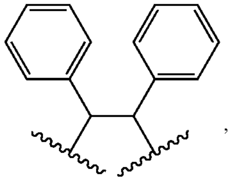, 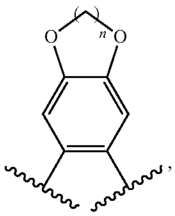, 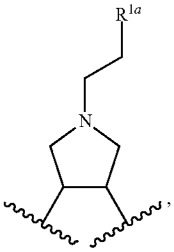, 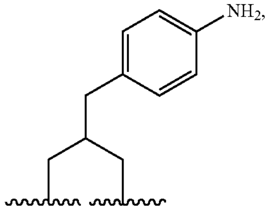 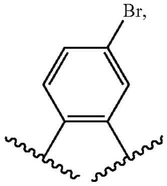

-continued

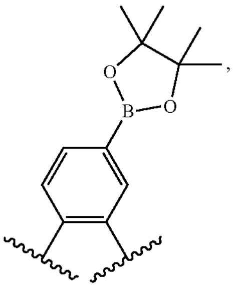

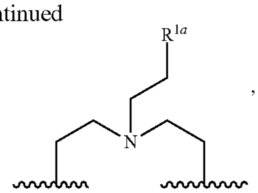

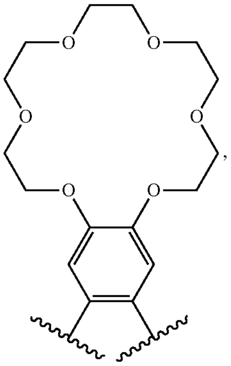

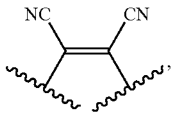

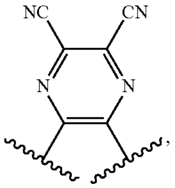

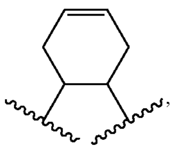

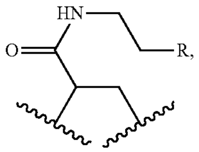

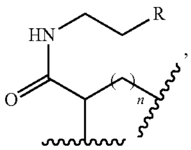

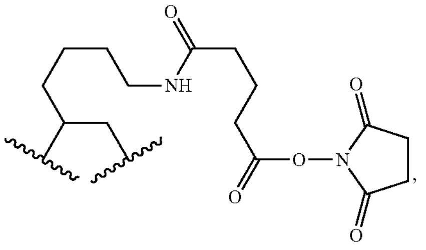

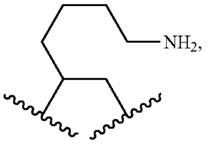

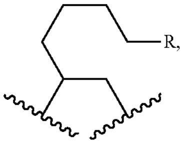

and

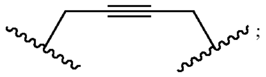

wherein n is an integer selected from 0, 1, 2, 3, 4, 5, and 6. Each R is as defined herein. $R^1$ and $R^{1a}$ are used interchangeably with reference with the structures above. In preferred embodiments, $R^{1a}$ is independently selected from H, substituted or unsubstituted alkyl, substituted or unsubstituted heteroalkyl, and a modifying moiety; X is O, S, or $CH_2$.

In a preferred embodiment, $L^{1a}$ is a member selected from 5 membered ring moieties and 6 membered ring moieties.

In another preferred embodiment, $L^{1a}$ is a member selected from 5 membered ring moieties and 6 membered ring moieties, wherein the 5 membered ring moiety or the 6 membered ring moiety is part of a fused ring system.

In another preferred embodiment according to paragraph [0058], any implied hydrogens can be selected from substituted or unsubstituted alkyl, and substituted or unsubstituted heteroalkyl of 1, 2, 3, 4, 5, 6, 7, 8, 9 members selected from C or a heteroatom.

In some embodiments, any implicit hydrogen atom in the $L^{1a}$ moieties shown above is optionally replaced by substituted or unsubstituted alkyl, substituted or unsubstituted heteroalkyl, or a modifying moiety.

In some embodiments, $L^{1a}$ is not unsubstituted $C_1$, $C_2$, or linear $C_3$ alkyl. In some embodiments, $L^{1a}$ is not an unsubstituted, linear alkyl. In some embodiments, $L^{1a}$ is not unsubstituted alkyl.

In a preferred embodiment, $L^{1a}$ is selected from:

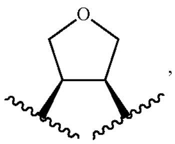

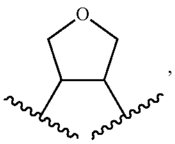

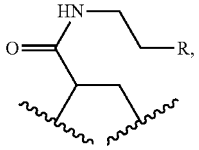

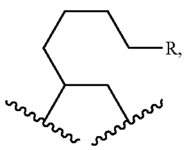

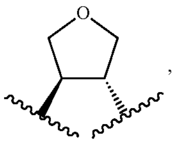

, and

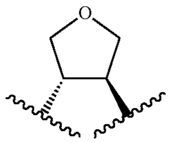

wherein R is as defined herein.

In another preferred embodiment, $L^{1a}$ is selected from:

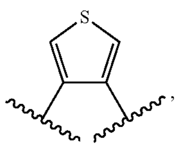

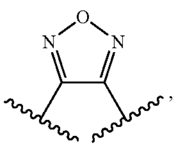

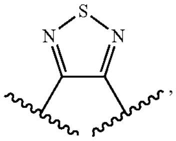

, and

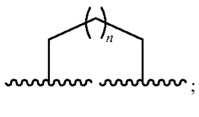

wherein n=0, 1, 2 or 3.

In another preferred embodiment, $L^{1a}$ is selected from:

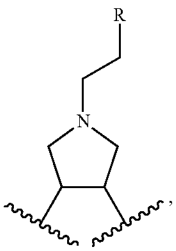,
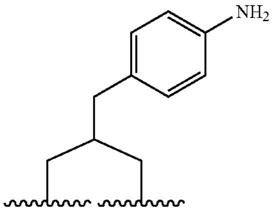,
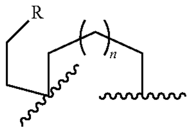, and
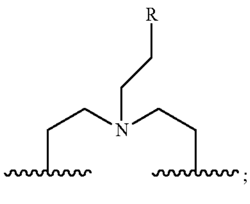;

wherein n=0, 1, 2 or 3; and R is as defined herein.

In another preferred embodiment, $L^{1a}$ has the structure:

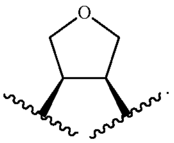 [SMILES: *[C@@H]1COC[C@@H]1*].

In some embodiments, $L^{1a}$ is selected from:

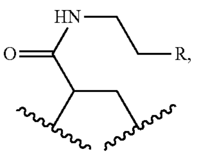,
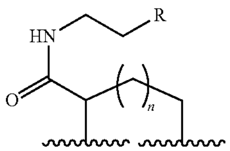,
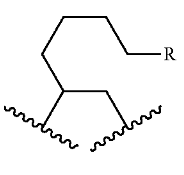
and
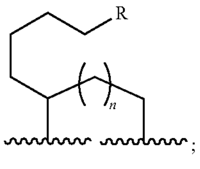;

wherein n is an integer selected from 0, 1, 2, 3, 4, 5, and 6; and R is as defined herein.

In some embodiments, $L^{1a}$ is substituted with a linker to a reactive functional group, or a linker to a targeting moiety.

In some embodiments, $L^1$b and $L^1$c are independently selected from a bond, —C(O)—, substituted or unsubstituted alkyl, and substituted or unsubstituted heteroalkyl.

In some embodiments, $L^1$b and $L^1$c are independently selected from a bond, —C(O)—, —$(CH_2)_aC(O)$—, and —$O(CH_2)_aC(O)$—; wherein a is an integer selected from 1, 2, 3, 4, 5, and 6.

In some embodiments, $L^1$b and $L^{1c}$ are each —C(O)—.

In some embodiments, $L^1$ has the structure:

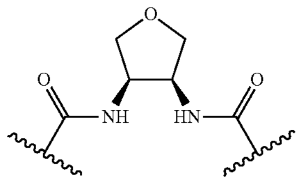 [SMILES: *C(=O)N[C@H]1COC[C@H]1NC(*)=O]

In some embodiments, $L^2$ has the structure:

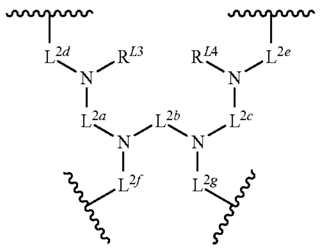

wherein $L^{2a}$, $L^{2b}$, $L^{2c}$, $L^{2d}$, $L^{2e}$, $L^{2f}$, $L^{2g}$, $R^{L3}$, and $R^{L4}$ are as defined herein. Any of the combinations of $L^{2a}$, $L^{2b}$, $L^{2c}$, $L^{2d}$, $L^{2e}$, $L^{2f}$, $L^{2g}$, $R^{L3}$, and $R^{L4}$ are encompassed by this disclosure and specifically provided by the invention.

In some embodiments, $L^2$ is substituted with a linker to a reactive functional group, or a linker to a targeting moiety.

In some embodiments, $L^2$ has the structure:

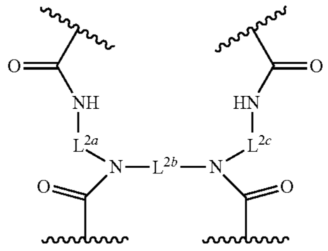

wherein $L^{2a}$, $L^{2b}$, and $L^2$c are as defined herein. Any of the combinations of $L^{2a}$, $L^{2b}$, and $L^2$c are encompassed by this disclosure and specifically provided by the invention.

In some embodiments, $A^{p1}$-$L^2$-$A^{p2}$ has the structure:

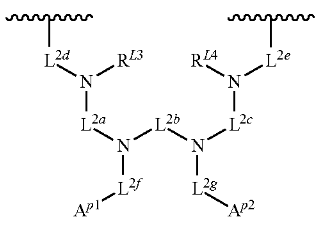

wherein $L^{2a}$, $L^{2b}$, $L^{2c}$, $L^{2d}$, $L^{2e}$, $L^{2f}$, $L^{2g}$, $R^{L3}$, $R^{L4}$, $A^{p1}$, and $A^{p2}$ are as defined herein. Any of the combinations of $L^{2a}$, $L^{2b}$, $L^{2c}$, $L^{2d}$, $L^{2e}$, $L^{2f}$, $L^{2g}$, $R^{L3}$, $R^{L4}$, $A^{p1}$, and $A^{p2}$ are encompassed by this disclosure and specifically provided by the invention.

In some embodiments, $A^{p1}$-$L^2$-$A^{p2}$ has the structure:

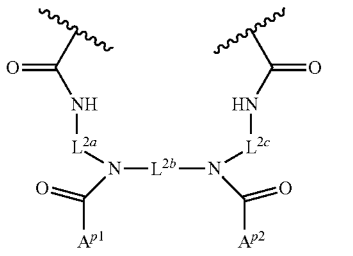

wherein $L^{2a}$, $L^{2b}$, $L^{2c}$, $A^{p1}$, and $A^{p2}$ are as defined herein. Any of the combinations of $L^{2a}$, $L^2$b $L^{2c}$, $A^{p1}$, and $A^{p2}$ are encompassed by this disclosure and specifically provided by the invention.

In some embodiments, $L^{2a}$, $L^2$b and $L^2$c are independently selected from substituted or unsubstituted alkyl and substituted or unsubstituted heteroalkyl.

In some embodiments, $L^{2a}$, $L^2$b and $L^2$c are independently selected from substituted or unsubstituted $C_1$-$C_8$ alkyl.

In some embodiments, $L^{2a}$ and $L^2$c are independently selected from substituted or unsubstituted $C_2$, $C_3$ and $C_4$ alkyl; and $L^2$b is selected from substituted or unsubstituted $C_2$, $C_3$, $C_4$, and $C_5$ alkyl.

In some embodiments, one or more of $L^{2a}$, $L^2$b and $L^2$c is substituted with a linker to a reactive functional group, or a linker to a targeting moiety. In some embodiments, $L^{2a}$ is substituted with a linker to a reactive functional group, or a linker to a targeting moiety. In some embodiments, $L^2$b is substituted with a linker to a reactive functional group, or a linker to a targeting moiety. In some embodiments, $L^2$c is substituted with a linker to a reactive functional group, or a linker to a targeting moiety.

In some embodiments, $L^{2d}$, $L^{2e}$, $L^2$f and $L^2$g are independently selected from a bond, —C(O)—, substituted or unsubstituted alkyl, and substituted or unsubstituted heteroalkyl. In some embodiments, $L^{2d}$, $L^{2e}$, $L^2$f and $L^2$g are independently selected from a bond, —C(O)—, —$(CH_2)_a$C(O)—, and —$O(CH_2)_a$C(O)—; wherein a is an integer selected from 1, 2, 3, 4, 5, and 6. In some embodiments, $L^{2d}$, $L^{2e}$, $L^2$f and $L^2$g are each —C(O)—.

In some embodiments, $R^{L3}$ and $R^{L4}$ are independently selected from hydrogen, substituted or unsubstituted alkyl, and substituted or unsubstituted heteroalkyl. In some embodiments, $R^{L3}$ and $R^{L4}$ are each H.

In some embodiments, $A^{p1}$-$L^2$-$A^{p2}$ has the structure:

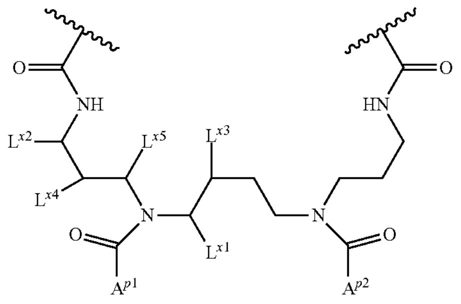

wherein $L^{x1}$, $L^{x2}$, $L^{x3}$, $L^{x4}$, and $L^{x5}$ are as defined herein.

In some embodiments, $L^{x1}$, $L^{x2}$, $L^{x3}$, $L^{x4}$, $L^{x5}$, and $L^{x6}$ are independently selected from H, a linker to a reactive functional group, and a linker to a targeting moiety. In some embodiments, at least one of $L^{x1}$, $L^{x2}$, $L^{x3}$, $L^{x4}$, $L^{x5}$, and $L^{x6}$ is a linker to a reactive functional group, or a linker to a targeting moiety.

In some embodiments, $L^{x1}$ is a linker to a reactive functional group, or a linker to a targeting moiety; and $L^{x2}$, $L^{x3}$, $L^{x4}$, $L^{x5}$, and $L^{x6}$ are each H.

In some embodiments, $L^{x2}$ is a linker to a reactive functional group, or a linker to a targeting moiety; and $L^{x1}$, $L^{x3}$, $L^{x4}$, $L^{x5}$, and $L^{x6}$ are each H. In some embodiments, $L^{x3}$ is a linker to a reactive functional group, or a linker to a targeting moiety; and $L^{x1}$, $L^{x2}$, $L^{x4}$, $L^{x5}$, and $L^{x6}$ are each H. In some embodiments, $L^{x4}$ is a linker to a reactive functional group, or a linker to a targeting moiety; and $L^{x1}$, $L^{x2}$, $L^{x3}$, $L^{x5}$, and $L^{x6}$ are each H. In some embodiments, $L^{x5}$ is a linker to a reactive functional group, or a linker to a targeting moiety; and $L^{x1}$, $L^{x2}$, $L^{x3}$, $L^{x4}$, and $L^{x6}$ are each H. In some embodiments, $L^{x6}$ is a linker to a reactive functional group, or a linker to a targeting moiety; and $L^{x1}$, $L^{x2}$, $L^{x3}$, $L^{x4}$, and $L^{x5}$ are each H.

In some embodiments, $A^{p1}$-$L^2$-$A^{p2}$ has the structure:

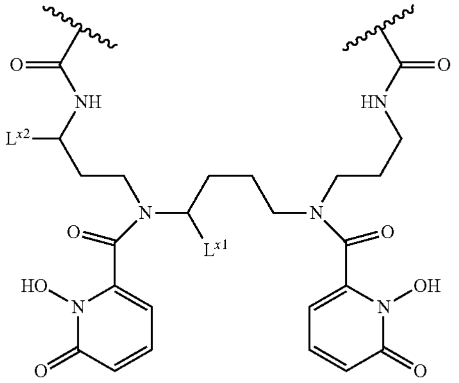

wherein $L^{x1}$ and $L^{x2}$ are as defined herein.

In various embodiments, the invention provides compounds selected from:

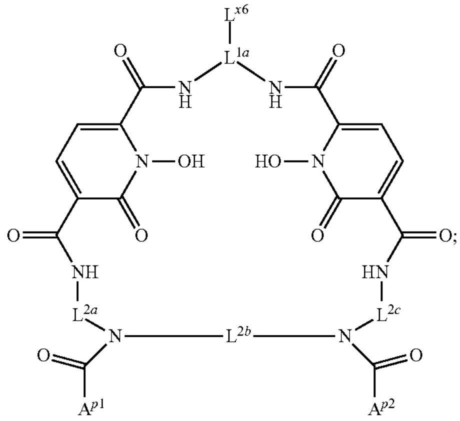

and

-continued

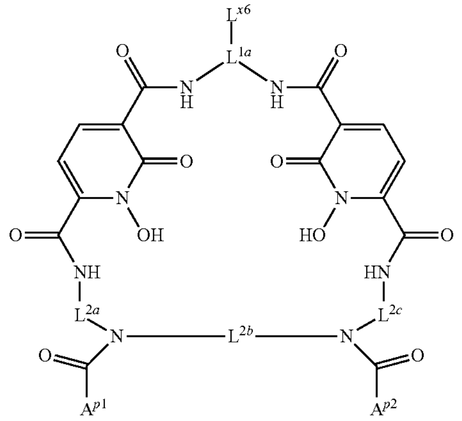

wherein $L^{1a}$ is selected from substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted heteroalkyl, substituted or unsubstituted heterocycloalkyl, substituted or unsubstituted aryl, substituted or unsubstituted arylalkyl, substituted or unsubstituted biaryl, substituted or unsubstituted heteroaryl, and a substituted or unsubstituted polycyclic ring system. $L^{x6}$ is selected from H, a linker to a reactive functional group, and a linker to a targeting moiety. $L^{2a}$, $L^{2}$b and $L^{2}$c are independently selected from substituted or unsubstituted alkyl and substituted or unsubstituted heteroalkyl.

In various embodiments, the invention provides compounds selected from:

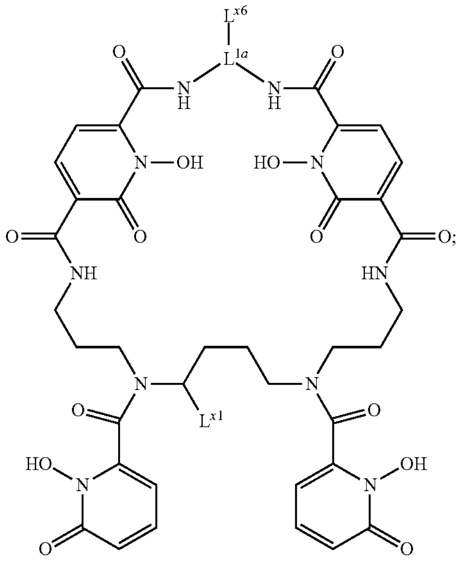

; and

-continued

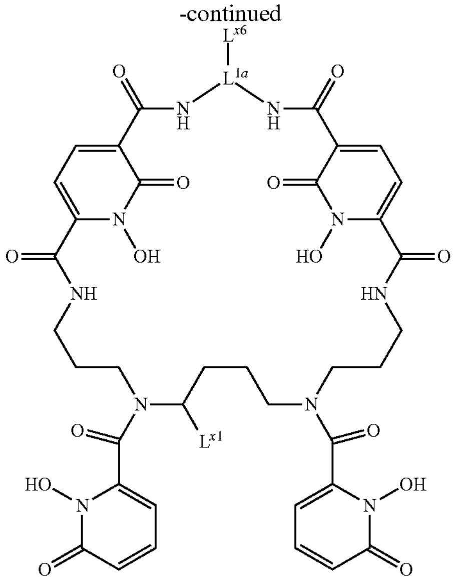

wherein $L^{x1}$ and $L^{x6}$ are independently selected from H, a linker to a reactive functional group, and a linker to a targeting moiety.

Precursors for the scaffold moieties, particularly $L^{2}$, can be synthesized as disclosed in WO 2016/106241 A1. The disclosure of which is incorporated herein by reference in its entirety.

Chelating Moieties

In some embodiments, $A^{b1}$, $A^{b2}$, $A^{P1}$, and $A^{P2}$ are independently selected from:

(I)

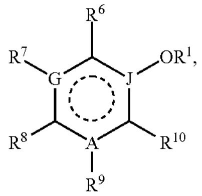

, (II)

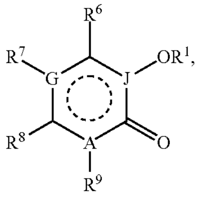

, and (III)

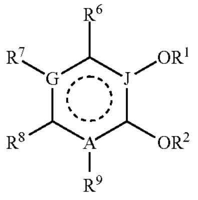

wherein A and G are independently selected from carbon, nitrogen and oxygen;

J is selected from carbon and nitrogen. Each $R^{1}$ and $R^{2}$ is independently selected from H, an enzymatically labile group, a hydrolytically labile group, a metabolically labile group, a photolytically labile group and a single negative charge. Each $R^6$, $R^7$, $R^8$, $R^9$, and $R^{10}$ is independently selected from a bond to $L^1$ or $L^2$, alkanediyl attached to $L^1$ or $L^2$, H, substituted or unsubstituted alkyl, substituted or unsubstituted heteroalkyl, halogen, CN, $-CF_3$, $-C(O)R^{17}$, $-SO_2NR^{17}R^{18}$, $-NR^{17}R^{18}$, $-OR^{17}$, $-S(O)_2R^{17}$, $-COOR^{17}$, $-S(O)_2OR^{17}$, $-OC(O)R^{17}$, $-C(O)NR^{17}R^{18}$, $-NR^{17}C(O)R^{18}$, $-NR^{17}SO_2R^{18}$, and $-NO_2$, wherein at least two of $R^6$, $R^7$, $R^8$, $R^9$, and $R^{10}$ are optionally joined to form a ring system selected from substituted or unsubstituted cycloalkyl, substituted or unsubstituted heterocycloalkyl, substituted or unsubstituted aryl and substituted or unsubstituted heteroaryl. $R^{17}$ and $R^{18}$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl; and $R^{17}$ and $R^{18}$, together with the atoms to which they are attached, are optionally joined to form a 5-, 6- or 7-membered ring. When A is oxygen, $R^9$ is not present; and when G is oxygen, $R^7$ is not present. $A^{b1}$ and $A^{b2}$ are attached to $L^1$ and $L^2$ through two members selected from $R^6$, $R^7$, $R^8$, $R^9$ and $R^{10}$; and $A^{P1}$ and $A^{P2}$ are attached to $L^2$ through a member selected from $R^6$, $R^7$, $R^8$, $R^9$ and $R^{10}$.

In some embodiments, when $A^{b1}$ has a structure according to formula (I), $A^{b1}$ is attached to $L^1$ and $L^2$ through $R^6$ and $R^{10}$; when $A^{b1}$ has a structure according to formula (II) or (III), $A^{b1}$ is attached to L' and $L^2$ through $R^6$ and $R^9$; when $A^{b2}$ has a structure according to formula (I), $A^{b2}$ is attached to $L^1$ and $L^2$ through $R^6$ and $R^{10}$; when $A^{b2}$ has a structure according to formula (II) or (III), $A^{b2}$ is attached to $L^1$ and $L^2$ through $R^6$ and $R^9$; when $A^{P1}$ has a structure according to formula (I), $A^{P1}$ is attached to $L^2$ through $R^6$ or $R^{10}$; when $A^{P1}$ has a structure according to formula (II) or (III), $A^{P1}$ is attached to $L^2$ through $R^6$ or $R^9$; when $A^{P2}$ has a structure according to formula (I), $A^{P2}$ is attached to $L^2$ through $R^6$ or $R^{10}$; and when $A^{P2}$ has a structure according to formula (II) or (III), $A^{P2}$ is attached to $L^2$ through $R^6$ or $R^9$.

In some embodiments, $A^{b1}$, $A^{b2}$, $A^{P1}$ and $A^{P2}$ are each independently selected from:

(1)

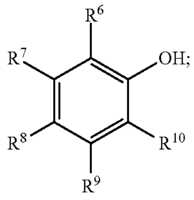

(2a)

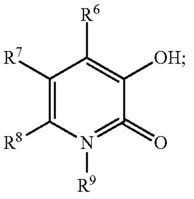

-continued (2b)

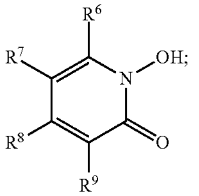

(3)

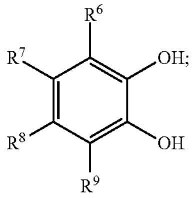

(4)

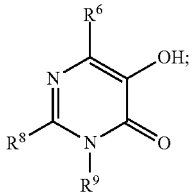

and (5)

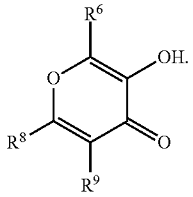

In some embodiments, when $A^{b1}$ has a structure according to formula (1), $A^{b1}$ is attached to $L^1$ and $L^2$ through $R^6$ and $R^{10}$; when $A^{b1}$ has a structure according to formula (2a), (2b), (3), (4) or (5), $A^{b1}$ is attached to $L^1$ and $L^2$ through $R^6$ and $R^9$; when $A^{b2}$ has a structure according to formula (1), $A^{b2}$ is attached to $L^1$ and $L^2$ through $R^6$ and $R^{10}$; when $A^{b2}$ has a structure according to formula (2a), (2b), (3), (4) or (5), $A^{b2}$ is attached to $L^1$ and $L^2$ through $R^6$ and $R^9$; when $A^{P1}$ has a structure according to formula (1), $A^{P1}$ is attached to $L^2$ through $R^6$ or $R^{10}$; and when $A^{P1}$ has a structure according to formula (2a), (2b), (3), (4) or (5), $A^{P1}$ is attached to $L^2$ through $R^6$ or $R^9$; when $A^{P2}$ has a structure according to formula (1), $A^{P2}$ is attached to $L^2$ through $R^6$ or $R^{10}$; and when $A^{P2}$ has a structure according to formula (2a), (2b), (3), (4) or (5), $A^{P2}$ is attached to $L^2$ through $R^6$ or $R^9$.

In a preferred embodiment, each $A^{b1}$, $A^{b2}$, $A^{P1}$ and $A^{P2}$ has a structure according to formula (2b).

In another preferred embodiment, each $A^{b1}$, $A^{b2}$, $A^{P1}$ and $A^{P2}$ has a structure according to formula (2a).

In another preferred embodiment, each $A^{b1}$, $A^{b2}$, $A^{P1}$ and $A^{P2}$ has a structure according to formula (1).

In various embodiments, there is provided a compound in which wherein $A^{b1}$ and $A^{b2}$ are members independently selected from:

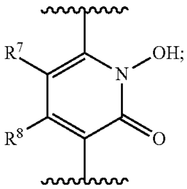

and

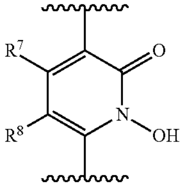

wherein each $R^7$, and $R^8$ is independently selected from a bond to $L^1$ or $L^2$, alkanediyl attached to $L^1$ or $L^2$, H, substituted or unsubstituted alkyl, substituted or unsubstituted heteroalkyl, halogen, CN, $—CF_3$, $—C(O)R^{17}$, $—SO_2NR^{17}R^{18}$, $—NR^{17}R^{18}$, $—OR^{17}$, $—S(O)_2R^{17}$, $—COOR^{17}$, $—S(O)_2OR^{17}$, $—OC(O)R^{17}$, $—C(O)NR^{17}R^{18}$, $—NR^{17}C(O)R^{18}$, $—NR^{17}SO_2R^{18}$, and $—NO_2$, wherein at least two of $R^6$, $R^7$, $R^8$, $R^9$, and $R^{10}$ are optionally joined to form a ring system selected from substituted or unsubstituted cycloalkyl, substituted or unsubstituted heterocycloalkyl, substituted or unsubstituted aryl and substituted or unsubstituted heteroaryl. $R^{17}$ and $R^{18}$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl; and $R^{17}$ and $R^{18}$, together with the atoms to which they are attached, are optionally joined to form a 5-, 6- or 7-membered ring.

In some embodiments, $A^{b1}$ and $A^{b2}$ are each independently selected from a moiety comrpising:

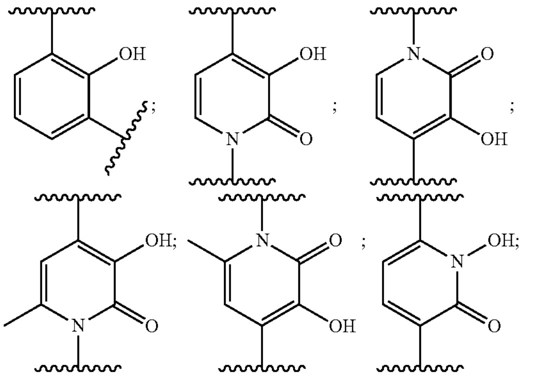

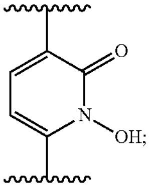

and

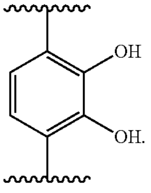 [SMILES: *c1ccc(*)c(O)c1O]

In some embodiments, a member selected from $A^{b1}$ and $A^{b2}$ and a combination thereof is not a moiety comprising:

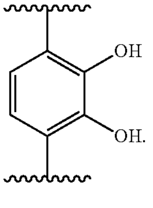

In some embodiments, $A^{b1}$ and $A^{b2}$ are each independently selected from a moiety comprising:

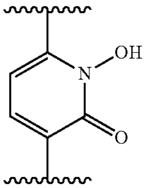

and

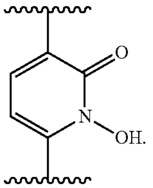

In some embodiments, $A^{p1}$ and $A^{p2}$ are each independently selected from a moiety comprising:

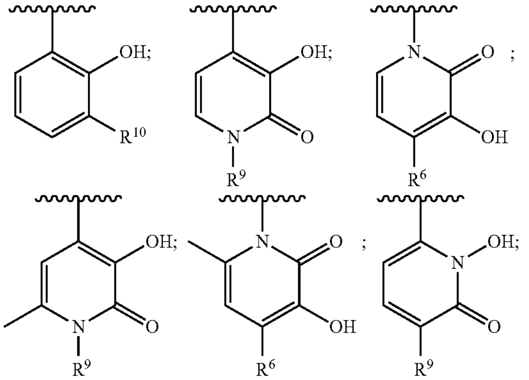

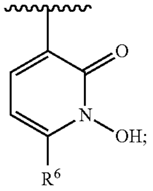

and

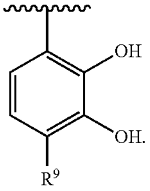

In some embodiments, $A^{p1}$ and $A^{p2}$ are each independently selected from a moiety comprising:

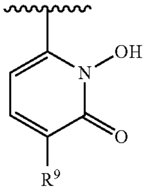

and

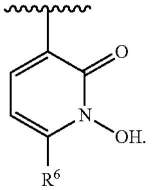

In some embodiments, $A^{p1}$ and $A^{p2}$ each are a moiety comprising:

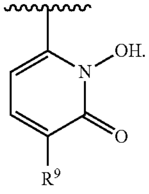

In some embodiments, one or both of $A^{p1}$ and $A^{p2}$ comprise a modifying moiety. Modifying moieties are as defined herein. In some embodiments, $R^9$ of $A^{p1}$, $A^{p2}$, or $A^{p1}$ and $A^{p2}$ comprises a modifying moiety. In some embodiments, $R^9$ of $A^{p1}$, $A^{p2}$, or $A^{p1}$ and $A^{p2}$ is —C(O)$NR^{17}R^{18}$, wherein $R^{17}$ is H and $R^{18}$ is a modifying moiety. In some embodiments, $R^6$ of $A^{p1}$, $A^{p2}$, or $A^{p1}$ and $A^{p2}$ comprises a modifying moiety. In some embodiments, $R^6$ of $A^{p1}$, $A^{p2}$, or $A^{p1}$ and $A^{p2}$ is —C(O)$NR^{17}R^{18}$, wherein $R^{17}$ is H and $R^{18}$ is a modifying moiety. In an exemplary embodiment, one or both of $R^6$ and $R^9$ is COOH, or COO.

Linker to Functional/Targeting Moiety

A "linker", "linking member", or "linking moiety" as used herein is a moiety that joins or potentially joins, covalently or noncovalently, a first moiety to a second moiety. In particular, a linker attaches or could potentially attach a ligand described herein to another molecule, such as a targeting moiety. In some embodiments, a linker attaches or could potentially attach a ligand described herein to a solid support. A linker comprising a reactive functional group that can be further reacted with a reactive functional group on a structure of interest in order to attach the structure of interest to the linker is referred to as a "functionalized linker". In exemplary embodiments, a linker is a functionalized linker. In exemplary embodiments, a ligand comprises one or more functionalized linkers. In some embodiments, a linker comprises a targeting moiety. In some embodiments, a linker to a targeting moiety comprises a bond to the targeting moiety.

In some embodiments, the linker is a linker to a functional moiety, or a linker to a targeting moiety. In some embodiments, the functional moiety is a reactive functional group or a protected functional group. In some embodiments, the linker is a linker to a reactive functional group, or a linker to a targeting moiety.

A linker can be any useful structure for that joins a ligand to a reactive functional group or a targeting moiety, such as an antibody. Examples of a linker include 0-order linkers (i.e., a bond), substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. Further exemplary linkers include substituted or unsubstituted ($C_1$, $C_2$, $C_3$, $C_4$, $C_5$, $C_6$, $C_7$, $C_8$, $C_9$ or $C_{10}$)alkyl, substituted or unsubstituted heteroalkyl, —C(O)NR'—, —C(O)O—, —C(O)S—, and —C(O)CR'R", wherein R' and R" are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, a linker includes at least one heteroatom. Exemplary linkers also include-C(O)NH—, —C(O), —NH—, —S—, —O—, and the like. In an exemplary embodiment, a linker is a heteroalkyl substituted with a reactive functional group.

Reactive Functional Groups

In one embodiment, a linker comprises a reactive functional group (or a "reactive functional moiety", used synonymously), which can be further reacted to covalently attach the linker to a targeting moiety. Reactive functional groups and classes of reactions useful in practicing the present invention are generally those that are well known in the art of bioconjugate chemistry. Currently favored classes of reactions available with reactive functional groups of the invention are those which proceed under relatively mild conditions. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions and Diels-Alder reactions). These and other useful reactions are discussed, for example, in March, Advanced Organic Chemistry (3rd Ed., John Wiley & Sons, New York, 1985); Hermanson, Bioconjugate Techniques (Academic Press, San Diego, 1996); and Feeney et al., Modification of Proteins, Advances in Chemistry Series, Vol. 198 (American Chemical Society, Washington, D.C., 1982).

In some embodiments, a reactive functional group refers to a group selected from olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds., Organic Functional Group Preparations, (Academic Press, San Diego, 1989)).

A reactive functional group can be chosen according to a selected reaction partner. As an example, an activated ester, such as an NHS ester will be useful to label a protein via lysine residues. Sulfhydryl reactive groups, such as maleimides can be used to label proteins via amino acid residues carrying an SH-group (e.g., cystein). Antibodies may be labeled by first oxidizing their carbohydrate moieties (e.g., with periodate) and reacting resulting aldehyde groups with a hydrazine containing ligand.

The reactive functional groups can be chosen such that they do not participate in, or interfere with, the reactions necessary to assemble the reactive ligand. Alternatively, a reactive functional group can be protected from participating in the reaction by means of a protecting group. Those of skill in the art understand how to protect a particular functional group so that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Amines and Amino-Reactive Groups

In one embodiment, a reactive functional group is selected from an amine, (such as a primary or secondary amine), hydrazine, hydrazide and sulfonylhydrazide. Amines can, for example, be acylated, alkylated or oxidized. Useful non-limiting examples of amino-reactive groups include N-hydroxysuccinimide (NHS) esters, sulfur-NHS esters, imidoesters, isocyanates, isothiocyanates, acylhalides, arylazides, p-nitrophenyl esters, aldehydes, sulfonyl chlorides, thiazolides and carboxyl groups.

NHS esters and sulfo-NHS esters react preferentially with primary (including aromatic)amino groups of a reaction partner. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide.

Imidoesters are the most specific acylating reagents for reaction with amine groups of a molecule such as a protein.

At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus cross-linking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the reaction partner attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of carboxylic acids are also useful amino-reactive groups. Although the reagent specificity is not very high, α- and ε-amino groups appear to react most rapidly.

Aldehydes react with primary amines of the conjugate components (e.g., ε-amino group of lysine residues). Although unstable, Schiff bases are formed upon reaction of the protein amino groups with the aldehyde. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product. Alternatively, a stable bond may be formed by reductive amination.

Aromatic sulfonyl chlorides react with a variety of sites of the conjugate components, but reaction with the amino groups is the most important, resulting in a stable sulfonamide linkage.

Free carboxyl groups react with carbodiimides, soluble in both water and organic solvents, forming pseudoureas that can then couple to available amines yielding an amide linkage. Yamada et al., *Biochemistry,* 1981, 20:4836-4842, e.g., teach how to modify a protein with carbodiimides.

Sulfhydryl and Sulfhydryl-Reactive Groups

In another embodiment, a reactive functional group is selected from a sulfhydryl group (which can be converted to disulfides) and sulfhydryl-reactive group. Useful non-limiting examples of sulfhydryl-reactive groups include maleimides, alkyl halides, acyl halides (including bromoacetamide or chloroacetamide), pyridyl disulfides, and thiophthalimides.

Maleimides react preferentially with the sulfhydryl group of the conjugate components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryl groups via disulfide exchange to give mixed disulfides. As a result, pyridyl disulfides are relatively specific sulfhydryl-reactive groups.

Thiophthalimides react with free sulfhydryl groups to also form disulfides.

Other Reactive Functional Groups

Other exemplary reactive functional groups include:

(i)carboxyl groups and various derivatives thereof including, but not limited to, N-hydroxybenztriazole esters, acid halides, acyl imidazoles, thioesters, p-nitrophenyl esters, alkyl, alkenyl, alkynyl and aromatic esters;

(ii) hydroxyl groups, which can be converted to esters, ethers, aldehydes, etc.;

(iii) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;

(iv) dienophile groups, which are capable of participating in Diels-Alder reactions such as, for example, maleimido groups;

(v) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(vi) alkenes, which can undergo, for example, cycloadditions, acylation, Michael addition, etc;

(vii) epoxides, which can react with, for example, amines and hydroxyl groups;

(ix) phosphoramidites and other standard functional groups useful in nucleic acid synthesis and (x) any other functional group useful to form a covalent bond between the functionalized ligand and a molecular entity or a surface.

Functional Groups with Non-specific Reactivities

In addition to the use of site-specific reactive moieties, the present invention contemplates the use of non-specific reactive groups to link a ligand to a targeting moiety. Non-specific groups include photoactivatable groups, for example.

Photoactivatable groups are ideally inert in the dark and are converted to reactive species in the presence of light. In one embodiment, photoactivatable groups are selected from precursors of nitrenes generated upon heating or photolysis of azides. Electron-deficient nitrenes are extremely reactive and can react with a variety of chemical bonds including N—H, O—H, C—H, and C═C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55:3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein cross-links.

In some embodiments, a linker joins a ligand to a reactive functional group. In exemplary embodiments, a linker joins a ligand to a targeting moiety. That is, in exemplary embodiments, a linker comprises a targeting moiety. In some embodiments, a ligand comprises a linker to a targeting moiety. Any linker described herein may be a linker comprising a reactive functional group that could react with a reactive functional group on a targeting moiety to join the linker to the targeting moiety. Any linker described herein may be a linker comprising a bond to a targeting moiety. The term "targeting moiety" refers to a moiety serves to target or direct the molecule to which it is attached (e.g., a ligand or a ligand complexed to a metal ion (such as a radionuclide)) to a particular location or molecule. Thus, for example, a targeting moiety may be used to target a molecule to a specific target protein or enzyme, or to a particular cellular location, to a particular cell type or to a diseased tissue. As will be appreciated by those in the art, the localization of proteins within a cell is a simple method for increasing effective concentration. For example, shuttling an imaging agent and/or therapeutic into the nucleus confines them to a smaller space thereby increasing concentration. Finally, the physiological target may simply be localized to a specific compartment, and the agents must be localized appropriately.

The targeting moiety can be a small molecule (e.g., MW<500D), which includes both non-peptides and peptides. Examples of a targeting moiety also include peptides, polypeptides (including proteins, and in particular antibodies, which includes antibody fragments), nucleic acids, oligonucleotides, carbohydrates, lipids, hormones (including proteinaceous and steroid hormones (for instance, estradiol)), growth factors, lectins, receptors, receptor ligands, cofactors and the like. Targets of a targeting moiety can include a complementary nucleic acid, a receptor, an antibody, an antigen or a lectin, for example.

In exemplary embodiments, a targeting moiety can bind to a target with high binding affinity. In other words, a targeting moiety with high binding affinity to a target has a high specificity for or specifically binds to the target. In some embodiments, a high binding affinity is given by a dissociation constant $K_d$ of about $10^{-7}$ M or less. In exemplary embodiments, a high binding affinity is given by a dissociation constant $K_d$ of about $10^{-8}$ M or less, about $10^{-9}$ M or less, about $10^{-10}$ M or less, about $10^{-11}$ M or less, about $10^{-12}$ M or less, about $10^{-13}$ M or less, about $10^{-14}$ M or less or about $10^{-15}$ M or less. A compound may have a high binding affinity for a target if the compound comprises a portion, such as a targeting moiety, that has a high binding affinity for the target.

In exemplary embodiments, a targeting moiety is an antibody. An "antibody" refers to a protein comprising one or more polypeptides substantially encoded by all or part of the recognized immunoglobulin genes. The recognized immunoglobulin genes, for example in humans, include the kappa (κ), lambda (λ) and heavy chain genetic loci, which together compose the myriad variable region genes, and the constant region genes mu (μ), delta (δ), gamma (γ), epsilon (ε) and alpha (α), which encode the IgM, IgD, IgG, IgE, and IgA isotypes respectively. Antibody herein is meant to include full length antibodies and antibody fragments, and may refer to a natural antibody from any organism, an engineered antibody or an antibody generated recombinantly for experimental, therapeutic or other purposes as further defined below. Antibody fragments include Fab, Fab', $F(ab')_2$, Fv, scFv or other antigen-binding subsequences of antibodies and can include those produced by the modification of whole antibodies or those synthesized de novo using recombinant DNA technologies. The term "antibody" refers to both monoclonal and polyclonal antibodies. Antibodies can be antagonists, agonists, neutralizing, inhibitory or stimulatory.

While a targeting moiety may be appended to a ligand in order to localize the compound to a specific region in an animal, certain ligands have a natural affinity for cells, tissue, organs or some other part of the animal. For example, a ligand disclosed herein might have a natural or intrinsic affinity for bone. Thus, in some embodiments, a ligand does not comprise a targeting moiety or a linker to a targeting moiety. A ligand lacking a targeting moiety can be used in any method that does not require specific targeting.

In some embodiments, a ligand comprises a linker to a solid support. That is, any linker described herein may be a linker comprising a reactive functional group that could react with a reactive functional group on a solid support to join the linker to the solid support. Any linker described herein may be a linker comprising a bond to a solid support. A "solid support" is any material that can be modified to contain discrete individual sites suitable for the attachment or association of a ligand. Suitable substrates include biodegradable beads, non-biodegradable beads, silica beads, magnetic beads, latex beads, glass beads, quartz beads, metal beads, gold beads, mica beads, plastic beads, ceramic beads, or combinations thereof. Of particular use are biocompatible polymers, including biodegradable polymers that are slowly removed from the system by enzymatic degradation. Example biodegradable materials include starch, cross-linked starch, poly(ethylene glycol), polyvinylpyrrolidine, polylactides (PLA), polyglycolides (PGA), poly(lactide-co-glycolides) (PLGA), polyanhydrides, polyorthoesters, poly(DTH iminocarbonate), poly(bisphenol A iminocarbonate), polycyanoacrylate, polyphosphazene, mixtures thereof and combinations thereof. Other suitable substances for forming the particles exist and can be used. In some embodiments, a solid support is a bead comprising a cross-linked starch, for example, cross-linked potato starch. Beads made from starch are completely biodegradable in the body, typically by serum amylase, a naturally occurring enzyme found in the body. In these embodiments, the ligand optionally further comprises a targeting moiety or a linker to a targeting moeity. In cases where a ligand that is attached to a solid support does not comprise a targeting moiety, the ligand can be localized directly by the practitioner, for example, by direct surgical implantation.

In some embodiments, a linker has the structure $-L^{11}-F^x$, wherein $L^{11}$ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and $F^x$ is selected from a reactive functional group, a protected functional group, or a targeting moiety.

In some embodiments, $L^{11}$ is selected from substituted or unsubstituted alkyl and substituted or unsubstituted heteroalkyl. In some embodiments, $L^{11}$ is heteroalkyl. In some embodiments, $L^{11}$ is ($C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ or $C_{20}$)alkyl in which 1, 2 or 3 atoms are replaced with a heteroatom, such as nitrogen or oxygen. In some embodiments, $L^{11}$ comprises a modifying moiety.

In some embodiments, $F^x$ is selected from —$NH_2$, —C(O)OH, alkyl ester (e.g., methyl ester), N-hydroxysuccinimide (NHS) ester, sulfo-NHS ester, isothiocyanate, and maleimide. In some embodiments, $F^x$ is selected from —$NH_2$ and —C(O) OH.

In some embodiments, $-L^{11}-F^x$ is selected from:

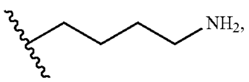

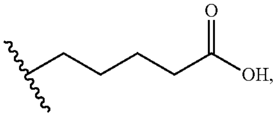

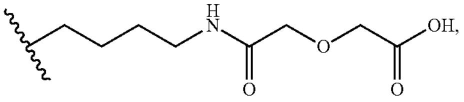

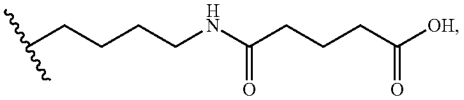

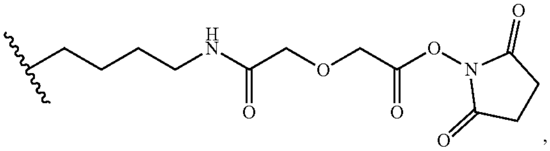
,

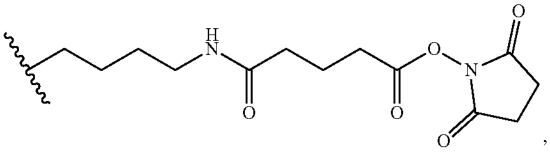
,

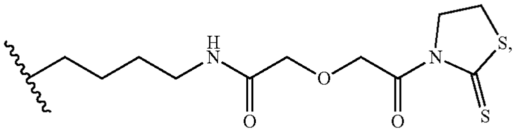

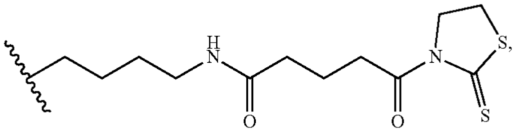

-continued

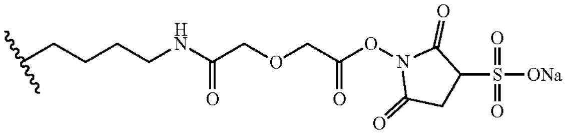

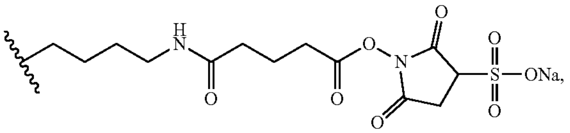

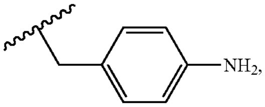

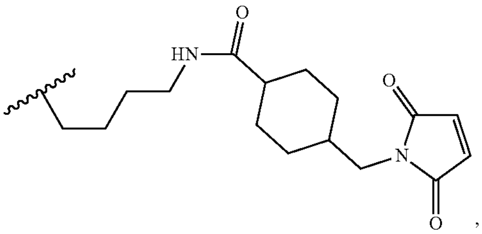
,

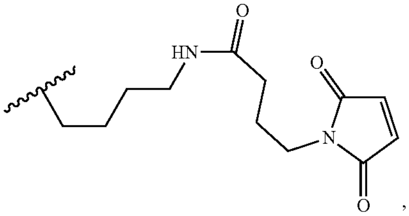
,

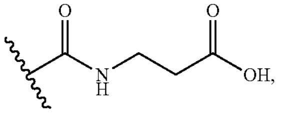

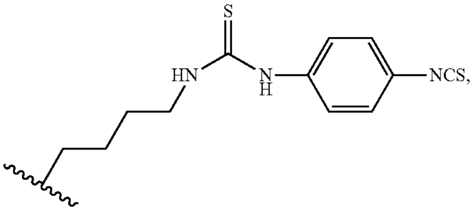

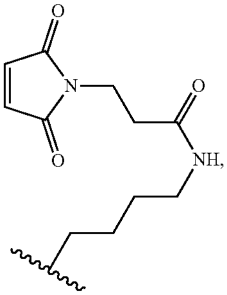

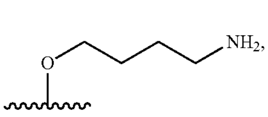

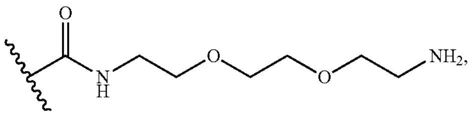

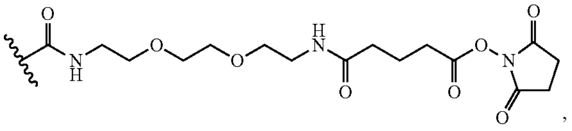
,

-continued

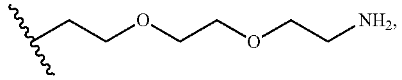

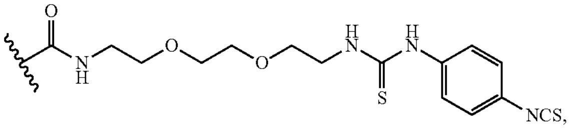

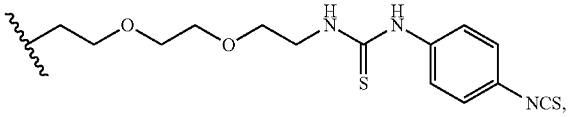

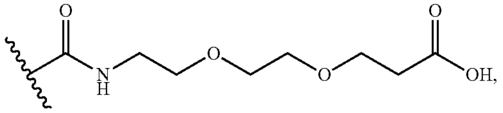

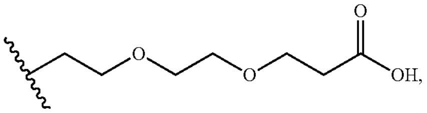

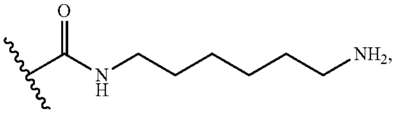

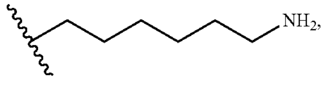

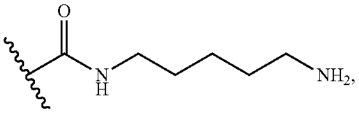

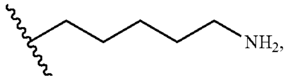

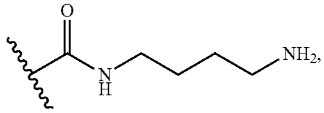

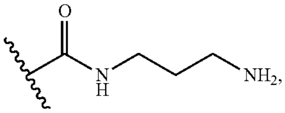
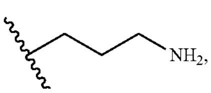

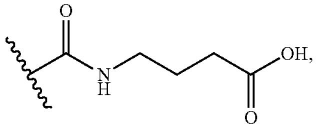

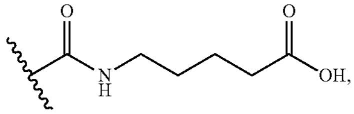

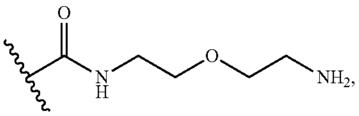

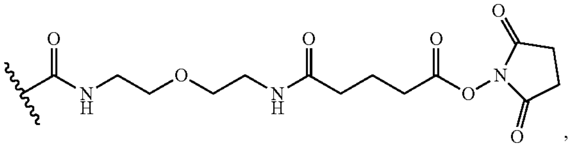
,

-continued

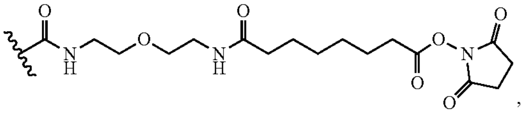
, and

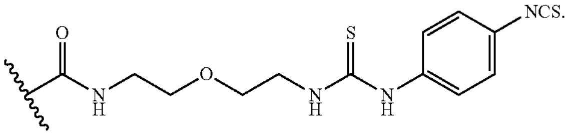

In a preferred embodiment according to paragraph [00139], any implied hydrogens can be selected from substituted or unsubstituted alkyl, and substituted or unsubstituted heteroalkyl of 1, 2, 3, 4, 5, 6, 7, 8, 9 members selected from C or a heteroatom.

In some embodiments, a linker has the structure:

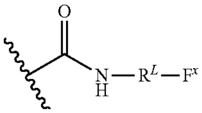

wherein $R^L$ is selected from substituted or unsubstituted alkyl, and substituted or unsubstituted heteroalkyl; and $F^x$ is as defined herein. In some embodiments, $R^L$ is a substituted or unsubstituted alkoxyalkyl. In some embodiments, $R^L$ is a substituted or unsubstituted monoether. In some embodiments, $R^L$ is a substituted or unsubstituted polyether. In some embodiments, the polyether has from 2 to 10 (i.e., 2, 3, 4, 5, 6, 7, 8, 9, or 10) ether groups. In some embodiments, $R^L$ comprises a modifying moiety.

In some embodiments, a linker has the structure:

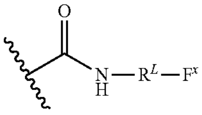

wherein $R^L$ is selected from:

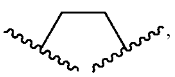
,
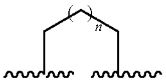
, and

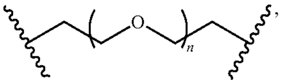

wherein n is an integer selected from 1, 2, 3, 4, 5, and 6; and $F^x$ is a reactive functional group (such as $NH_2$) or a protected functional group.

In some embodiments, a linker has a structure selected from:

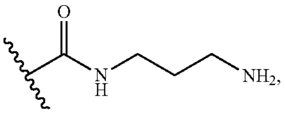,
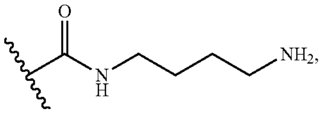,
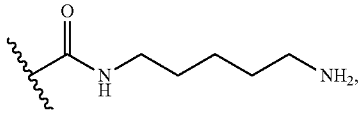,
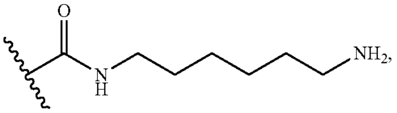,
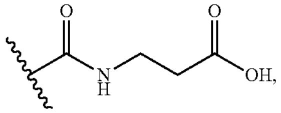,
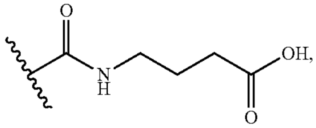,
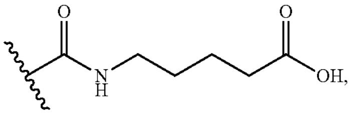,
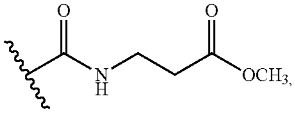,
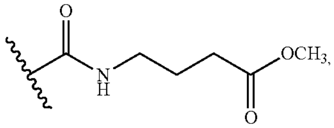,
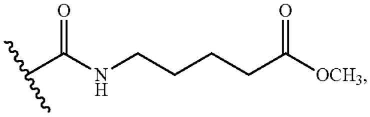,
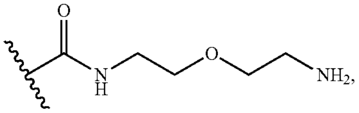,
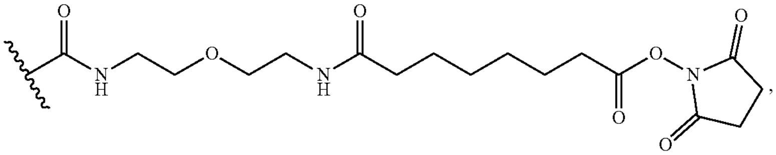, and
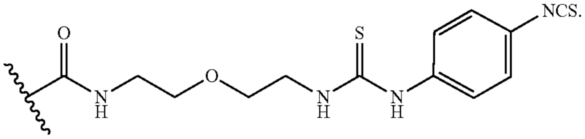.
In a preferred embodiment, a linker has a structure selected from:
In another preferred embodiment, a linker has a structure selected from:
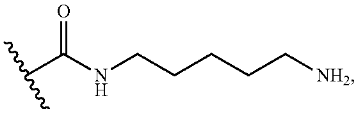,
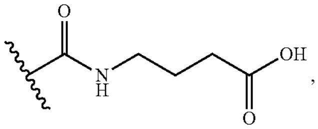,
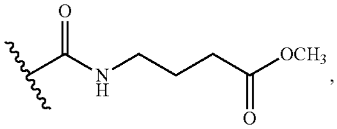,
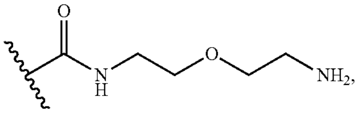,
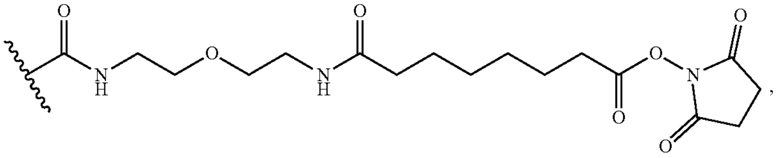,
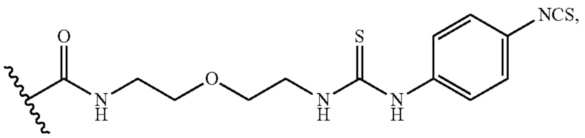, and
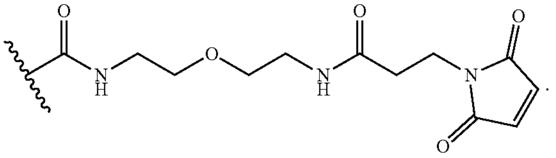.

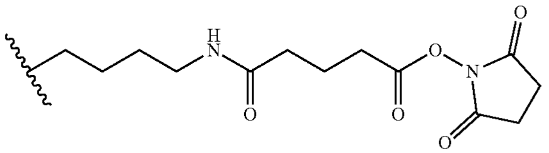

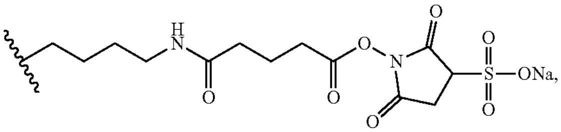

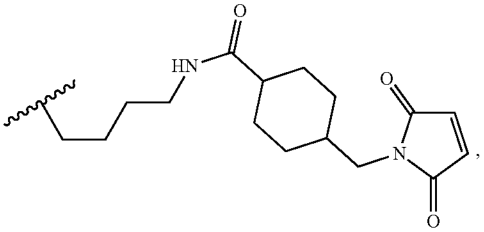

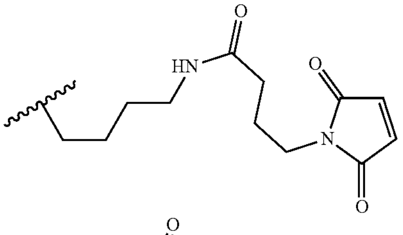
, and

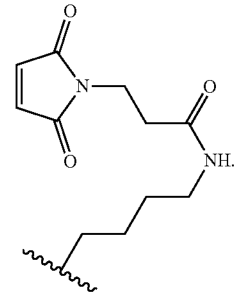

In another preferred embodiment, a linker has a structure selected from:

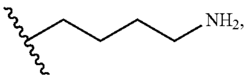

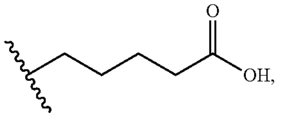
and

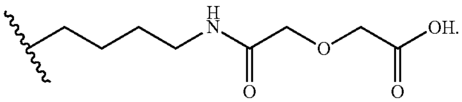

In exemplary embodiments, $F^x$ is a targeting moiety.

In exemplary embodiments, a linker is a linker to a targeting moiety. In some embodiments, the targeting moiety is selected from a polypeptide, a nucleic acid, a lipid, a polysaccharide, a small molecule, a cofactor and a hormone. In exemplary embodiments, the targeting moiety is an antibody or antibody fragment.

In a linker with multiple reactive functional groups, a particular functional group can be chosen such that it does not participate in, or interfere with, the reaction controlling the attachment of the functionalized spacer component to another ligand component. Alternatively, the reactive functional group can be protected from participating in the reaction by the presence of a protecting group. Those of skill in the art understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

Modifying Moiety

In some embodiments, the compound (ligand) comprises one or more modifying moieties. In some embodiments, one or more of $L^1$, $L^2$, $A^{b1}$, $A^{b2}$, $A^{p1}$, and $A^{p2}$ comprise(s) a modifying moiety. In some embodiments, one or more of $L^{1a}$, $L^{1b}$, $L^{1c}$, $R^{L1}$, and $R^{L2}$, $L^{2a}$, $L^{2b}$, $L^{2c}$, $L^{2d}$, $L^{2e}$, $L^{2f}$, $L^{2g}$, $R^{L3}$, $R^{L4}$, $A^{b1}$, $A^{b2}$, $A^{p1}$, and $A^{p2}$ comprise(s) a modifying moiety. In some embodiments, a linker to a reactive functional group, or a linker to a targeting moiety comprises a modifying moiety. Each of the modifying moieties can be the same or different.

The modifying moiety modifies various properties of the ligand and/or a complex formed between the ligand and a metal ion, such as solubility, charge, or affinity. In some embodiments, the modifying moiety does not interact with the metal when the ligand is complexed to a metal. In some embodiments, the modifying moiety is a solubilizing group, a hormone-derived moiety, a prodrug moiety (for example, with a cleavable moiety), an oligonucleotide, ssDNA, dsDNA, RNA, or a peptide. The solubilizing group improves solubility of the ligand and/or a complex formed between the ligand and a metal ion in aqueous media. In some embodiments, the hormone (of the homone-derived moiety) is a steroid. In some embodiments, the steroid is estradiol. In some embodiments, the modifying moiety is an estradiol-derived moiety. Peptides of a hydrophilic and hydrophobic nature by virtue of their amino acid composition may be used to tune solubility of the ligand and/or a complex formed between the ligand and a metal ion.

In some embodiments, the modifying moiety is substituted or unsubstituted heteroalkyl. In some embodiments, the modifying moiety is a substituted or unsubstituted alkoxyalkyl. In some embodiments, the modifying moiety is a substituted or unsubstituted monoether. In some embodiments, the modifying moiety is a substituted or unsubstituted polyether. In some embodiments, the modifying moiety comprises an estradiol-derived moiety. In some embodiments, the modifying moiety is a polyether substituted with an estradiol-derived moiety.

In some embodiments, the modifying moiety is selected from:

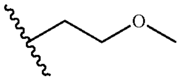
;
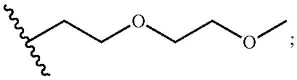
;
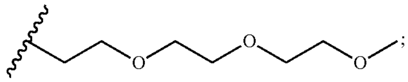
;

-continued

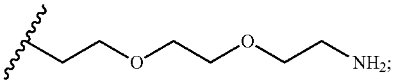

and

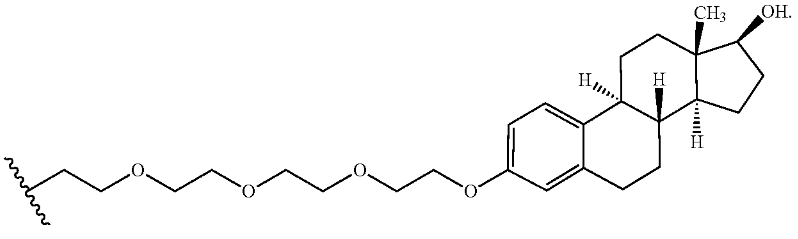

In some embodiments, the modifying moiety is a peptide.

In some embodiments, the modifying moiety is:

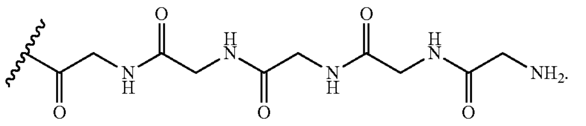 [SMILES: *C(=O)CNC(=O)CNC(=O)CNC(=O)CNC(=O)CN]

In some embodiments, the modifying moiety comprises an oligonucleotide.

In some embodiments, the modifying moiety is selected from:

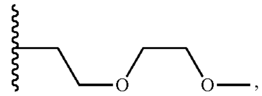

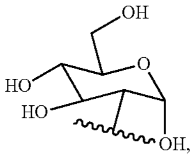

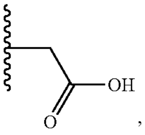

,

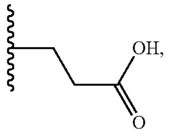

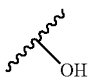

,

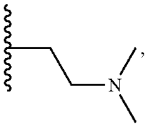

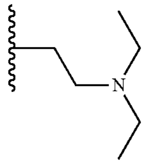

, and

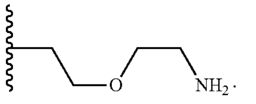

Exemplary Ligands

In some embodiments, the invention provides a ligand having the structure:

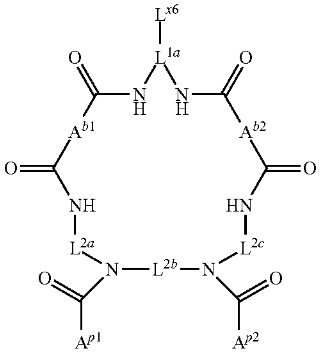

wherein $L^{1a}$, $L^{2a}$, $L^{2b}$, $L^{2c}$, $L^{x6}$, $A^{b1}$, $A^{b2}$, $A^{p1}$, and $A^{p2}$ are as defined herein.

In some embodiments, the invention provides a ligand having the structure:

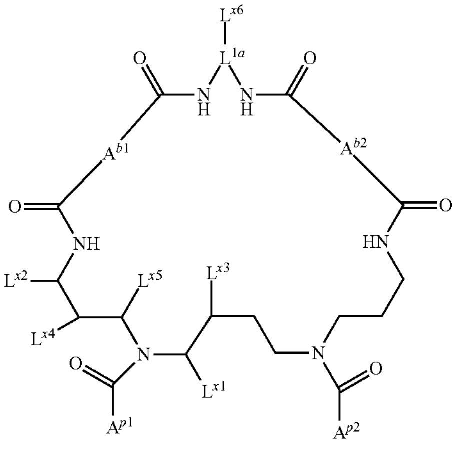

wherein $L^{1a}$, $L^{x1}$, $L^{x2}$, $L^{x3}$, $L^{x4}$, $L^{x5}$, $L^{x6}$, $A^{b1}$, $A^{b2}$, $A^{p1}$, and $A^{p2}$ are as defined herein.

In some embodiments, the invention provides a ligand having the structure:

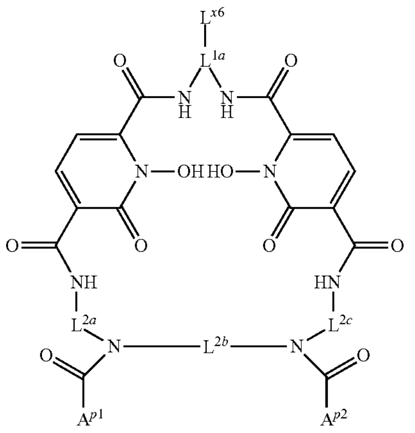

or

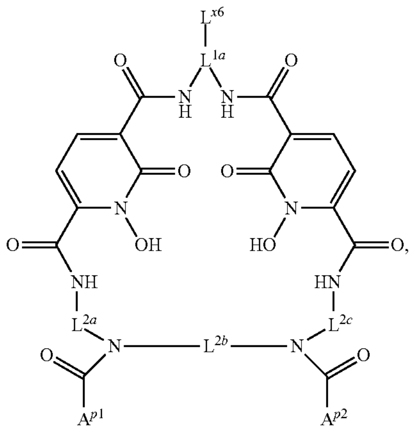

, wherein $L^{1a}$, $L^{2a}$, $L^{2b}$, $L^{2c}$, $L^{x6}$, $A^{p1}$, and $A^{p2}$ are as defined herein.

In some embodiments, the invention provides a ligand having the structure:

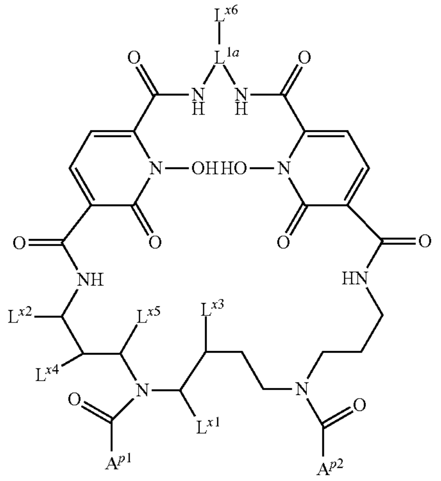

or

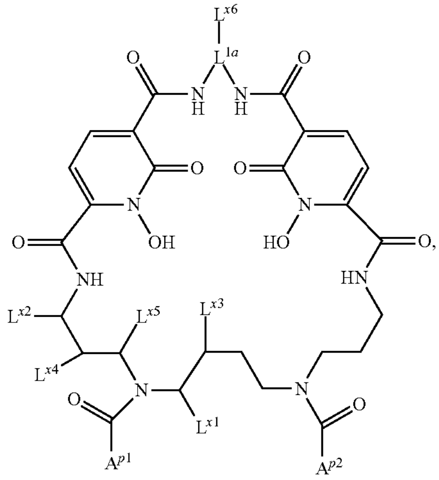

, wherein $L^{1a}$, $L^{x1}$, $L^{x2}$, $L^{x3}$, $L^{x4}$, $L^{x5}$, $L^{x6}$, $A^{p1}$, and $A^{p2}$ are as defined herein.

In some embodiments, the invention provides a ligand having the structure:

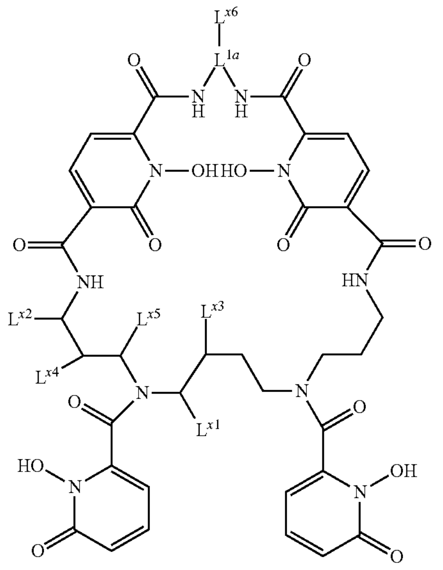

or

-continued

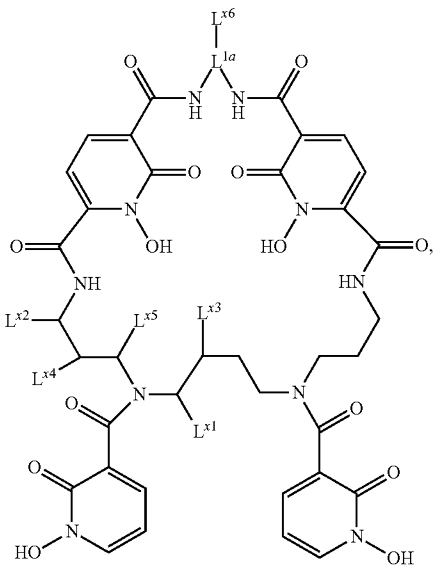

wherein $L^{1a}$, $L^{x1}$, $L^{x2}$, $L^{x3}$, $L^{x4}$, $L^{x5}$ and $L^{x6}$ are as defined herein.

In some embodiments, the invention provides a ligand having the structure:

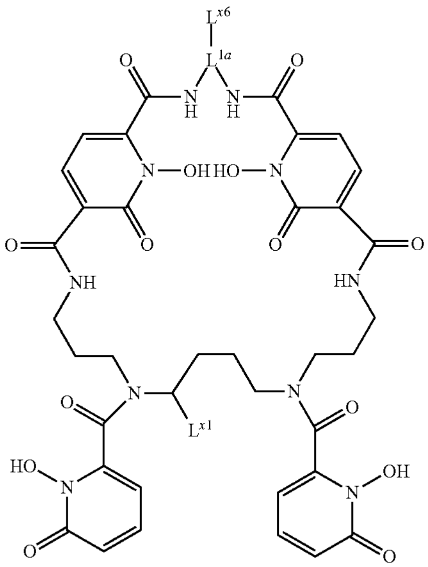

or

-continued

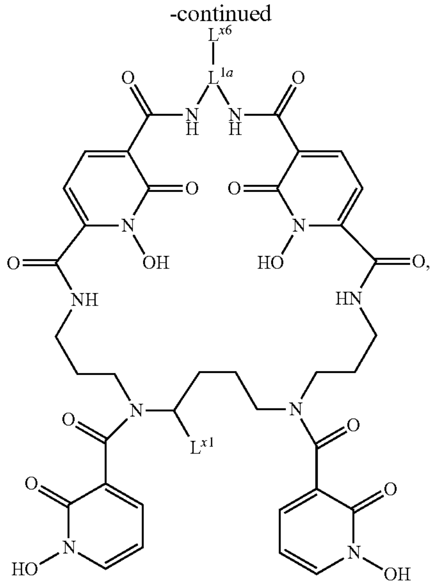

wherein $L^{1a}$, $L^{x6}$, and $L^{x1}$ are as defined herein.

Additional exemplary ligands are shown in the Examples.

Complexes

In one aspect, the invention provides a complex of a compound (ligand) disclosed herein with a metal ion.

In a preferred embodiment, the complex is a complex of a +2 metal cation, e.g., $Ca^{+2}$ or $Mg^{+2}$. In a preferred embodiment, the +2 metal cation protects a reactive moiety on a reagent contacting the complex from unproductive reaction with the complex during the course of modification of the complex with the reagent. An exemplary reactive moiety is an imide moiety, e.g, N-hydoxysuccinimide (NHS). In a preferred embodiment, the complex of the +2 metal cation is converted to an NHS ester by contacting the complex with a reagent comprising a NHS moiety. In a preferred embodiment, the +2 metal cation is displaced following reaction with the reagent, e.g., following NHS ester formation, by a cation of valence higher than +2, e.g., +3 or +4. In a preferred embodiment, the cation of higher valence is selected from an ion of lanthanides, transition metals and actinides.

Any of the combinations of compounds (ligands) disclosed herein and a metal ion disclosed herein are encompassed by this disclosure and specifically provided by the invention.

In some embodiments, the complex is luminescent.

In some embodiments, the complex includes a metal ion that is a known radioisotope.

Exemplary complexes are shown in the Examples.

In another aspect, the invention provides a complex of a compound (ligand) disclosed herein with an element, or ion thereof, from periods 4, 5, 6 and 7 and/or from groups 13, 14, 15, 16. In another aspect, the invention provides a complex of a compound (ligand) disclosed herein with an element, or ion thereof, from periods 3, 4, 7, 8, 9, 10, 11, 13, 14, and 15. In some embodiments, the invention provides a complex of a compound (ligand) disclosed herein with an element, or ion thereof, from periods 3, 4, and 13.

In some embodiments, complexes disclosed in WO 2013/187971 A2 are excluded.

Metals

In some embodiments, the metal complexed by a ligand of the invention is an actinide. In some embodiments, the actinide is thorium (Th). In some embodiments, the metal is a lanthanide. In some embodiments, the lanthanide is terbium (Tb). In some embodiments, the lanthanide is europium (Eu). In some embodiments, the lanthanide is dysprosium (Dy). In some embodiments, the lanthanide is lutetium (Lu). In some embodiments, the lanthanide is gadolinium (Gd). In some embodiments the metal is yttrium (Y). In some embodiments, the metal is zirconium (Zr). In some embodiments, the metal ion is yttrium(III). In some embodiments, the metal ion is europium(III). In some embodiments, the metal ion is terbium(III). In some embodiments, the metal ion is zirconium(IV). In some embodiments, the metal ion is thorium(IV). In some embodiments, the metal ion is selected from $Th^{4+}$, $Zr^{4+}$, $Eu^{3+}$, $Dy^{3+}$, $Tb^{3+}$, $Lu^{3+}$, and $Y^{3+}$. In some embodiments, the metal (ion) is a radionuclide. In some embodiments, the metal ion is $^{227}$Th(IV). In some embodiments, the metal ion is $^{89}$Zr(IV).

In some embodiments, the metal complexed by a ligand of the invention is $^{177}$Lu. In some embodiments, the metal is $^{166}$Ho. In some embodiments, the metal is $^{153}$Sm. In some embodiments, the metal is $^{90}$Y. In some embodiments, the metal is $^{86}$Y. In some embodiments, the metal is $^{166}$Dy. In some embodiments, the metal is $^{165}$Dy. In some embodiments, the metal is $^{169}$Er. In some embodiments, the metal is $^{175}$Yb. In some embodiments, the metal is $^{225}$Ac. In some embodiments, the metal is $^{149}$Tb. In some embodiments, the metal is $^{153}$Gd. In some embodiments, the metal is $^{230}$U.

In some embodiments, the metal complexed by a ligand of the invention is $^{111}$In. In some embodiments, the metal is $^{67}$Ga. In some embodiments, the metal is $^{67}$Cu. In some embodiments, the metal is $^{64}$Cu. In some embodiments, the metal is $^{186}$Re. In some embodiments, the metal is $^{188}$Re. In some embodiments, the metal is $^{111}$Ag. In some embodiments, the metal is $^{109}$Pd. In some embodiments, the metal is $^{212}$Pb. In some embodiments, the metal is $^{203}$Pb. In some embodiments, the metal is $^{212}$Bi. In some embodiments, the metal is $^{213}$Bi. In some embodiments, the metal is $^{195m}$Pt. In some embodiments, the metal is $^{201}$Tl. In some embodiments, the metal is $^{55}$Co. In some embodiments, the metal is $^{99m}$Tc.

In some embodiments, the metal complexed by a ligand of the invention is selected from yttrium (Y), a lanthanoid, an actinoid, zirconium (Zr), iron (Fe), and indium (In). In some embodiments, the metal is selected from zirconium (Zr), iron (Fe), indium (In), europium (Eu), holmium (Ho), lutetium (Lu), yttrium (Y), terbium (Tb), ytterbium (Yb), gadolinium (Gd), samarium (Sm), dysprosium (Dy), erbium (Er), and thorium (Th). In some embodiments, the metal is selected from Eu, Tb, Sm, and Dy. In some embodiments, the metal is Gd.

In some embodiments, the metal ion complexed by a ligand of the invention is selected from Zr(IV), Fe(III), Ga(III), In(III), Eu(III), Ho(III), Lu(III), Y(III), Tb(III), Yb(III), Gd(III), Sm(III), Dy(III), Er(III), and Th(IV). In some embodiments, the metal ion is selected from $^{227}$Th (IV), $^{89}$Zr(IV), and $^{177}$Lu(III).

In some embodiments, the metal is a radionuclide.

Radionuclides

The chelating moieties disclosed herein can be used to bind metal ions, in particular, a radionuclide. The term "radionuclide" or "radioisotope" refers to a radioactive isotope or element with an unstable nucleus that tends to undergo radioactive decay. Numerous decay modes are known in the art and include alpha decay, proton emission, neutron emission, double proton emission, spontaneous fission, cluster decay, $\beta^-$ decay, positron emission ($\beta^+$ decay), electron capture, bound state beta decay, double beta decay, double electron capture, electron capture with positron emission, double positron emission, isomeric transition and internal conversion.

Exemplary radionuclides include alpha-emitters, which emit alpha particles during decay. In some embodiments, a radionuclide is an emitter of a gamma ray or a particle selected from an alpha particle, an electron and a positron.

In some embodiments, the radionuclide is an actinide. In some embodiments, the radionuclide is a lanthanide. In some embodiments, the radionuclide is a $3^+$ ion. In some embodiments, the radionuclide is a $4^+$ ion. In some embodiements the radionuclide is a $2^+$ ion.

Of particular use in the complexes provided herein are radionuclides selected from isotopes of U, Pu, Fe, Cu, Sm, Gd, Tb, Dy, Ho, Er, Yb, Lu, Y, Th, Zr, In, Ga, Bi, Ra, At and Ac. In some embodiments, a radionuclide is selected form radium-223, thorium-227, astatine-211, bismuth-213, Lutetium-177, and actinium-225. Other useful radioisotopes include bismuth-212, iodine-123, copper-64, iridium-192, osmium-194, rhodium-105, samarium-153, and yttrium-88, yttrium-90, and yttrium-91. In exemplary embodiments, the radionuclide is thorium, particularly selected from thorium-227 and thorium-232. In some embodiments, thorium-226 is excluded. In some embodiments, U is excluded. In some embodiments, uranium-230 is excluded. That is, in some embodiments, a radionuclide is not U, or a radionuclide is not uranium-230 or a radionuclide is not thorium-226.

In a preferred embodiment, the radionuclide is selected from Th(IV)-227, Zr(IV)-89, Lu(III)-177, Y(III)-90, Y(III)-86, and In(III)-111.

In another preferred embodiment, the radionuclide is Ac(III)-225.

In some embodiments, the radionuclide is selected from Tb(III)-149, Sc(III)-47, Dy(III)-166, Er(III)-169, Gd(III)-153, Ho(III)-166, Sm(III)-153, Yb(III)-175, Ac(III)-225, Bi(III)-212 and Bi(III)-213.

In a preferred embodiment, the complex is luminescent and comprises a metal ion which is selected from Tb(III), Eu(III), Sm(III), Dy(III), and Yb(III).

$^{232}$Th exists in nature as an a-emitter with a half life of $1.4\times10^{10}$ yr. In aqueous solution, Th(IV) is the only oxidation state. Thorium(IV) ion is bigger than Pu(IV) and usually forms complexes with 9 or higher coordination number. For example, the crystal structure of both Th(IV) complexes of simple bidentate 1,2-HOPO and Me-3,2-HOPO have been determined as nine coordinated species.

Similar to other actinide ions, thorium(IV) prefers forming complexes with oxygen, especially negative oxygen donor ligands. Thorium(IV) also prefers octadentate or higher multidentate ligands:

| Ligand | Acac | NTA | HEDTA* | EDTA** | DTPA | TTHA |
|---|---|---|---|---|---|---|
| Ligand Type | Bi-dentate | Tetra- | Hexa- | Hexa- | Octa- | Deca- |
| Log $K_1$ | 7.85 | 16.9 | 18.5 | 25.3 | 30.34 | 31.9 |

*with one alcoholic oxygen and three carboxyl groups;
**with four carboxyl groups.

Other radionuclides with diagnostic and therapeutic value that can be used with the compounds disclosed herein can be found, for example, in U.S. Pat. Nos. 5,482,698 and 5,601,800; and Boswell and Brechbiel, Nuclear Medicine and Biology, 2007 October, 34 (7): 757-778 and the manuscript thereof made available in PMC 2008 Oct. 1.

Uses

The ligands and complexes disclosed herein can be used in a wide variety of therapeutic and diagnostic settings.

In one aspect, the invention provides a method of treating a disease in an animal comprising administering a complex disclosed herein to the animal, whereby the disease is ameliorated or eliminated.

In one aspect, the invention provides a method of diagnosing a disease in an animal comprising (a) administering a complex disclosed herein to the animal and (b) detecting the presence or absence of a signal emitted by the complex. In some embodiments, the detecting step comprises obtaining an image based on the signal.

In some embodiments, the disease is cancer.

In some embodiments, the complex comprises a linker to a targeting moiety and the method further comprises localizing the complex to a targeting site in the animal by binding the targeting moiety to the targeting site.

The compounds disclosed herein are particularly well suited for the preparation of stable, pre-labeled antibodies for use in the diagnosis and treatment of cancer and other diseases. For example, antibodies expressing affinity for specific tumors or tumor-associated antigens are labeled with a diagnostic radionuclide-complexed chelate, and the labeled antibodies can be further stabilized through lyophilization. Where a chelate is used, it generally is covalently attached to the antibody. The antibodies used can be polyclonal or monoclonal, and the radionuclide-labeled antibodies can be prepared according to methods known in the art. The method of preparation will depend upon the type of radionuclide and antibody used. A stable, lyophilized, radiolabeled antibody can be reconstituted with suitable diluent at the time of intended use, thus greatly simplifying the on site preparation process. The methods of the invention can be applied to stabilize many types of pre-labeled antibodies, including, but not limited to, polyclonal and monoclonal antibodies to tumors associated with melanoma, colon cancer, breast cancer, prostate cancer, etc. Such antibodies are known in the art and are readily available.

EXAMPLES

The compounds and complexes of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, but it is not intended to limit the scope of reactions or reaction sequences that are useful in preparing the compounds of the present invention.

Example 1

Synthesis of Bridging 1,2-HOPO Intermediate 8

Scheme 1. Synthetic scheme of bridging 1,2-HOPO intermediate 8.

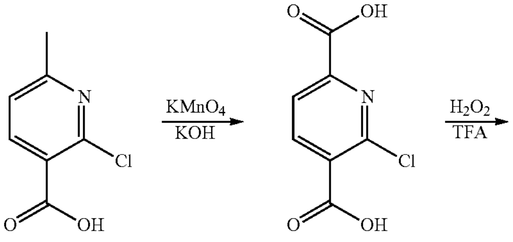

1 2

-continued

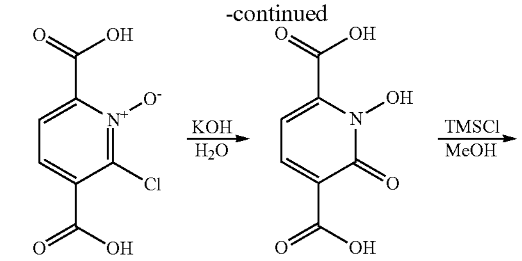

3 4

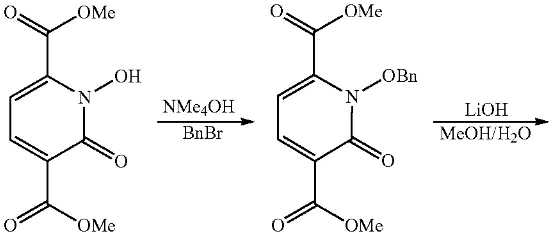

5 6

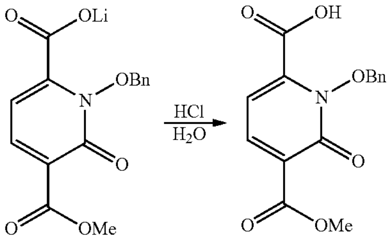

7 8

The precursor 2-chloro-6-methylnicotinic acid (1) was purchased from A2Z Chemical (Irvine, CA). All other solvents and reagents were purchased from commercial sources and used as received unless otherwise noted. $^1$H-NMR and $^{13}$C-NMR spectra were obtained at 300/75 MHz, 400/100 MHz, or 500/125 MHz using a Bruker AV-300, AVB-400, or DRX-500 spectrometer as noted below. $^1$H(or $^{13}$C) chemical shifts are reported relative to residual solvent signals, taken as 7.24 (77.23) and 2.50 (39.51) ppm for $CDCl_3$ and DMSO-$d_6$ respectively. High resolution electrospray ionization mass spectra (HRMS-ESI) were performed by the Microanalytical Laboratory at the University of California, Berkeley.

6-Chloropyridine-2,5-dicarboxylic acid (2). Potassium hydroxide (112 g, 2 mol) was dissolved into water (1.5 L), and then 2-chloro-6-methylnicotinic acid (1, 100 g, 0.583 mol) was dissolved into the basic solution. The reaction was heated to 90° C. with stirring, and potassium permanganate (316·g, 2 mol) was then added in ~50 g portions over a period of 6 hours. The reaction was left to stir at 90° C. overnight. The reaction mixture was cooled to room temperature, and the dark suspension was filtered to remove $MnO_2$ solids. The filter cake was washed with water (3×200 mL), and the colorless filtrates were combined and concentrated under vacuum to ~1.5 L total volume. Concentrated HCl (165.3 mL, 2 mol) was added slowly, liberating a large amount of gas as the crude product precipitates from solution. The crude product was filtered (without additional washing) and dried under a stream of air. The crude product was recrystallized by dissolving it into a solution of potassium hydroxide (44.8 g, 0.800 mol) in water (1 L), and then concentrated HCl (66.1 mL 0.800 mol) was added all at once. The product slowly crystallized at room temperature for several hours, and then the flask was cooled to 4° C. and left standing in a refrigerator overnight. The recrystallized product was isolated by filtration, washed with isopropyl alcohol (4×100 mL), and dried under vacuum overnight to give a white, free-flowing solid of 2. Yield: 105.3 g, 89.6%. $^{1}$H NMR (500 MHZ, DMSO-$d_6$) δ 13.85 (br s, 2H), 8.34 (d, J=7.5 Hz, 1H) 8.12 (d, J=7.5 Hz, 1H). $^{13}$C NMR (125 MHz, DMSO-$d_6$) δ 165.8, 164.6, 150.0, 147.7, 141.4, 131.4, 124.1. HRMS-ESI (m/z, [M−H]$^-$) Calcd for $C_7H_3{}^{35}ClNO_4$: 199.9756, Found: 199.9750.

3,6-Dicarboxy-2-chloropyridine 1-oxide (3). The starting material 6-chloropyridine-2,5-dicarboxylic acid (2, 103.3 g, 512.5 mmol) was dissolved into trifluoroacetic acid (1.5 L) while the reaction vessel was being heated to 80° C. with stirring. As soon as all of the starting material dissolved, a fresh sample of concentrated (34-37% technical grade) $H_2O_2$ (207 mL) was added all at once, and the reaction was maintained at 80° C. with relatively slow stirring for 4 hours. The reaction was then cooled to room temperature, and the trifluoroacetic acid was removed under vacuum. Cold water was added until the final volume reached ~500 mL, causing precipitation of the desired product. The product was recovered by filtration, washed with cold water (3×50 mL), and dried under vacuum to give a dense white crystalline solid of 3. Yield 98.1 g, 88.0%. $^{1}$H NMR (300 MHz, DMSO-$d_6$) δ 8.21 (d, J=7.4 Hz, 1H) 8.06 (d, J=7.4 Hz, 1H). $^{13}$C NMR (75 MHz, DMSO-$d_6$) δ 163.6, 160.3, 140.5, 139.9, 133.8, 130.6, 125.9. HRMS-ESI (m/z, [M+H]$^+$) Calcd for $C_7H_5{}^{35}ClNO_5$: 217.9856, Found: 217.9850.

1-Hydroxy-6-oxo-1,6-dihydropyridine-2,5-dicarboxylic acid (4). The starting material 3,6-dicarboxy-2-chloropyridine 1-oxide (3, 97.8 g, 449.5 mmol) was dissolved into water (1 L) containing potassium hydroxide (300 g, 5.35 mol), and the reaction was heated to 80° C. with stirring overnight. The reaction was cooled to room temperature, and then concentrated hydrochloric acid (500 mL, 6.05 mol) was added in portions to avoid excessive production of heat. The product precipitated initially as a fluffy yellow powder, which became a dense brown solid as more HCl was added. The dense, dark brown solid was collected by filtration, washed with cold water (3×50 mL), and then dried under vacuum to give a dense, free-flowing brown powder of 4. Yield 74.8 g, 83.6%. $^{1}$H NMR (300 MHZ, DMSO-$d_6$) δ 15.35 (br s, 2H) 8.06 (d, J=7.5 Hz, 1H) 7.19 (d, J=7.5 Hz, 1H). $^{13}$C NMR (75 MHz, $D_2O$-NaOD) δ 175.2, 170.3, 160.8, 148.1, 133.3, 123.3, 102.6. HRMS-ESI (m/z, [M−H]$^-$) Calcd for $C_7H_4NO_6$: 198.0044, Found: 198.0044.

Dimethyl 1-hydroxy-6-oxo-1,6-dihydropyridine-2,5-dicarboxylate (5). The starting material 1-hydroxy-6-oxo-1,6-dihydropyridine-2,5-dicarboxylic acid (4, 74.2 g, 372.6 mmol) was suspended in methanol (800 mL), and trimethylsilyl chloride (200 mL, 171.2 g, 1.576 mol) was added all at once. The suspension was stirred at room temperature for 3 days. Once the reaction was complete, the suspension was filtered to remove a solid byproduct, and the filtrate was evaporated under vacuum to give the desired compound as a hardened solid residue of 5. Yield 71.2 g, 84.1%. $^{1}$H NMR (300 MHz, DMSO-$d_6$) δ 8.56 (d, J=8.4 Hz, 1H) 7.81 (d, J=8.4 Hz, 1H), 3.99 (s, 3H), 3.92 (s, 3H). $^{13}$C NMR (75 MHz, DMSO-$d_6$) δ 161.7, 157.9, 154.9, 142.3, 135.3, 117.9, 116.6, 54.8, 53.8. HRMS-ESI (m/z, [M+Na]$^+$) Calcd for $C_9H_9NO_6Na$: 250.0322, Found: 250.0320.

Dimethyl 1-(benzyloxy)-6-oxo-1,6-dihydropyridine-2,5-dicarboxylate (6). The starting material dimethyl 1-hydroxy-6-oxo-1,6-dihydropyridine-2,5-dicarboxylate (5, 70.70 g, 311.2 mmol) was dissolved into methanol (800 mL) containing benzyl bromide (55.9 g, 326.8 mmol). Tetramethylammonium hydroxide pentahydrate (56.40 g, 311.2 mmol) was separately dissolved into methanol (200 mL) and added dropwise to the first solution with stirring at room temperature. The reaction was stirred at room temperature overnight, and then the solvent was removed under vacuum. Water (500 mL) and dichloromethane (500 mL) were then added to the residue, and the dichloromethane layer was washed with water (3×300 mL) to remove tetramethylammonium bromide. The dichloromethane layer was then concentrated and loaded onto a large silica gel column, and the desired product was eluted with dichloromethane. The solvent was removed and the residue was subjected to high vacuum overnight to remove residual benzyl bromide, yielding the desired product 6 as a hardened off-white solid. Yield 95.1 g, 96.3%. $^{1}$H NMR (400 MHZ, $CDCl_3$) δ 8.07 (d, J=7.4 Hz, 1H), 7.51 (dd, J=6.3, 2.8 Hz, 2H), 7.36-7.28 (m, 3H), 6.43 (d, J=7.4 Hz, 1H), 5.36 (s, 2H), 3.88 (s, 3H), 3.83 (s, 3H). $^{13}$C NMR (100 MHZ, $CDCl_3$) δ 164.60, 159.96, 155.81, 142.86, 142.55, 133.39, 130.34, 129.43, 128.63, 124.93, 105.19, 79.00, 53.62, 52.76. HRMS-ESI (m/z, [M+H]$^+$) Calcd for $C_{16}H_{16}NO_6$: 318.0972, Found: 318.0979.

Lithium 1-(benzyloxy)-5-(methoxycarbonyl)-6-oxo-1,6-dihydropyridine-2-carboxylate (7). The starting material dimethyl 1-(benzyloxy)-6-oxo-1,6-dihydropyridine-2,5-dicarboxylate (6, 94.5 g, 297.8 mmol) was dissolved into a minimal amount of dichloromethane, and the resulting solution was concentrated under vacuum until the residue was noticeably viscous (like maple syrup). The residue was then dissolved into methanol (1 L), and cooled on an ice bath. Separately, lithium hydroxide monohydrate (12.50 g, 297.8 mmol) was dissolved in water (200 mL), diluted with methanol (600 mL), and allowed to cool to room temperature for 1 hour prior to use. The lithium hydroxide solution was then added dropwise to the cooled methanolic solution of the starting material with efficient stirring. Upon completion of the addition, the stirbar was removed and the reaction was allowed to stand at 0° C. for 1 hour. The crude product was recovered by filtration, washed with methanol (3×100 mL), and dried under a flow of air. The crude product was recrystallized several times by heating a stirred suspension of the crude in a 1:20 water: methanol mixture (500 mL) overnight. The solids were collected the next morning after cooling the suspension to room temperature, washing with methanol (3×100 mL) as before and drying under vacuum. Recrystallization was ceased once the product was >99.5% pure (measuring at 315 nm) by HPLC, yielding a dense white crystalline solid of 7. Yield 65.2 g, 70.8%. $^{1}$H NMR (500 MHz, DMSO-$d_6$) δ 8.04 (d, J=7.5 Hz, 1H), 7.61-7.52 (m, 2H), 7.45-7.34 (m, 3H), 6.02 (d, J=7.5 Hz, 1H), 5.30 (s, 2H), 3.75 (s, 3H), 3.48 (s, 2H). $^{13}$C NMR (125 MHz, DMSO-$d_6$) δ 165.10, 161.30, 155.91, 155.18, 144.52, 134.51, 129.93, 128.88, 128.31, 115.81, 98.72, 77.82, 51.72. HRMS-ESI (m/z, [M−Li]$^-$) Calcd for $C_{15}H_{12}NO_6$: 302.0670, Found: 302.0663.

1-(Benzyloxy)-5-(methoxycarbonyl)-6-oxo-1,6-dihydropyridine-2-carboxylic acid (8). The starting material lithium 1-(benzyloxy)-5-(methoxycarbonyl)-6-oxo-1,6-dihydropyridine-2-carboxylate (7, 10.0 g, 32.3 mmol) was suspended in water (200 mL) with stirring. Concentrated hydrochloric acid (8.26 mL, 100 mmol) was diluted to a final volume of 50 mL, and then added dropwise to the stirring suspension. The suspension was stirred for 2 hours at room temperature, and then the solids were collected by filtration, washed with dilute HCl (3×50 mL), and dried under vacuum overnight to yield a free flowing white powder of 8. Yield 9.6 g, 98.0%. $^{1}$H NMR (500 MHZ, DMSO-$d_6$) δ 8.10 (d, J=7.4 Hz, 1H), 7.54-7.47 (m, 2H), 7.46-7.39 (m, 3H), 6.60 (d, J=7.4 Hz, 1H), 5.28 (s, 2H), 3.80 (s, 3H). $^{13}$C NMR (125

MHz, DMSO-$d_6$) δ 164.18, 161.24, 154.57, 144.63, 142.96, 133.58, 129.81, 129.29, 128.61, 123.28, 103.50, 78.39, 52.23. HRMS-ESI (m/z, $[M+Na]^+$) Calcd for $C_{15}H_{13}NO_6Na$: 326.0635, Found: 326.0633.

Example 2. Crystal Data and Structure of Key Intermediate 7

Single crystals suitable for X-ray diffraction of key intermediate compound 7 were grown by slowly cooling a heated, concentrated solution of 7 dissolved in 1:9 methanol: water. Single crystal X-ray diffraction data were collected on a Rigaku diffractometer equipped with a Pilatus 200K CCD detector at the Small Molecule X-ray Crystallography Facility at the University of California, Berkeley. Structures were solved with SIR-97, refined with SHELX-97, and the refined atomic positions are displayed as 50% thermal ellipsoids using Mercury (FIG. 1). Publication materials were generated with WinGX. The crystal structure confirms which one of the two methyl esters present in compound 6 is selectively hydrolyzed at low temperature by lithium hydroxide. The crystal data and structure refinement statistics are summarized in the following tables.

TABLE 1

Crystal data and structure refinement for 7•$H_2O$

| | | |
|---|---|---|
| Identification code | 7•$H_2O$ | |
| Empirical formula | C15 H14 Li N O7 | |
| Formula weight | 327.21 | |
| Temperature | 100(2) K | |
| Wavelength | 1.54184 Å | |
| Crystal system | Monoclinic | |
| Space group | P2(1)/c | |
| Unit cell dimensions | a = 7.38170(10) Å | α = 90° |
| | b = 11.5916(2) Å | β = 92.9770(10)° |
| | c = 17.5938(3) Å | γ = 90° |
| Volume | 1503.39(4) $Å^3$ | |
| Z | 4 | |
| Density (calculated) | 1.446 $Mg/m^3$ | |
| Absorption coefficient | 0.975 $mm^{-1}$ | |
| F(000) | 680 | |
| Crystal size | 0.15 × 0.12 × 0.10 $mm^3$ | |
| Theta range for data collection | 4.57 to 79.27° | |
| Index ranges | −9 <= h <= 9, −14 <= k <= 12, −22 <= l <= 16 | |
| Reflections collected | 16383 | |
| Independent reflections | 3179 [R(int) = 0.0373] | |
| Completeness to theta = 67.00° | 99.8% | |
| Absorption correction | Semi-empirical from equivalents | |
| Max. and min. transmission | 0.9088 and 0.8675 | |
| Refinement method | Full-matrix least-squares on $F^2$ | |
| Data/restraints/parameters | 3179/0/219 | |
| Goodness-of-fit on $F^2$ | 1.095 | |
| Final R indices [I > 2sigma(I)] | R1 = 0.0455, wR2 = 0.1289 | |
| R indices (all data) | R1 = 0.0480, wR2 = 0.1315 | |
| Largest diff. peak and hole | 0.609 and −0.552 e.$Å^{-3}$ | |

TABLE 2

XRD measured Cartesian coordinates of 7•$H_2O$

| Atom | X (Å) | Y (Å) | Z (Å) |
|---|---|---|---|
| O | 2.125048 | 4.991343 | 4.666958 |
| O | 3.325835 | 6.479241 | 6.847051 |
| O | 1.904459 | −0.16112 | 4.674514 |
| O | 1.386767 | 6.323102 | 7.935165 |
| O | 2.339358 | −0.55431 | 6.835455 |

TABLE 2-continued

XRD measured Cartesian coordinates of 7•$H_2O$

| Atom | X (Å) | Y (Å) | Z (Å) |
|---|---|---|---|
| O | 1.982343 | 2.499844 | 3.930597 |
| O | 6.131239 | 6.241149 | 7.186505 |
| H | 5.713697 | 6.112251 | 7.91531 |
| H | 6.614891 | 6.923663 | 7.335499 |
| N | 2.153092 | 3.98867 | 5.630852 |
| C | 2.100669 | 2.677776 | 5.15277 |
| C | 2.252598 | 4.372583 | 6.932442 |
| C | 2.329842 | 5.867784 | 7.246946 |
| C | 2.134466 | 0.25687 | 5.798821 |
| C | 0.845814 | 6.31974 | 3.214618 |
| C | 2.194041 | 1.680202 | 6.187647 |
| C | 2.311656 | 3.40538 | 7.897565 |
| H | 2.360826 | 3.637444 | 8.797327 |
| C | 2.296539 | 2.063884 | 7.512605 |
| H | 2.357367 | 1.40722 | 8.168319 |
| C | 0.745716 | 5.250531 | 4.257927 |
| H | 0.214784 | 5.553536 | 5.01098 |
| H | 0.339424 | 4.450015 | 3.891768 |
| C | 2.275989 | −1.97243 | 6.553631 |
| H | 2.941854 | −2.19893 | 5.900025 |
| H | 1.405697 | −2.19197 | 6.212772 |
| H | 2.438522 | −2.46669 | 7.360097 |
| C | 0.88719 | 7.654049 | 3.578669 |
| H | 0.822763 | 7.885765 | 4.47685 |
| C | 1.100499 | 8.306888 | 1.279627 |
| H | 1.180748 | 8.96958 | 0.630765 |
| C | 0.939779 | 5.982425 | 1.871914 |
| H | 0.9228 | 5.088712 | 1.616445 |
| C | 1.021777 | 8.650231 | 2.623034 |
| H | 1.059361 | 9.543364 | 2.879732 |
| C | 1.059185 | 6.971652 | 0.910129 |
| H | 1.111874 | 6.738197 | 0.010542 |
| Li | 4.879882 | 6.647783 | 5.808485 |
| O | 5.020374 | 5.634677 | 4.110515 |
| O | 4.942489 | 8.295644 | 4.854431 |
| Li | 2.044951 | 0.851983 | 2.976543 |

Example 3. Synthesis of an Exemplary Parent Ligand 16·

Scheme 2. Synthetic scheme of an exemplary parent ligand 16.

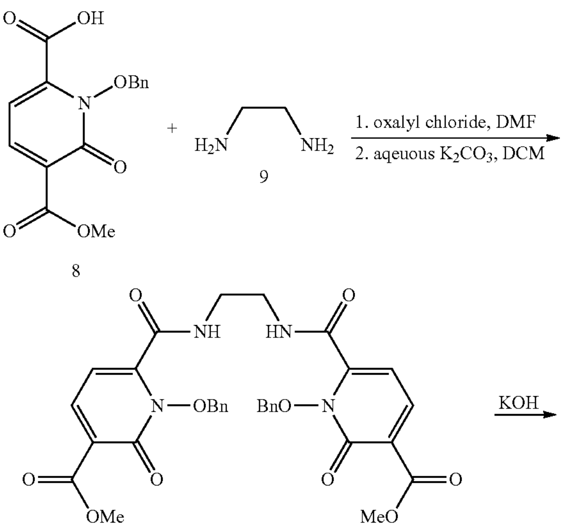

8

9

10

-continued

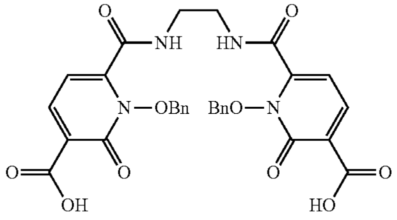

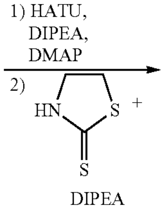

11

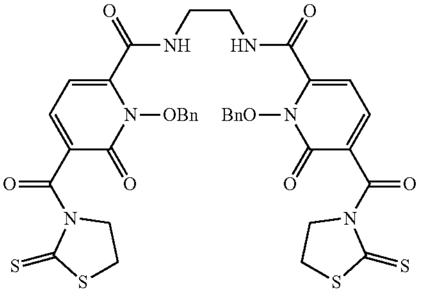

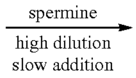

12

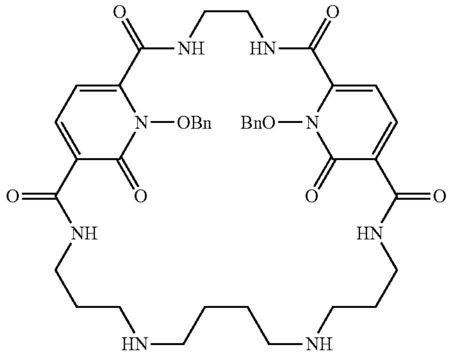

+

13

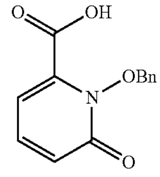

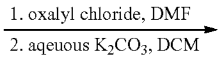

14

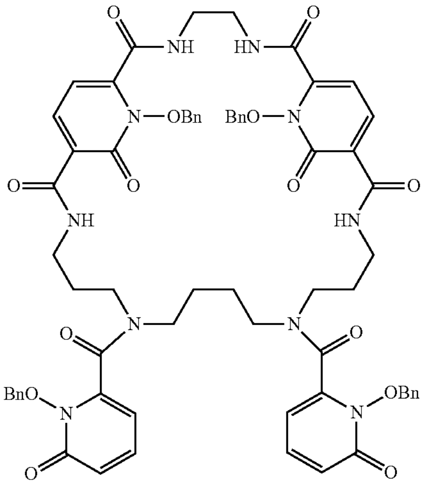

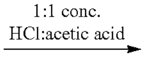

15

-continued

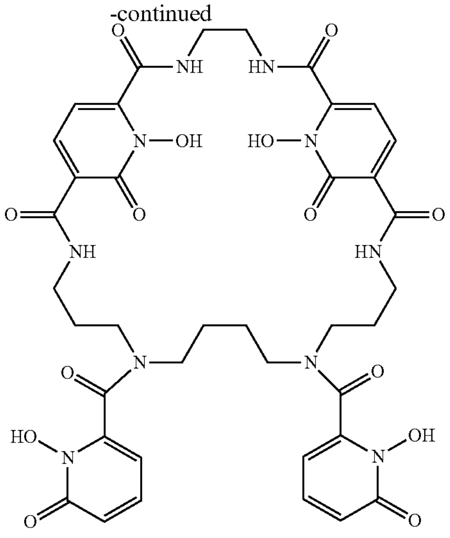

16

6-oxo-1,6-dihydropyridine-2-carboxylic acid (14) was synthesized according to previously reported methods (Xu, J.; Durbin, P. W.; Kullgren, B.; Ebbe, S. N.; Uhlir, L. C.; Raymond, K. N. J. Med. Chem. 2002, 45, 3963.). All other solvents and reagents were purchased from commercial sources and used as received unless otherwise noted. $^{1}$H-NMR and $^{13}$C-NMR spectra were obtained at 300/75 MHz, 400/100 MHz, or 500/125 MHz using a Bruker AV-300, AVB-400, or DRX-500 spectrometer as noted below. $^{1}$H (or $^{13}$C) chemical shifts are reported relative to residual solvent signals, taken as 7.24 (77.23), 2.50 (39.51), and 3.31 (49.15) ppm for $CDCl_3$, DMSO-$d_6$, and methanol-$d_4$ respectively. High resolution electrospray ionization mass spectra (HRMS-ESI) were performed by the Microanalytical Laboratory at the University of California, Berkeley.

Dimethyl 6,6'-((ethane-1,2-diylbis(azanediyl))bis(carbonyl))bis(1-(benzyloxy)-2-oxo-1,2-dihydropyridine-3-carboxylate) (10). Oxalyl chloride (4.8 g, 37.8 mmol) was added to a suspension of 8 (4.814 g, 15.87 mmol) in dichloromethane (50 mL), followed by 2 drops of dry N,N-dimethylformamide (DMF). The solution became homogenous within 30 min, and the reaction was stirred at room temperature for 3 hours total. The solvent was then removed under vacuum overnight. The residue was dissolved into dichloromethane (20 mL) and added dropwise to a solution of 9 (372.6 mg, 6.20 mmol) dissolved in dichloromethane (20 mL) and 20 mL of aqueous $K_2CO_3$ (2.76 g, 20 mmol) at 0° C. with vigorous stirring. The desired product precipitated within 1 hour and was collected by filtration, washed with dichloromethane (3×50 mL), washed with water (3×50 mL), and dried under vacuum overnight to yield a free flowing white powder of 10. Yield 3.7 g, 94.6%. $^{1}$H NMR (500 MHz, DMSO-$d_6$) δ 9.22 (s, 2H), 8.10 (d, J=7.3 Hz, 2H), 7.55-7.34 (m, 10H), 6.44 (d, J=7.2 Hz, 2H), 5.28 (s, 4H), 3.80 (s, 6H), 3.41 (s, 4H). $^{13}$C NMR (125 MHz, DMSO-$d_6$) δ 164.29, 159.98, 154.52, 147.70, 143.18, 133.66, 129.77, 129.24, 128.58, 122.21, 102.58, 78.80, 52.18, 38.53. HRMS-ESI (m/z, $[M+Na]^+$) Calcd for $C_{32}H_{30}N_4O_{10}Na_1$: 653.1854, Found: 653.1852.

6,6'-((Ethane-1,2-diylbis(azanediyl))bis(carbonyl))bis(1-(benzyloxy)-2-oxo-1,2-dihydropyridine-3-carboxylic acid) (11). Potassium hydroxide (1.30 g, 23.2 mmol) was dissolved into water (20 mL) and added to a suspension of 10 (3.65 g, 5.79 mmol) in methanol (100 mL), and the reaction was stirred at room temperature overnight. The next day, water (100 mL) was added and the suspension resolved to a homogenous purple colored solution. The solvent was removed under vacuum and the resulting residue was dissolved into water (200 mL). Dilute HCl was added dropwise with stirring until the solution was acidic by litmus test. The desired product was collected by filtration, washed with dilute HCl and dried under vacuum overnight to yield a white powder of 11. Yield: 3.10 g, 88.9%. $^1$H NMR (500 MHz, DMSO-$d_6$) δ 13.55 (s, 2H), 9.23 (s, 2H), 8.33 (d, J=7.2 Hz, 2H), 7.61-7.30 (m, 10H), 6.70 (d, J=7.2 Hz, 2H), 5.35 (s, 4H), 3.44 (s, 4H). $^{13}$C NMR (125 MHz, DMSO-$d_6$) δ 164.12, 159.56, 158.67, 147.45, 143.77, 133.30, 129.89, 129.43, 128.66, 120.74, 105.32, 79.54, 38.61. HRMS-ESI (m/z, $[M-H]^-$) Calcd for $C_{30}H_{25}N_4O_{10}$: 601.1576, Found: 601.1567.

N,N'-(ethane-1,2-diyl)bis(1-(benzyloxy)-6-oxo-5-(2-thioxothiazolidine-3-carbonyl)-1,6-dihydropyridine-2-carboxamide) (12). Starting material 11 (1.50 g, 2.49 mmol), N-[(Dimethylamino)-1H-1,2,3-triazolo-[4,5-b]pyridin-1-ylmethylene]-N-methylmethanaminium hexafluorophosphate N-oxide (HATU, 1.99 g, 5.23 mmol), and 4-dimethylaminopyridine (DMAP, 30.4 mg, 0.249 mmol) were dissolved in dimethylformamide (10 mL). N,N-Diisopropylethylamine (DIPEA, 643.5 mg, 4.979 mmol) was added dropwise to the solution, and the reaction was stirred at room temperature for 1 hour. Next, 2-mercaptothiazoline (712 mg, 5.97 mmol) was added to the homogenous solution, followed by more DIPEA (1.287 g, 9.96 mmol). The reaction was stirred for an additional 20 minutes at room temperature, and then the reaction mixture was evaporated to dryness overnight under vacuum. The residue was dissolved in dichloromethane and then washed with water 3×75 mL to remove the bulk of the urea byproduct, concentrated, and then loaded onto a 6 inch tall×1 inch wide silica gel column. Following a 2-propanol/dichloromethane gradient elution, the desired product was collected using 5% 2-propanol in dichloromethane. The solvent was removed under vacuum, and the residue was dissolved into 100 mL dichloromethane. The organic solution was again washed with water 3×75 mL to remove final traces of the urea byproduct, and the silica gel chromatography was repeated as described above. Removal of the solvent under vacuum gave the desired compound as a yellow powder of 12. Yield: 1.72 g, 85.8%. $^1$H NMR (500 MHZ, $CDCl_3$) δ 7.43 (s, 2H), 7.41-7.36 (m, 6H), 7.33-7.27 (m, 6H), 6.30 (d, J=7.2 Hz, 2H), 5.18 (s, 4H), 4.55 (t, J=7.3 Hz, 4H), 3.46-3.37 (m, 8H). $^{13}$C NMR (125 MHz, $CDCl_3$) δ 202.32, 165.52, 160.34, 155.62, 144.51, 138.98, 133.20, 130.49, 130.38, 129.71, 128.86, 105.70, 79.35, 55.74, 39.79, 29.52. HRMS-ESI (m/z, $[M+Na]^+$) Calcd for $C_{36}H_{32}N_6O_8{}^{32}S_4Na$: 827.1057, Found: 827.1055.

Compound 13. Spermine (386.4 mg, 1.910 mmol) was dissolved into 2-propanol (50 mL) and 12 (1.614 g, 2.005 mmol) was separately dissolved into dichloromethane (50 mL). Using syringe pumps, the two solutions were dripped (1 mL/hour) into a large flask containing 1:1 dichloromethane: 2-propanol (1 L) over two days. The reaction was stirred for an additional day at room temperature, followed by removal of the solvent under vacuum. The crude residue of compound 13 was used directly in the next reaction without further purification.

Compound 15. Oxalyl chloride (4.00 g, 31.5 mmol) was added to a suspension of 14 (3.92 g, 16.0 mmol) in dichloromethane (50 mL), followed by 2 drops of dry dimethylformamide. The solution became homogenous within 30 min, and the reaction was stirred at room temperature for 3 hours total. The solvent was then removed under vacuum overnight. The residue was dissolved into dichloromethane (40 mL) and added dropwise to a solution of crude 13 (assumed 1.469 g, 1.910 mmol) dissolved in dichloromethane (40 mL) and 20 mL of aqueous $K_2CO_3$ (4.42 g, 32 mmol) at 0° C. with vigorous stirring. The dichloromethane layer was loaded directly onto a 4 inch tall×1 inch wide silica gel column. Following a methanol/dichloromethane gradient elution, the desired product was collected using 4% methanol in dichloromethane. The solvent was removed under vacuum, and the crude product was again dissolved in dichloromethane and the column chromatography was repeated twice in the same way. After the final column chromatography step, the solvent was removed once more to yield a colorless foam of 15. Yield 1.69 g, 72.3% over two steps. $^1$H NMR (500 MHz, methanol-$d_4$) δ 9.74-9.41 (m, 2H), 8.22-7.94 (m, 2H), 7.62-7.02 (m, 22H), 6.78-5.89 (m, 6H), 5.62-4.91 (m, 8H), 3.77-2.84 (m, 16H), 1.93-0.98 (m, 10H). HRMS-ESI (m/z, $[M+Na]^+$) Calcd for $C_{66}H_{66}N_{10}O_{14}Na$: 1245.4652, Found: 1245.4626.

Compound 16·Compound 15 (1.63 g, 1.33 mmol) was dissolved into a 1:1 mixture of concentrated HCl and glacial acetic acid (50 mL). The homogenous solution was left capped at room temperature for 30 days in the dark. Upon reaction completion, the solvent was removed under vacuum. Residual solvent was removed by co-evaporation with water, followed by methanol. A concentrated methanolic solution of the product was dripped into diethyl ether to yield a beige solid of 16·Purity was assessed by HPLC by first adding a 5-fold molar excess of $EuCl_3$ to the sample dissolved in methanol. Quantitative yield and >95% purity. HRMS-ESI (m/z, $[M+H]^+$) Calcd for $C_{38}H_{43}N_{10}O_{14}$: 863.2955, Found: 863.2949.

Example 4. Crystal Structure of [Eu-16][NMe4] Salt

Figure 2:
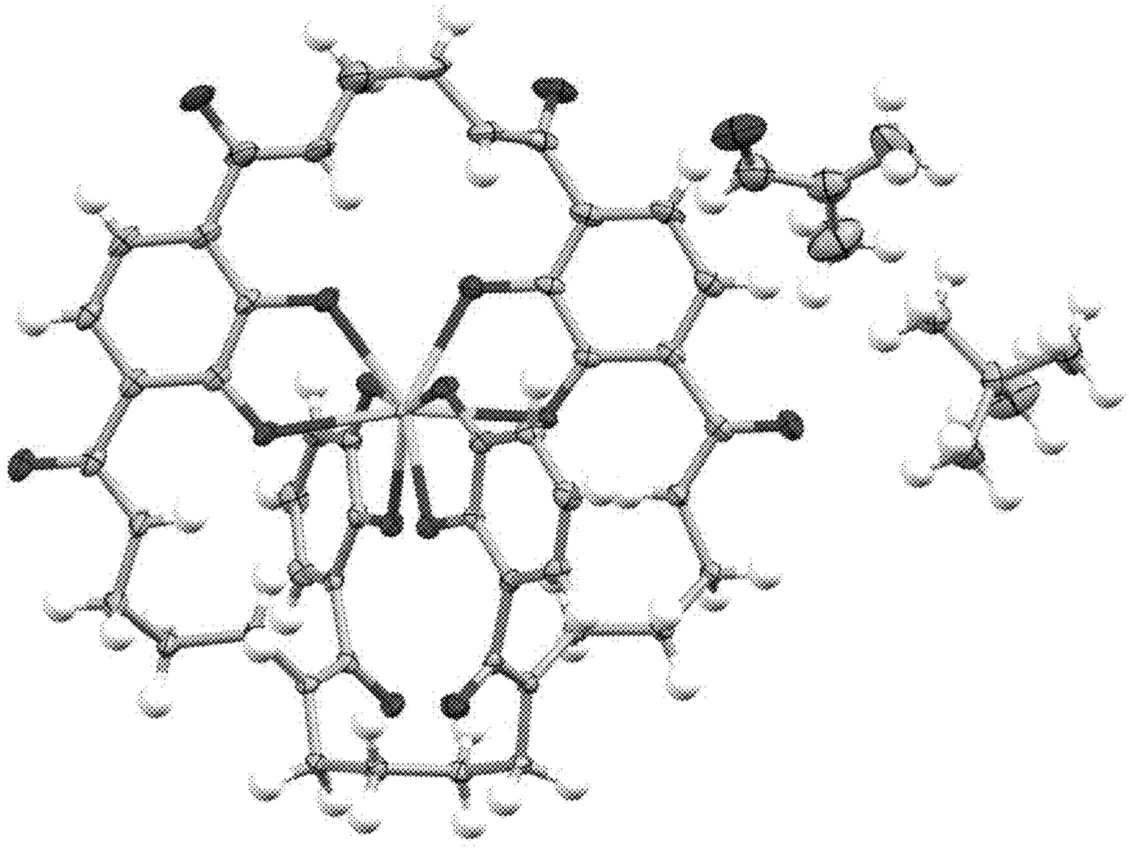
FIG. 2 shows the crystal structure ORTEP of [Eu-16] [NMe4]·DMF

Single crystals suitable for X-ray diffraction of [Eu-16][NMe4] were grown by vapor diffusion of diethyl ether into a DMF solution containing Eu·16 and tetramethylammonium hydroxide (1.5 molar equivalents). Single crystal X-ray diffraction data were collected on a Rigaku diffractometer equipped with a Pilatus 200K CCD detector at the Small Molecule X-ray Crystallography Facility at the University of California, Berkeley. Structures were solved with SIR-97, refined with SHELX-97, and the refined atomic positions are displayed as 50% thermal ellipsoids using Mercury (FIG. 2). Publication materials were generated with WinGX. The refinement tool SQUEEZE was used to remove disordered solvent electron density from the .hkl file used for final refinement. The crystal structure confirms the expected structure of Eu·16, and the orientations of the bridging 1,2-HOPO units are consistent with the crystal structure determined for key intermediate 7 (Example 2). The crystal data and structure refinement statistics are summarized in the following tables.

TABLE 3

| Crystal data and structure refinement for [Eu-16][$NMe_4$]•DMF | |
|---|---|
| Identification code | [Eu-16][$NMe_4$]•DMF |
| Empirical formula | C45 H57 Eu N12 O15 |
| Formula weight | 1157.99 |
| Temperature | 100(2) K |
| Wavelength | 0.71073 Å |
| Crystal system | Monoclinic |
| Space group | I2/a |

TABLE 3-continued

| Crystal data and structure refinement for [Eu-16][NMe$_4$]•DMF | | |
|---|---|---|
| Unit cell dimensions | a = 18.2333(5) Å | α = 90° |
| | b = 27.4104(7) Å | β = 107.170(3)° |
| | c = 22.5818(6) Å | γ = 90° |
| Volume | 10783.0(5) Å$^3$ | |
| Z | 8 | |
| Density (calculated) | 1.427 Mg/m$^3$ | |
| Absorption coefficient | 1.237 mm$^{-1}$ | |
| F(000) | 4752 | |
| Crystal size | 0.13 × 0.09 × 0.02 mm$^3$ | |
| Theta range for data collection | 3.17 to 28.95°. | |
| Index ranges | −22 <= h <= 22, −33 <= k <= 36, −29 <= l <= 27 | |
| Reflections collected | 57823 | |
| Independent reflections | 12313 [R(int) = 0.0482] | |
| Completeness to theta = 25.00° | 99.8% | |
| Absorption correction | Semi-empirical from equivalents | |
| Max. and min. transmission | 0.9757 and 0.8557 | |
| Refinement method | Full-matrix least-squares on F$^2$ | |
| Data/restraints/parameters | 12313/0/658 | |
| Goodness-of-fit on F$^2$ | 1.035 | |
| Final R indices [I > 2sigma(I)] | R1 = 0.0360, wR2 = 0.0866 | |
| R indices (all data) | R1 = 0.0494, wR2 = 0.0906 | |
| Largest diff. peak and hole | 2.248 and −0.720 e·Å$^{-3}$ | |

TABLE 4

XRD measured Cartesian coordinates of [Eu-16][NMe$_4$]•DMF

| Atom | X (Å) | Y (Å) | Z (Å) |
|---|---|---|---|
| C | 8.143087 | 21.36175 | 14.37375 |
| C | 9.415502 | 21.95107 | 14.62424 |
| C | 10.49805 | 21.11533 | 14.90148 |
| H | 11.34708 | 21.49798 | 15.08768 |
| C | 10.36056 | 19.75111 | 14.9086 |
| H | 11.11534 | 19.20373 | 15.09415 |
| C | 9.13495 | 19.16261 | 14.64883 |
| C | 9.022787 | 17.66463 | 14.5964 |
| C | 7.739806 | 15.74755 | 13.93339 |
| H | 8.518753 | 15.25663 | 14.29802 |
| H | 7.753881 | 15.65408 | 12.94955 |
| C | 6.488443 | 15.13876 | 14.46631 |
| H | 6.425671 | 14.20681 | 14.13836 |
| H | 6.544811 | 15.10861 | 15.4523 |
| C | 4.583867 | 15.68176 | 12.95301 |
| C | 3.398074 | 16.59837 | 12.75322 |
| C | 2.137789 | 16.08716 | 12.53488 |
| H | 1.999577 | 15.14973 | 12.47705 |
| C | 1.067653 | 16.97088 | 12.39981 |
| H | 0.193681 | 16.62441 | 12.2613 |
| C | 1.245307 | 18.33399 | 12.46217 |
| C | 2.556772 | 18.85808 | 12.64469 |
| C | 0.050208 | 19.23059 | 12.28719 |
| C | −0.65245 | 21.60844 | 12.09582 |
| H | −1.56415 | 21.25402 | 12.24404 |
| H | −0.59929 | 21.9338 | 11.16311 |
| C | −0.39476 | 22.7679 | 13.05398 |
| H | −0.57466 | 22.46831 | 13.98086 |
| H | −1.02263 | 23.50442 | 12.84599 |
| C | 1.036754 | 23.29034 | 12.9666 |
| H | 1.661739 | 22.55602 | 13.18688 |
| H | 1.219102 | 23.57294 | 12.03476 |
| C | 1.686752 | 24.25108 | 15.14183 |
| C | 1.784183 | 22.84109 | 15.67863 |
| C | 0.855284 | 22.38361 | 16.58889 |
| H | 0.118744 | 22.93154 | 16.83528 |
| C | 1.003803 | 21.11341 | 17.14446 |
| H | 0.357878 | 20.79079 | 17.76087 |
| C | 2.077564 | 20.32728 | 16.80573 |
| H | 2.173533 | 19.46687 | 17.19559 |
| C | 3.040099 | 20.78613 | 15.88338 |
| C | 1.05272 | 25.76441 | 13.34158 |
| H | 0.933038 | 26.39073 | 14.09952 |
| H | 0.216962 | 25.76304 | 12.81147 |
| C | 2.200746 | 26.25067 | 12.46389 |
| H | 2.46342 | 25.52182 | 11.84921 |
| H | 1.880679 | 27.00747 | 11.91178 |
| C | 3.429256 | 26.698 | 13.24773 |
| H | 3.675506 | 25.9878 | 13.8924 |
| H | 3.202482 | 27.51182 | 13.7651 |
| C | 4.634335 | 26.99623 | 12.35062 |
| H | 4.321419 | 27.46522 | 11.53637 |
| H | 5.250647 | 27.60227 | 12.83089 |
| C | 5.11326 | 25.20523 | 10.77109 |
| C | 5.932152 | 24.00877 | 10.35317 |
| C | 6.755068 | 24.08607 | 9.253041 |
| H | 6.855465 | 24.90783 | 8.78766 |
| C | 7.439317 | 22.95265 | 8.824769 |
| H | 8.012822 | 23.00281 | 8.069199 |
| C | 7.288796 | 21.76468 | 9.487781 |
| H | 7.75587 | 20.99637 | 9.178174 |
| C | 6.454222 | 21.65833 | 10.62092 |
| C | 6.318536 | 25.27431 | 12.94136 |
| H | 6.433714 | 24.30206 | 12.79637 |
| H | 5.941318 | 25.40122 | 13.84709 |
| C | 7.690828 | 25.94669 | 12.87922 |
| H | 7.576236 | 26.92798 | 12.82226 |
| H | 8.170577 | 25.64517 | 12.06712 |
| C | 8.516129 | 25.59857 | 14.12239 |
| H | 9.440011 | 25.93572 | 14.01322 |
| H | 8.11957 | 26.0344 | 14.91723 |
| C | 9.637109 | 23.4326 | 14.56145 |
| Eu | 5.073161 | 20.77741 | 13.36684 |
| N | 8.073 | 19.98109 | 14.41647 |
| N | 7.856373 | 17.1304 | 14.27666 |
| H | 7.136709 | 17.63585 | 14.27428 |
| N | 5.259365 | 15.85911 | 14.08205 |
| H | 4.947589 | 16.4572 | 14.6497 |
| N | 3.581271 | 17.94203 | 12.80176 |
| N | 2.836403 | 22.04454 | 15.34529 |
| N | 0.31791 | 20.54629 | 12.29474 |
| H | 1.152965 | 20.78531 | 12.43175 |
| N | 1.293538 | 24.41664 | 13.86457 |
| N | 5.364276 | 25.78935 | 11.95622 |
| N | 8.544244 | 24.16282 | 14.31938 |
| H | 7.776031 | 23.73467 | 14.27644 |
| N | 5.775052 | 22.8134 | 10.98555 |
| O | 7.059436 | 21.9804 | 14.12369 |
| O | 6.845652 | 19.47262 | 14.20718 |
| O | 4.810482 | 18.44281 | 12.98731 |
| O | 2.886079 | 20.091 | 12.68655 |
| O | 4.070293 | 20.14692 | 15.48855 |
| O | 3.741467 | 22.48996 | 14.4443 |
| O | 4.925769 | 22.72103 | 12.02289 |
| O | 6.266796 | 20.62112 | 11.31781 |
| O | 10.76262 | 23.92352 | 14.69608 |
| O | 10.03669 | 17.00815 | 14.83675 |
| O | 4.826473 | 14.80792 | 12.1271 |
| O | −1.07757 | 18.75995 | 12.16874 |
| O | 1.873137 | 25.17289 | 15.93127 |
| O | 4.307506 | 25.64901 | 9.952084 |
| C | −2.97036 | 16.16035 | 12.99486 |
| H | −2.88889 | 15.29226 | 12.54825 |
| H | −2.94579 | 16.03234 | 13.96576 |
| H | −2.22698 | 16.73953 | 12.72517 |
| C | −5.38404 | 15.90132 | 13.04664 |
| H | −5.29759 | 15.0346 | 12.59572 |
| H | −6.24376 | 16.30645 | 12.81363 |
| H | −5.33577 | 15.77194 | 14.01754 |
| C | −4.30797 | 17.00541 | 11.13959 |
| H | −4.22693 | 16.13924 | 10.68845 |
| H | −3.56453 | 17.58377 | 10.86969 |
| H | −5.15683 | 17.42479 | 10.8891 |
| C | −4.39437 | 18.11773 | 13.28397 |
| H | −4.36615 | 17.98945 | 14.25487 |
| H | −5.24511 | 18.53491 | 13.0337 |
| H | −3.65264 | 18.69663 | 13.00781 |
| N | −4.27079 | 16.80285 | 12.60845 |

TABLE 4-continued

| XRD measured Cartesian coordinates of [Eu-16][NMe4]•DMF | | | |
|---|---|---|---|
| Atom | X (Å) | Y (Å) | Z (Å) |
| C | 2.357822 | 15.05516 | 6.496352 |
| H | 2.980759 | 15.70068 | 6.185667 |
| C | 1.068958 | 15.68697 | 4.571827 |
| H | 0.237293 | 15.45398 | 4.112271 |
| H | 1.826984 | 15.54992 | 3.965558 |
| H | 1.037662 | 16.62441 | 4.85015 |
| C | 0.270959 | 13.88885 | 6.08642 |
| H | −0.45313 | 13.89707 | 5.426213 |
| H | −0.09237 | 14.09991 | 6.973169 |
| H | 0.685482 | 13.00349 | 6.107995 |
| N | 1.229849 | 14.84301 | 5.73884 |
| O | 2.61352 | 14.48256 | 7.527656 |

Example 5. Synthesis of Exemplary Scaffold Amine 23

Scheme 3. Synthetic scheme of exemplary scaffold amine 23.

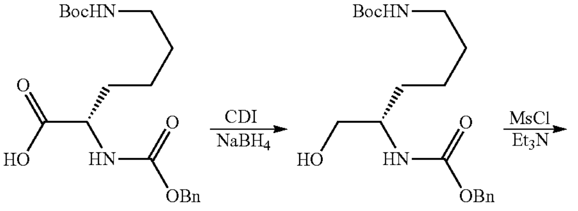

17 18

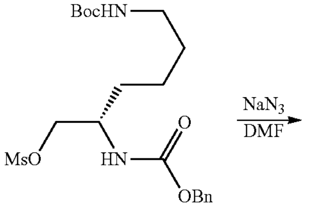

19

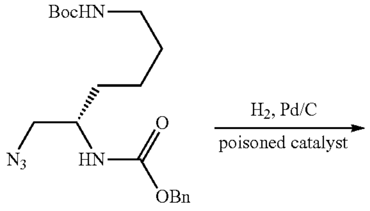

20

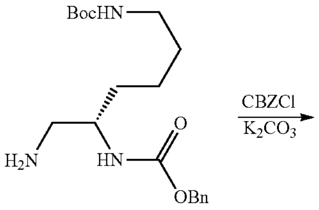

21

-continued

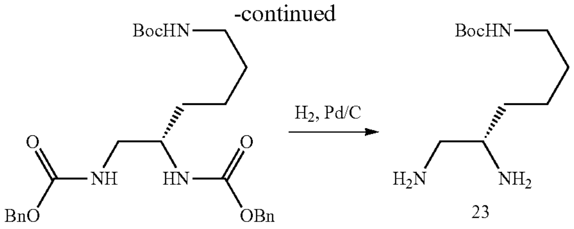

22 23

The precursor(S)-2-(((benzyloxy)carbonyl)amino)-6-((tert-butoxycarbonyl)amino) hexanoic acid (17, $N^{\alpha}$—Z—$N^{\varepsilon}$-Boc-L-lysine) was purchased from Chem-Impex (Wood Dale, IL). All other solvents and reagents were purchased from commercial sources and used as received unless otherwise noted. $^{1}$H-NMR and $^{13}$C-NMR spectra were obtained at 300/75 MHz, 400/100 MHZ, or 500/125 MHz using a Bruker AV-300, AVB-400, or DRX-500 spectrometer as noted below. $^{1}$H (or $^{13}$C) chemical shifts are reported relative to residual solvent signals, taken as 7.24 (77.23), 2.50 (39.51), and 3.31 (49.15) ppm for $CDCl_3$, DMSO-$d_6$, and methanol-$d_4$ respectively. High resolution electrospray ionization mass spectra (HRMS-ESI) were performed by the Microanalytical Laboratory at the University of California, Berkeley.

(S)-Benzyl tert-butyl (6-hydroxyhexane-1,5-diyl)dicarbamate (18). The reagent 1,1'-carbonyldiimidazole (CDI, 5.1 g, 31.5 mmol) was added to a stirred solution of the starting material(S)-2-(((benzyloxy)carbonyl)amino)-6-((tert-butoxycarbonyl)amino) hexanoic acid (17, $N^{\alpha}$—Z—$N^{\varepsilon}$-Boc-L-lysine, 11.4 g, 30 mmol) dissolved in THF (70 mL) at room temperature. After 20 minutes, the THF solution was transferred slowly via a Teflon cannula (ϕ=2 mm) to a stirred solution of sodium borohydride (2.25 g, 60 mmol) dissolved in water (10 mL) in a 1 L round flask immersed in a water bath at 5-10° C. The addition caused a strong evolution of hydrogen gas, and the mixture was stirred for three hours. The volatiles were then removed on a rotovap, and the residue was dissolved in ethyl acetate (150 mL). The ethyl acetate solution was extracted successively with cold 1 N HCl (2×50 mL), saturated sodium bicarbonate solution (2×50 mL), and brine (100 mL). The washed ethyl acetate solution was dried with anhydrous sodium sulfate, and the dried ethyl acetate solution was then passed through a one inch silica gel column, eluting with ethyl acetate. The solvent was removed under vacuum to provide a colorless solid of 18. Yield 9.9 g, 90%. TLC $R_f$=0.24 (95:5:2 EtOAc:MeOH:$H_2O$). $^{1}$H NMR (500 MHZ, $CDCl_3$) δ 7.40-7.22 (m, 5H), 5.15 (s, 1H), 5.06 (s, 2H), 4.62 (s, 1H), 3.72-3.49 (m, 3H), 3.18-2.97 (m, 2H), 1.64-1.52 (m, 1H), 1.52-1.21 (m, 15H). $^{13}$C NMR (125 MHz, $CDCl_3$) δ 156.7, 156.4, 136.4, 128.5, 128.1, 128.0, 79.2, 66.7, 64.8, 52.9, 39.7, 29.8, 28.4, 22.6.

(S)-2-(((benzyloxy)carbonyl)amino)-6-((tert-butoxycarbonyl)amino) hexyl methanesulfonate (19). The starting material(S)-benzyl tert-butyl (6-hydroxyhexane-1,5-diyl)dicarbamate (18, 9.9 g, 27 mmol), triethylamine (7.1 g mL, 70 mmol), and a catalytic amount of DMAP (100 mg, 0.819 mmol,) were dissolved in dichloromethane (350 mL) at 0° C. Freshly distilled methanesulfonyl chloride (MsCl, 4.0 g, 35 mmol) dissolved in DCM (50 mL) was then added dropwise to the starting material solution over 30 min. Upon completion of the MsCl addition, the reaction mixture was warmed to room temperature and stirred under $N_2$ for 2 hours. The reaction mixture was again cooled to 0° C., and the excess reagent was quenched by addition of 5% $KHSO_4$ solution until the aqueous phase had a pH of 3-4. The dichloromethane phase was washed successively with $H_2O$ (100 mL) and brine (3×100 mL). The organic portion was dried over $Na_2SO_4$, filtered and concentrated under reduced pressure to give a pink solid of 19 Yield 10.8 g, 90%. $^1H$ NMR (300 MHz, $CDCl_3$) δ 7.43-7.25 (m, 5H), 5.57-5.42 (m, 1H), 5.18-5.03 (m, 2H), 4.88-4.71 (m, 1H), 4.29-4.08 (m, 2H), 3.99-3.77 (m, 1H), 3.18-3.00 (m, 2H), 2.95 (s, 3H), 1.64-1.51 (m, 2H), 1.50-1.23 (m, 13H). $^{13}C$ NMR (75 MHZ, $CDCl_3$) δ 162.33, 156.18, 136.35, 128.50, 128.15, 128.08, 79.02, 70.92, 66.74, 50.19, 39.90, 37.12, 30.35, 29.61, 28.38, 22.70.

(S)-Benzyl tert-butyl (6-azidohexane-1,5-diyl)dicarbamate (20). The starting material 1-(S)-2-(((benzyloxy)carbonyl)amino)-6-((tert-butoxycarbonyl)amino) hexyl methanesulfonate (19, 10.7 g, 24 mmol) was dissolved in DMF (100 mL), and then solid sodium azide (2.40 g, 36.9 mmol) was added. The suspension was heated to 70° C. and stirred under $N_2$ overnight. The reaction mixture was concentrated under reduced pressure to give a sticky white foam, which was dissolved in 250 mL of ethyl acetate and washed successively with $H_2O$ (3×100 mL) and brine (1×100 mL). The organic fraction was dried over $Na_2SO_4$, filtered, and concentrated under reduced pressure to give a crude colorless syrup. The syrup was loaded onto a silica gel column, eluted with 25-50% ethyl acetate/hexanes, and then concentrated under vacuum to give a colorless syrup of 20. Yield 8.9 g, 95%, $^1H$ NMR (300 MHz, $CDCl_3$) δ 7.46-7.26 (m, 5H), 5.26-5.03 (m, 3H), 4.70 (s, 1H), 3.77 (s, 1H), 3.50-3.25 (m, 2H), 3.10 (s, 2H), 1.61-1.25 (m, 15H). $^{13}C$ NMR (75 MHz, $CDCl_3$) δ 156.24, 156.11, 136.44, 128.60, 128.23, 128.16, 79.21, 66.87, 54.78, 50.88, 40.07, 31.72, 29.82, 28.48, 22.95.

(S)-Benzyl tert-butyl (6-aminohexane-1,5-diyl)dicarbamate (21). The azido group in the(S)-benzyl tert-butyl (6-azidohexane-1,5-diyl)dicarbamate (20) starting material was selectively reduced to primary amine by catalytic hydrogenation using a poisoned 5% Pd/C catalyst. The CBZ protecting group was not affected under these conditions. To prepare the poisoned 5% Pd/C catalyst, the Pd/C catalyst was suspended in methanol containing 2-mercapto-thioazoline (20% by weight), and the mixture was stirred for 10 min at room temperature. The solvent was filtered off, and the catalyst bed was washed thoroughly with methanol and used directly for the selective hydrogenation. A solution of starting material 20 (8.9 g, 22.7 mmol) in methanol (40 mL) was added to an appropriately sized glass container, followed by 1g of the poisoned 5% Pd/C catalyst. The container was placed into a Parr bomb, $H_2$ (500 psi) was added, and the solution was stirred under high pressure $H_2$ at room temperature overnight. After depressurizing the bomb and removing the reaction vessel, TLC analysis showed no starting material remained, and litmus test shows that the solution is strongly basic. The solvent was removed under vacuum to give a think, colorless oil of 21. The raw yield was quantitative. $^1H$ NMR (300 MHz, $CDCl_3$) δ 7.41-7.26 (m, 5H), 5.47 (d, J=8.7 Hz, 1H), 5.10 (s, 2H), 5.03-4.87 (m, 1H), 3.65-3.51 (m, 1H), 3.17-2.95 (m, 2H), 2.76 (dd, J=13.0, 4.2 Hz, 1H), 2.64 (dd, J=13.0, 6.5 Hz, 1H), 1.60-1.16·(m, 17H). $^{13}C$ NMR (75 MHz, $CDCl_3$) δ 156.66, 156.14, 136.62, 128.46, 128.02, 128.01, 78.89, 66.50, 53.47, 45.83, 40.09, 32.10, 29.77, 28.41, 23.02.

(S)-Dibenzyl tert-butyl hexane-1,2,6-triyltricarbamate (22). The starting material (S)-benzyl tert-butyl (6-aminohexane-1,5-diyl)dicarbamate (21, 8.2 g, 22.5 mmol) was suspended in dichloromethane (100 mL), and an aqueous solution of $K_2CO_3$ (4M, 50 mL) was added. The two-phase suspension was stirred vigorously at 0° C., and then a solution of benzyl chloroformate (CBZCl, 5.80 g, 34 mmol) dissolved in dry DCM (50 mL) was added dropwise over 1 hour. The reaction mixture was stirred with warming to room temperature overnight, resulting in the precipitation of a fluffy white solid. The reaction mixture was filtered, and the solids were washed with methanol to yield a 1st batch of product. The organic phase was then separated, the solvent was evaporated to dryness, and the residue was treated with methanol. The methanol treatment resulted in precipitation of more desired product, which was collected by filtration and washed with methanol to give a 2nd batch of product. The combined 1st and 2nd batch products were dried under vacuum to afford a white solid of 22. Yield 9.9 g, 87%. $^1H$ NMR (300 MHZ, $CDCl_3$) δ 7.42-7.19 (m, 10H), 5.30 (d, J=8.5 Hz, 1H), 5.06 (d, J=2.4 Hz, 4H), 4.60 (s, 1H), 3.67 (s, 1H), 3.38-3.25 (m, 1H), 3.26-3.13 (m, 1H), 3.13-2.96 (m, 2H), 1.79 (s, 1H), 1.59-1.21 (m, 15H). $^{13}C$ NMR (75 MHz, $CDCl_3$) δ 157.26, 156.80, 156.40, 136.65, 136.63, 128.69, 128.69, 128.29, 128.29, 128.25, 128.25, 79.40, 66.98, 66.94, 51.99, 45.21, 40.06, 32.05, 30.00, 28.59, 22.89. HRMS-ESI (m/z, $[M+Na]^+$) Calcd for $C_{27}H_{37}N_3O_6Na$: 522.2575, Found: 522.2565.

(S)-Tert-butyl (5,6-diaminohexyl)carbamate (23). In an appropriately sized glass container, the starting material(S)-dibenzyl tert-butyl hexane-1,2,6-triyltricarbamate (22, 2.5 g, 5 mmol) was dissolved into a 1:1 methanol: acetic acid mixture (40 mL), and 5% Pd/C (300 mg) was added. The reaction vessel was placed into a Parr bomb, which was pressurized with $H_2$ (500 psi). The pressurized reaction was stirred with a large egg-shaped stirbar overnight at room temperature. The reaction completion was verified by TLC, which showed no starting material remained. The solvent was removed under vacuum, and the crude product acetate salt was obtained as clear colorless thick oil. The oil was dissolved in small amount water, and the crude product was subjected to ion-exchange chromatography to yield the free amine product 23 as colorless oil that solidified upon cooling. Yield 0.95 g, 82%. $^1H$ NMR (300 MHz, $CDCl_3$) δ 5.19-4.75 (m, 1H), 3.00-2.76 (m, 2H), 2.63-2.35 (m, 2H), 2.30-2.13 (m, 1H), 1.52-0.91 (m, 19H). $^{13}C$ NMR (75 MHz, $CDCl_3$) δ 155.97, 78.62, 53.34, 48.40, 40.15, 35.06, 30.02, 28.28, 23.20. HRMS-ESI (m/z, $[M+H]^+$) Calcd for $C_{11}H_{26}N_3O_2$: 232.2025, Found: 232.2019.

Example 6. Synthesis of Exemplary Bifunctional Chelator 29

Scheme 4. Synthesis of exemplary bifunctional chelaltor 29.

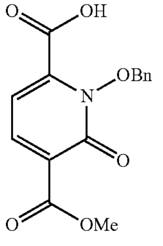

8

+

-continued

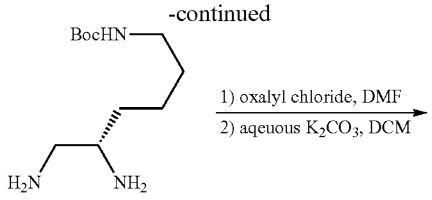

23

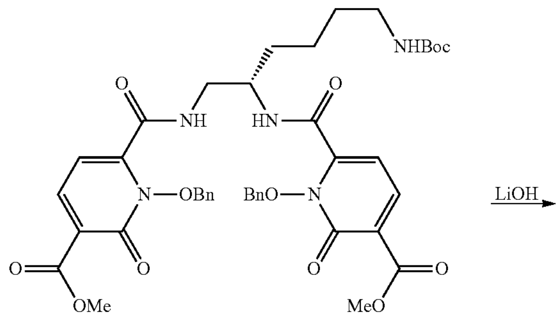

24

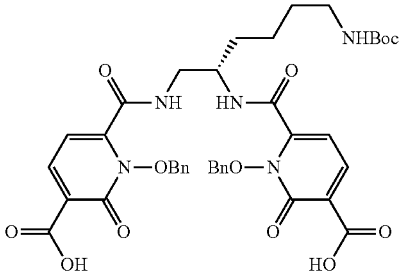

25

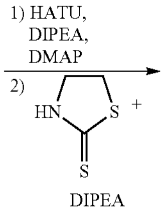

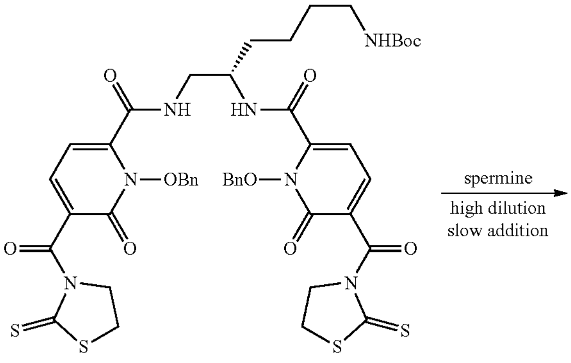

26

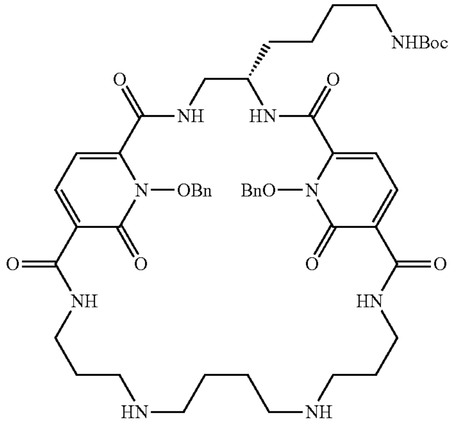

27

+

-continued

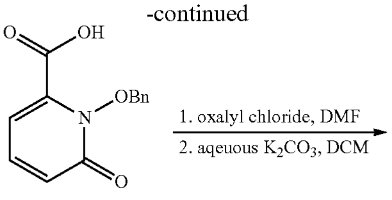

14

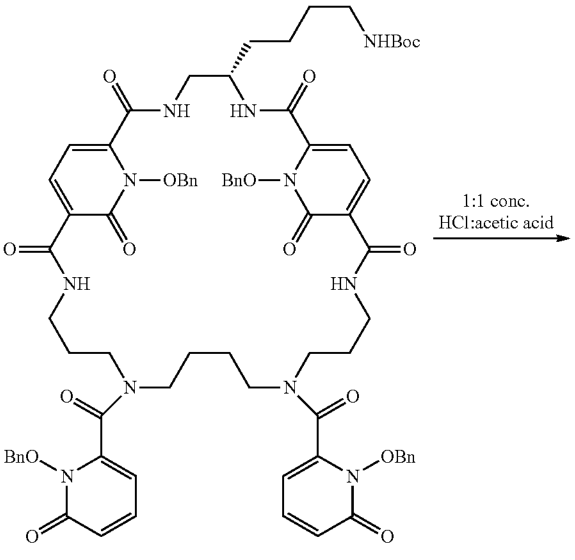

28

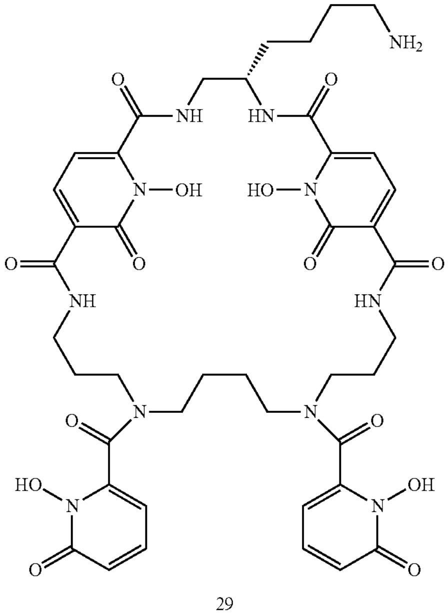

29

$^1$H-NMR and $^{13}$C-NMR spectra were obtained at 300/75 MHz, 400/100 MHZ, or 500/125 MHz using a Bruker AV-300, AVB-400, or DRX-500 spectrometer as noted below. $^1$H(or $^{13}$C) chemical shifts are reported relative to residual solvent signals, taken as 7.24 (77.23), 2.50 (39.51), and 3.31 (49.15) ppm for $CDCl_3$, DMSO-$d_6$, and methanol-$d_4$ respectively. High resolution electrospray ionization mass spectra (HRMS-ESI) were performed by the Microanalytical Laboratory at the University of California, Berkeley.

Compound 24. Oxalyl chloride (1.00 g, 7.88 mmol) was added to a suspension of 8 (910 mg, 3.00 mmol) in dichloromethane (15 mL), followed by 1 drop of dry dimethylformamide. The solution became homogenous within 30 min, and the reaction was stirred at room temperature for 3 hours total. The solvent was then removed under vacuum overnight. The residue was dissolved into dichloromethane (50 mL) and added dropwise to a solution of 23 (0.23 g, 1.0 mmol) dissolved in dichloromethane (40 mL) and aqueous $K_2CO_3$ (4 M, 30 mL) at 0° C. with vigorous stirring. The dichloromethane layer was loaded directly onto a 4 inch tall×1 inch wide silica gel column. Following a methanol/dichloromethane gradient elution, the desired product was collected using 3-4% methanol in dichloromethane. The solvent was removed under vacuum to yield a colorless foam of 24. Yield 720 mg, 90%. $^1$H NMR (300 MHz, $CDCl_3$) δ 8.17-8.07 (m, 1H), 7.98 (d, J=8.7 Hz, 1H), 7.76 (d, J=7.4 Hz, 1H), 7.67 (d, J=7.4 Hz, 1H), 7.40-7.11 (m, 10H), 6.13 (d, J=7.4 Hz, 1H), 6.03 (d, J=7.4 Hz, 1H), 5.31-5.00 (m, 5H), 4.31-4.08 (m, 1H), 3.77-3.57 (m, 7H), 3.48-3.28 (m, 1H), 2.90-2.72 (m, 2H), 1.69-1.05 (m, 15H). $^{13}$C NMR (75 MHz, $CDCl_3$) δ 164.43, 164.26, 162.40, 160.37, 159.75, 156.04, 155.79, 155.73, 148.18, 147.95, 143.29, 133.30, 133.26, 130.06, 130.03, 129.32, 129.24, 128.53, 128.48, 121.32, 103.21, 103.10, 79.63, 79.54, 79.15, 78.87, 52.65, 52.54, 50.40, 42.86, 40.20, 31.05, 29.38, 28.46, 22.94. HRMS-ESI (m/z, $[M+Na]^+$) Calcd for $C_{41}H_{47}N_5O_{12}Na$: 824.3119, Found: 824.3098.

Compound 25. Lithium hydroxide monohydrate (147 mg, 3.5 mmol) was dissolved into water (12 mL), and then it was added all at once to a suspension of 24 (1.00 g, 1.25 mmol) in methanol (12 mL). The reaction was stirred at room temperature overnight. The solvents were then removed under vacuum, and the residue was dissolved in water (25 mL). The solution was adjusted to pH=5-6 with 2N HCl, and then a 5% $KHSO_4$ solution was added until the pH was dropped to 3-4, causing precipitation of the product. The precipitate was washed with a small amount of cold water, and it was dried under vacuum overnight to yield a white powder of 25. The product was used directly in the next reaction without further purification. $^1$H NMR (300 MHz, $CDCl_3$) δ 8.35-7.70 (m, 4H), 7.64-7.21 (m, 10H), 6.77-6.32 (m, 2H), 5.60-5.22 (m, 4H), 4.69 (s, 1H), 4.32 (s, 1H), 4.00-3.44 (m, 2H), 3.18-2.59 (m, 2H), 1.79-1.10 (m, 15H). $^{13}$C NMR (75 MHz, $CDCl_3$) δ 171.27, 164.97, 164.89, 160.50, 159.75, 159.40, 156.25, 147.88, 147.53, 144.18, 144.08, 132.68, 132.63, 130.49, 130.41, 129.86, 129.78, 128.74, 119.64, 119.49, 106.33, 106.00, 80.72, 80.61, 79.16, 50.55, 39.78, 30.89, 29.45, 28.40, 22.73. HRMS-ESI (m/z, $[M+Na]^+$) Calcd for $C_{39}H_{43}N_5O_{12}Na$: 796.2800, Found: 796.2803.

Compound 26. The entire batch of compound 25 (assumed 965 mg, 1.25 mmol) was dissolved in DMF (10 mL), and HATU (1.20 g, 3.15 mmol) and DIPEA (390 mg, 3.00 mmol) were added sequentially. The solution was stirred at room temperature for 15 minutes, after which time 2-mercaptothiazoline (352 mg, 3.00 mmol) and DIPEA (390 mg, 3.00 mmol) were added sequentially. The reaction mixture was stirred at room temperature overnight, then the reaction was evaporated to dryness and dissolved in dichloromethane (50 mL). The dichloromethane solution was washed with 5% $KHSO_4$ (1×50 mL), brine (3×40 mL), and loaded onto a 4 inch tall×1 inch wide silica gel column. Following a 2-propanol/dichloromethane gradient elution, the desired product was collected using 5% 2-propanol in dichloromethane. The solvent was removed under vacuum to yield a yellow foam of 26. Yield: 0.70 g, 57% over two steps. $^1$H NMR (300 MHz, $CDCl_3$) δ 7.60 (s, 1H), 7.52-7.14 (m, 13H), 6.38-6.11 (m, 2H), 5.36-5.07 (m, 4H), 4.54 (t, J=7.1 Hz, 5H), 4.10 (s, 1H), 3.62-3.21 (m, 6H), 3.01-2.72 (m, 2H), 1.41 (s, 11H), 1.22 (s, 4H). $^{13}$C NMR (75 MHz, $CDCl_3$) δ 202.12, 165.56, 165.50, 160.60, 160.16, 156.21, 155.53, 145.14, 144.92, 138.87, 133.45, 130.11, 130.05, 129.44, 128.69, 105.17, 104.84, 79.16, 55.67, 50.60, 43.26, 39.93, 31.18, 29.61, 29.46, 28.53, 22.86. HRMS-ESI (m/z, $[M+Na]^+$) Calcd for $C_{45}H_{49}N_7O_{10}S_4Na$: 998.2322, Found: 998.2319.

Compound 27. Following the same procedure as used for compound 13, using 26 (747.7 mg, 0.766 mmol) and spermine (147.6 mg, 0.7294 mmol) as starting materials. Similarly, the residue was used without further purification directly in the next reaction.

Compound 28. Following the same procedure as used for compound 15, using 27 (assumed 685.7 mg, 0.7294 mmol) and 14 (1.43 g, 5.84 mmol) as starting materials. Yield: 653 mg, 64.2% over two steps. $^1$H NMR (500 MHZ, methanol-$d_4$) δ 9.72-9.43 (m, 2H), 8.31-7.81 (m, 2H), 7.65-7.07 (m, 24H), 6.83-5.90 (m, 6H), 5.67-4.91 (m, 8H), 4.31-4.07 (m, 1H) 3.91-2.80 (m, 16H), 1.97-1.04 (m, 24H). HRMS-ESI (m/z, $[M+Na]^+$) Calcd for $C_{75}H_{83}N_{11}O_{16}Na$: 1416.5911, Found: 1416.5937.

Compound 29. Following the same procedure as used for compound 16, using 28 (600 mg, 0.430 mmol) as the starting material. Quantitative yield and >95% purity. HRMS-ESI (m/z, $[M+H]^+$) Calcd for $C_{42}H_{52}N_{11}O_{14}$: 934.3690, Found: 934.3701.

Example 7. Synthesis of Exemplary Bifunctional Chelator 33

Scheme 5. Synthetic scheme of exemplary bifunctional chelator 33.

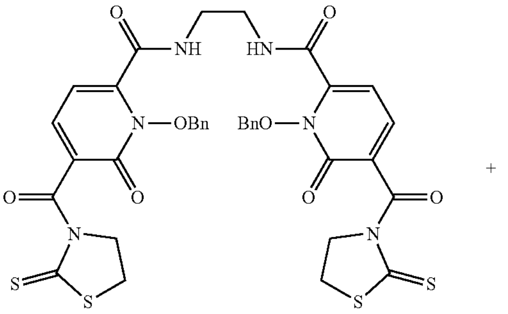

12

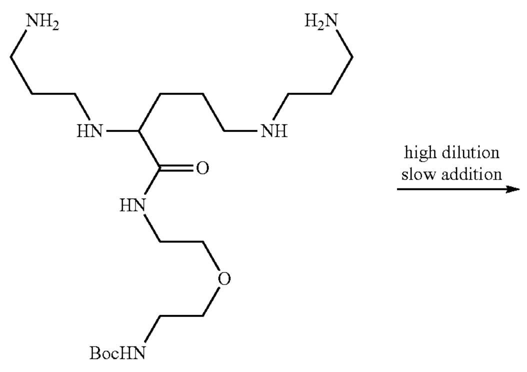

30

-continued

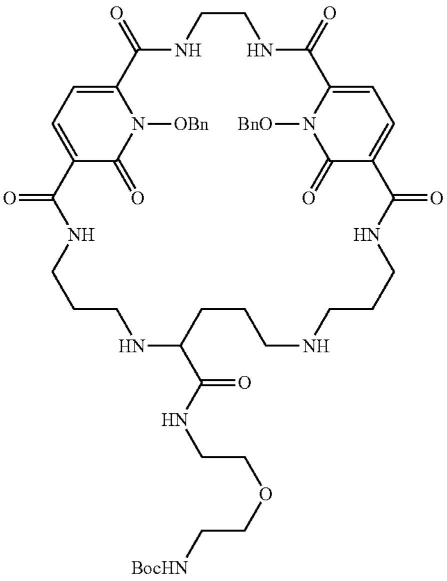

31

+

-continued

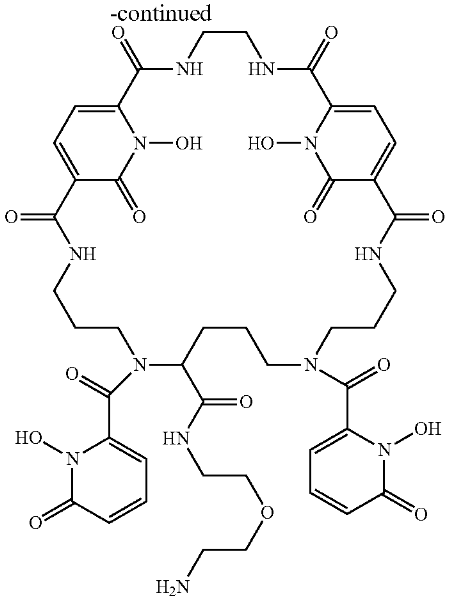

33

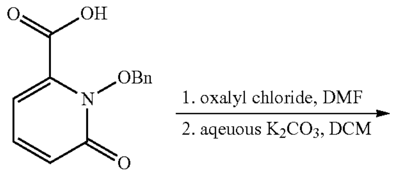

14

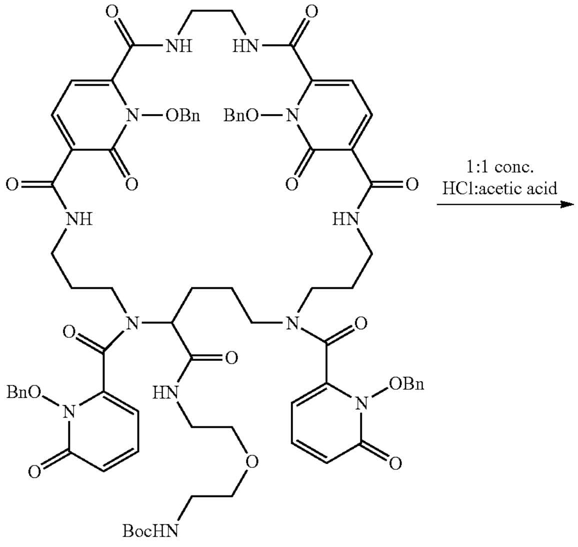

32

The precursor tert-butyl (2-(2-(2,5-bis((3-aminopropyl) amino) pentanamido) ethoxy)ethyl)carbamate (30) was synthesized according to previously reported methods (WO2016106241). All other solvents and reagents were purchased from commercial sources and used as received unless otherwise noted. $^{1}$H-NMR and $^{13}$C-NMR spectra were obtained at 300/75 MHz, 400/100 MHz, or 500/125 MHz using a Bruker AV-300, AVB-400, or DRX-500 spectrometer as noted below. $^{1}$H(or $^{13}$C) chemical shifts are reported relative to residual solvent signals, taken as 7.24 (77.23), 2.50 (39.51), and 3.31 (49.15) ppm for $CDCl_3$, DMSO-$d_6$, and methanol-$d_4$ respectively. High resolution electrospray ionization mass spectra (HRMS-ESI) were performed by the Microanalytical Laboratory at the University of California, Berkeley.

Compound 31. Following the same procedure as used for compound 13, using 12 (916.8 g, 1.139 mmol) and 30 (469.3 mg, 1.085 mmol) as starting materials. Similarly, the residue was used without further purification directly in the next reaction.

Compound 32. Following the same procedure as used for compound 15, using 31 (assumed 1.084 g, 1.085 mmol) and 14 (2.29 g, 8.68 mmol) as starting materials. Yield: 834 mg, 52.9% over two steps. $^{1}$H NMR (500 MHZ, methanol-$d_4$) δ 10.03-9.32 (m, 2H), 8.32-7.81 (m, 2H), 7.81-6.95 (m, 24H), 6.85-5.85 (m, 6H), 5.69-4.56 (m, 8H), 4.14-2.61 (m, 24H), 2.23-1.02 (m, 18H). HRMS-ESI (m/z, $[M+Na]^+$) Calcd for $C_{76}H_{84}N_{12}O_{18}Na$: 1475.5919, Found: 1475.5925.

Compound 33. Following the same procedure as used for compound 16, using 32 (750 mg, 0.516·mmol) as the starting material. Quantitative yield and >95% purity. HRMS-ESI (m/z, $[M-H]^-$) Calcd for $C_{43}H_{51}N_{12}O_{16}$: 991.3551, Found: 991.3510.

Example 8. Synthesis of an Exemplary Parent Ligand 40
Scheme 6. Synthetic scheme of an exemplary parent ligand 40.
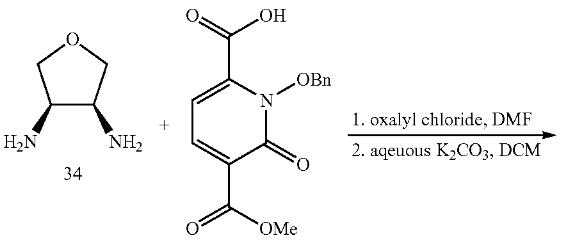
34
8
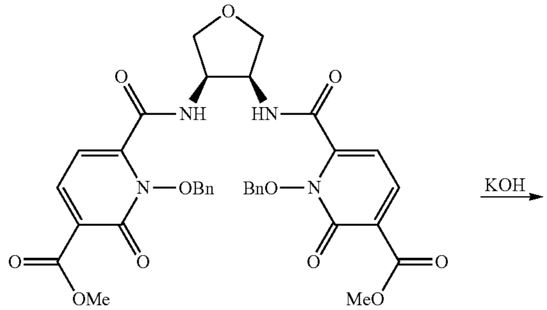
35
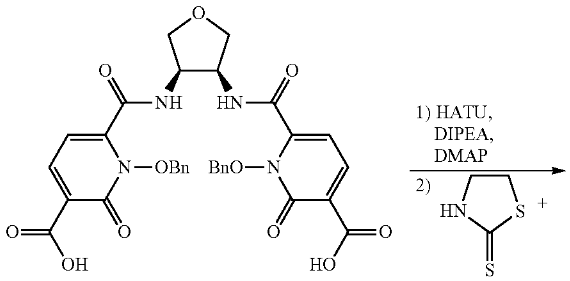
36
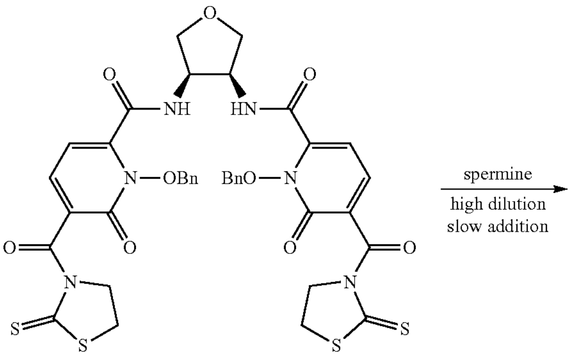
37
-continued
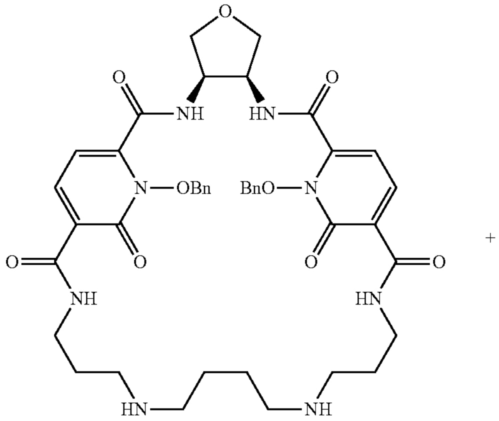
38
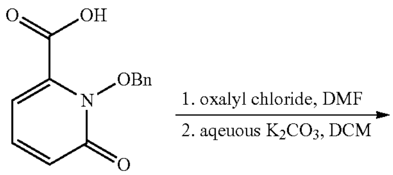
14
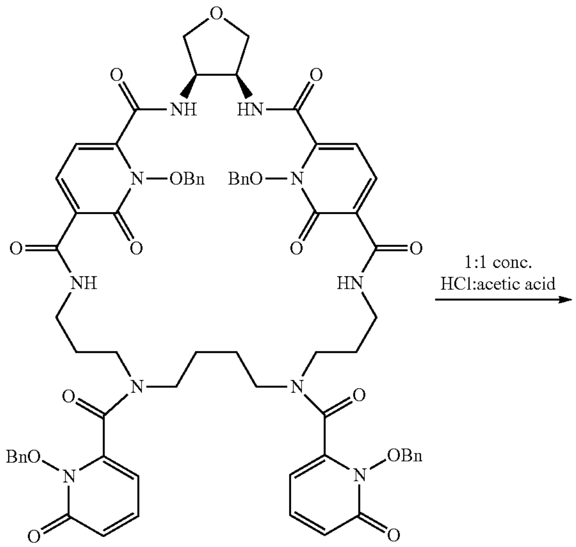
39

-continued

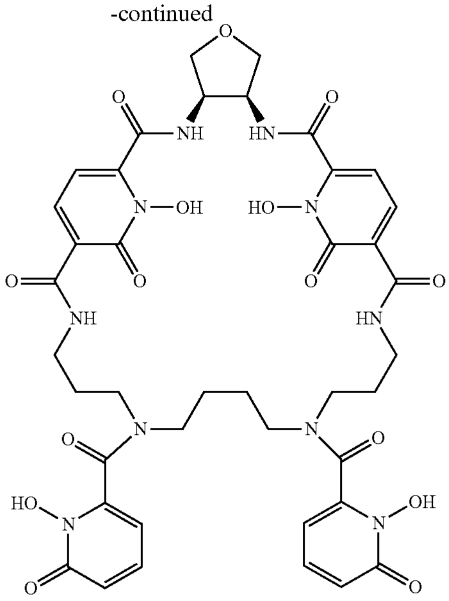

40

General Methods.

The precursors (3R,4S)-tetrahydrofuran-3,4-diamine (34) and 1-(benzyloxy)-6-oxo-1,6-dihydropyridine-2-carboxylic acid (14) were synthesized according to previously reported methods (Zhang, Z.; Du, X.; Chopiuk, G. Heteropolycyclic Inhibitors. WO0202562 (A2), Jan. 10, 2002; Xu, J.; Durbin, P. W.; Kullgren, B.; Ebbe, S. N.; Uhlir, L. C.; Raymond, K. N. J. Med. Chem. 2002, 45, 3963.). All other solvents and reagents were purchased from commercial sources and used as received unless otherwise noted. $^{1}$H-NMR and $^{13}$C-NMR spectra were obtained at 600/150 MHz or 500/125 MHz using either a Bruker AV-600 or DRX-500 spectrometer as noted below. $^{1}$H (or $^{13}$C) chemical shifts are reported relative to residual solvent signals, taken as 7.24 (77.23) and 2.50 (39.51) ppm for $CDCl_3$ and DMSO-$d_6$ respectively. High resolution electrospray ionization mass spectra (HRMS-ESI) were performed by the Microanalytical Laboratory at the University of California, Berkeley.

Dimethyl 6,6'-((((3R,4S)-tetrahydrofuran-3,4-diyl)bis(azanediyl))bis(carbonyl))bis(1-(benzyloxy)-2-oxo-1,2-dihydropyridine-3-carboxylate) (35). Oxalyl chloride (4.10 g, 32.3 mmol) was added to a suspension of 8 (4.10 g, 13.5 mmol) in dichloromethane (40 mL), followed by 2 drops of dry DMF. The solution became homogenous within 30 min, and the reaction was stirred at room temperature for 3 hours total. The solvent was then removed under vacuum overnight. The residue was dissolved into dichloromethane (20 mL) and added dropwise to a solution of 34 (580 mg, 5.7 mmol) dissolved in dichloromethane (20 mL) and 40% aqueous $K_2CO_3$ (20 mL) at 0° C. with vigorous stirring. The reaction was stirred with warming to room temperature overnight. The dichloromethane layer was loaded directly onto a 4 inch tall×1 inch wide silica gel column. Following a methanol/dichloromethane gradient elution, the desired product was collected using 2.5% methanol in dichloromethane. The solvent was removed under vacuum to yield the desired product as a hardened glass. Recrystallization from methanol followed by filtration and washing with 2-propanol yielded a free flowing white powder of 35. Yield: 3.2 g, 83%. $^{1}$H NMR (600 MHZ, $CDCl_3$) δ 8.16·(s, 2H), 7.73 (d, J=7.3 Hz, 2H), 7.36-7.29 (m, 6H), 7.28-7.23 (m, 4H), 6.07 (d, J=7.2 Hz, 2H), 5.22 (d, J=8.2 Hz, 2H), 5.02 (d, J=7.8 Hz, 2H), 4.95-4.85 (m, 2H), 4.09 (dd, J=9.0, 6.3 Hz, 2H), 3.73 (dd, J=8.5, 4.2 Hz, 2H), 3.67 (s, 6H). $^{13}$C NMR (150 MHz, $CDCl_3$) δ 164.03, 160.01, 155.80, 147.39, 143.25, 132.88, 130.30, 129.42, 128.54, 121.43, 103.67, 79.80, 71.22, 52.43, 51.13. HRMS-ESI (m/z, $[M+H]^+$) Calcd for $C_{34}H_{33}N_4O_{11}$: 673.2140, Found: 673.2148.

6,6'-((((3R,4S)-tetrahydrofuran-3,4-diyl)bis(azanediyl))bis(carbonyl))bis(1-(benzyloxy)-2-oxo-1,2-dihydropyridine-3-carboxylic acid) (36). Potassium hydroxide (934 mg, 16.6 mmol) was added to a suspension of 35 (2.80 g, 4.16·mmol) in 2:2:1 THF: MeOH: water (50 mL), and the reaction was heated to 50° C. overnight with stirring. The solvent was removed under vacuum and the resulting residue was dissolved into water (250 mL). Dilute HCl was added dropwise with stirring until the solution was acidic by litmus test. The desired product was collected by filtration, washed with dilute HCl and dried under vacuum overnight to yield a white powder of 36. Yield: 2.3 g, 86%. $^{1}$H NMR (600 MHZ, DMSO-$d_6$) δ 13.53 (s, 2H), 9.19 (d, J=7.0 Hz, 2H), 8.28 (d, J=7.4 Hz, 2H), 7.53-7.47 (m, 4H), 7.47-7.39 (m, 6H), 6.59 (d, J=7.4 Hz, 2H), 5.37 (d, J=8.6 Hz, 2H), 5.27 (d, J=8.6 Hz, 2H), 4.80-4.70 (m, 2H), 3.99 (dd, J=8.8, 6.3 Hz, 2H), 3.60 (dd, J=9.0, 4.8 Hz, 2H). $^{13}$C NMR (150 MHz, DMSO-$d_6$) δ 163.98, 159.36, 158.61, 147.09, 143.63, 133.23, 129.73, 129.31, 128.55, 120.56, 105.44, 79.52, 69.53, 51.29. HRMS-ESI (m/z, $[M-H]^-$) Calcd for $C_{32}H_{27}N_4O_{11}$: 643.1682, Found: 643.1684.

N,N'-((3R,4S)-tetrahydrofuran-3,4-diyl)bis(1-(benzyloxy)-6-oxo-5-(2-thioxothiazolidine-3-carbonyl)-1,6-dihydropyridine-2-carboxamide) (37). HATU (2.40 g, 6.3 mmol), 36 (1.93 g, 3.00 mmol), and DMAP (73.3 mg, 0.6 mmol) were suspended in dichloromethane (75 mL). DIPEA (776 mg, 6 mmol) was added dropwise to the suspension, and the reaction was stirred at room temperature for 2 hours. Upon completion 2-mercaptothiazoline (894 mg, 7.5 mmol) was added to the homogenous solution, followed by DIPEA (1.5 g, 11.6 mmol). The reaction was stirred for an additional 1.5 hours at room temperature. The reaction mixture was then washed with water 3×75 mL to remove the bulk of the urea byproduct, concentrated, and then loaded onto a 6 inch tall×1 inch wide silica gel column. Following a 2-propanol/dichloromethane gradient elution, the desired product was collected using 5% 2-propanol in dichloromethane. The solvent was removed under vacuum, and the residue was dissolved into 100 mL dichloromethane. The organic solution was again washed with water 3×75 mL to remove final traces of the urea byproduct, and the organic solution was concentrated to a volume of 10 mL. Addition of 2-propanol caused precipitation of the desired product, which was collected by evaporation of the solvent to give a yellow powder of 37. Yield: 1.83 g, 72%. $^{1}$H NMR (500 MHZ, $CDCl_3$) δ 7.57 (d, J=5.0 Hz, 2H), 7.44-7.37 (m, 4H), 7.37-7.28 (m, 6H), 7.25 (d, J=7.0 Hz, 2H), 6.20 (d, J=7.0 Hz, 2H), 5.26 (d, J=8.7 Hz, 2H), 5.08 (d, J=8.7 Hz, 2H), 4.79-4.68 (m, 2H), 4.57-4.41 (m, 4H), 3.98 (dd, J=9.1, 6.0 Hz, 2H), 3.62 (dd, J=9.2, 3.8 Hz, 2H), 3.49-3.33 (m, 4H). $^{13}$C NMR (125 MHz, $CDCl_3$) δ 202.05, 165.47, 159.87, 155.36, 144.03, 138.67, 132.91, 130.27, 130.07, 129.61, 128.70, 105.73, 79.43, 70.99, 55.60, 51.75, 29.38. HRMS-ESI (m/z, $[M+H]^+$) Calcd for $C_{38}H_{35}N_6O_9{}^{32}S_4$: 847.1343, Found: 847.1338.

Compound 38. Spermine (229 mg, 1.13 mmol) was dissolved into 2-propanol (50 mL) and 37 (957 mg, 1.13 mmol) was separately dissolved into dichloromethane (50 mL). Using syringe pumps, the two solutions were dripped (0.5 mL/hour) into a large flask containing 1:1 dichloromethane: 2-propanol (1 L) over four days. The reaction was stirred for an additional day at room temperature, followed by removal of the solvent under vacuum. The residue was dissolved into dichloromethane (200 mL) and extracted with aqueous potassium hydroxide to remove the 2-mercaptothiazoline byproduct. Removal of the solvent afforded the desired product as a viscous oil of 38, which was used without further purification in the next reaction. $^{1}$H NMR (600 MHZ, $CDCl_3$) δ 9.60 (s, 2H), 8.08 (s, 2H), 7.64-7.11 (m, 12H), 6.05 (s, 2H), 5.35-5.08 (m, 4H), 4.81 (s, 2H), 4.09 (s, 2H), 3.85 (s, 2H), 3.69-3.22 (m, 4H), 2.96-2.37 (m, 8H), 1.97-1.39 (m, 8H). $^{13}$C NMR (150 MHZ, $CDCl_3$) δ 162.97, 160.18, 158.11, 144.85, 141.33, 132.93, 130.44, 129.73, 128.73, 123.83, 104.66, 79.89, 71.46, 51.59, 49.65, 47.25, 37.26, 29.53, 27.30. HRMS-ESI (m/z, $[M+H]^+$) Calcd for $C_{42}H_{51}N_8O_9$: 811.3774, Found: 811.3768.

Compound 39. Oxalyl chloride (1.1 g, 8.7 mmol) was added to a suspension of 14 (1.11 g, 4.52 mmol) in dichloromethane (40 mL), followed by 1 drop of dry DMF. The solution became homogenous within 30 min, and the reaction was stirred at room temperature for 3 hours total. The solvent was then removed under vacuum overnight. The residue was dissolved into dichloromethane (20 mL) and added dropwise to a solution of 38 (1.13 mmol) dissolved in dichloromethane (20 mL) and 40% aqueous $K_2CO_3$ (20 mL) at 0° C. with vigorous stirring. The reaction was stirred with warming to room temperature overnight. The dichloromethane layer was loaded directly onto a 4 inch tall×1 inch wide silica gel column. Following a methanol/dichloromethane gradient elution, the desired product was collected using 4% methanol in dichloromethane. The solvent was removed under vacuum to yield the desired product as a hardened glass of 39. Yield: 520 mg, 36% over two steps. $^{1}$H NMR (600 MHz, $CDCl_3$) δ 9.60-8.98 (m, 2H), 8.43-7.83 (m, 4H), 7.80-7.05 (m, 20H), 7.05-5.54 (m, 8H), 5.49-4.98 (m, 6H), 4.98-4.69 (m, 2H), 4.28-3.98 (m, 2H), 3.93-2.75 (m, 14H), 2.05-1.16·(m, 10H). HRMS-ESI (m/z, $[M+H]^+$) Calcd for $C_{68}H_{69}N_{10}O_{15}$: 1265.4938, Found: 1265.4901.

Compound 40. Compound 39 (63 mg, 0.070 mmol) was dissolved into a 1:1 mixture of concentrated HCl and glacial acetic acid (5 mL). The homogenous solution was stirred at room temperature for 3 weeks in the dark. Upon reaction completion, the solvent was removed under vacuum. Residual solvent was removed by co-evaporation with water, followed by methanol, and finally diethyl ether to yield a beige solid of 40. Purity was assessed by HPLC by first adding a 5-fold molar excess of $EuCl_3$ to the sample dissolved in methanol. Quantitative yield and >95% purity. $^{1}$H NMR (500 MHZ, DMSO-$d_6$) δ 9.82-9.33 (m, 2H), 9.07-7.94 (m, 4H), 7.52-7.15 (m, 2H), 6.86-6.44 (m, 4H), 6.40-6.05 (m, 2H), 4.74 (s, 2H), 4.03 (s, 2H), 3.86-2.76 (m, 14H), 1.97-1.17 (m, 8H). HRMS-ESI (m/z, $[M+H]^+$) Calcd for $C_{40}H_{45}N_{10}O_{15}$: 905.3060, Found: 905.3053.

Example 9. Synthesis of Exemplary Bifunctional Chelator 43

Scheme 7. Synthetic scheme of exemplary bifunctional chelator 43.

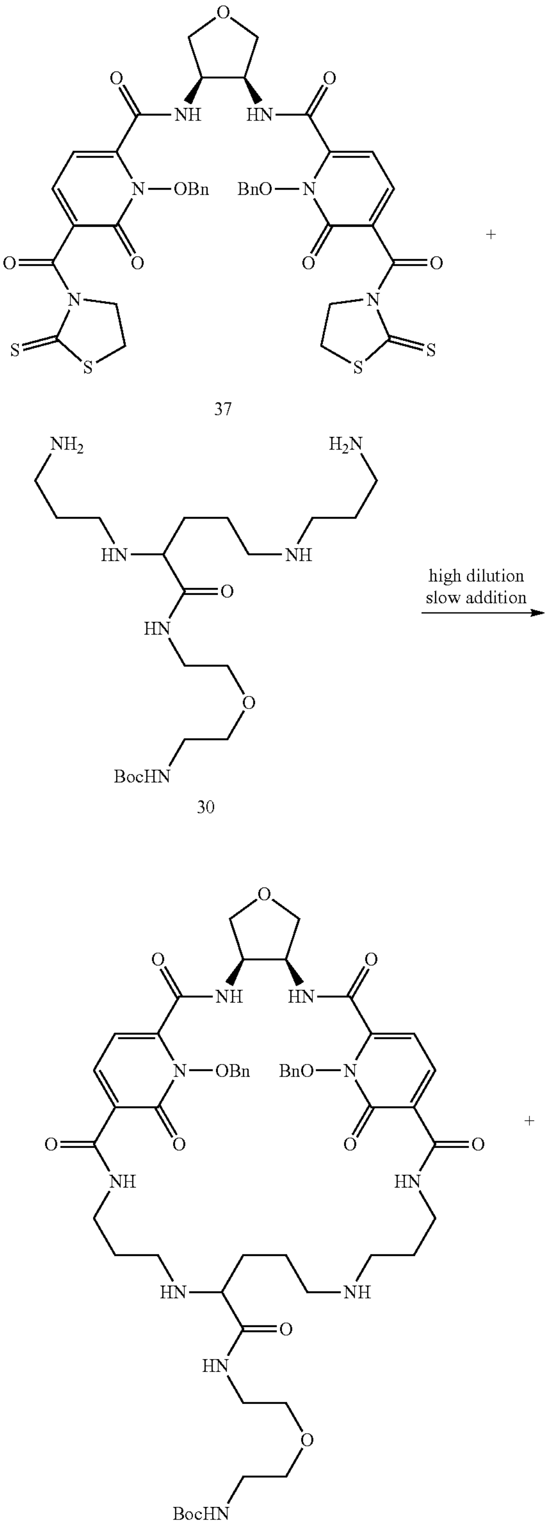

37

30

41

-continued

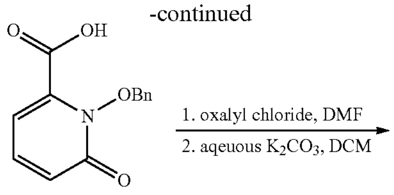

14

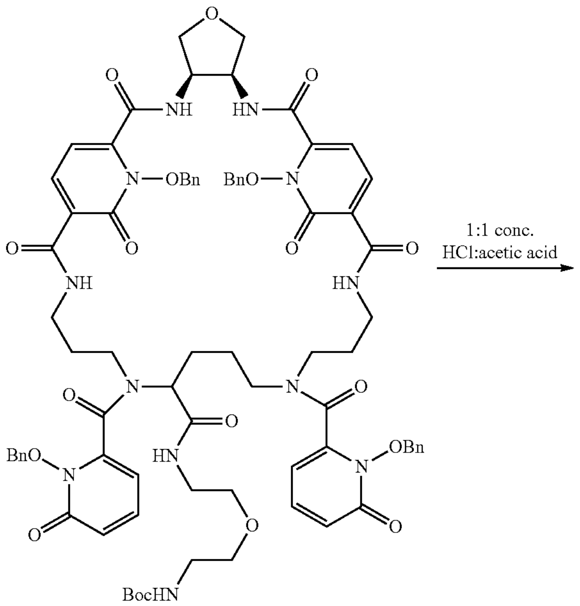

42

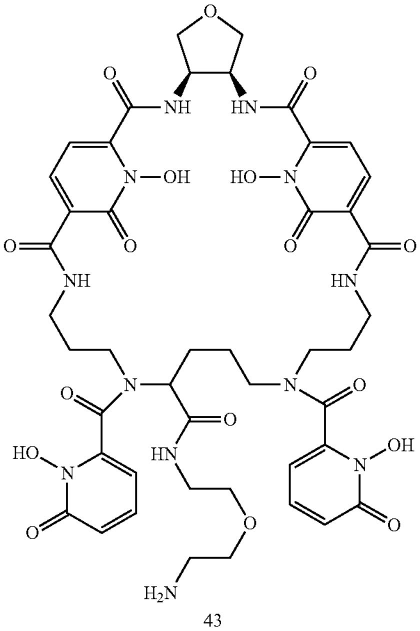

43

The precursor tert-butyl (2-(2-(2,5-bis((3-aminopropyl) amino) pentanamido) ethoxy)ethyl)carbamate (30) was synthesized according to previously reported methods (WO2016106241). All other solvents and reagents were purchased from commercial sources and used as received unless otherwise noted. $^1$H-NMR and $^{13}$C-NMR spectra were obtained at 600/150 MHz or 500/125 MHz using either a Bruker AV-600 or DRX-500 spectrometer as noted below. $^1$H (or $^{13}$C) chemical shifts are reported relative to residual solvent signals, taken as 7.24 (77.23) and 2.50 (39.51) ppm for $CDCl_3$ and DMSO-$d_6$ respectively. High resolution electrospray ionization mass spectra (HRMS-ESI) were performed by the Microanalytical Laboratory at the University of California, Berkeley.

Compound 41. Following the same procedure as used for compound 38, using 37 (1.30 g, 1.54 mmol) and 30 (668 mg, 1.54 mmol) as starting materials. Similarly, the residue was used washed with base and used without further purification in the next reaction. $^1$H NMR (500 MHZ, $CDCl_3$) δ 9.89-9.45 (m, 2H), 8.43-7.62 (m, 6H), 7.62-7.09 (m, 10H), 6.49-5.92 (m, 2H), 5.59-4.51 (m, 6H), 4.11-2.24 (m, 23H), 2.10-1.03 (m, 17H). HRMS-ESI (m/z, $[M+H]^+$) Calcd for $C_{52}H_{69}N_{10}O_{13}$: 1041.5040, Found: 1041.5031.

Compound 42. Following the same procedure as used for compound 39, using 41 (1.54 mmol) and 14 (1.51 g, 6.16·mmol) as starting materials. Yield: 1.08 g, 47% over two steps. $^1$H NMR (500 MHZ, $CDCl_3$) δ 9.69-8.96 (m, 2H), 8.61-6.93 (m, 28H), 6.89-6.01 (m, 4H), 5.98-4.66 (m, 12H), 4.29-2.65 (m, 23H), 2.56-1.04 (m, 17H). HRMS-ESI (m/z, $[M+Na]^+$) Calcd for $C_{78}H_{86}N_{12}O_{19}Na$: 1517.6024, Found: 1517.6063.

Compound 43. Following the same procedure as used for compound 40, using 42 (92 mg, 0.062 mmol) as the starting material. Quantitative yield and >95% purity. $^1$H NMR (500 MHz, DMSO-$d_6$) δ 9.79-9.26 (m, 2H), 8.85-7.79 (m, 5H), 7.61-7.19 (m, 2H), 6.75-6.40 (m, 4H), 6.37-6.02 (m, 2H), 4.74 (s, 2H), 4.04 (s, 2H), 3.75-2.85 (m, 21H), 1.94-1.29 (m, 8H). HRMS-ESI (m/z, $[M-H]^-$) Calcd for $C_{45}H_{53}N_{12}O_{17}$: 1033.3657, Found: 1033.3646.

Example 10. Characterization of Metal Complexes for Ligands 16, 29, 33, 40, and 43

Metal complexes of compounds 16, 29, 33, 40, and 43 may be prepared readily, for example, by treatment with an appropriate metal salt dissolved in methanol as described below. A stock solution was prepared by dissolving compound 16, 29, 33, 40, or 43 (~2 mg, 1 μmol) in methanol (1 mL), and then dividing the solution into several aliquots. Stock solutions of the metal salts were prepared in methanol (1 mL) at concentrations ranging from 5 to 20 mM. For each metal salt, a volume corresponding to 1.5 molar equivalents was added to one of the aliquots containing 16, 29, 33, 40, or 43. The solvent was removed by evaporation in a stream of compressed air, and the samples were analyzed in methanol or 1:10 DMSO: methanol by mass spectrometry, with results reported below. Metal salts tested include zirconium (IV) acetylacetonate, iron(III) nitrate nonahydrate, indium (III) chloride tetrahydrate, europium(III) chloride hexahydrate, holmium(III) chloride hexahydrate, lutetium(III) chloride hexahydrate, lanthanum(III) chloride heptahydrate, scandium(III) chloride hexahydrate, yttrium(III) chloride hexahydrate, terbium(III) chloride hexahydrate, ytterbium trifluoromethanesulfonate, gadolinium(III) chloride hexahydrate, samarium(III) chloride hexahydrate, dysprosium(III) chloride hexahydrate, erbium(III) chloride hexahydrate, and thorium(IV) nitrate hydrate (99.8%).

16·Zr: FTMS-pESI: calculated for $C_{38}H_{37}N_{10}O_{14}{}^{90}Zr$ $[M-H]^-$947.1543, found 947.1514.

16·Sc: FTMS-pESI: calculated for $C_{38}H_{38}N_{10}O_{14}{}^{45}Sc$ $[M]^-$903.2134, found 903.2111.

16·La: FTMS-pESI: calculated for $C_{38}H_{38}N_{10}O_{14}{}^{139}La$ $[M]^-$997.1638, found 997.1617.

16·Y: FTMS-pESI: calculated for $C_{38}H_{38}N_{10}O_{14}{}^{89}Y$ $[M]^-$947.1633, found 947.1602.

16·Lu: FTMS−pESI: calculated for $C_{38}H_{38}N_{10}O_{14}{}^{175}Lu$ $[M]^-$1033.1982, found 1033.1973.

16·In: FTMS−pESI: calculated for $C_{38}H_{38}N_{10}O_{14}{}^{115}In$ $[M]^-$973.1613, found 973.1585.

16·Eu: FTMS−pESI: calculated for $C_{38}H_{38}N_{10}O_{14}{}^{151}Eu$ $[M]^-$1009.1773, found 1009.1765.

16·Th: FTMS+pESI: calculated for $C_{38}H_{39}N_{10}O_{14}{}^{232}Th$ $[M+H]^+$1091.3022, found 1091.2992.

29·Eu: FTMS−pESI: calculated for $C_{42}H_{47}N_{11}O_{14}{}^{151}Eu$ $[M]^-$1080.2508, found 1080.2480.

29·Th: FTMS+pESI: calculated for $C_{42}H_{48}N_{11}O_{14}{}^{232}Th$ $[M+H]^+$1162.3757, found 1162.3778.

33·Eu: FTMS−pESI: calculated for $C_{43}H_{48}N_{12}O_{16}{}^{151}Eu$ $[M]^-$1139.2515, found 1139.2500.

33·Th: FTMS+pESI: calculated for $C_{43}H_{49}N_{12}O_{16}{}^{232}Th$ $[M+H]^+$1221.3765, found 1221.3738.

40·Th: FTMS+pESI: calculated for $C_{40}H_{41}N_{10}O_{15}{}^{232}Th$ $[M+H]^+$1133.3128, found 1133.3118.

43·Zr: FTMS+pESI: calculated for $C_{45}H_{51}N_{12}O_{17}{}^{90}Zr$ $[M+H]^+$1121.2537, found 1121.2554.

43·Fe: FTMS+pESI: calculated for $C_{45}H_{52}N_{12}O_{17}{}^{56}Fe$ $[M+2H]^+$1088.2917, found 1088.2921.

43·In: FTMS−pESI: calculated for $C_{45}H_{50}N_{12}O_{17}{}^{115}In$ $[M]^-$1145.2461, found 1145.2462.

43·Eu: FTMS−pESI: calculated for $C_{45}H_{50}N_{12}O_{17}{}^{151}Eu$ $[M]^-$1181.2621, found 1181.2619.

43·Ho: FTMS−pESI: calculated for $C_{45}H_{50}N_{12}O_{17}{}^{165}Ho$ $[M]^-$1195.2726, found 1195.2730.

43·Lu: FTMS−pESI: calculated for $C_{45}H_{50}N_{12}O_{17}{}^{175}Lu$ $[M]^-$1205.2830, found 1205.2836.

43·Y: FTMS−pESI: calculated for $C_{45}H_{50}N_{12}O_{17}{}^{89}Y$ $[M]^-$1119.2481, found 1119.2476.

43·Tb: FTMS−pESI: calculated for $C_{45}H_{50}N_{12}O_{17}{}^{159}Tb$ $[M]^-$1189.2676, found 1189.2677.

43·Yb: FTMS−pESI: calculated for $C_{45}H_{50}N_{12}O_{17}{}^{174}Yb$ $[M]^-$1204.2811, found 1204.2812.

43·Gd: FTMS−pESI: calculated for $C_{45}H_{50}N_{12}O_{17}{}^{158}Gd$ $[M]^-$1188.2663, found 1188.2677.

43·Sm: FTMS−pESI: calculated for $C_{45}H_{50}N_{12}O_{17}{}^{152}Sm$ $[M]^-$1182.2620, found 1182.2647.

43·Dy: FTMS−pESI: calculated for $C_{45}H_{50}N_{12}O_{17}{}^{164}Dy$ $[M]^-$1194.2714, found 1194.2737.

43·Er: FTMS−pESI: calculated for $C_{45}H_{50}N_{12}O_{17}{}^{166}Er$ $[M]^-$1196.2725, found 1196.2737.

43·Th: FTMS+pESI: calculated for $C_{45}H_{51}N_{12}O_{17}{}^{232}Th$ $[M+H]^+$1263.3870, found 1263.3835.

Figure 3:
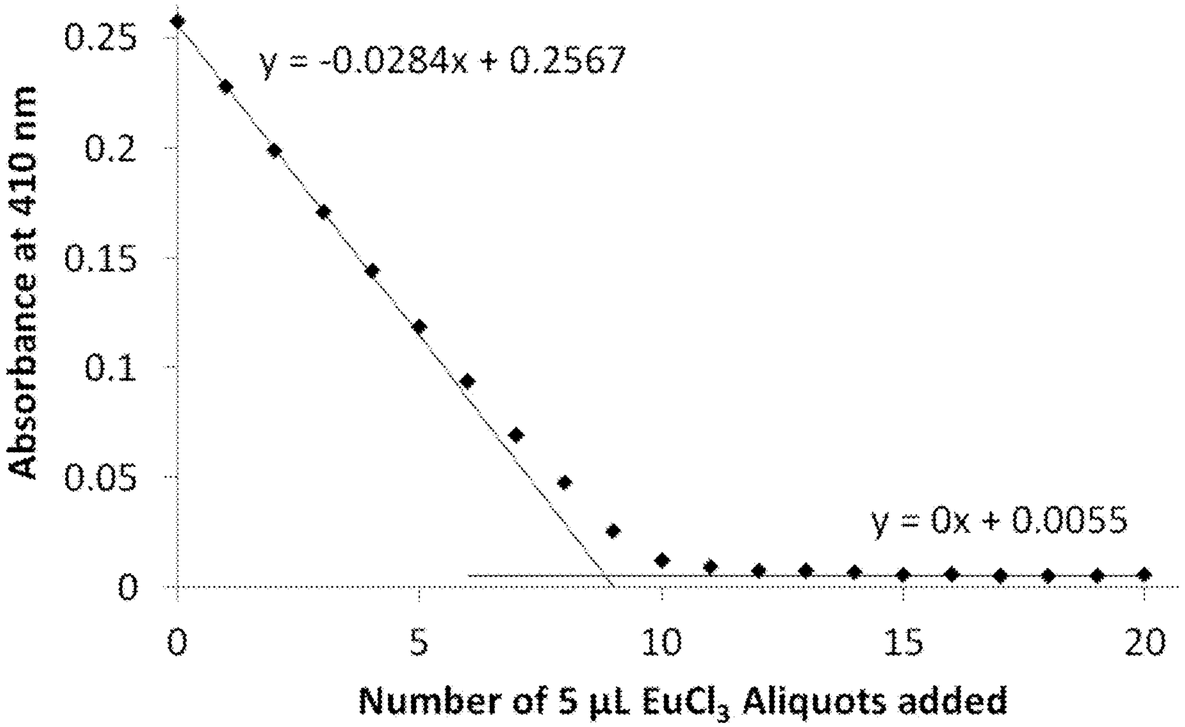
FIG. 3 shows the UV-vis titration of ligand 16 with europium chloride.

Example 11. Europium Titration Experiments for Determining Extinction Coefficients In order to determine accurate extinction coefficients for 16 and 16·Eu, titration experiments using europium chloride as the titrant were performed. Europium chloride hexahydrate (13.22 mg, 0.03608 mmol) was dissolved into 5 mM citrate buffer (pH=4) using a 100 mL volumetric flask to give a 0.3608 mM europium chloride solution, which was then titrated into a 0.5 mL solution of 16 in TBS buffer (Tris-buffered saline, 50 mM Tris, 150 mM NaCl, pH=7.6) using 5 μL aliquots. The UV-vis spectra were adjusted for the increase in solvent volume due to each injection. The results of the UV-vis titration are plotted in FIG. 3.

From the UV-vis titration (FIG. 3), it was found that 46.28 μL of the 0.3608 mM europium chloride solution was required to reach the equivalence point. The volume of europium chloride corresponds to 16.70 nmol of europium, meaning the starting concentration of ligand 16 was 33.40 μM. The lambda max absorbances of 16 and 16·Eu were found to be 0.454 at 382 nm (500 μL total volume) and 0.431 at 361 nm (555 μL total volume) for the ligand and complex respectively. These absorbance and concentration values yield extinction coefficients of 13,600 $M^{-1}$ $cm^{-1}$ and 14,300 $M^{-1}$ $cm^{-1}$ for the ligand 16 and the complex 16·Eu respectively.

Figure 4:
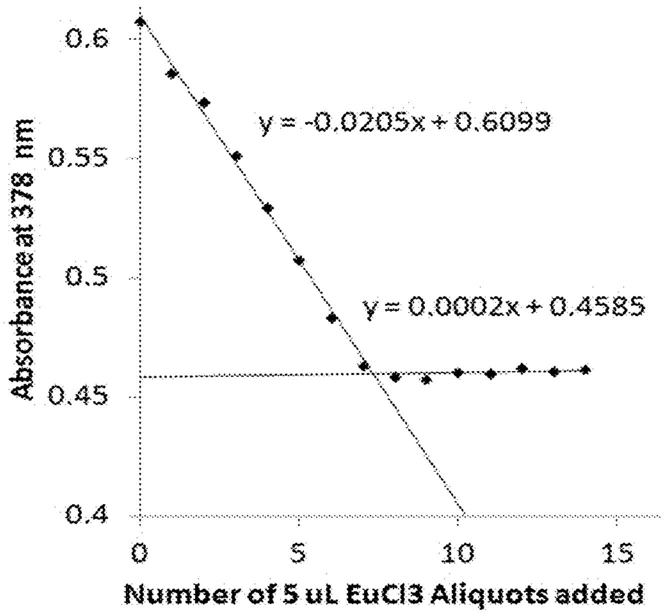
FIG. 4 shows the UV-vis titration of ligand 43 with europium chloride.

In order to determine accurate extinction coefficients for 43 and 43 Eu, titration experiments using europium chloride as the titrant were performed. Europium chloride hexahydrate (47.58 mg, 0.1299 mmol) was dissolved into 50 mM citrate buffer (pH=4) using a 10 mL volumetric flask to give a 12.99 mM europium chloride solution, which was then transferred to a 100 mL volumetric flask and diluted 1:10 with water. The resulting 1.299 mM europium chloride solution (in 5 mM citrate buffer) was then titrated into a 1 mL solution of 43 in TBS buffer using 5 μL aliquots. The UV-vis spectra were adjusted for the increase in solvent volume due to each injection. The results of the UV-vis titration are plotted in FIG. 4.

From the UV-vis titration (FIG. 4), it was found that 36.55 μL of the 1.299 mM europium chloride solution was required to reach the equivalence point. The volume of europium chloride corresponds to 47.46 nmol of europium, meaning the starting concentration of ligand 43 was 47.46 μM. The lambda max absorbances of 43 and 43·Eu were found to be 0.618 at 383 nm and 0.607 at 357 nm for the ligand and complex respectively. These absorbance and concentration values yield extinction coefficients of 13,000 $M^{-1}$ $cm^{-1}$ and 12,800 $M^{-1}$ $cm^{-1}$ for the ligand and complex respectively.

Figure 5:
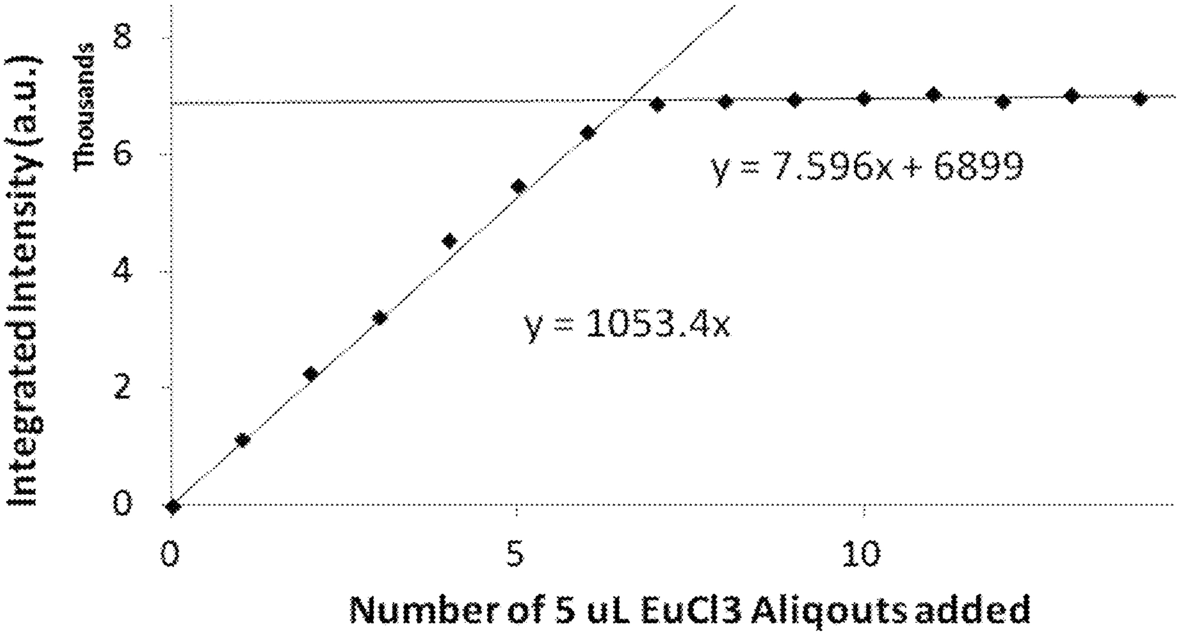
FIG. 5 shows the photoluminescent titration of ligand 43 with europium chloride.
Figure 6:
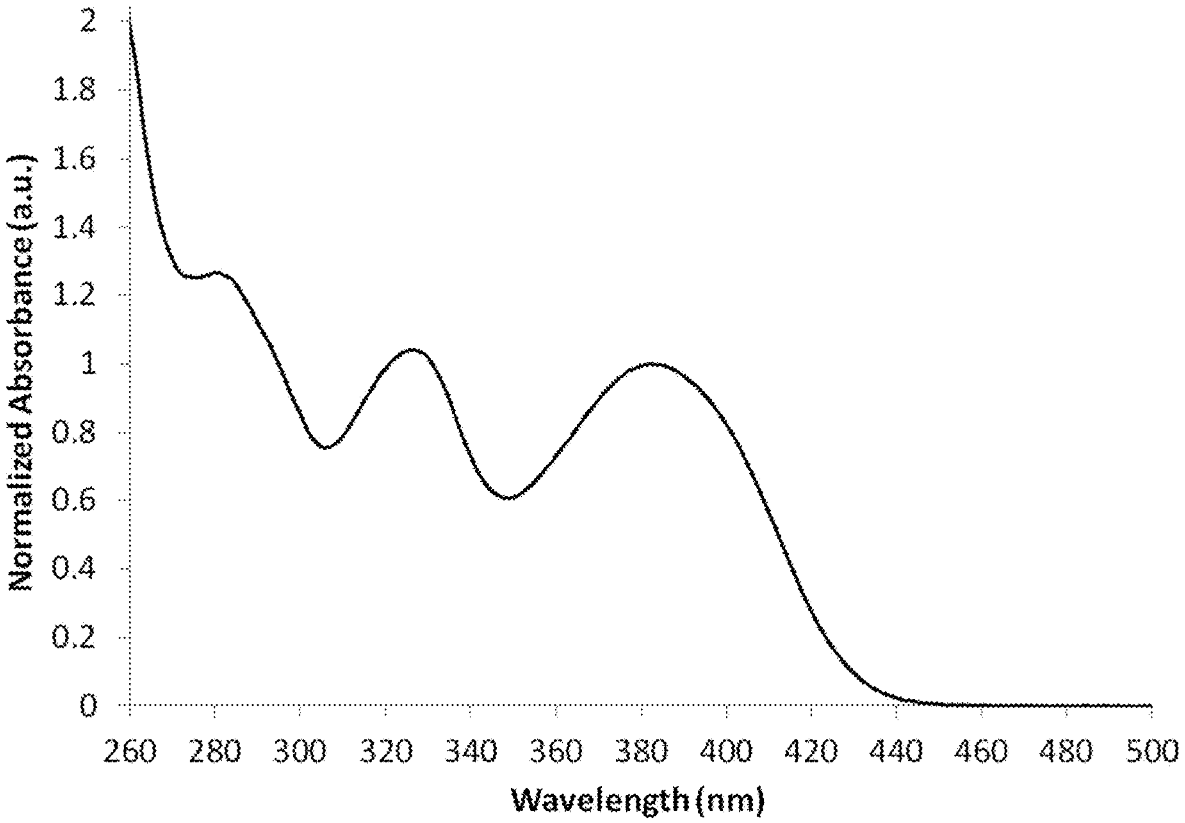
FIG. 6 shows the UV-vis absorption spectrum of 16·measured in TBS buffer, pH=7.6.
Figure 7:
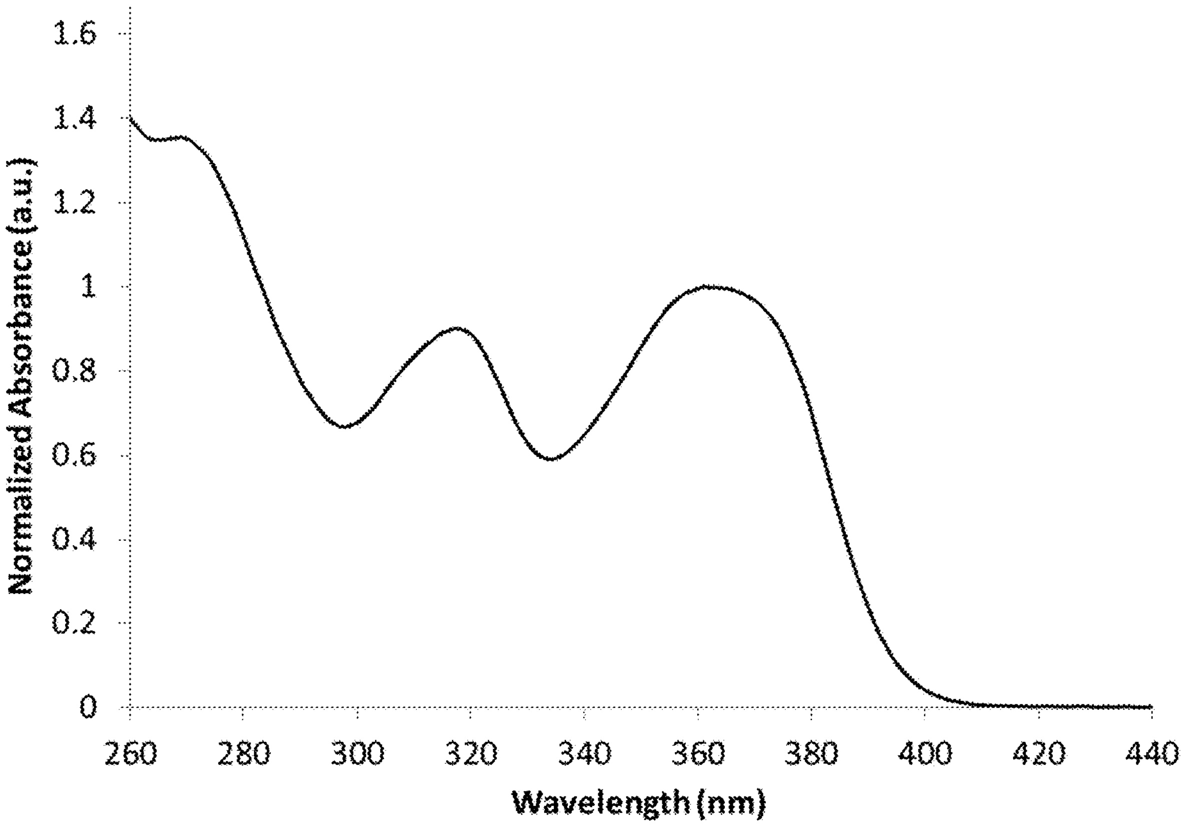
FIG. 7 shows the UV-vis absorption spectrum of 16·Eu measured in TBS buffer, pH 7.6.
Figure 8:
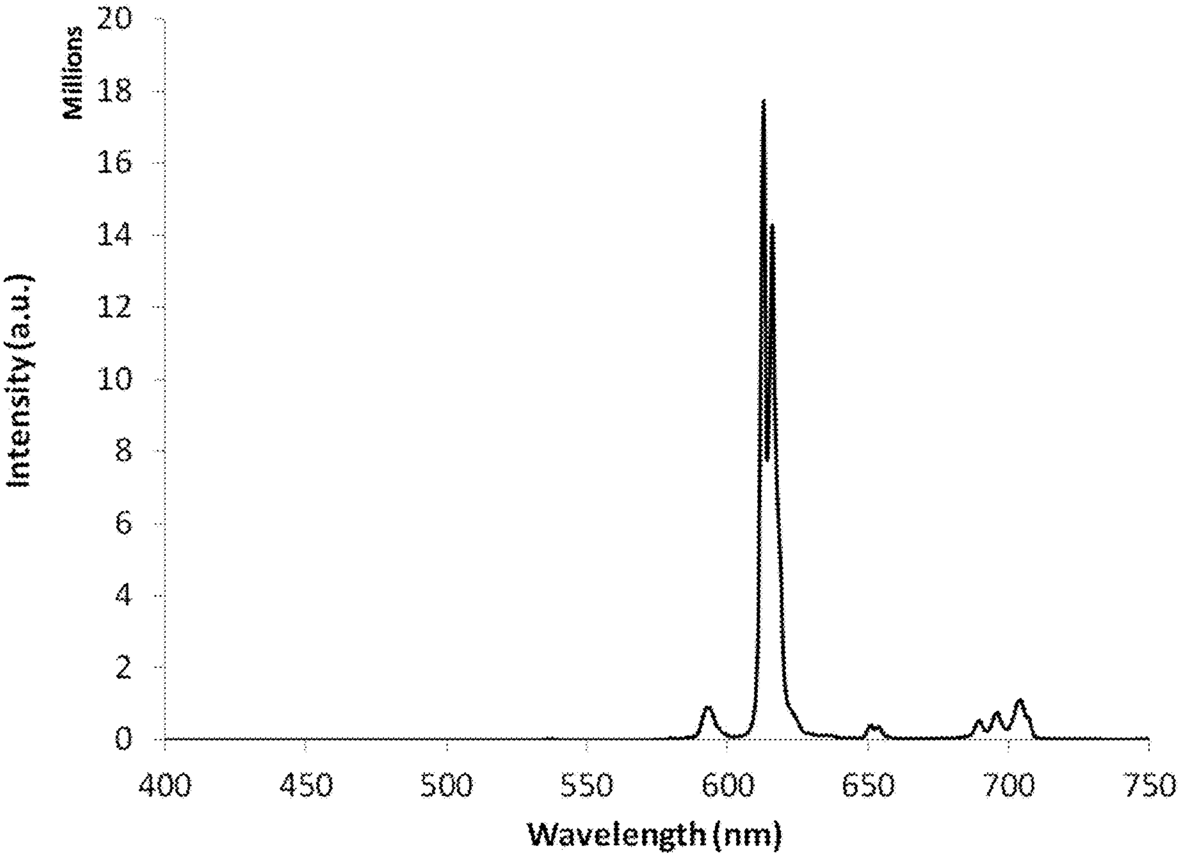
FIG. 8 shows the photoluminescence spectrum of 16·Eu measured in TBS buffer, pH 7.6.
Figure 9:
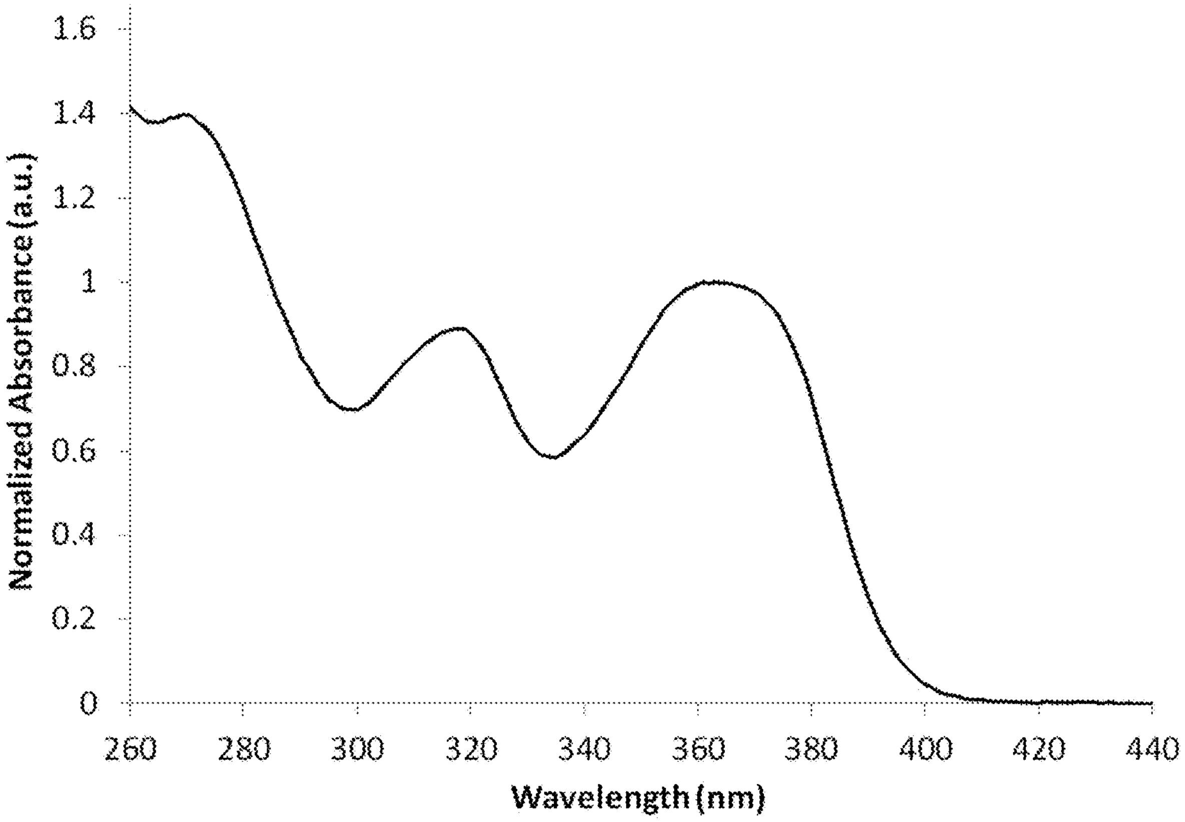
FIG. 9 shows the UV-vis absorption spectrum of 29 Eu measured in TBS buffer, pH 7.6.
Figure 10:
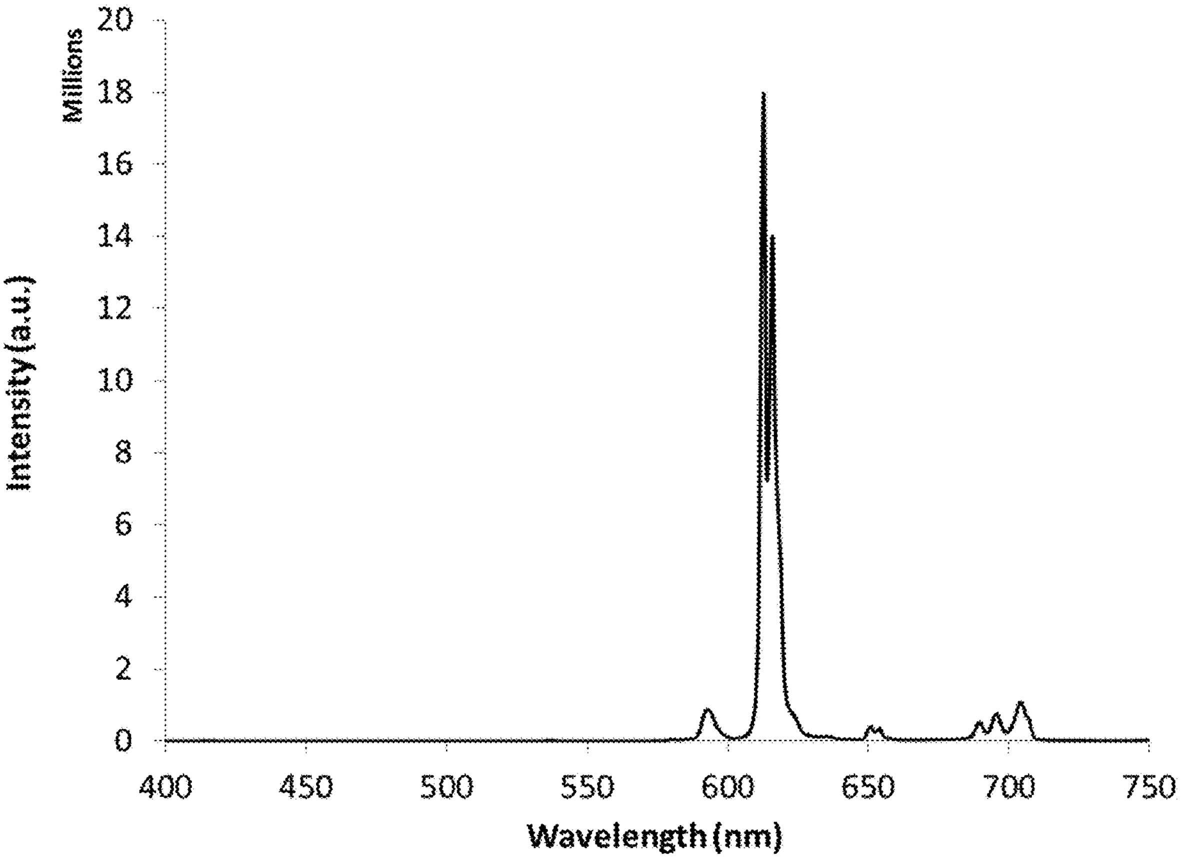
FIG. 10 shows the photoluminescence spectrum of 29 Eu measured in TBS buffer, pH 7.6.
Figure 11:
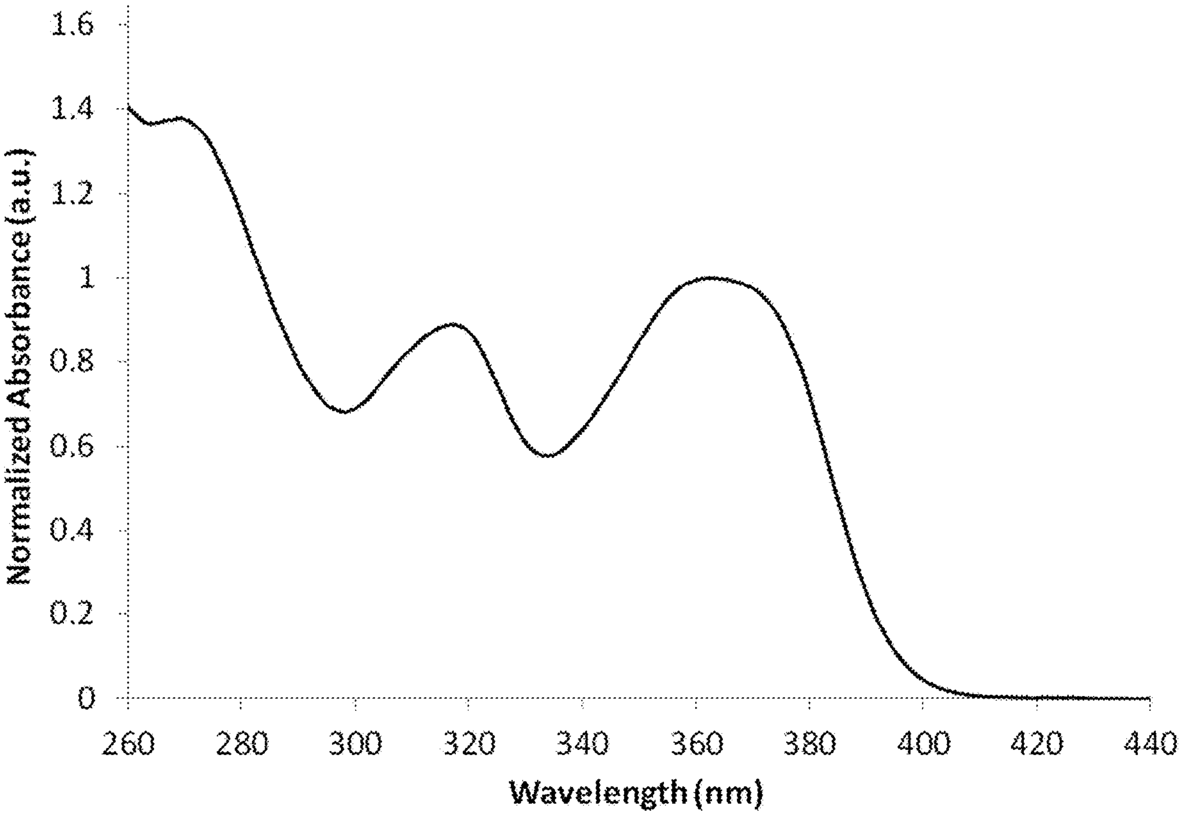
FIG. 11 shows the UV-vis absorption spectrum of 33·Eu measured in TBS buffer, pH 7.6.
Figure 12:
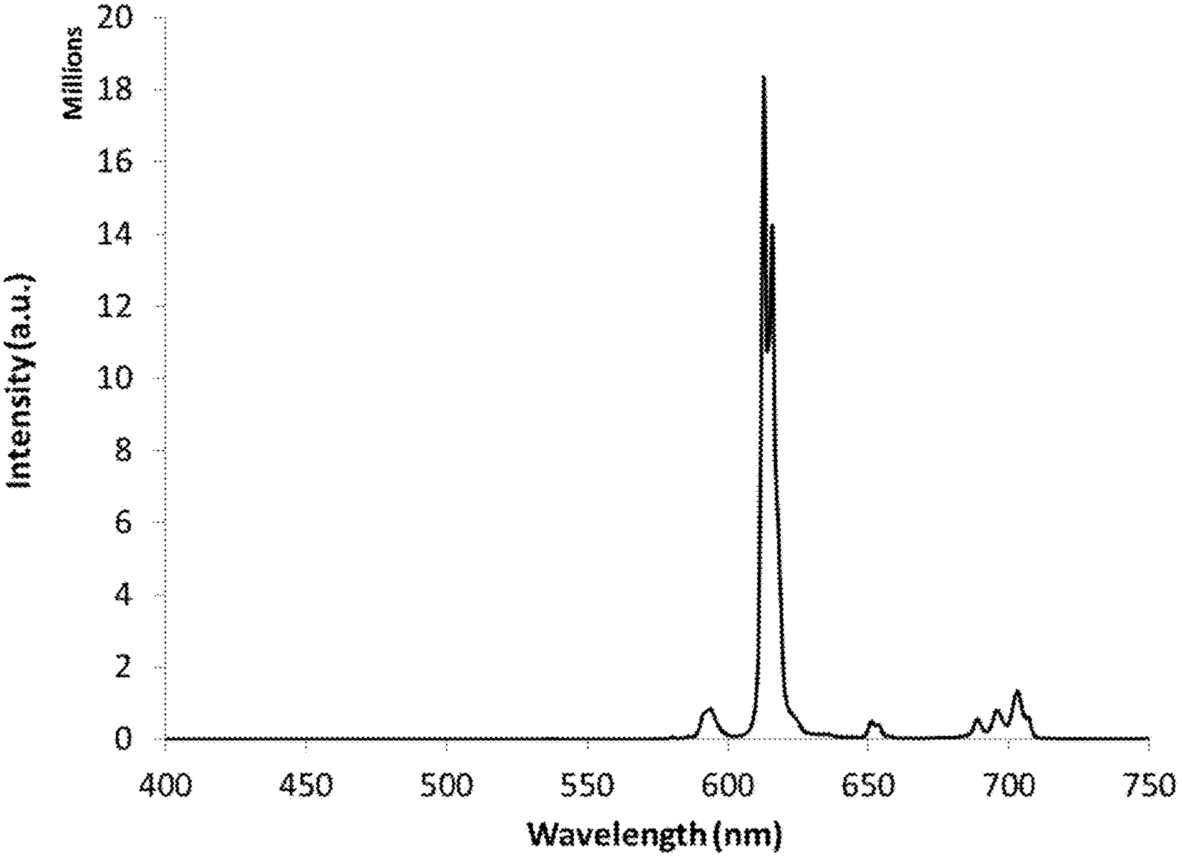
FIG. 12 shows the photoluminescence spectrum of 33·Eu measured in TBS buffer, pH 7.6.
Figure 13:
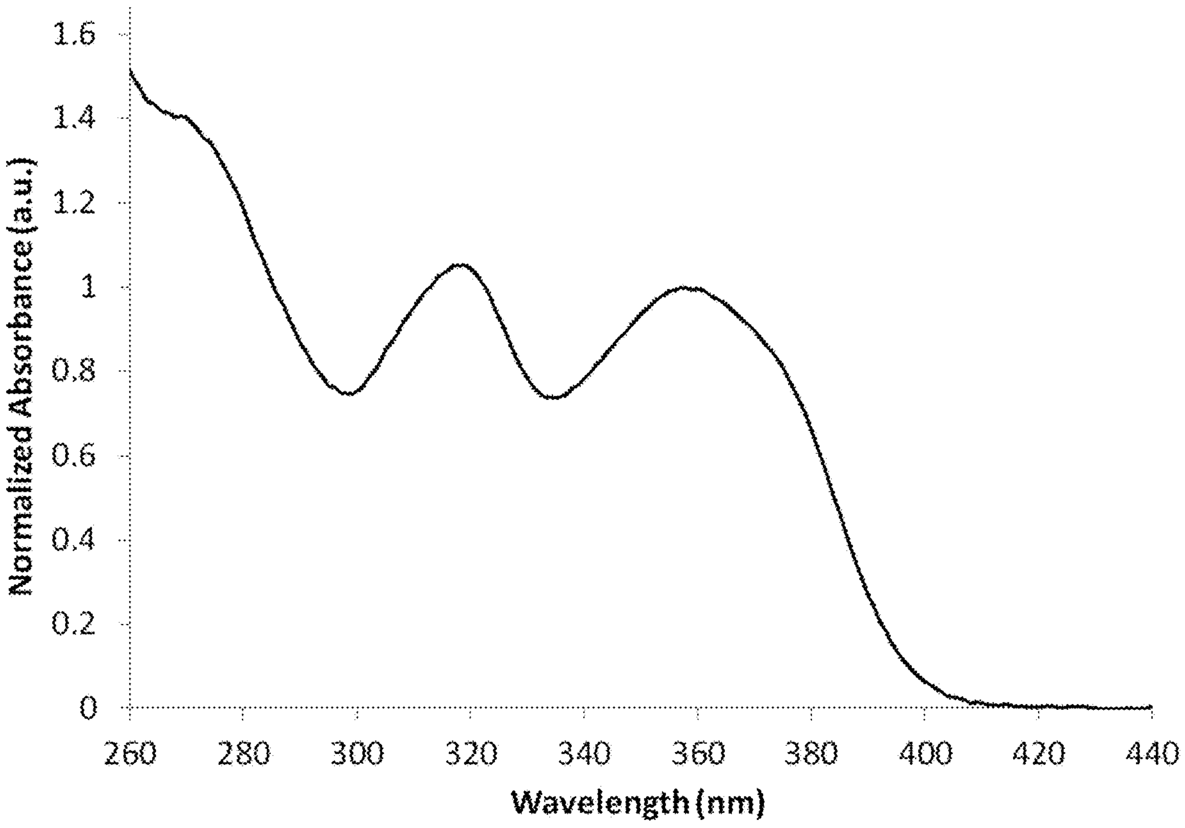
FIG. 13 shows the UV-vis absorption spectrum of 40 Eu measured in TBS buffer, pH 7.6.
Figure 14:
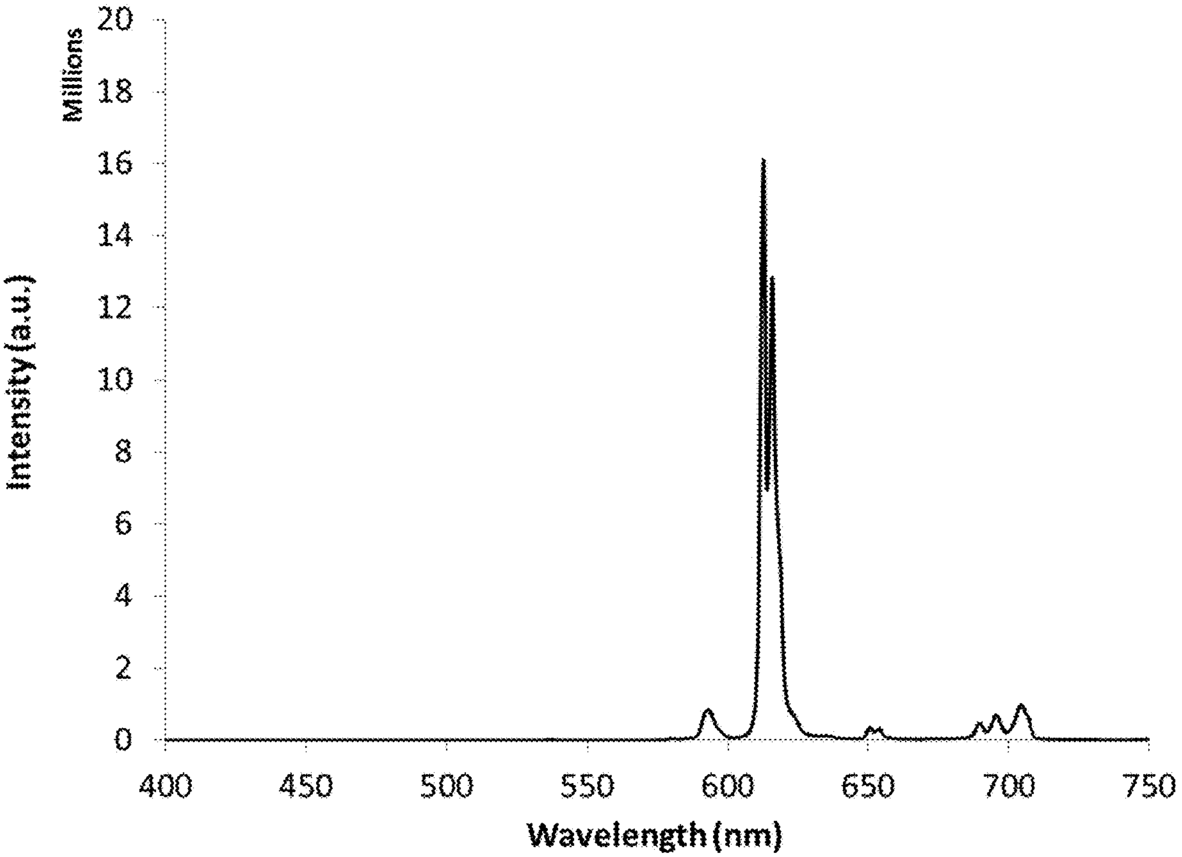
FIG. 14 shows the photoluminescence spectrum of 40 Eu measured in TBS buffer, pH 7.6.
Figure 15:
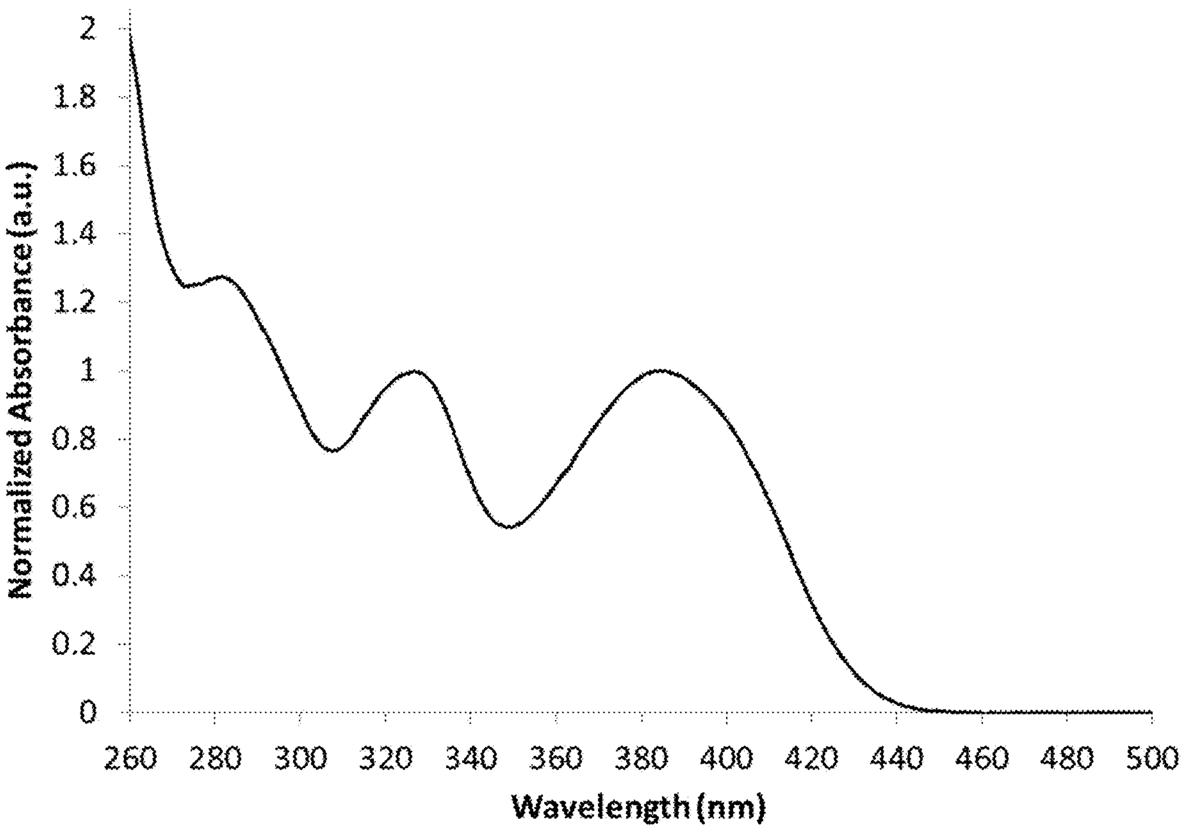
FIG. 15 shows the UV-vis absorption spectrum of 43 measured in TBS buffer, pH 7.6.
Figure 16:
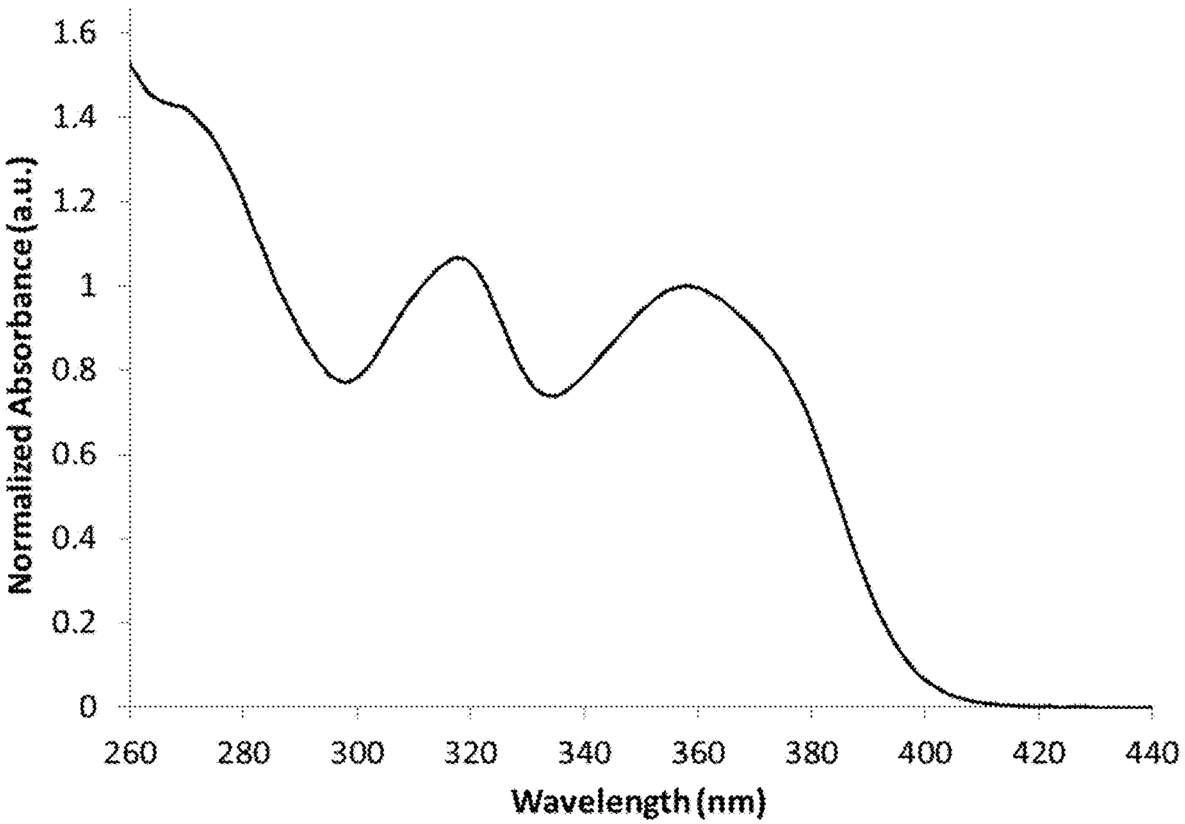
FIG. 16 shows the UV-vis absorption spectrum of 43 Eu measured in TBS buffer, pH 7.6.
Figure 17:
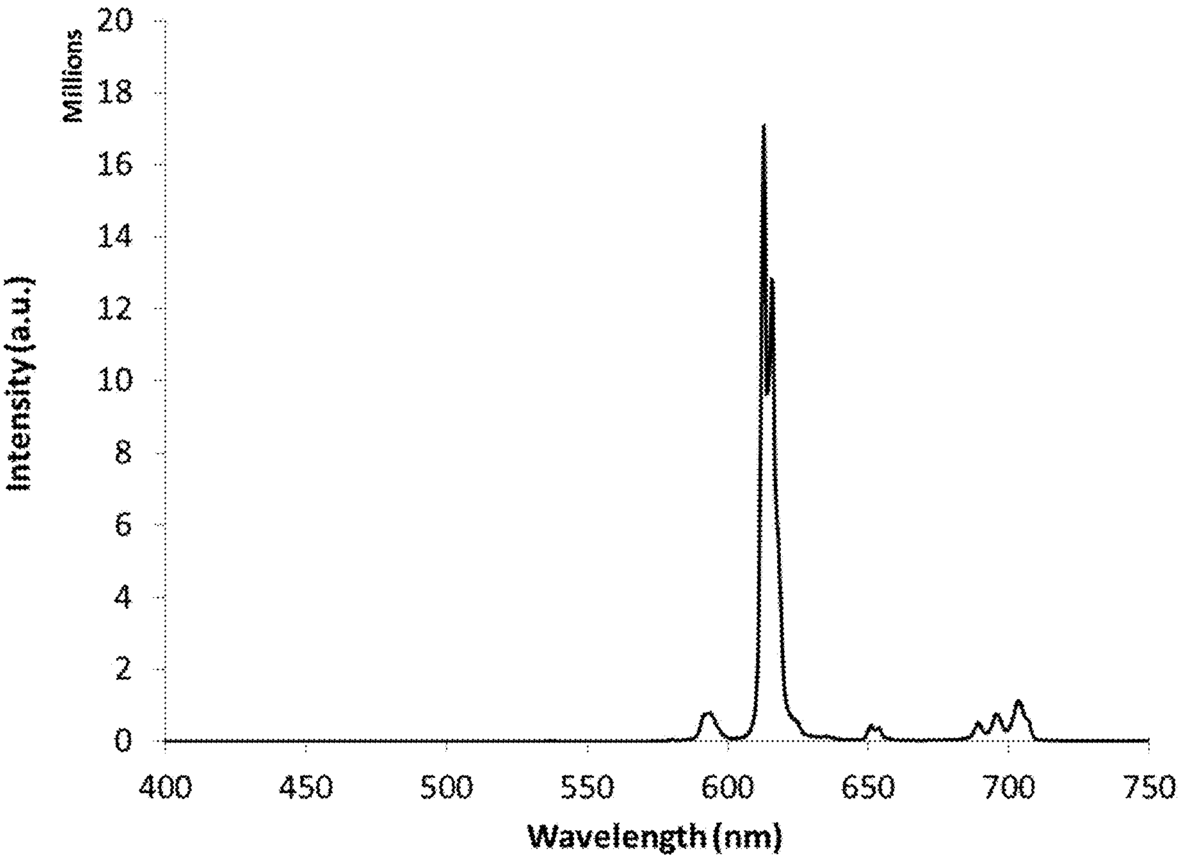
FIG. 17 shows the photoluminescence spectrum of 43 Eu measured in TBS buffer, pH 7.6.
Figure 18:
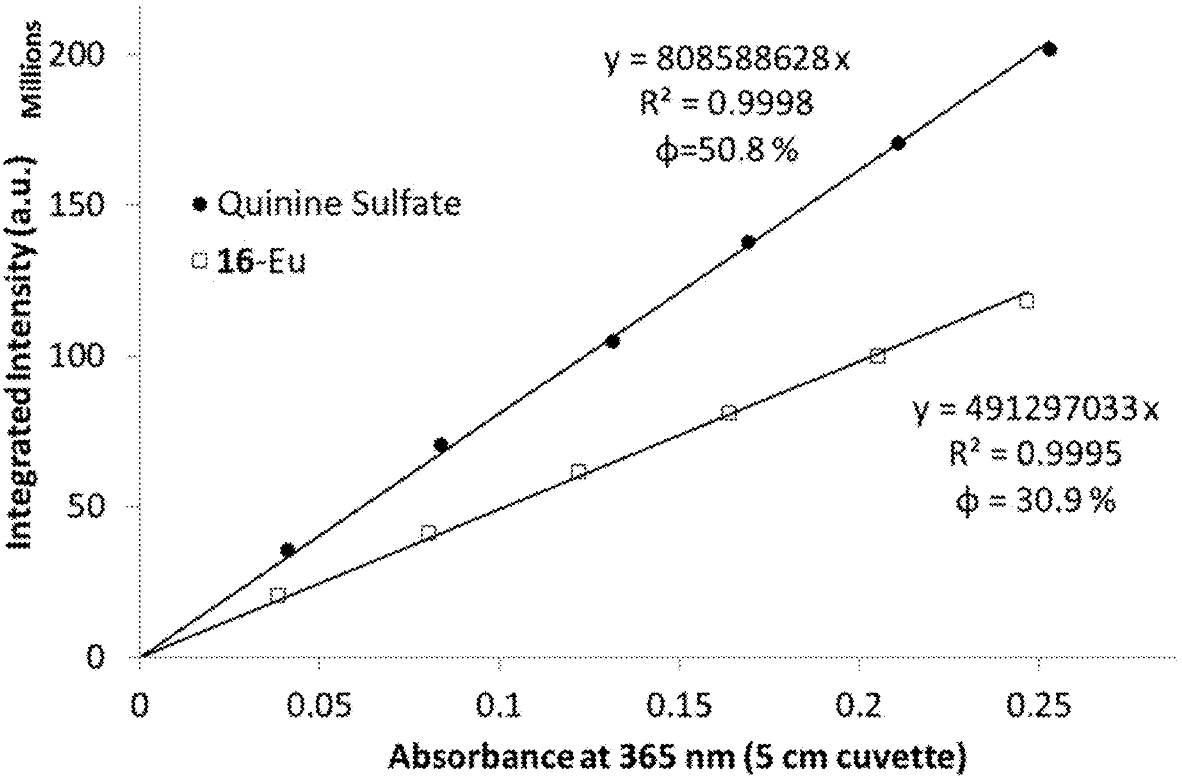
FIG. 18 shows quantum yield determination of 16·Eu.
Figure 19:
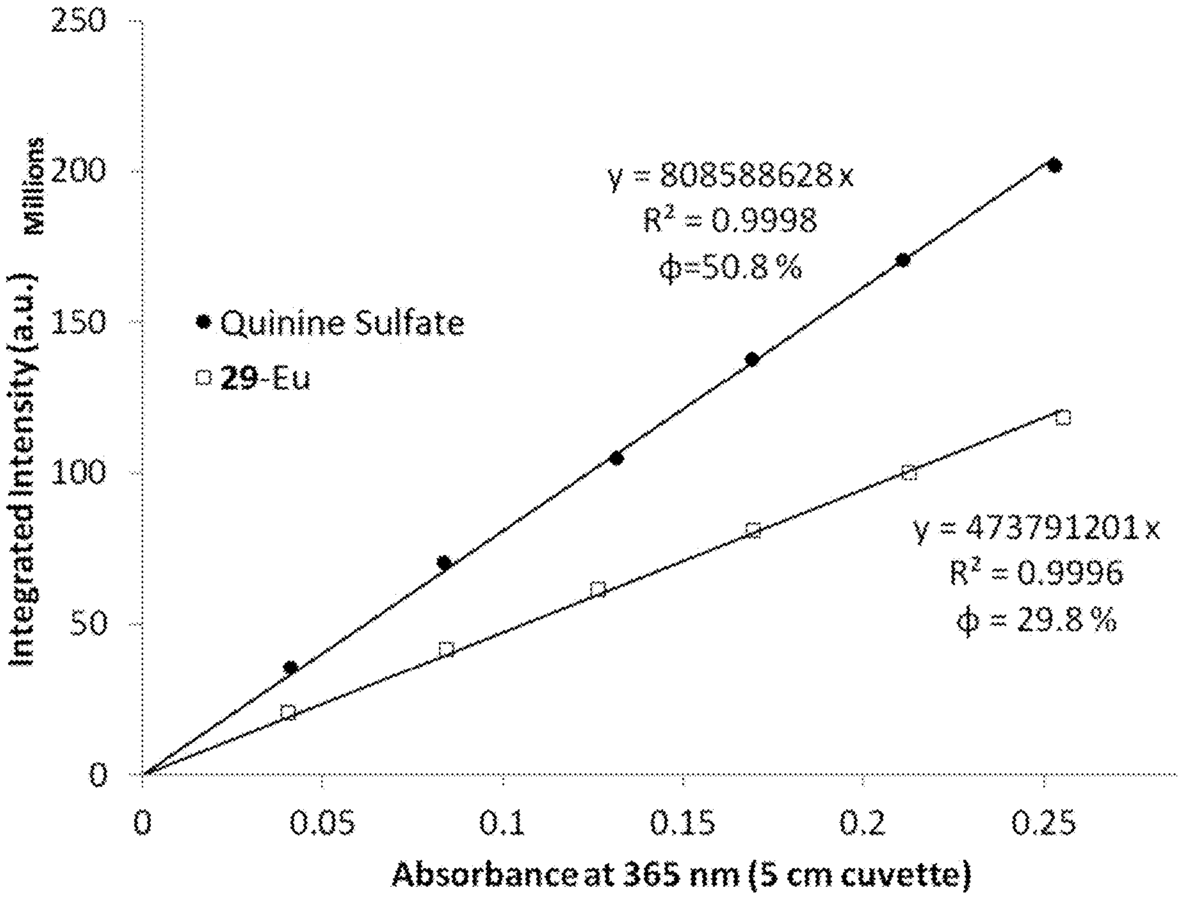
FIG. 19 shows quantum yield determination of 29·Eu.
Figure 20:
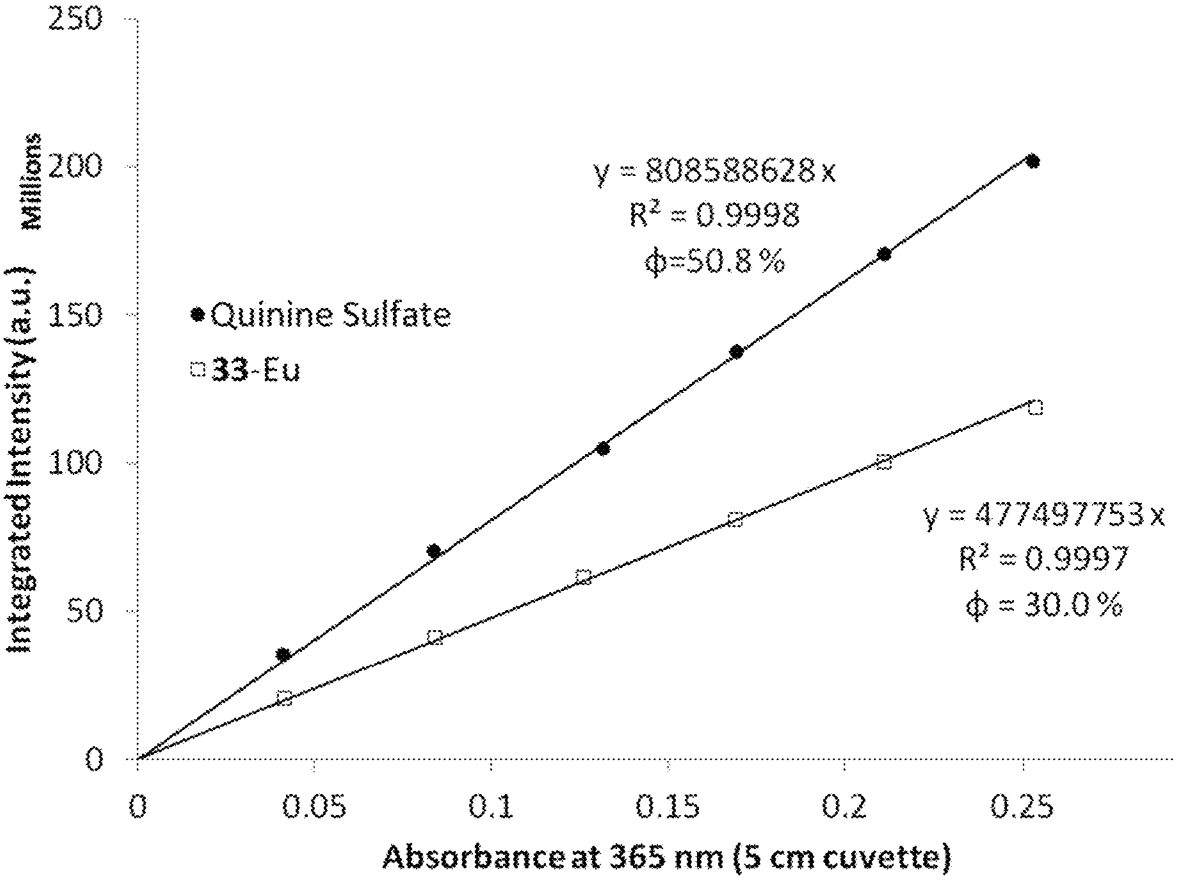
FIG. 20 shows quantum yield determination of 33·Eu.
Figure 21:
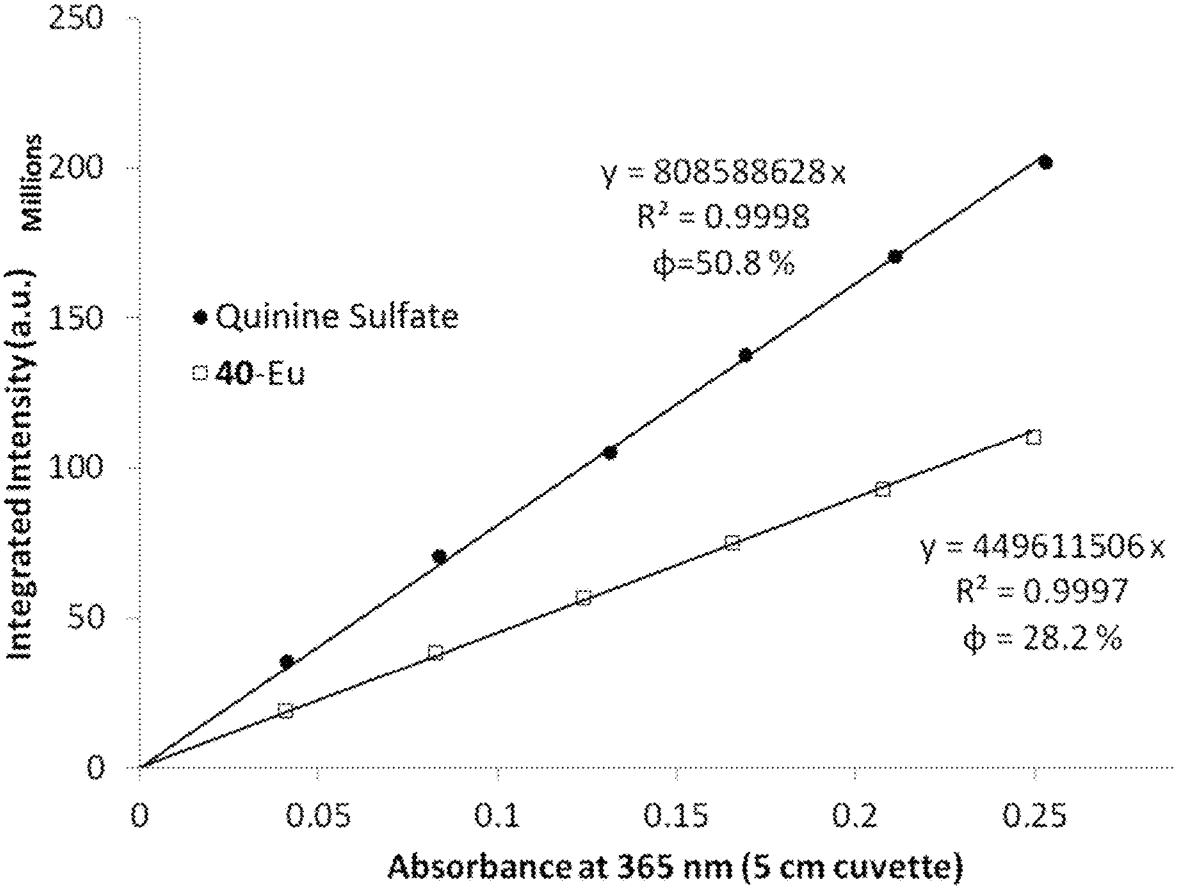
FIG. 21 shows quantum yield determination of 40·Eu.
Figure 22:
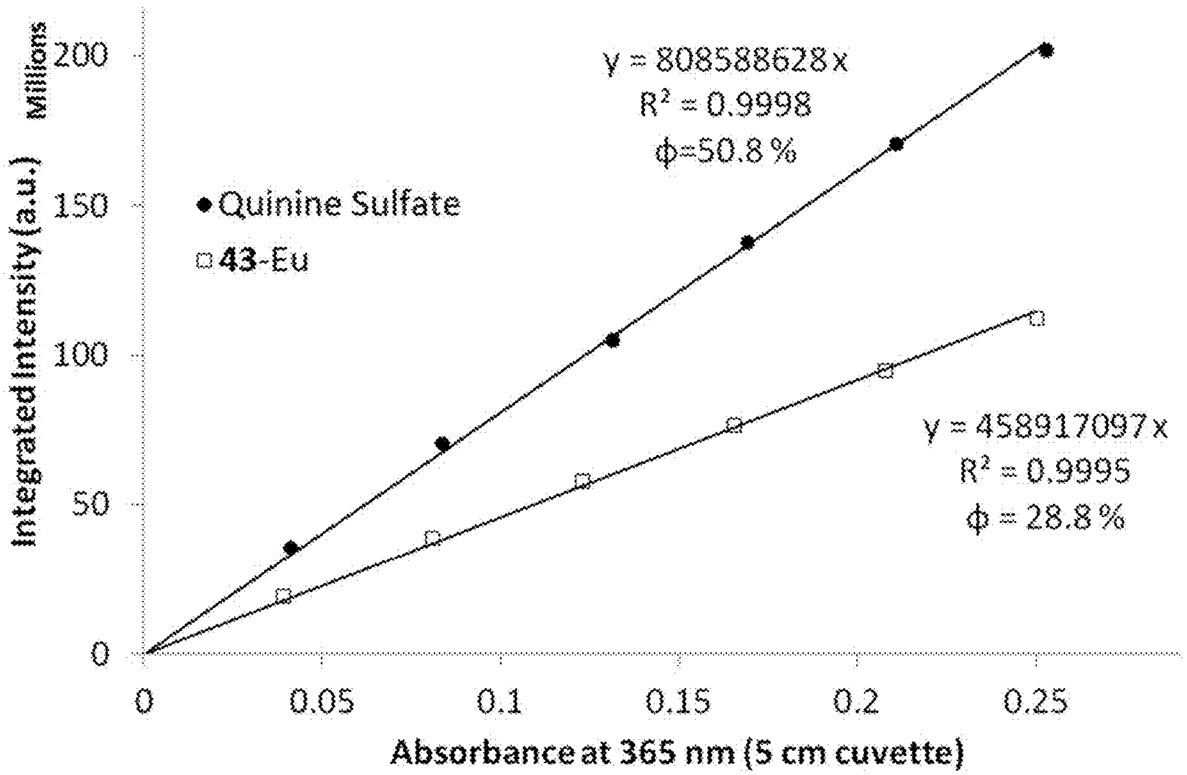
FIG. 22 shows quantum yield determination of 43·Eu.

Titration of ligand 43 was also performed by luminescence (FIG. 5), monitoring the europium signal at 612 nm upon photoexcitation of the solution at 340 nm. The ligand solution used for the UV-vis titration of 43 mentioned above was first diluted 1:10 in TBS buffer. Similarly, the 1.299 mM stock europium solution was separately diluted 1:10 with water. The results of the luminescence titration are shown in FIG. 5. It was found that 32.99 μL of the 0.1299 mM europium chloride solution was required to reach the equivalence point. The 32.99 μL equivalence point gives extinction coefficients of 14,400 $M^{-1}$ $cm^{-1}$ at 383 nm and 14,200 $M^{-1}$ $cm^{-1}$ at 357 nm for 43 and 43 Eu respectively. Averaging the values from both UV-vis and luminescence titration experiments of 43 yields extinction coefficients of 13,700 $M^{-1}$ $cm^{-1}$ at 383 nm and 13,500 $M^{-1}$ $cm^{-1}$ at 357 nm for 43 and 43 Eu respectively.

Example 12. Photophysical Characterization of 16·Eu, 29·Eu, 33·Eu, 40 Eu, and 43·Eu The europium complexes of ligands 16, 29, 33, 40, and 43 were prepared by separately dissolving each ligand (2 mg) into methanol (200 μL). Excess europium chloride hexahydrate (~5 equivalents) was dissolved in methanol (200 μL) and the full volume was added to each of the ligand solutions. The solvent was removed, and the residue was dissolved into DMF (50 μL). The europium complexes were then purified by semi-prep HPLC on an Agilent 1260 Infinity instrument using an Eclipse XDB-C18 column (5 μm, 9.4×250 mm). The mobile phase was 10 to 30% acetonitrile in water containing 0.1% trifluoroacetic acid. The volatiles were removed from the HPLC eluents under vacuum, and the residues were separately dissolved into methanol (500 μL) to give methanolic stock solutions of each europium complex with greater than 98% purity. A few drops of these methanolic solutions were evaporated to dryness, and then the residue was dissolved into TBS buffer at a concentration of ca. 3 μM to make aqueous stock solutions (20 mL) with an absorbance of 0.05 (1 cm path length) at 365 nm. Five dilutions (1/6, 2/6, 3/6, 4/6, and 5/6) were made from these aqueous stock solutions to yield six samples with evenly spaced concentrations (3 mL volume each). Quinine sulfate dissolved in 0.05 M sulfuric acid was similarly diluted to a final absorbance of 0.05 at 365 nm, and this solution was similarly (1/6, 2/6, 3/6, 4/6, and 5/6) diluted to afford six quinine sulfate reference samples of evenly spaced concentration. Quinine sulfate in 0.05 M sulfuric acid was used as the quantum yield standard ($\Phi$=0.508). By measuring the absorbance and luminescence of these dilute solutions, the quantum yields of the new Eu complexes were determined. A 5 cm path-length quartz cell was used to measure the absorbance of these dilute solutions in order to improve the UV-vis signal-to-noise. Steady state photoluminescence measurements were collected in a 1 cm fluorescence cuvette at 365 nm excitation wavelength, 1 nm resolution, 10 nm excitation slit width, 1 nm emission slit width, and 0.2 sec integration time on an instrument that has been described elsewhere (D'Aleo, A.; Moore, E. G.; Szigethy, G.; Xu, J.; Raymond, K. N. Inorg. Chem. 2009, 48, 9316·). Absorption spectra were measured at 1 nm resolution, and the absorbance of each sample was taken as the average absorbance measured from 360-370 nm to reflect the 10 nm excitation slit width used for luminescence measurements. The UV-vis spectra, luminescence spectra, and quantum yield linear regression data are shown in FIGS. 6 through 22. The data derived from these experiments, and from the titration experiments in example 11 are tabulated below.

TABLE 5

Summary of photophysical data for ligands 16 and 43, and for HPLC purified Eu complexes of 16, 29, 33, 40, and 43.

| Sample | $\lambda_{max}$ (nm) | $\varepsilon$ at $\lambda_{max}$ ($M^{-1}cm^{-1}$) | $\varepsilon_{260}/\varepsilon$ at $\lambda_{max}$ | $\varepsilon_{280}/\varepsilon$ at $\lambda_{max}$ | $\Phi_{total}$ at 365 nm excitation (%) | Lifetime (μs) |
|---|---|---|---|---|---|---|
| 16 | 382 | 13,600 | 1.98 | 1.27 | — | — |
| 16•Eu | 361 | 14,300 | 1.40 | 1.12 | 30.9 | 716 |
| 29•Eu | 363 | 14,300* | 1.42 | 1.18 | 29.8 | 716 |
| 33•Eu | 363 | 14,300* | 1.40 | 1.14 | 30.0 | 723 |
| 40•Eu | 357 | 13,500* | 1.51 | 1.19 | 28.2 | 729 |
| 43 | 383 | 13,700 | 1.96 | 1.27 | — | — |
| 43•Eu | 358 | 13,500 | 1.52 | 1.20 | 28.8 | 734 |

*these values are assumed equal to those measured by titration for 16•Eu or 43•Eu

Example 13. Stability of the Europium Complexes of 16, 29, 33, 40, and 43 in the Presence of Various Competitors In order for a luminescent metal complex to be useful in a practical sense, it must be stable in the presence of common competitive metal cations and chelating ligands. We measured the stability of 43·Eu(ca. 7 μM) dissolved in TBS buffer, with various competitors present at ca. 25 mM concentration. Specifically, manganese dichloride tetrahydrate (14.8 mg, 74.8 μmol) was dissolved into TBS buffer (100 μL), and added to an aliquot of 43·Eu(3 mL), making the final concentration of Mn(II) 24.1 mM. Magnesium chloride hexahydrate (33.6 mg, 165 μmol) was dissolved into TBS buffer (200 μL), and 100 μL was added to an aliquot of 43·Eu(3 mL), making the final concentration of Mg(II) 26.7 mM. Calcium chloride hexahydrate (55.8 mg, 255 μmol) was dissolved into TBS buffer (300 μL), and 100 μL was added to an aliquot of 43·Eu(3 mL), making the final concentration of Ca(II) 27.4 mM. For DTPA, first KOH(95.9 mg, 1.71 mmol) was dissolved into 1 mL of water, and 389 μL of this basic solution (5 equivalents) was used to dissolve DTPA (52.3 mg, 133 μmol). Then, 219 μL of this DTPA solution was added to an aliquot of 43·Eu(3 mL), making the final concentration of DTPA 23.4 mM. EDTA (0.5 M, pH=8, 150 μL) was added to an aliquot of 43·Eu(3 mL), making the final concentration of EDTA 23.8 mM. For phosphate competition, the methanolic stock of 43·Eu was diluted to ca. 7 μM in 25 mM phosphate buffer (pH=8).

Figure 23:
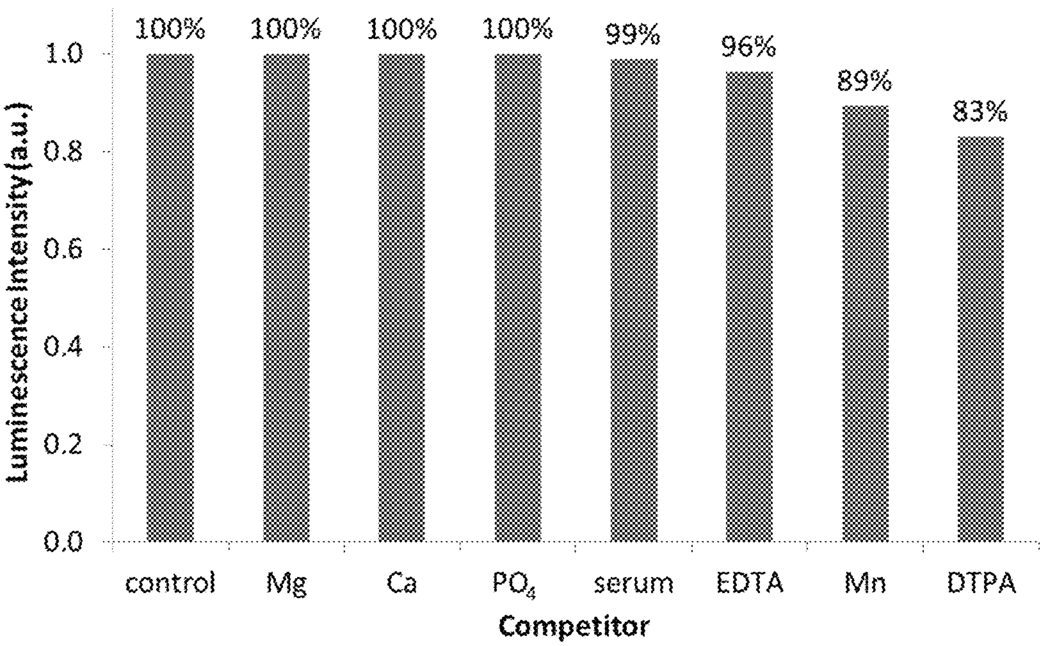
FIG. 23 shows changes in integrated luminescence intensity over one day in the presence of ca. 25 mM competitors. Competition conditions: 5 μM concentration of Eu·43, ~25 mM indicated competitor, TBS buffer pH=7.6. All samples were incubated for 24 hours at room temperature.

From the results of the stability study (FIG. 23), it is clear that most of the competitors have no significant effect on the brightness of 43·Eu over the course of 24 hours. Specifically, magnesium, calcium, and phosphate cause no detectable change in sample brightness. A small drop in brightness was noted for the EDTA containing solution (4% drop to 96%) and the manganese containing solution (11% drop to 89%). The DTPA solution showed a steady decrease in luminescence steadily, reaching 83% the original brightness after 24 hours.

Figure 24:
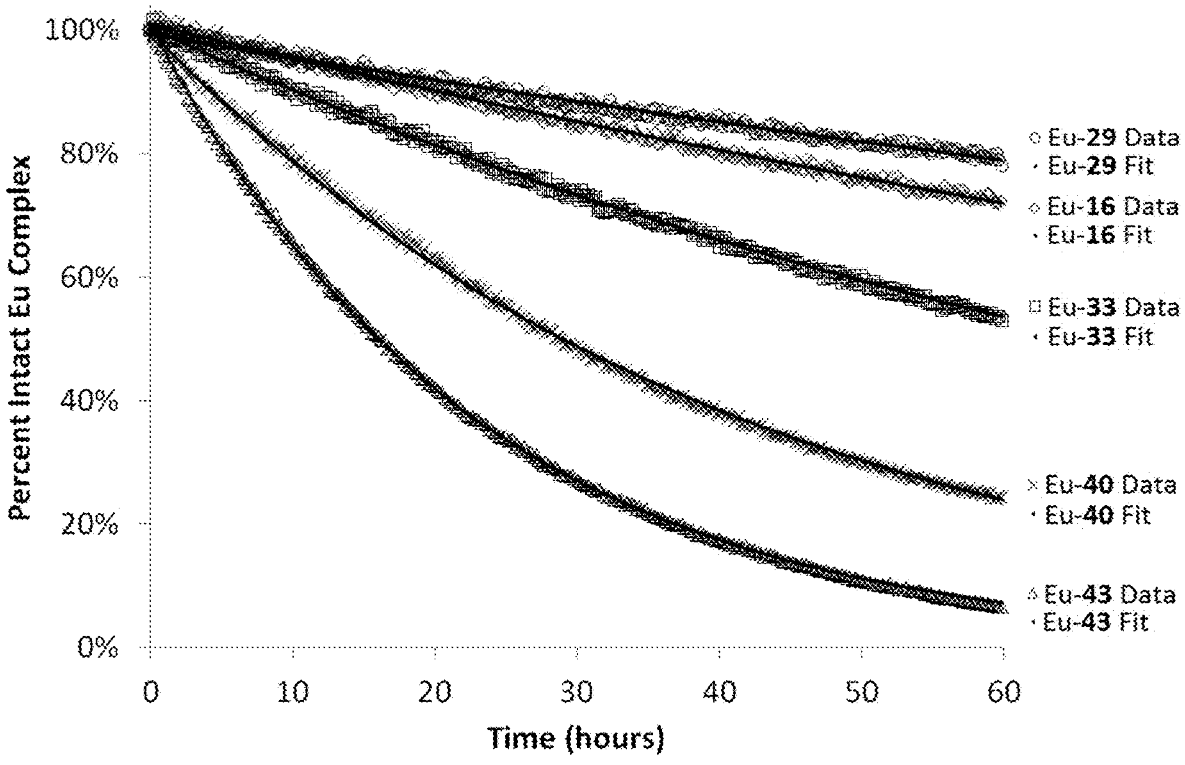
FIG. 24 shows changes in the integrated luminescence intensity at 612 nm (360 nm excitation) over time in the presence of 250 mM DTPA, pH=7.6.

From these experiments, it is clear that 43·Eu is remarkably stable to a wide range of competitive metal ions and chelators. The competitor concentrations mentioned above are a good way to assess the kinetic stability of the complex in various assay conditions. DTPA is an exceptionally good ligand for lanthanide ions, and thus it is not typically used in practical assays. However, DTPA competition offers an excellent way to benchmark the kinetic stability of the complexes reported here. In general, the decorporation of europium by ~25 mM DTPA was found to be too slow to measure reliably. In order to compare the kinetic stability of the complexes reported here, a 750 mM stock solution (25 mL) of DTPA was prepared by dissolving DTPA (7.375 g, 18.75 mmol) into water (20 mL) containing potassium hydroxide (5.26 g, 93.75 mmol). The pH of the DTPA solution was adjusted to pH=7.6 by addition of concentrated hydrochloric acid, and then the solution was diluted to a final volume of 25 mL to give a 750 mM DTPA stock solution at pH=7.6. HPLC purified europium complexes of 16, 29, 33, 40, and 43 were separately diluted to 11 μM in TBS buffer, pH=7.6. For each DTPA competition experiment, 1 mL of the 750 mM DTPA solution was added to 2 mL of the 11 μM europium complex solution. The luminescence at 612 nm (365 nm excitation) was monitored for these five separate solutions containing 250 mM DTPA and 7.1 μM of each europium complex as a function of time. The results are summarized in the following table and in FIG. 24.

TABLE 6

Summary of 250 mM DTPA competition experiments for the HPLC purified Eu complexes of 16, 29, 33, 40, and 43.

| Sample | Half-life in 250 mM DTPA (hours) | $R^2$ |
|---|---|---|
| 16•Eu | 122 | 0.995 |
| 29•Eu | 180 | 0.991 |
| 33•Eu | 66 | 0.998 |
| 40•Eu | 29 | 0.9993 |
| 43•Eu | 16 | 0.9997 |

In general, the decoporation of europium from these complexes in 250 mM DTPA occurs at ~10× the rate of the decorporation of europium in 25 mM DTPA, as expected for a pseudo first order kinetic process. Comparing 16·Eu(no sidearm) and 33 Eu(spermine-based sidearm) shows that introduction of the spermine-based sidearm reduces the kinetic stability by two fold. Likewise, comparing 40·Eu(no sidearm) and 43·Eu(spermine-based sidearm) shows the same ~2× reduction in the kinetic stability upon introduction of the spermine-based sidearm. In general, the europium complexes of the ethylenediamine-based macrocycles (29·Eu and 33·Eu) are ~5× more kinetically stable than the m-tetrahydrofurandiamine-based macrocycles (40·Eu and 43·Eu). This result is surprising given that the m-tetrahydrofurandiamine-based macrocycles are more rigid, and thus would be expected to have greater kinetic stability than the ethylenediamine-based macrocycles. Even more surprising was the fact that the ethylenediamine-based macrocycle with a sidearm coming off of the ethylenediamine unit (29·Eu) was found to be the most kinetically stable complex measured here. It is surprising that it appears to be more stable than the ethylenediamine-based macrocycle with no sidearm (16·Eu). It was surprisingly found that the 29·Eu complex is at least an order of magnitude more kinetically stable than 43·Eu to challenge by DTPA. This result is remarkable, given that 43·Eu has been shown to have excellent stability with regard to a variety of competitive metal ions and chelators as shown above.

Example 14

There are several diamines one could envision using within the existing synthetic scheme rather than the ethylenediamine (9), (S)-tert-butyl (5,6-diaminohexyl)carbamate (23), and (3R,4S)-tetrahydrofuran-3,4-diamine (34) reported here. Representative examples of these new diamines for the formation of new monomacrocyclic ligands (n=0, 1, 2 or 3; X=O, S, or $CH_2$) are tabulated below, sorted into rows:

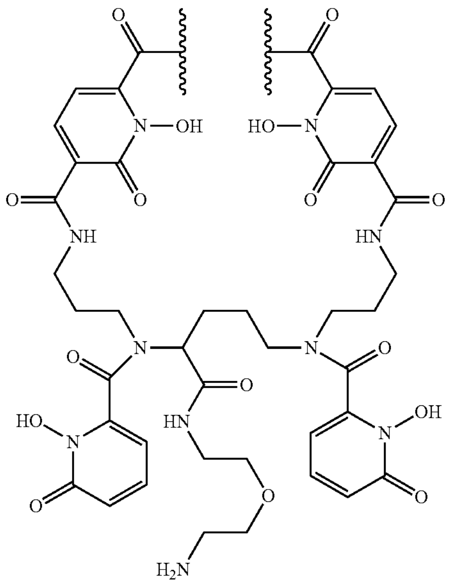

A

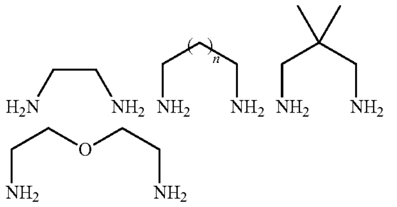

-continued

B

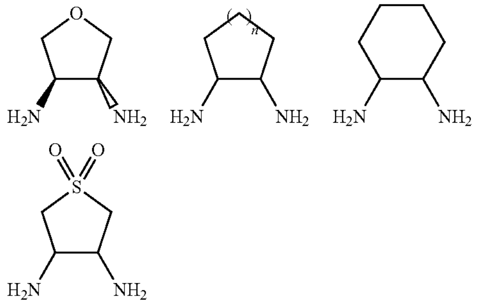

C

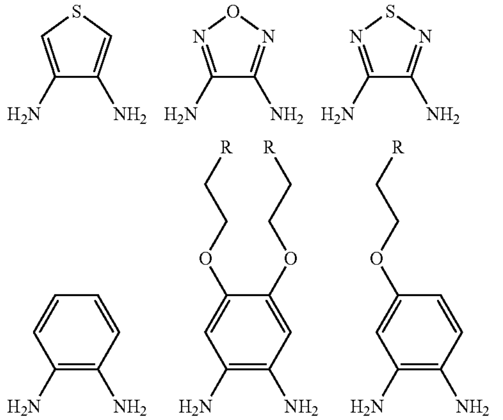

D

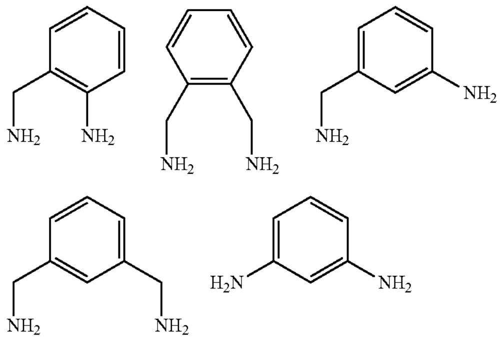

E

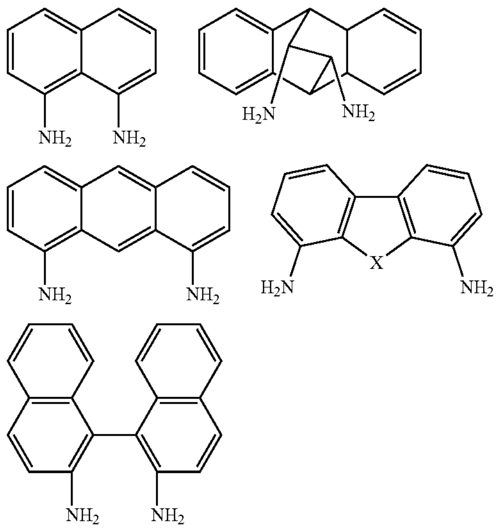

-continued

F

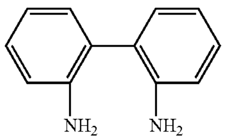

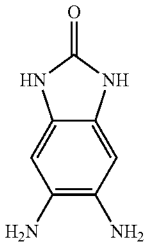

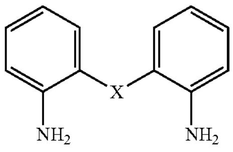

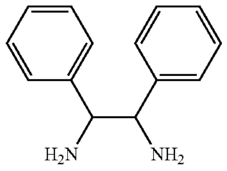

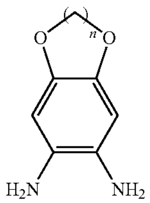

G

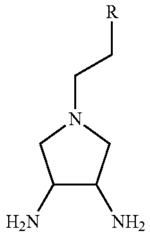

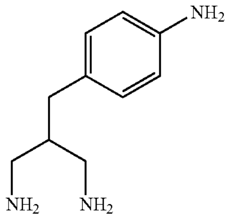

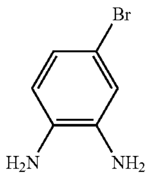

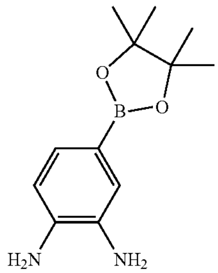

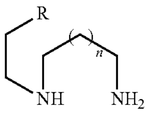

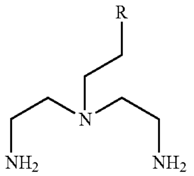

-continued

H

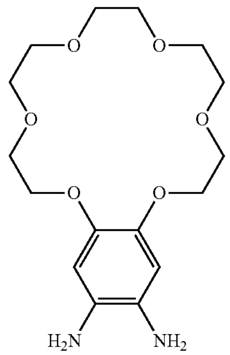

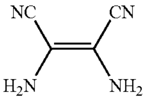

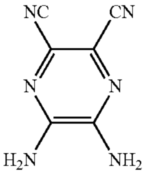

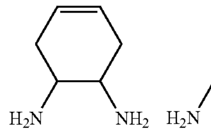

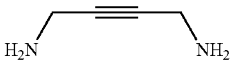

Row A consists of several acyclic, aliphatic linkers that may enhance or alter the photophysical properties of the Eu complexes, by affecting the geometry of the ligand around the metal ion. Similarly, the binding of other radiologically important metals ions may be altered or enhanced. Row B contains other cyclic, aliphatic diamine linkers. The cyclic structure of these examples may enhance the rigidity of the ligand structure, which may enhance the stability of the metal complexes formed. Row C contains cyclic, aromatic diamine linkers, which all have 2-carbon bridges much like the 2-carbon diamine bridges synthesized here. These aromatic diamines might extend the electronic conjugation of the 1,2-HOPO units, which can affect the photophysical characteristics of the ligand. The final entry in row C can also include polyethylene glycol units for enhanced solubility. Rows D, E, and F contain additional examples of cyclic, aromatic systems that may enhance the stability of the metal complexes by altering the ligand geometry. Row G contains a variety of diamine bridges, which all have a functional handle that can be used for linking these metal monomacrocycle complexes to a species of interest. The linkers on each of these diamines may be used to add functional handles to the metal complexes. Row H contains diamine bridges that may offer a way to sense or react with species of interest. The first entry contains an 18-crown-6 ether functionality, which should bind potassium ions. The cyano and cyclohexene examples may bind certain transition metals, while the butyne diamine might facilitate reaction with an organic azide.

Example 15

Representative new functional groups for attachment to pendant 1,2-HOPO units for solubility and additional points of attachment are shown below:

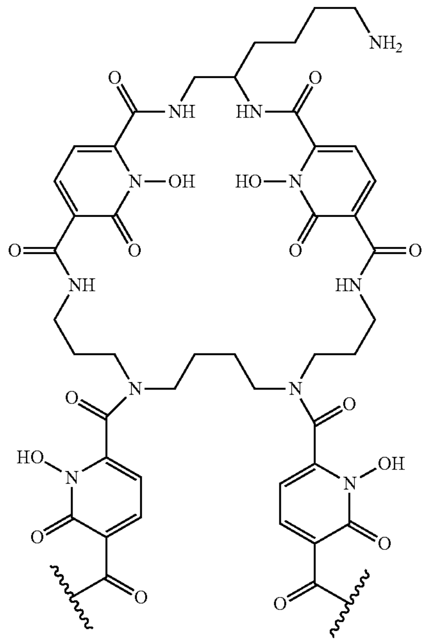

or

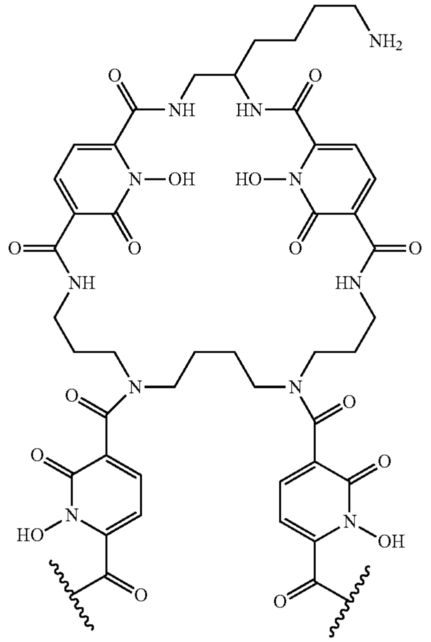

-continued

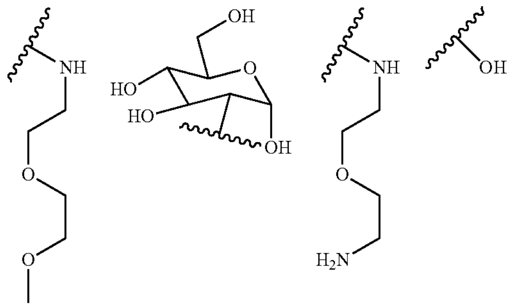

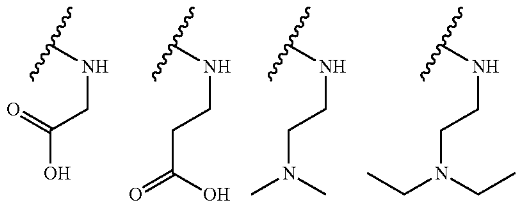

Reacting 8 (or derivatives thereof), instead of 14, with, for example, 27 can lead to structures like the one shown above. Such a species allow for solubilizing groups such as aminopolyethylene glycol, glucosamine, 2-aminoacetic acid, 3-aminopropanoic acid, $N^1$,$N^1$-dimethylethane-1,2-diamine, and $N^1$,$N^1$-diethylethane-1,2-diamine (shown above) to be added onto the ligand, enhancing the solubility of the metal complexes in water. Adding diamines (or similar bifunctional moieties) engenders ligands with additional attachment points. Additionally, use of the 1,2-HOPO diamide chromophores at all four sites (as shown above) may engender improved photophyiscal properties by more closely matching the absorption bands of the two types of 1,2-HOPO chromophores.

Example 16
Scheme 8. Representative synthetic scheme of compound 33b of the invention and precursors thereof. Synthesis of 30b has been previously reported (WO2016106241).
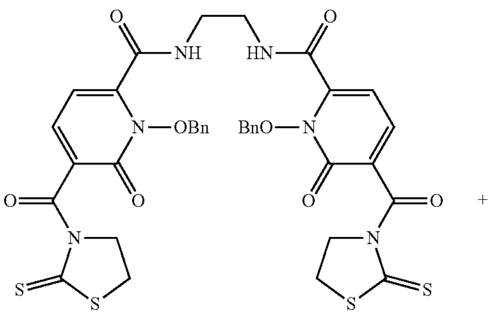
12
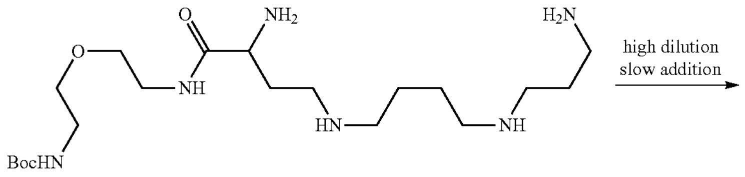
30b
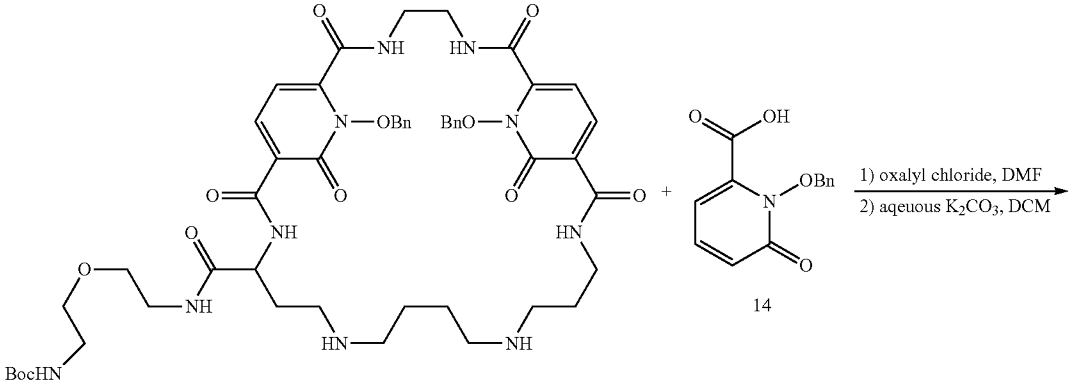
31b
14
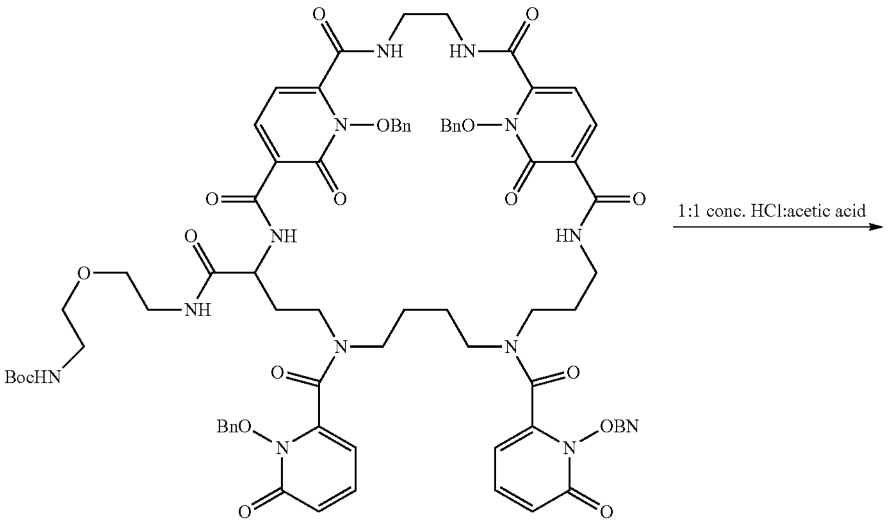
32b -continued
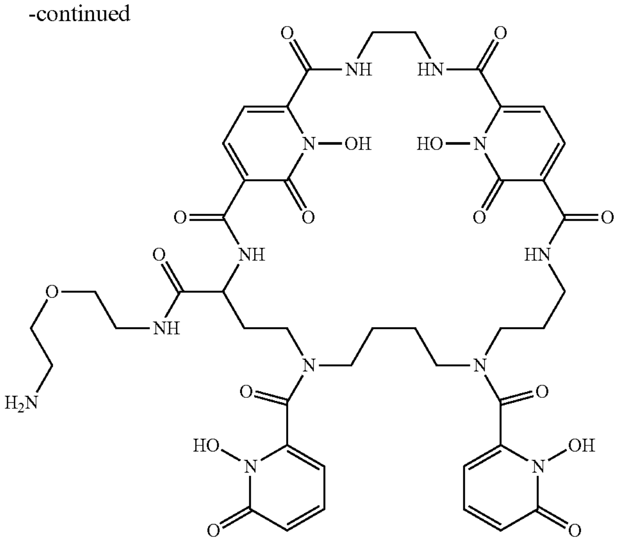
33b
Example 17
Scheme 9. Representative synthetic scheme of an exemplary scaffold precursor.
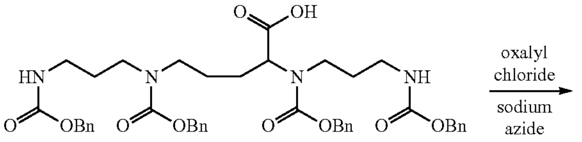
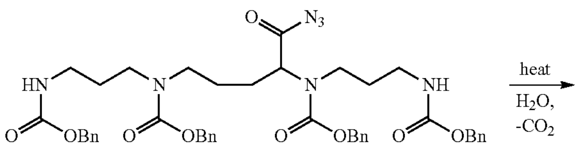
-continued
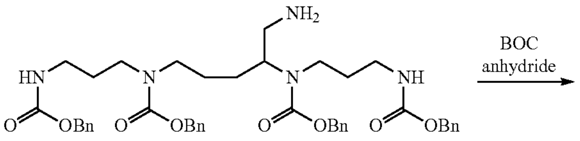
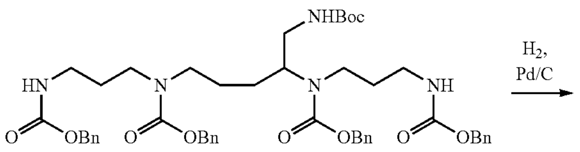
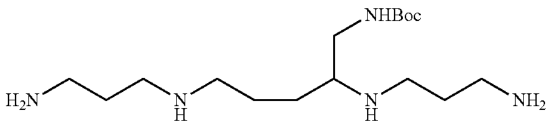

Example 18
Scheme 10. Representative synthetic scheme of HOPO-Lys-cyclic-RDGyK.
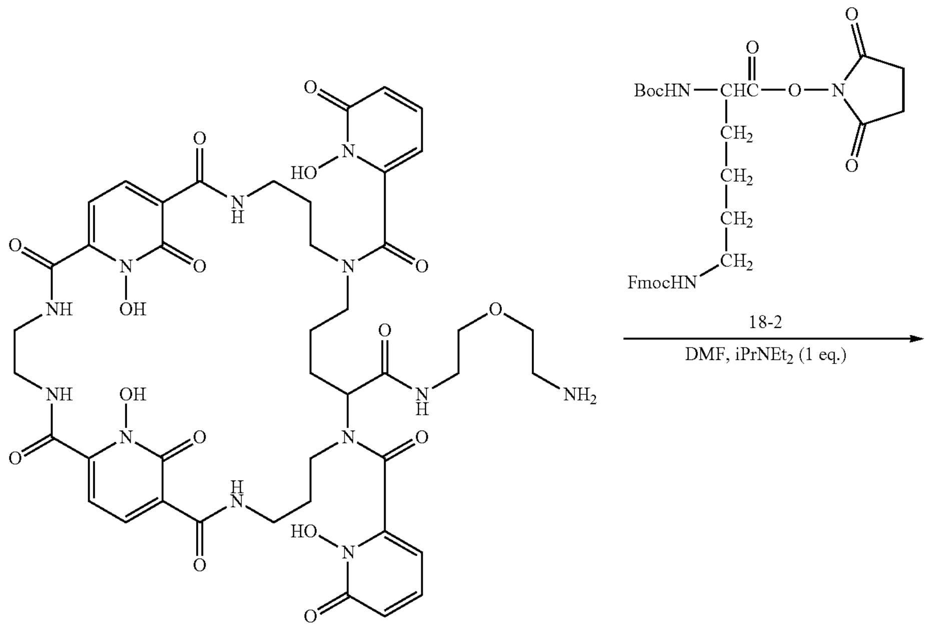
18-1
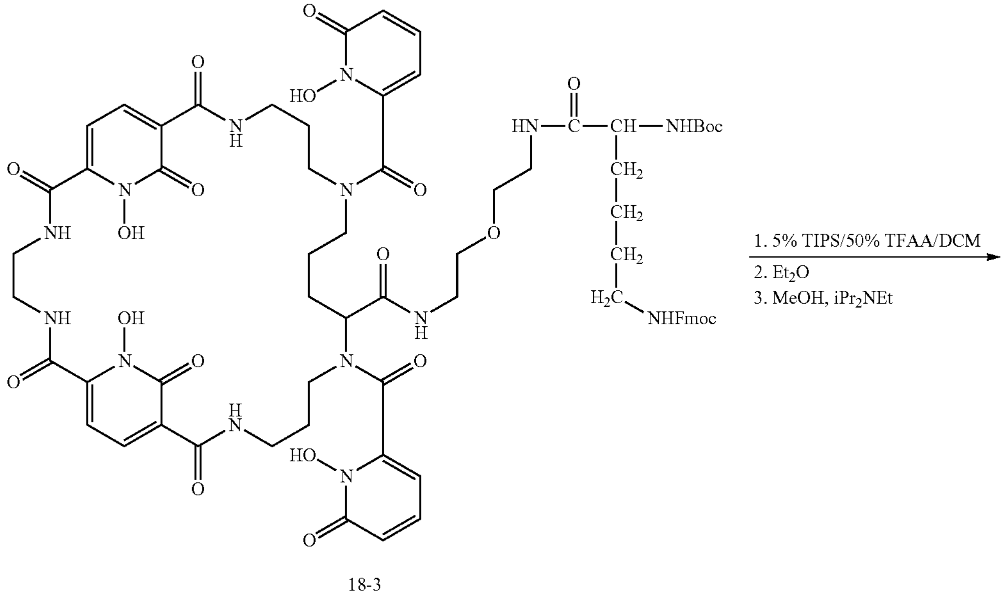
18-3

-continued
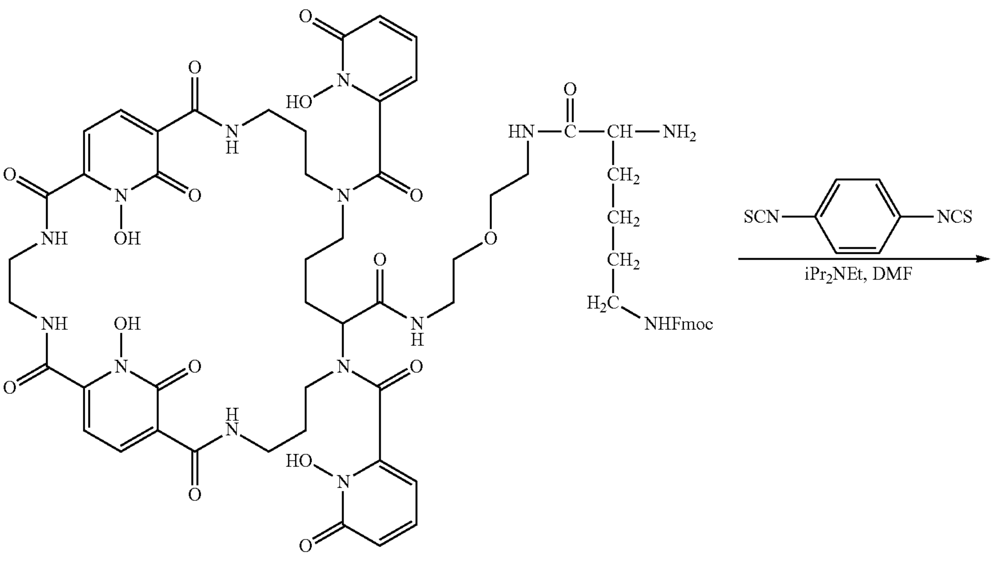
18-4
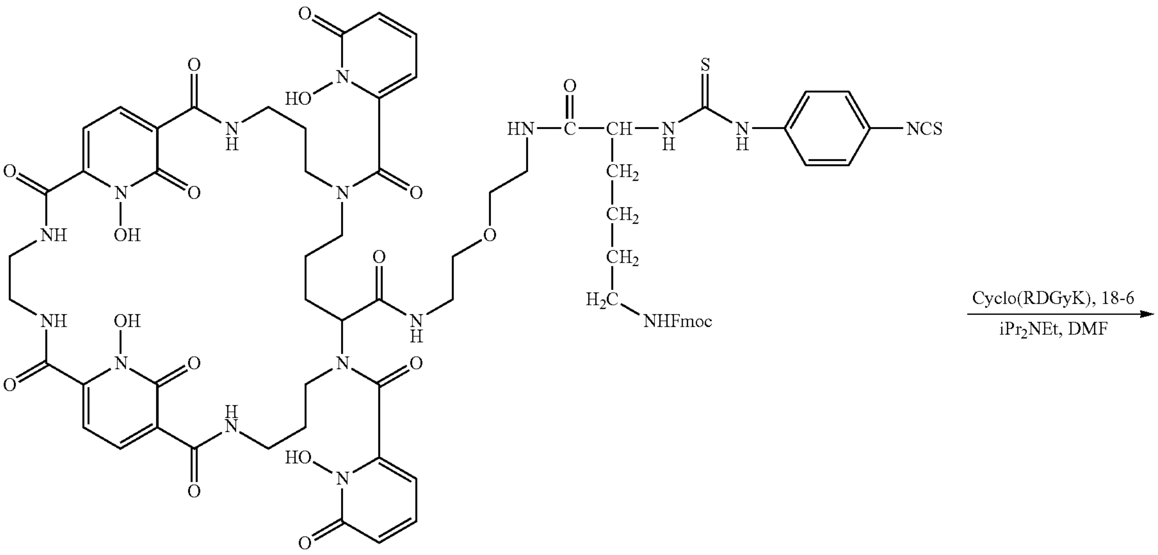
18-5
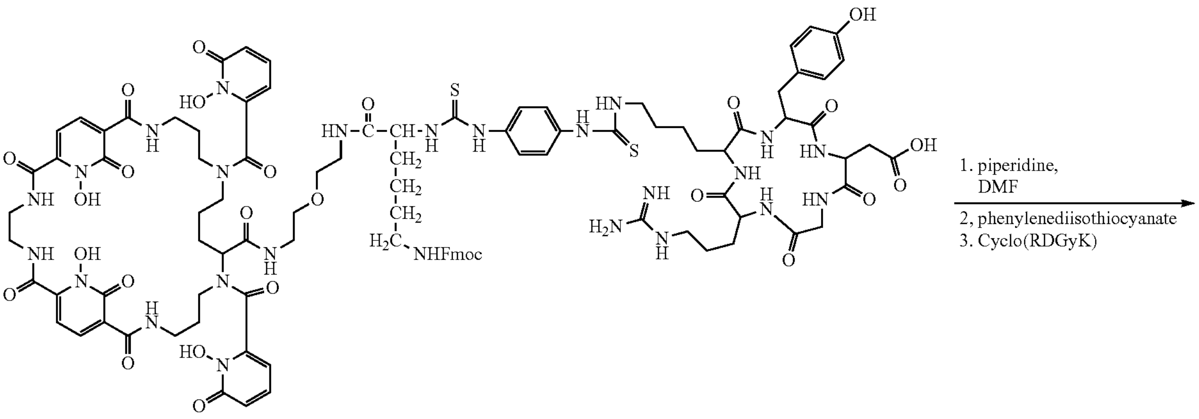
18-7

-continued

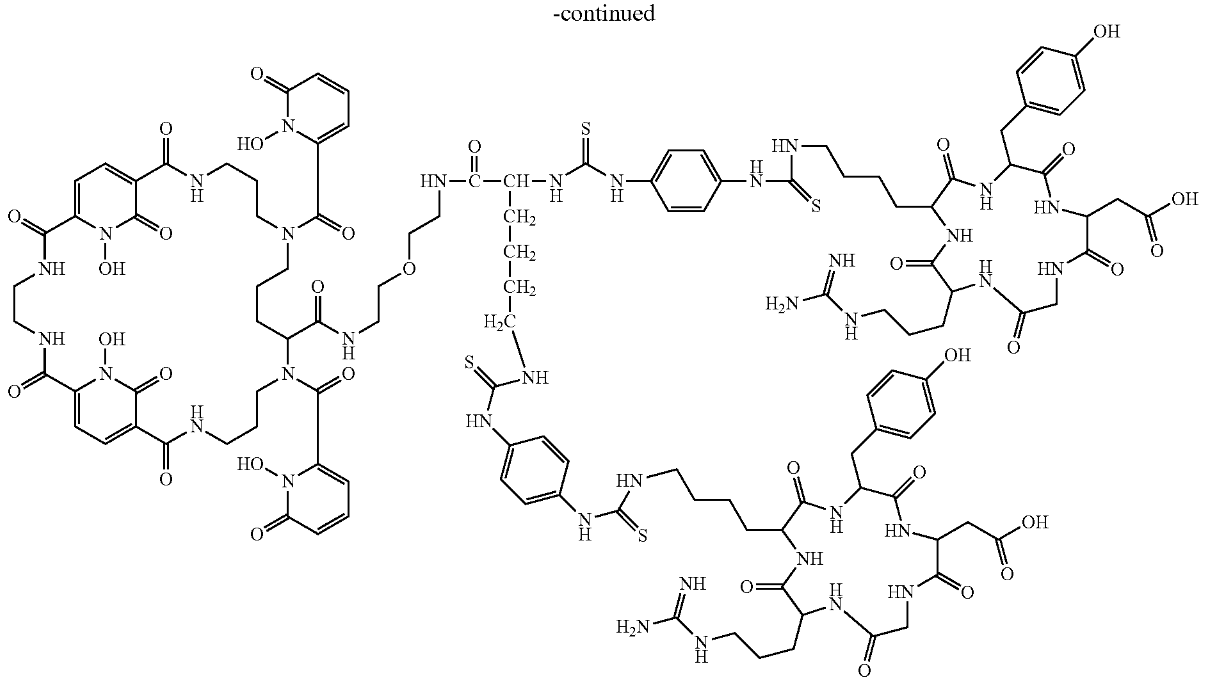

18-8

The divalent peptide conjugate HOPO-Lys-cyclic-RDGyK can be synthesized according as outlined in Scheme 5. Cyclo(RDGyK) is a peptide that binds αvβ3 integrin, overexpressed in pancreatic cancer, available from Anaspec.

Example 19

Scheme 11. Representative synthetic scheme of compound 23b.

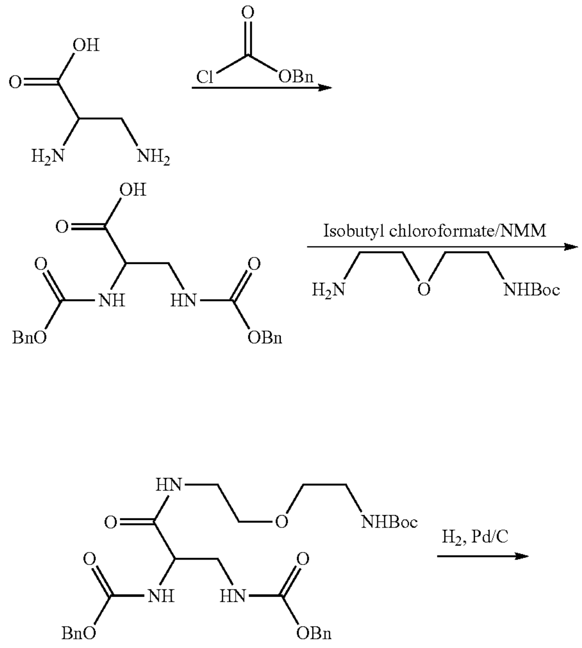

-continued

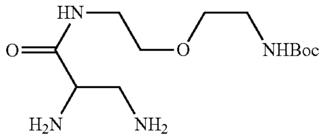

23b

Example 20

Scheme 12. Representative synthetic scheme of compound 29b of the invention and precusors thereof.

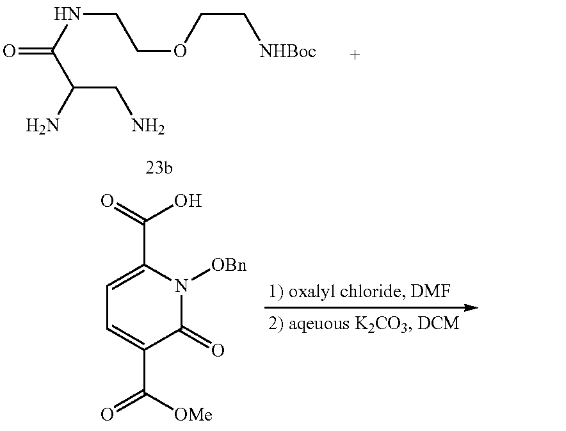

23b

8

-continued
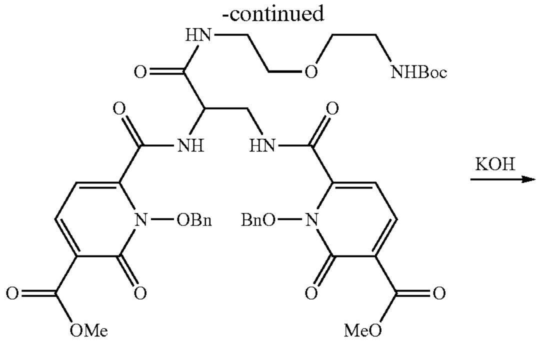
24b
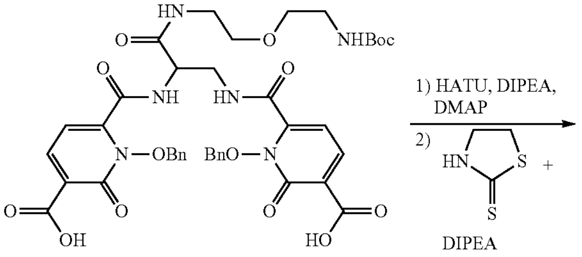
25b
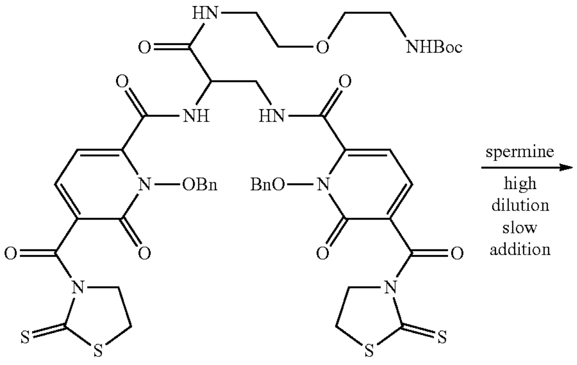
26b
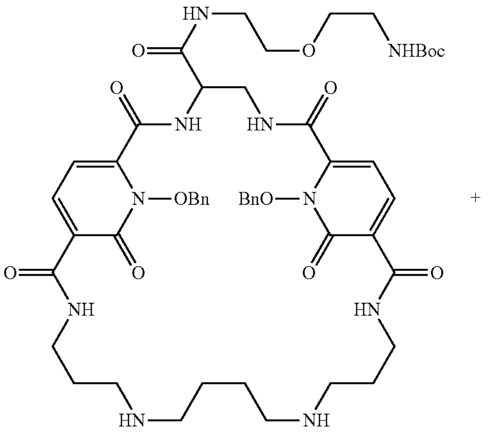
27b
-continued
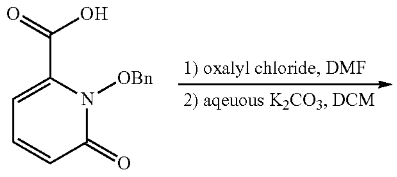
14
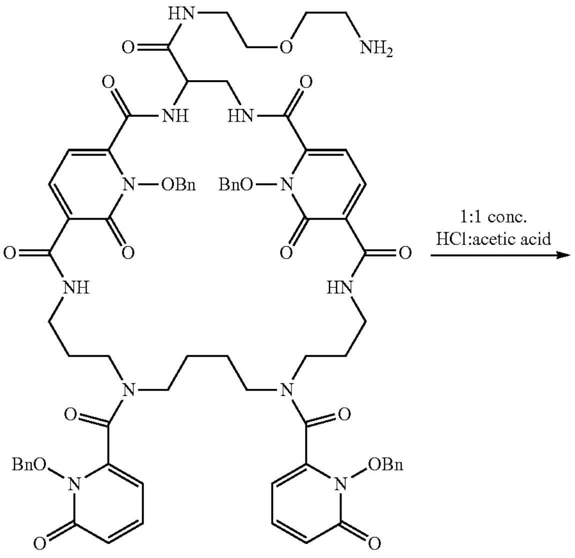
28b
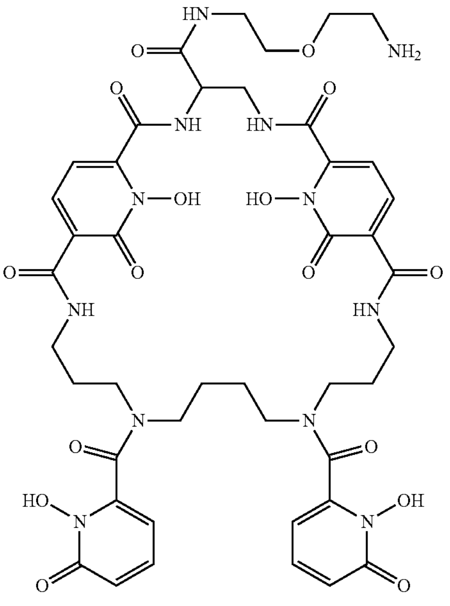
29b

Example 21 Synthesis of compound 29-Eu—NHS as a representative example of useful species that can be generated from compounds 29, 33, and 43

Scheme 13. Synthetic scheme of compound 29-Eu-NHS as a representative example of useful species that can be generated from compounds 29, 33, and 43.

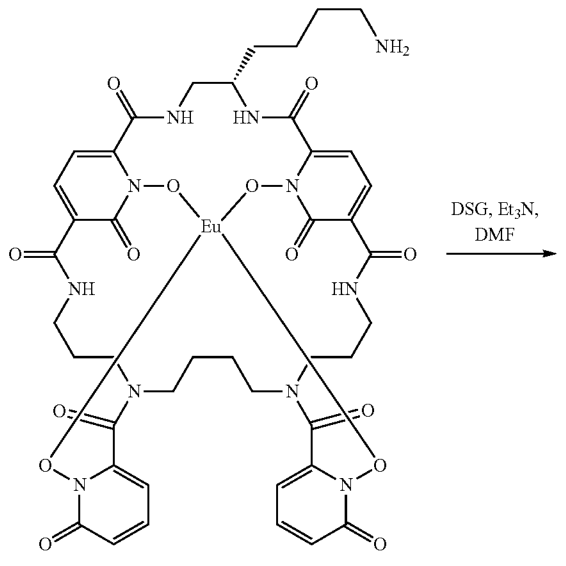

29-Eu

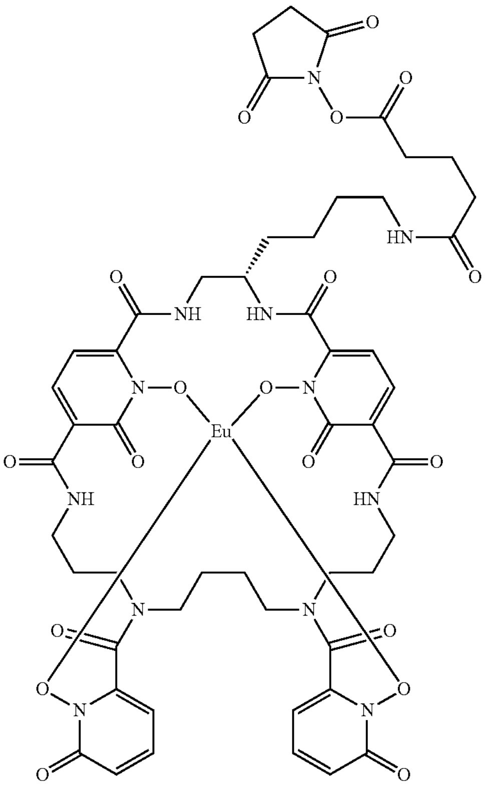

29-Eu-NHS

The reactive NHS esters of complexes Eu·29, Eu·33, and Eu·43 can be generated by treatment of the appropriate Eu complex with excess (10 eq.)di(N-succinimidyl) glutarate (DSG) in DMF and triethylamine. The reactive NHS esters are useful for attaching the metal complexes to lysine residues on proteins, or to amines of other targeting groups of interest. For example, Eu·29 (20 mg, 18.5 μmol) was dissolved into DMF (200 μL). Separately, DSG (60.2 mg, 185 μmol) was dissolved into DMF (200 μL) and then triethylamine (18.7 mg, 185 μmol) was added to the DSG solution. The solution of Eu·29 was added to the DSG solution dropwise with shaking. The reaction proceeded with shaking for 1 hour at room temperature. The product was isolated by precipitating the product four times from DMF using diethyl ether (4 mL per precipitation) and isolating the precipitate by centrifugation and decanting. The crude product was then similarly dissolved into dichloromethane (1 mL) and precipitated with ether (1 mL) four times. After the final decanting step, the residual solvent was removed under vacuum overnight to give Eu·29-NHS as a white powder. Yield 22.1 mg, 92.5%. HRMS-ESI (m/z, $[M]^-$) Calcd for $C_{51}H_{56}EuN_{12}O_{19}$: 1291.2989, Found: 1291.2986.

Example 22 Synthesis of Exemplary Parent Compound

Scheme 14. Synthetic scheme for parent compound 40′

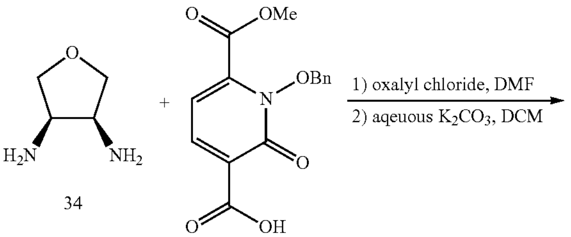

34

8′

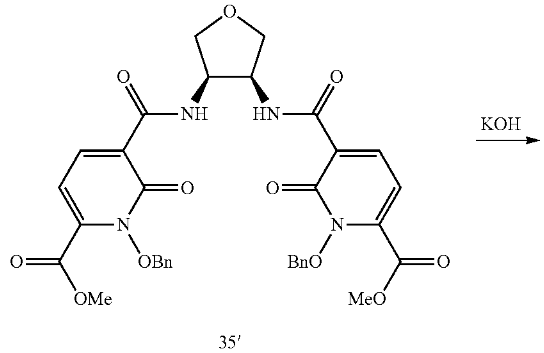

35′

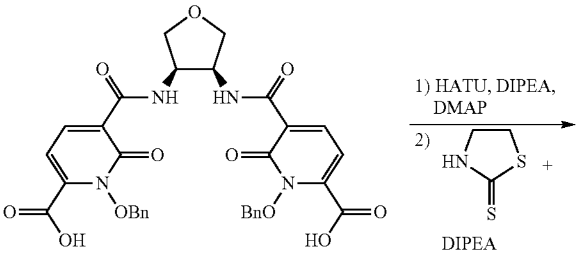

36′

-continued

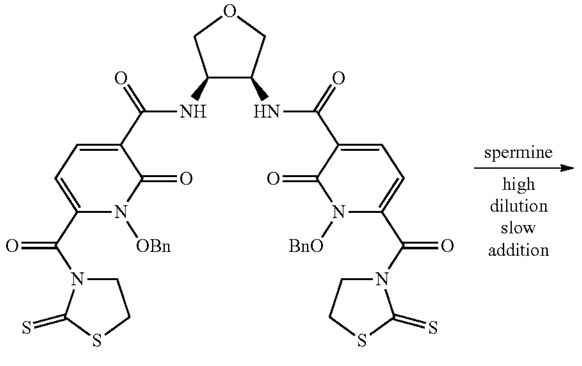

37′

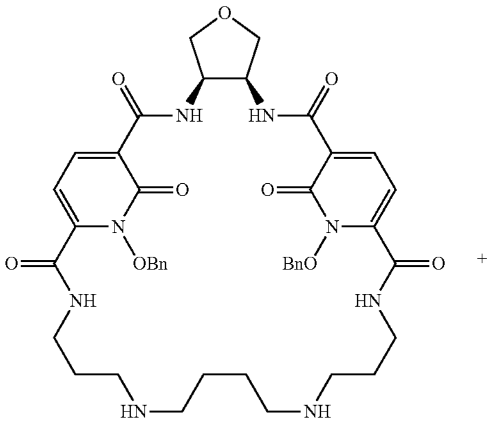

38′

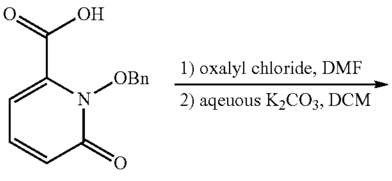

14

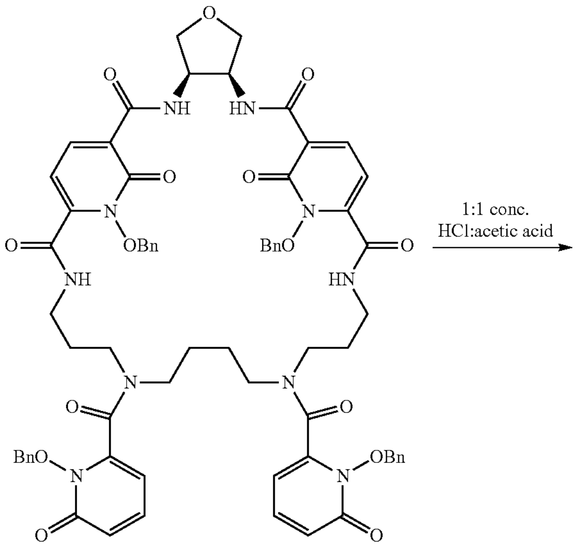

39′

-continued

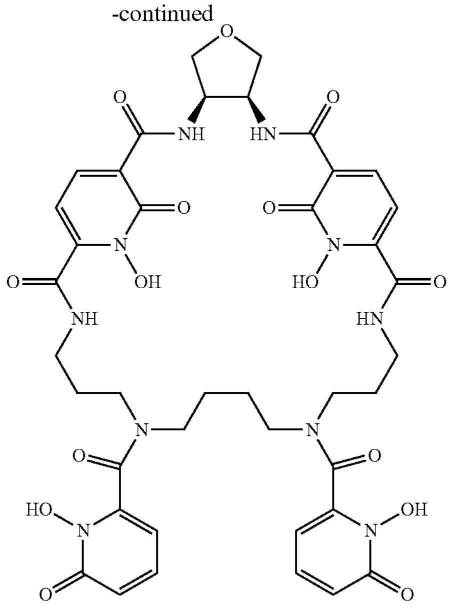

40′

General Methods.

The precursors (3R,4S)-tetrahydrofuran-3,4-diamine (34), 1-(benzyloxy)-6-(methoxycarbonyl)-2-oxo-1,2-dihydropyridine-3-carboxylic acid (8'), 1-(benzyloxy)-6-oxo-1,6-dihydropyridine-2-carboxylic acid (14), and tert-butyl (2-(2-(2,5-bis((3-aminopropyl)amino) pentanamido) ethoxy) ethyl)carbamate (30) are synthesized according to previously reported methods. All other solvents and reagents are purchased from commercial sources and used as received unless otherwise noted.

Dimethyl 5,5'-((((3R,4S)-tetrahydrofuran-3,4-diyl)bis (azanediyl))bis(carbonyl))bis(1-(benzyloxy)-6-oxo-1,6-dihydropyridine-2-carboxylate) (35'). Oxalyl chloride (4.10 g, 32.3 mmol) is added to a suspension of 8' (4.10 g, 13.5 mmol) in dichloromethane (40 mL), followed by 1 drop of dry DMF. The solution becomes homogenous within 30 min, and the reaction is stirred at room temperature for 3 hours total. The solvent is then removed under vacuum overnight. The residue is dissolved into dichloromethane (20 mL) and added dropwise to a solution of 34 (580 mg, 5.7 mmol) dissolved in dichloromethane (20 mL) and 40% aqueous $K_2CO_3$ (20 mL) at 0° C. with vigorous stirring. The reaction is stirred with warming to room temperature overnight. The dichloromethane layer is loaded directly onto a 4 inch tall×1 inch wide silica gel column. Following a methanol/dichloromethane gradient elution, the desired product is collected using 2.5% methanol in dichloromethane. The solvent is removed under vacuum to yield the desired product as a hardened glass of 35'.

5,5'-((((3R,4S)-tetrahydrofuran-3,4-diyl)bis(azanediyl)) bis(carbonyl))bis(1-(benzyloxy)-6-oxo-1,6-dihydropyridine-2-carboxylic acid) (36'). Potassium hydroxide (934 mg, 16.6 mmol) is added to a suspension of 35' (2.80 g, 4.16 mmol) in 2:2:1 THF: MeOH: water (50 mL), and the reaction is heated to 50° C. overnight with stirring. The solvent is removed under vacuum and the resulting residue is dissolved into water (250 mL). Dilute HCl is added dropwise with stirring until the solution is acidic by litmus test. The desired product is collected by filtration, washed with dilute HCl and dried under vacuum overnight to yield a white powder of 36'.

N,N'-((3R,4S)-tetrahydrofuran-3,4-diyl)bis(1-(benzyloxy)-2-oxo-6-(2-thioxothiazolidine-3-carbonyl)-1,2-dihydropyridine-3-carboxamide) (37'). HATU (2.40 g, 6.3 mmol), 36' (1.93 g, 3.00 mmol), and DMAP (73.3 mg, 0.6 mmol) are suspended in dichloromethane (75 mL). DIPEA (776 mg, 6 mmol) is added dropwise to the suspension, and the reaction is stirred at room temperature for 2 hours. Upon completion 2-mercaptothiazoline (894 mg, 7.5 mmol) is added to the homogenous solution, followed by DIPEA (1.5 g, 11.6 mmol). The reaction is stirred for an additional 1.5 hours at room temperature. The reaction mixture is then washed with water 3×75 mL to remove the bulk of the urea byproduct, concentrated, and then loaded onto a 6 inch tall×1 inch wide silica gel column. Following a 2-propanol/dichloromethane gradient elution, the desired product is collected using 5% 2-propanol in dichloromethane. The solvent is removed under vacuum, and the residue is dissolved into 100 mL dichloromethane. The organic solution is again washed with water 3×75 mL to remove final traces of the urea byproduct, and the organic solution is concentrated to a volume of 10 mL. Addition of 2-propanol causes precipitation of the desired product, which is collected by evaporation of the solvent to give a yellow powder of 37'.

Compound 38'. Spermine (229 mg, 1.13 mmol) is dissolved into 2-propanol (50 mL) and 37' (957 mg, 1.13 mmol) is separately dissolved into dichloromethane (50 mL). Using syringe pumps, the two solutions are dripped (0.5 mL/hour) into a large flask containing 1:1 dichloromethane: 2-propanol (1 L) over four days. The reaction is stirred for an additional day at room temperature, followed by removal of the solvent under vacuum. The residue is dissolved into dichloromethane (200 mL) and extracted with aqueous potassium hydroxide to remove the 2-mercaptothiazoline byproduct. Removal of the solvent affords the desired product as a viscous oil of 38', which is used without further purification in the next reaction.

Compound 39'. Oxalyl chloride (1.1 g, 8.7 mmol) is added to a suspension of 14 (1.11 g, 4.52 mmol) in dichloromethane (40 mL), followed by 1 drop of dry DMF. The solution becomes homogenous within 30 min, and the reaction is stirred at room temperature for 3 hours total. The solvent is then removed under vacuum overnight. The residue is dissolved into dichloromethane (20 mL) and added dropwise to a solution of 38' (1.13 mmol) dissolved in dichloromethane (20 mL) and 40% aqueous $K_2CO_3$ (20 mL) at 0° C. with vigorous stirring. The reaction is stirred with warming to room temperature overnight. The dichloromethane layer is loaded directly onto a 4 inch tall×1 inch wide silica gel column. Following a methanol/dichloromethane gradient elution, the desired product is collected using 4% methanol in dichloromethane. The solvent is removed under vacuum to yield the desired product as a hardened glass of 39'.

Compound 40'. Compound 39' (63 mg, 0.070 mmol) is dissolved into a 1:1 mixture of concentrated HCl and glacial acetic acid. The homogenous solution is stirred at room temperature for 3 weeks in the dark. Upon reaction completion, the solvent is removed under vacuum. Residual solvent is removed by co-evaporation with water, followed by methanol, and finally diethyl ether to yield a beige solid of 40'. Purity is assessed by HPLC by first adding a 5-fold molar excess of $EuCl_3$ to the sample dissolved in methanol.

Example 23. Synthesis of Exemplary Bifunctional Chelator

Scheme 15. Synthetic scheme for attachment point containing compound 43'

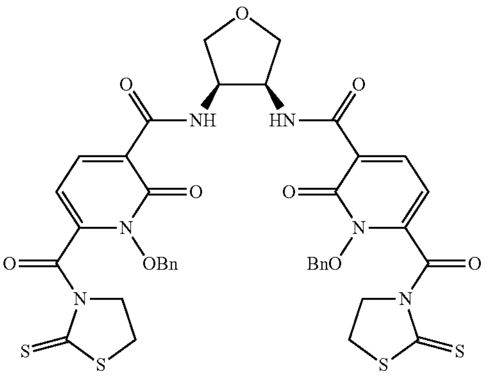

37'

+

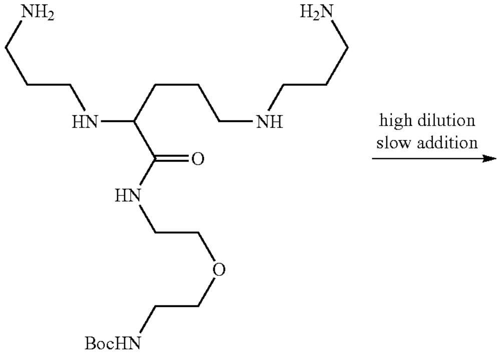

30

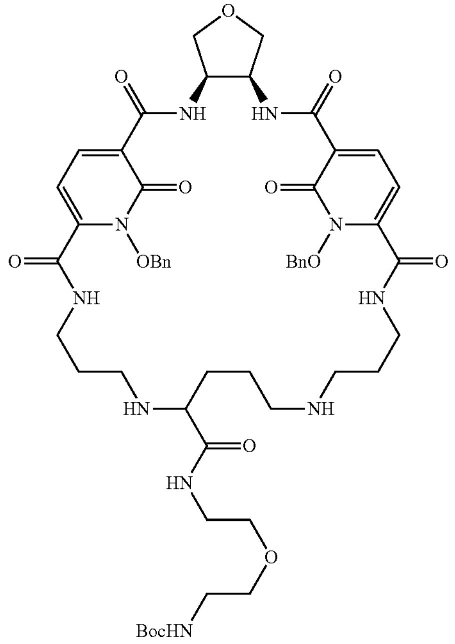

+

41'

-continued

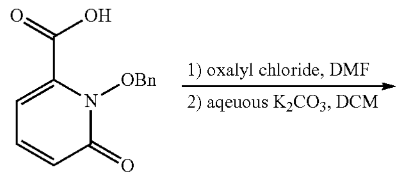

14

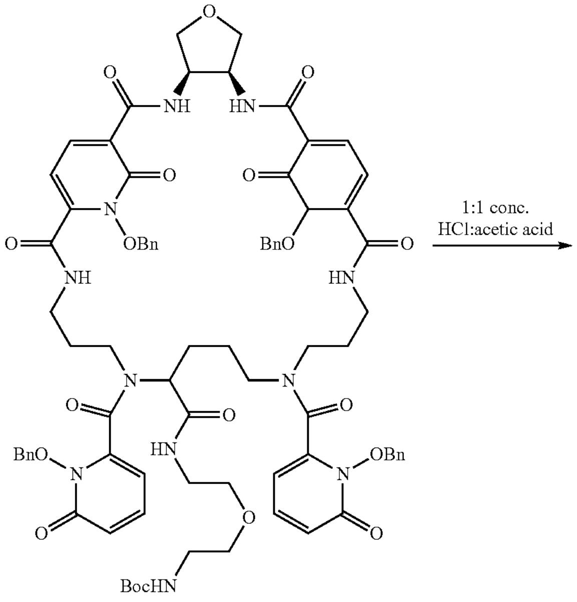

42'

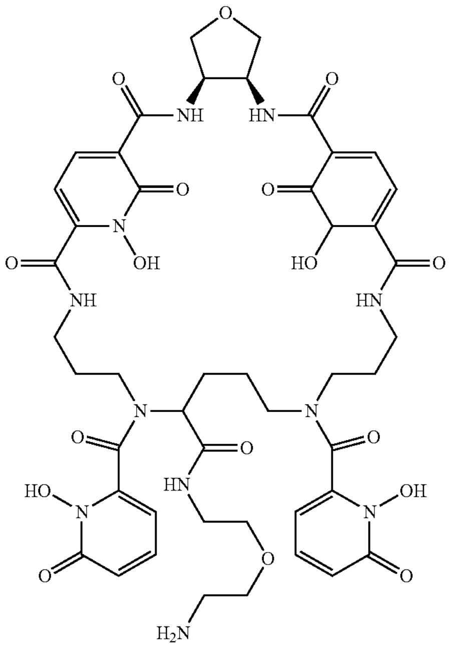

43'

Compound 41'. Following the same procedure as used for compound 38', using 37' (1.30 g, 1.54 mmol) and 30 (668 mg, 1.54 mmol) as starting materials. Similarly, the residue is washed with base and used without further purification in the next reaction.

Compound 42'. Following the same procedure as used for compound 39', using 41' (1.54 mmol) and 14 (1.51 g, 6.16·mmol) as starting materials.

Compound 43'. Following the same procedure as used for compound 40', using 42' (92 mg, 0.062 mmol) as the starting material.

Example 24

There are several diamines one could envision using within the existing synthetic scheme rather than the (3R, 4S)-tetrahydrofuran-3,4-diamine (34) reported here. Representative examples of these new diamines for the formation of new monomacrocyclic ligands (n=0, 1, 2 or 3; X=O, S, or $CH_2$) are tabulated below, sorted into rows:

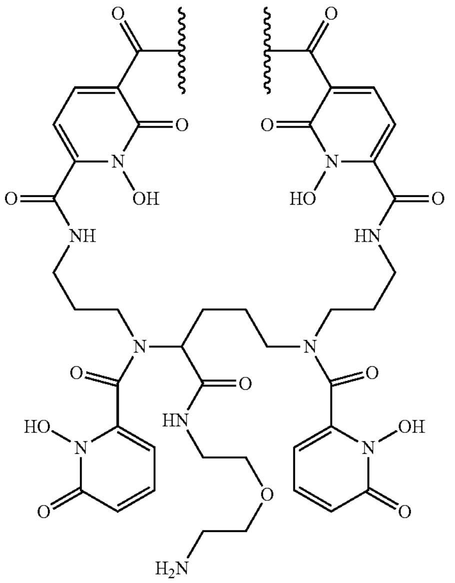

A

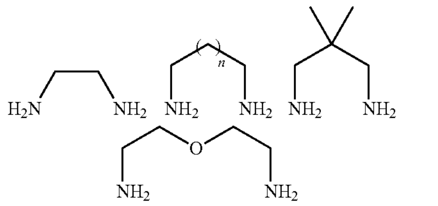

B

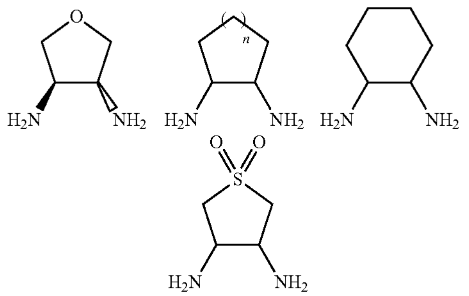

C

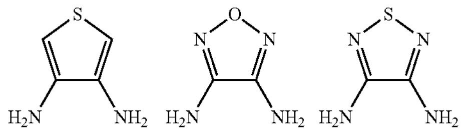

-continued

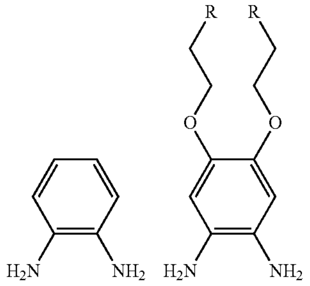

D

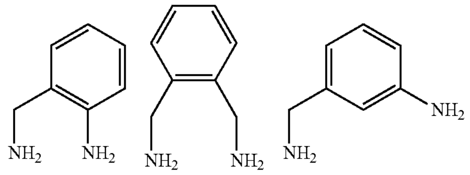

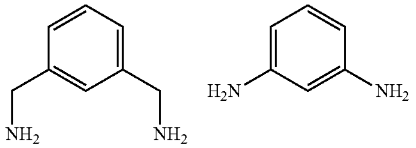

E

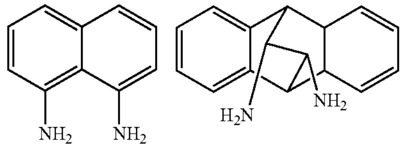

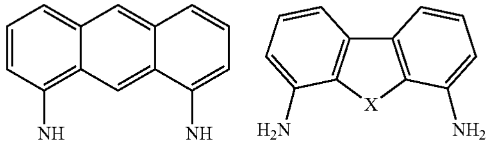

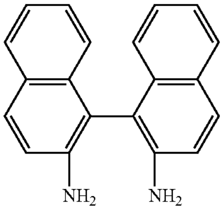

F

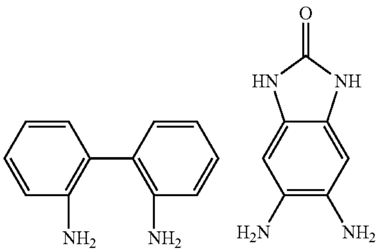

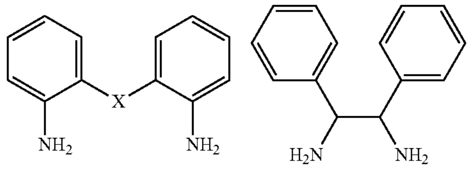

-continued

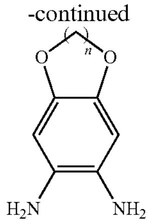

G

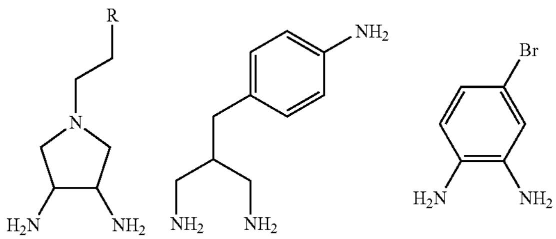

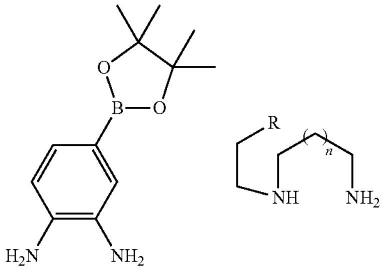

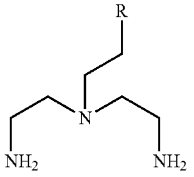

H

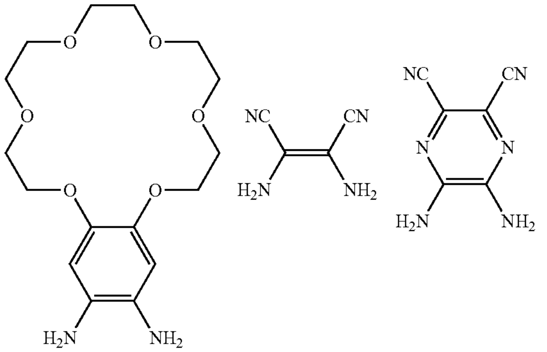

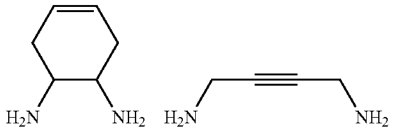

Row A consists of several acyclic, aliphatic linkers that may enhance or alter the photophysical properties of the analogous 43·' Eu complex, by affecting the geometry of the ligand around the metal ion. Similarly, the binding of other radiologically important metals ions may be altered or enhanced. Row B contains other cyclic, aliphatic diamine linkers. The cyclic structure of these examples may enhance the rigidity of the ligand structure, which may enhance the stability of the metal complexes formed. Row C contains cyclic, aromatic diamine linkers, which all have 2-carbon bridges much like the (3R,4S)-tetrahydrofuran-3,4-diamine 2-carbon bridge reported here. These aromatic diamines might extend the electronic conjugation of the 1,2-HOPO units, which can affect the photophysical characteristics of the ligand. The final entry in row C can also include polyethylene glycol units for enhanced solubility. Rows D, E, and F contain additional examples of cyclic, aromatic systems that may enhance the stability of the metal complexes by altering the ligand geometry. Row G contains a variety of diamine bridges, which all have a functional handle that can be used for linking 43·' Eu-type complexes to a species of interest. The linkers on each of these diamines may be used to give 43·' Eu-type complexes an additional functional handle, or they may be used as the sole functional group linker in 40·Eu-type complexes. Row H contains diamine bridges that may offer a way to sense or react with species of interest. The first entry contains an 18-crown-6 ether functionality, which should bind potassium ions. The cyano and cyclohexene examples may bind certain transition metals, while the butyne diamine might facilitate reaction with an organic azide.

Example 25

Representative new functional groups for attachment to pendant 1,2-HOPO units for solubility and additional points of attachment are shown below:

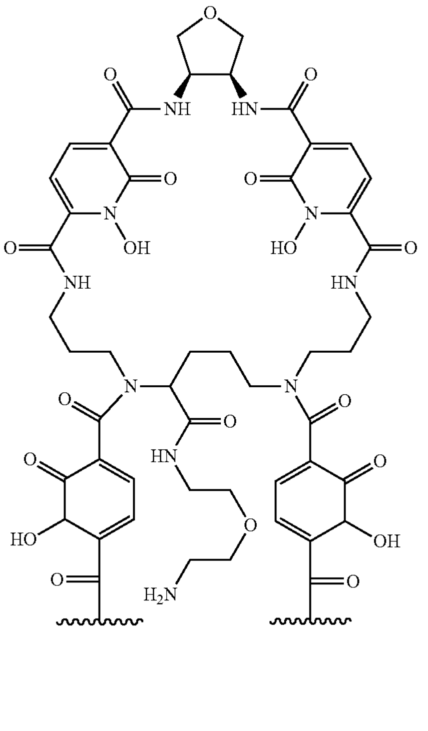

or

-continued

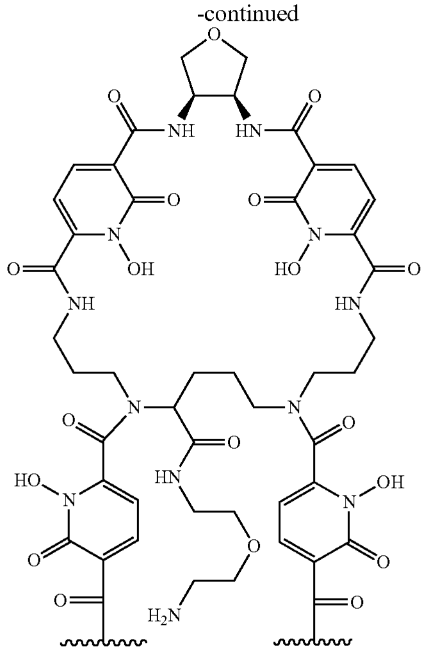

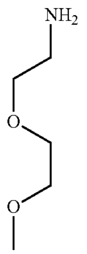

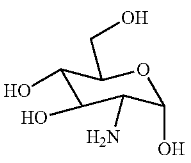

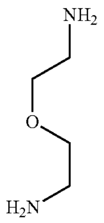

Reacting 8' (or derivatives thereof), instead of 14, with 38' or 41', can lead to the structures shown above. Such species allow for solubilizing groups such as aminopolyethylene glycol and glucosamine (shown above) to be added onto the ligand, enhancing the solubility of the metal complexes in water. Adding diamines (or similar bifunctional moieties) engenders ligands with additional attachment points.

Example 26
Scheme 16. Representative synthetic scheme of compound 43b′ of the invention and precursors thereof.
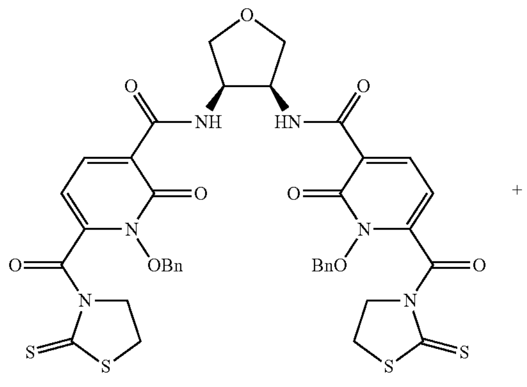
37′
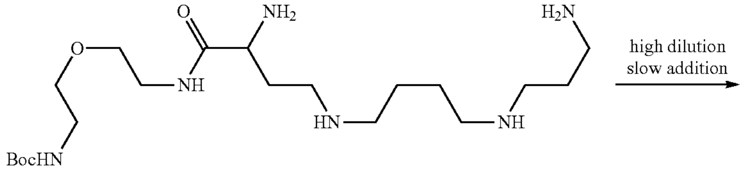
30b
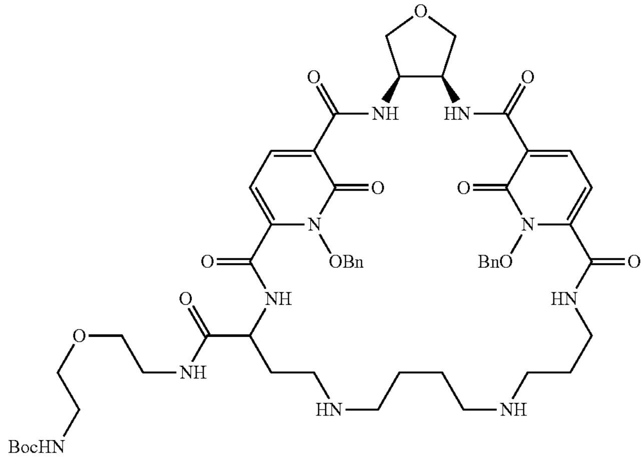
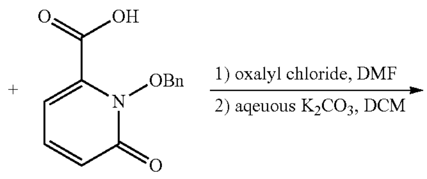
14
41b′

-continued
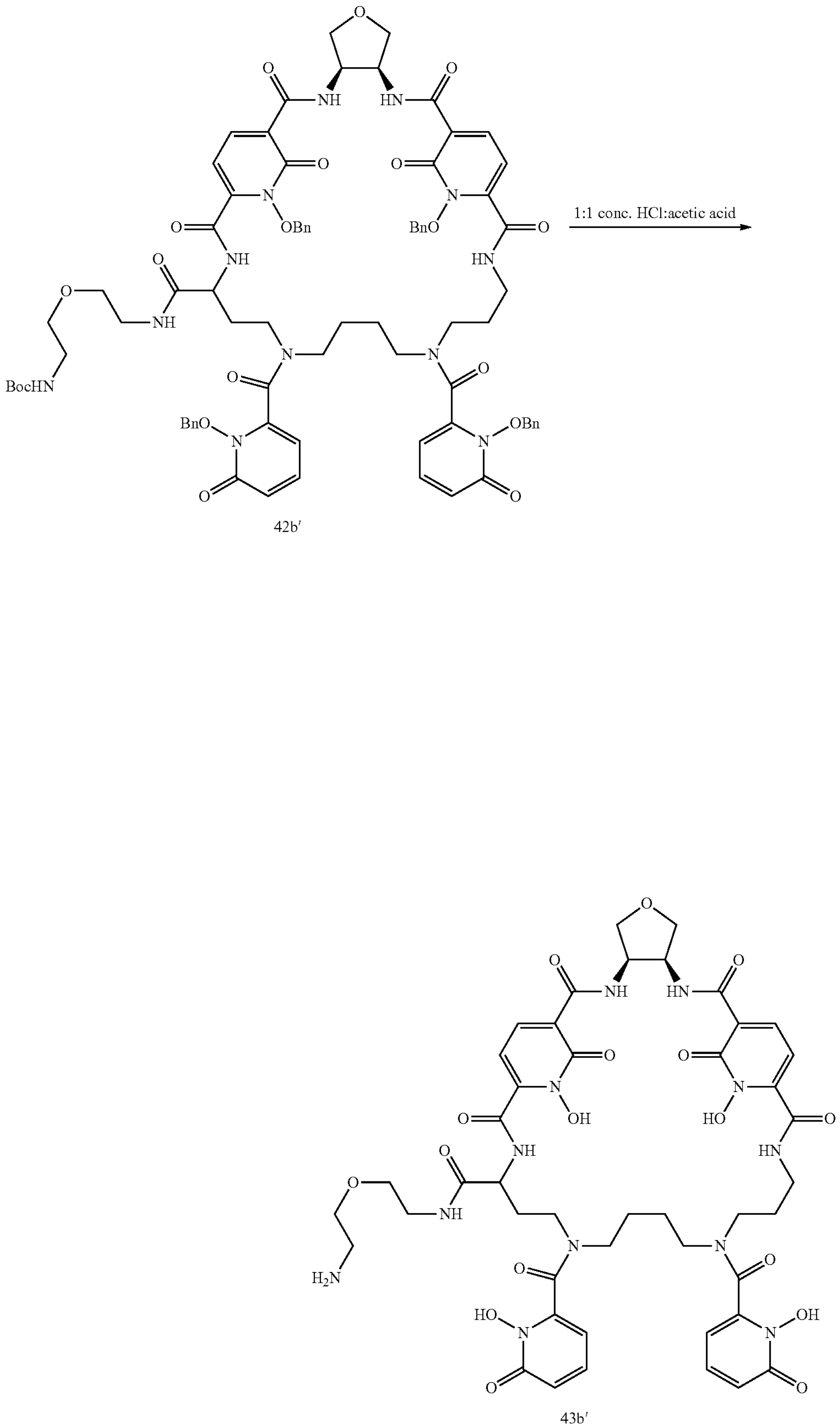
42b′
43b′

Example 27
Scheme 17. Representative synthetic scheme of HOPO-Lys-cyclic-RDGyK.
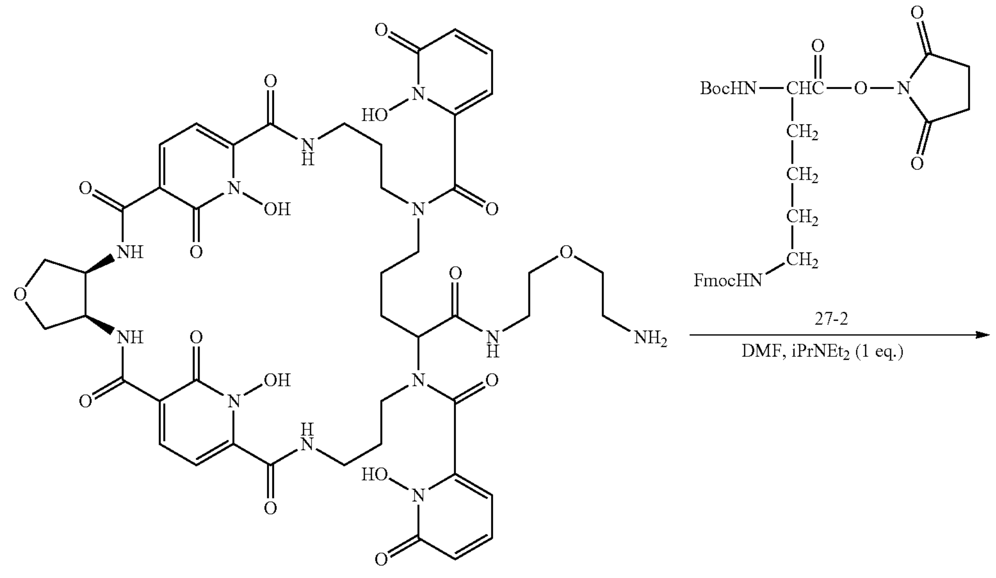
27-1
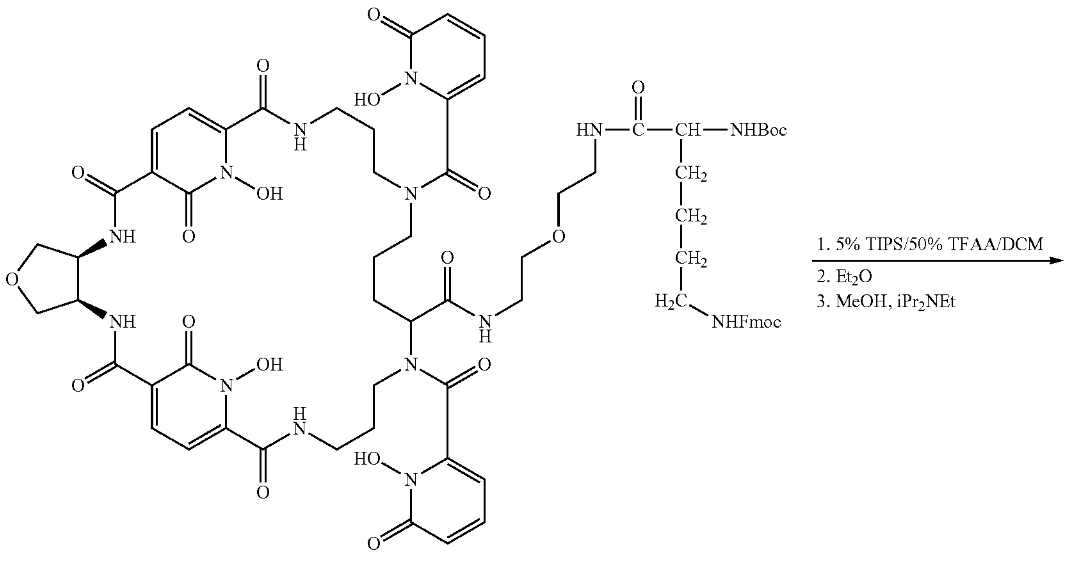
27-3

-continued
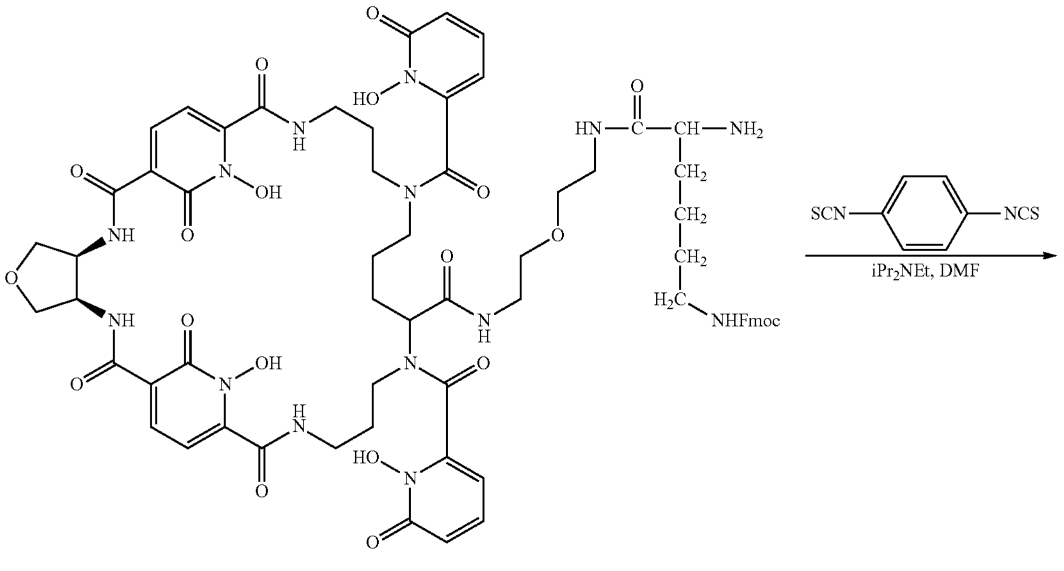
27-4
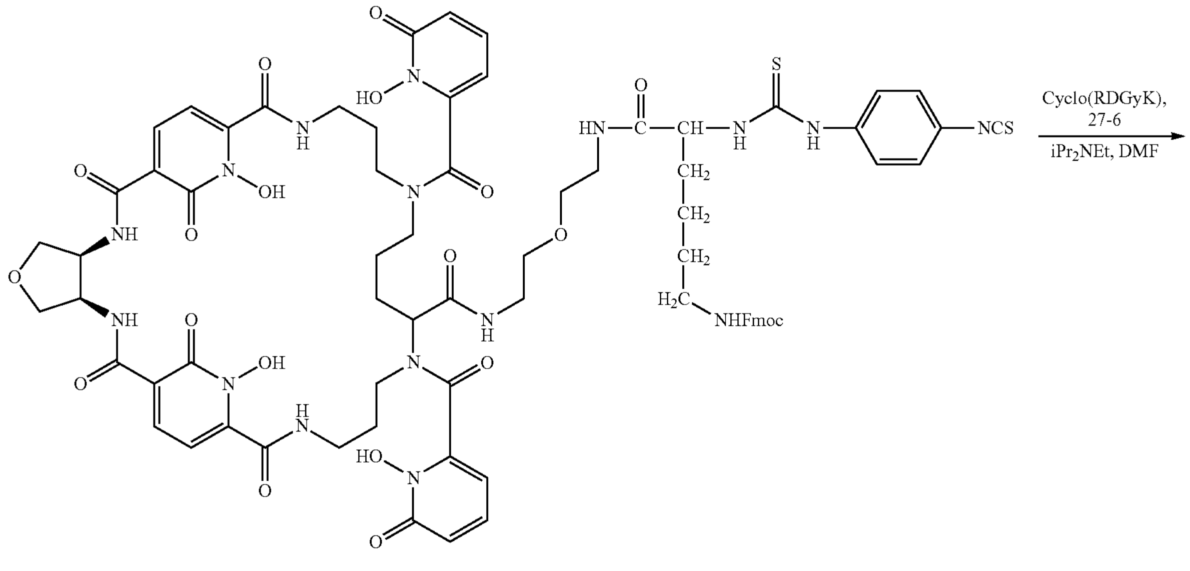
27-5
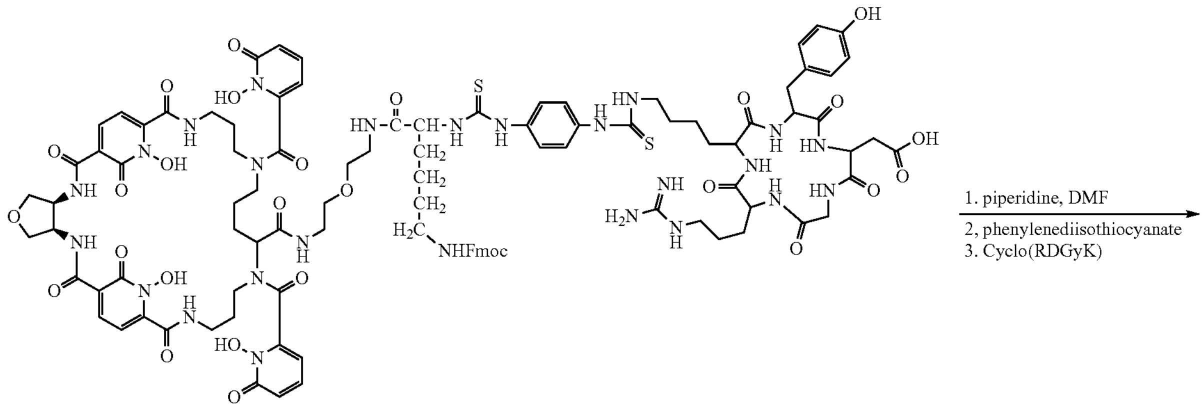
27-7

-continued
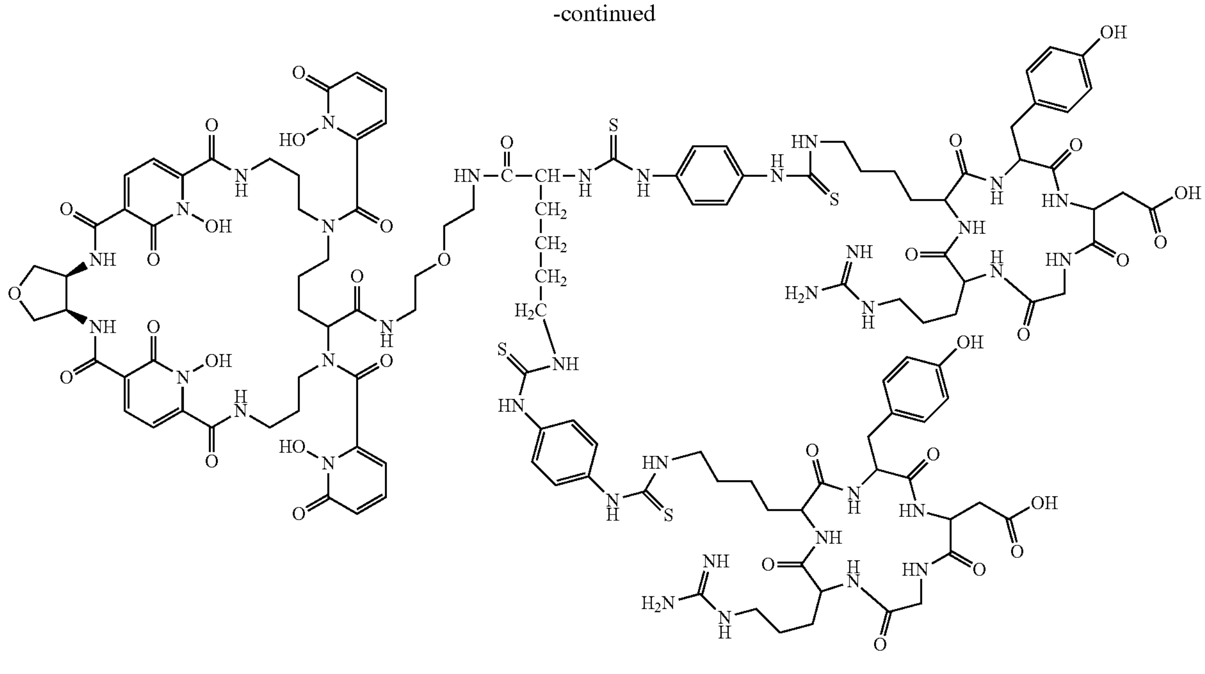
27-8
The divalent peptide conjugate HOPO-Lys-cyclic-RDGyK is synthesized as outlined in Scheme 17. Cyclo (RDGyK) is a peptide that binds αvβ3 integrin, overexpressed in pancreatic cancer, available from Anaspec.
Example 28
Scheme 18. Representative synthetic scheme of compound 29b′ of the invention and precusors thereof.
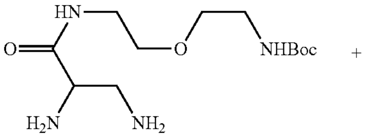
23b
-continued
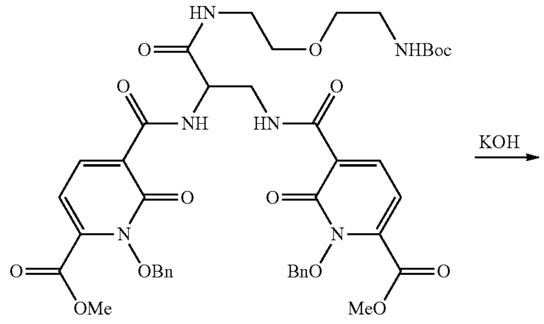
24b′
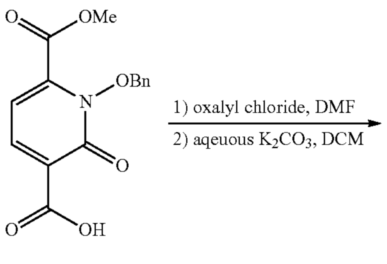
8′
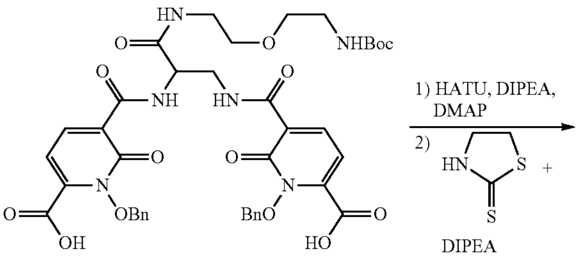
25b′

-continued
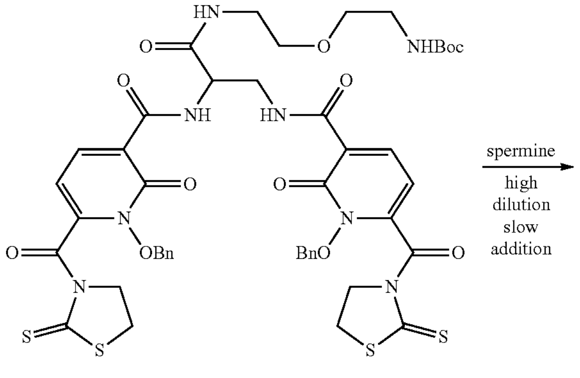
26b'
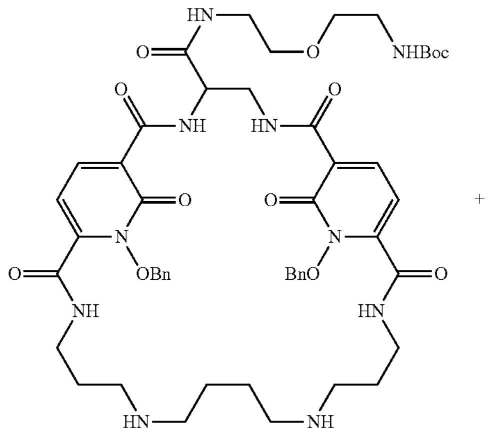
27b'
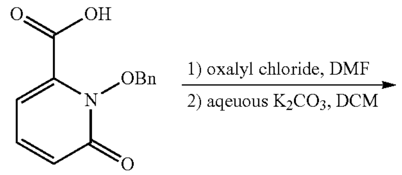
14
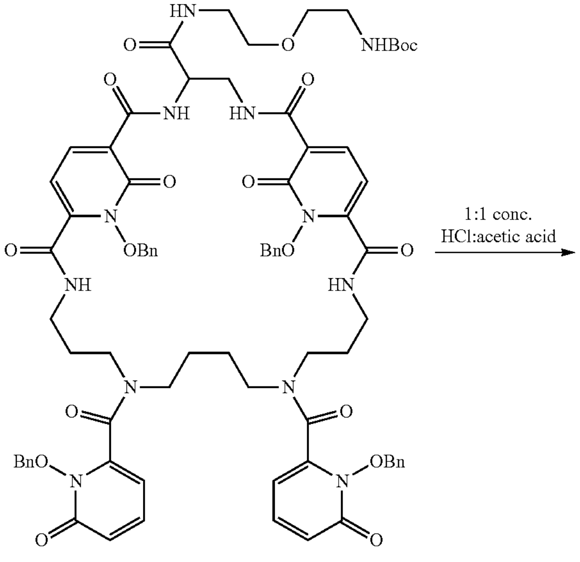
28b'
-continued
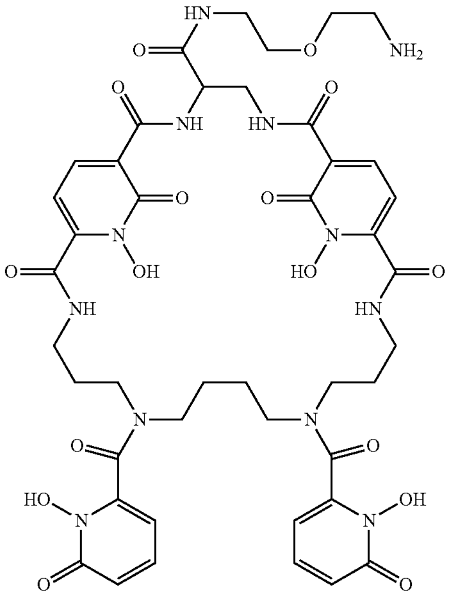
29b'
Example 29
Synthesis of compound 29-Ca—NHS as a representative example of useful species that can be generated from compounds 29, 33, and 43.
Scheme 19. Synthetic scheme of compound 29•Ca or 29•Mg as a representative example of complexes that can be generated from compounds 29, 33, and 43.
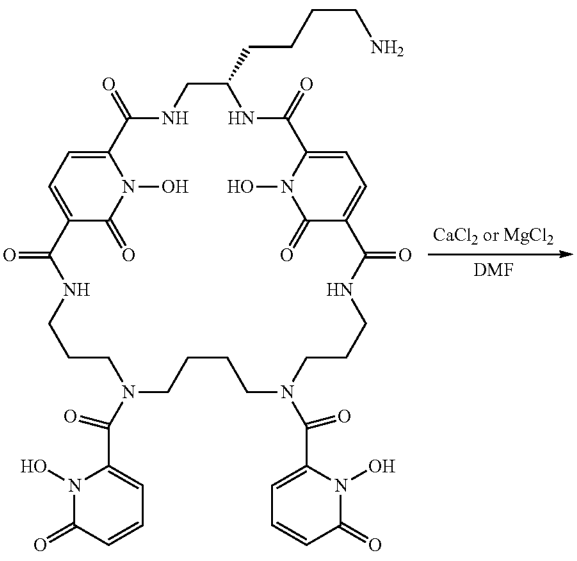

-continued

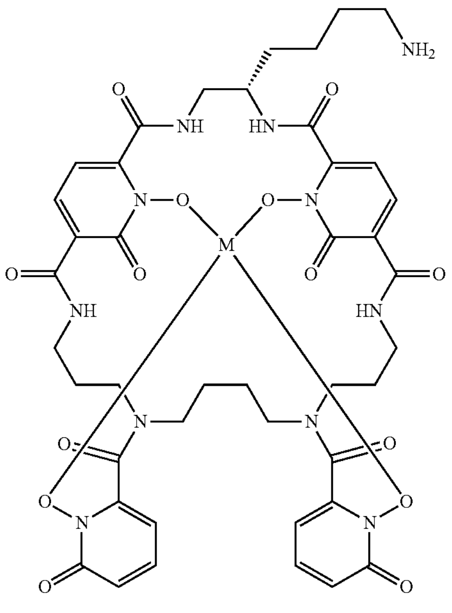

where M = Ca or Mg

For example, Ca·29 (or Mg·29) can be prepared by first mixing 29 with 1.2 molar equivalents of $CaCl_2$) (or $MgCl_2$) in DMF, followed by removing the solvent under vacuum.

Scheme 20. Synthetic scheme of compound 29-Ca-NHS as a representative example of useful species that can be generated from compounds 29, 33, and 43.

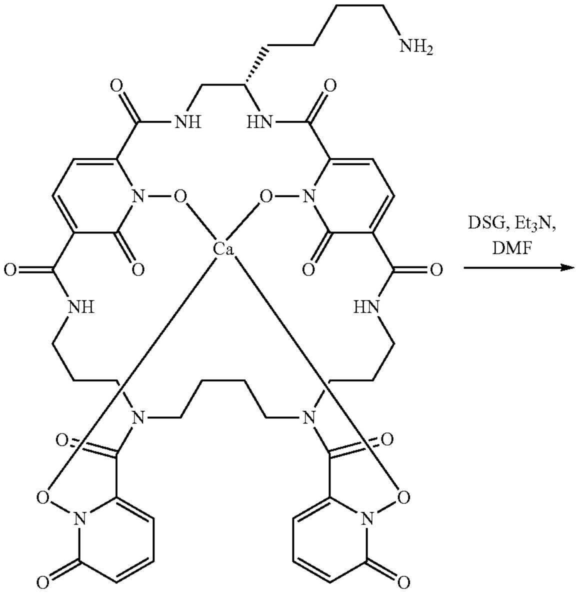

29-Ca

-continued

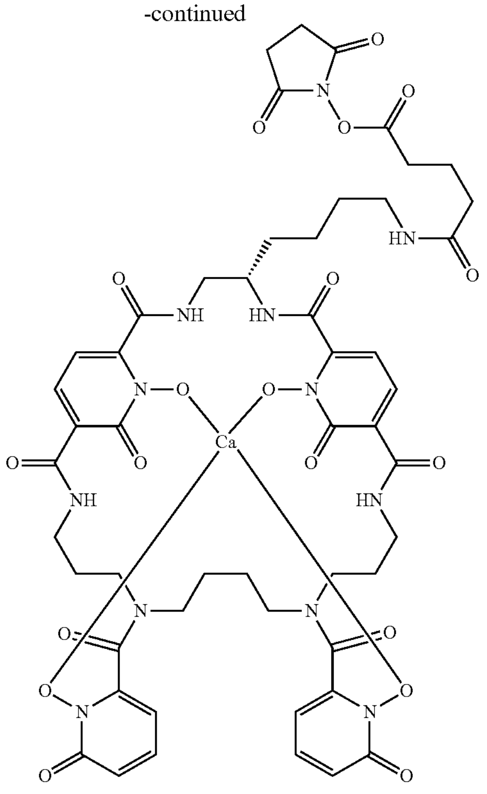

29-Ca-NHS

The reactive NHS esters of complexes Ca·29, Ca·33, and Ca·43 can be generated by treatment of the appropriate Ca(II) complex with excess (10 eq.)di(N-succinimidyl) glutarate (DSG) in DMF and triethylamine. The reactive NHS esters are useful for attaching the metal complexes to lysine residues on proteins, or to amines of other targeting groups of interest. For example, Ca·29 can be prepared by first mixing 29 with 1.2 molar equivalents of $CaCl_2$) in DMF, followed by removing the solvent under vacuum. The Ca·29 complex prepared in this way can then be reacted with excess DSG in DMF as described for Eu·29 in Example 21. HRMS-ESI (m/z, $[M+H]^-$) Calcd for $C_{51}H_{57}CaN_{12}O_{19}$: 1181.3494, Found: 1181.3502. Forming the Ca(II) complex before reaction with DSG protects the chelate from reacting nonproductively with the NHS functional group. It should also be noted that Mg(II) can be used successfully for the same purpose. Both Ca(II) and Mg(II) can be readily displaced by higher valent (oxidation state III or IV) metal ions that bind more tightly than Ca(II) or Mg(II), such as lanthanides (including Eu(III) and Lu(III)), actinides (including Th(IV)), and transition metals (including Zr(IV)). The Ca(II) or Mg(II) complexes are therefore very useful for affording a conveniently reactive bifunctional chelator that can be labeled with radioisotopes of interest.

In order to demonstrate the usefulness of first forming the Ca(II) or Mg(II) complex toward preventing the degradation of the 29-NHS, 33-NHS, or 43-NHS, we first show the results of forming 33-NHS without added Ca or Mg and the resulting stability in DMF solution in the following figure. Note that all of the following HPLC chromatograms in this example are collected after adding 10 molar equivalents of $EuCl_3$ 5 min prior to injection for convenience of analysis.

Figures 25A, 25B, 25C:
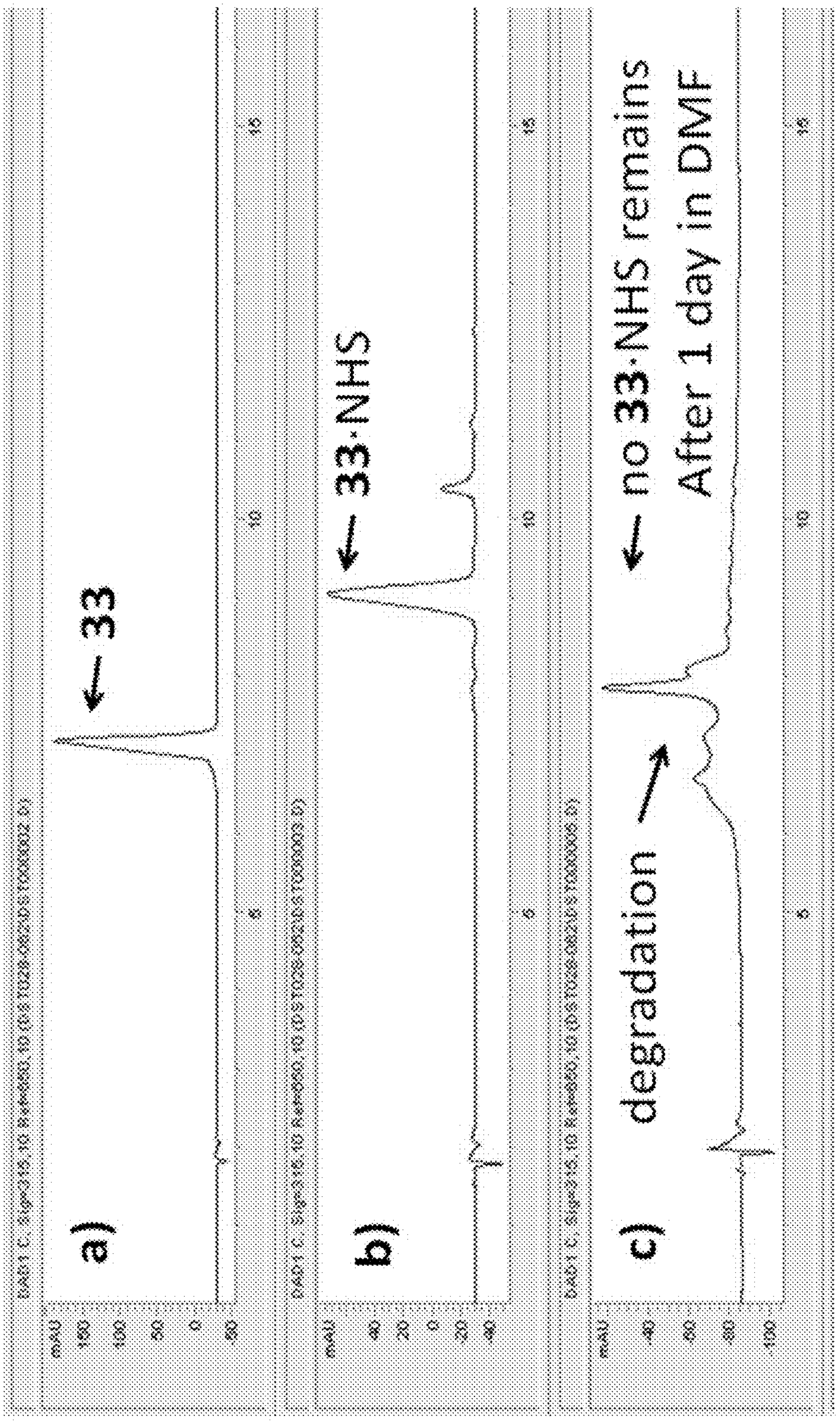
FIG. 25A-FIG. 25C. The HPLC chromatograms collected at 315 nm for a) the 33 starting material, b) the 33·NHS reaction product, and c) the 33·NHS reaction product dissolved in DMF at RT for 1 day. Note that all of the desired 33·NHS reaction product is consumed by unknown side reactions within the 1 day incubation.
Figures 26A, 26B, 26C:
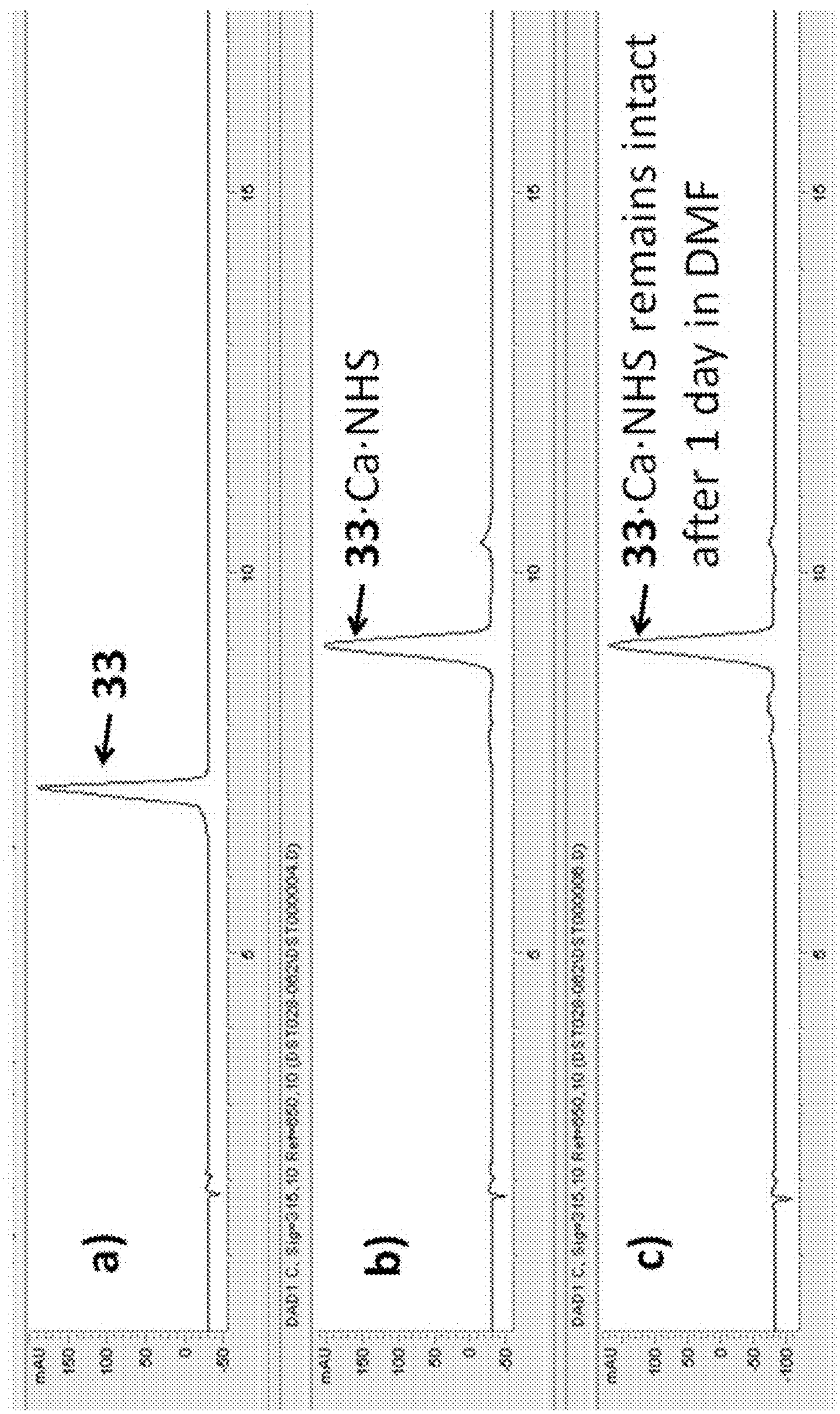
FIG. 26A-FIG. 26C. The HPLC chromatograms collected at 315 nm for a) the 33·Ca starting material, b) the 33·Ca·NHS reaction product, and c) the 33·Ca·NHS reaction product dissolved in DMF at RT for 1 day. Note that, unlike the previous experiment, the 33·Ca·NHS reaction product remains intact after incubation for 1 day.
Figures 27A, 27B:
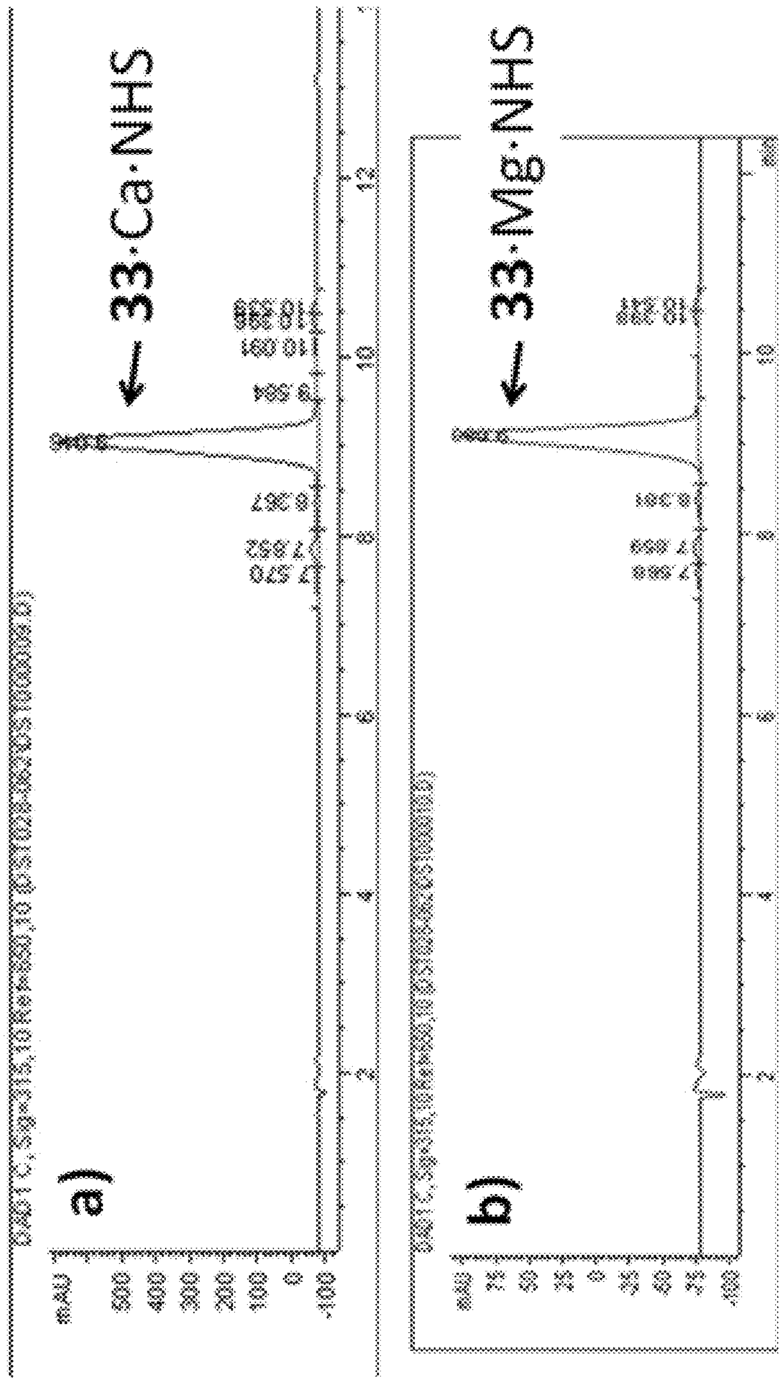
FIG. 27A-FIG. 27B. The HPLC chromatograms collected at 315 nm for 33·Ca·NHS (top) and 33· Mg. NHS (bottom) dissolved in DMF at RT for 1 day.

It is clear from the HPLC data shown in FIG. 25 that, while it is possible to form and isolate 33. NHS in the absence of Ca(II) or Mg(II), the resulting 33·NHS product is remarkably unstable. There is no measureable amount of the desired 33·NHS product remaining in solution once the 33·NHS product has been dissolved in DMF and incubated at RT for one day. For comparison, the exact same experiment was performed using the 33·Ca complex as shown in FIG. 26.

It is clear from the HPLC data that the forming the Ca complex of 33 (as a representative example) yields a 33·Ca·NHS reaction product with enhanced stability toward degradation in solution relative to the 33. NHS reaction product. In the following figure we show the HPLC data for both the 33·Ca·NHS and 33·Mg·NHS reaction products after incubation in DMF at RT for 1 day, which demonstrates that Mg can be used for the same protective purpose as Ca.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A compound according to the formula:

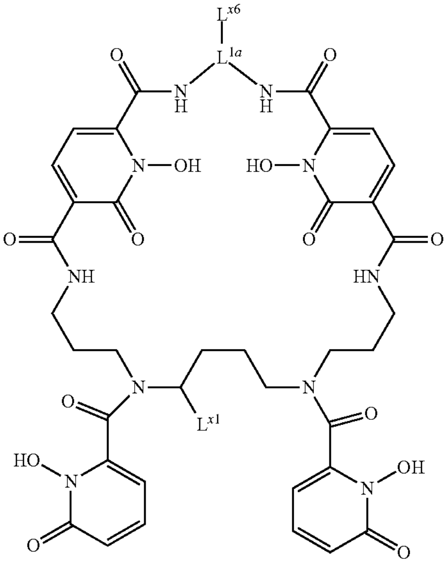

wherein

- $L^{1a}$ is selected from substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted heteroalkyl, substituted or unsubstituted heterocycloalkyl, substituted or unsubstituted aryl, substituted or unsubstituted arylalkyl, substituted or unsubstituted biaryl, substituted or unsubstituted heteroaryl, and a substituted or unsubstituted polycyclic ring system; and
- $L^{x1}$ and $L^{x6}$ are independently selected from H, a linker to a reactive functional group, and a linker to a targeting moiety.

2. The compound according to claim 1, wherein $L^{1a}$ is selected from:

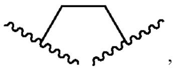, 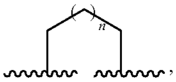, 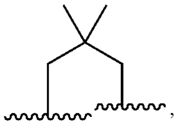,

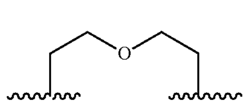, 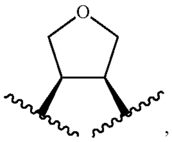,

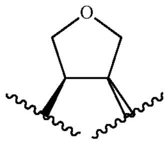, 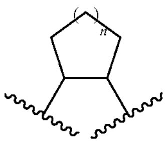, 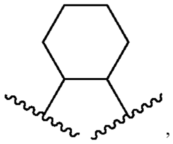,

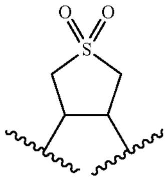, 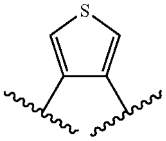, 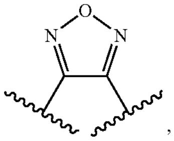,

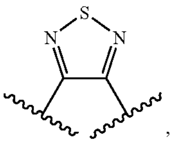, 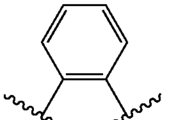, 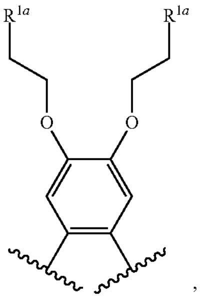,

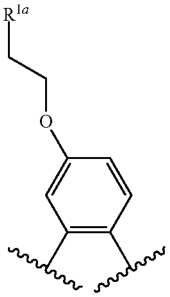, 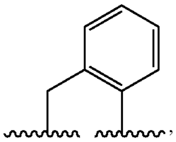, 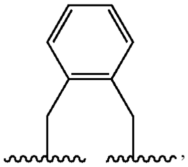,

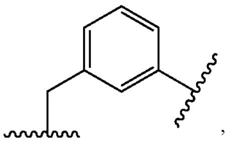, 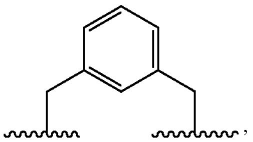,

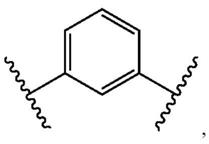, 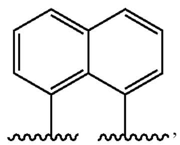,

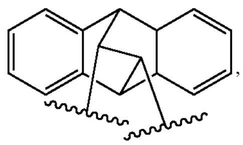, 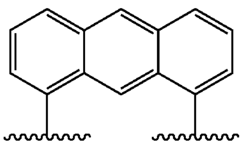,

-continued
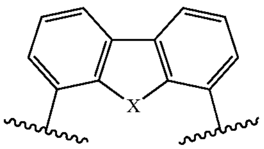,
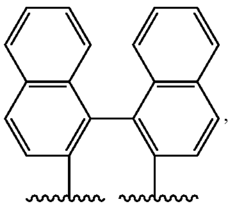,
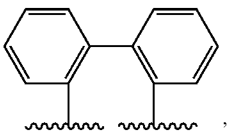,
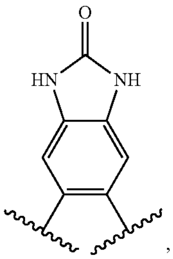,
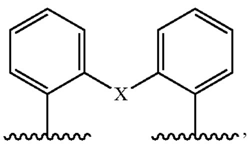,
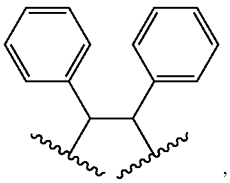,
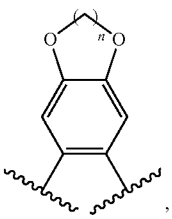,
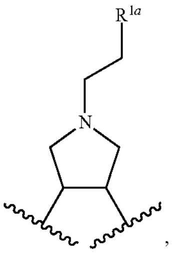,
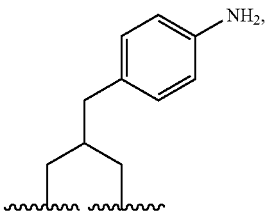
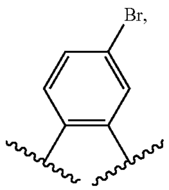
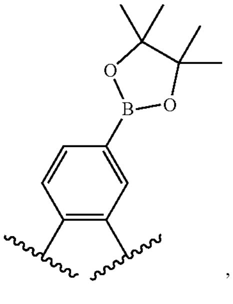,
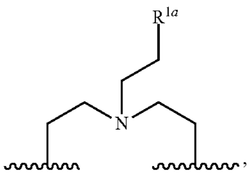,
-continued
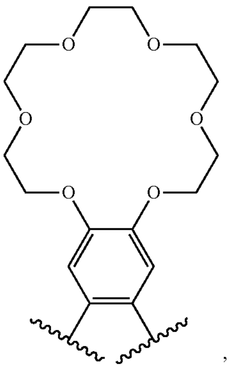,
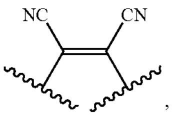,
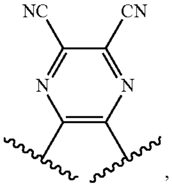,
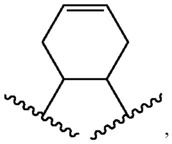,
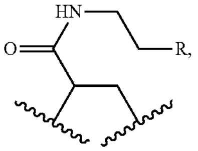
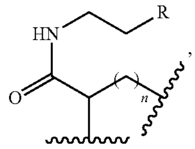,
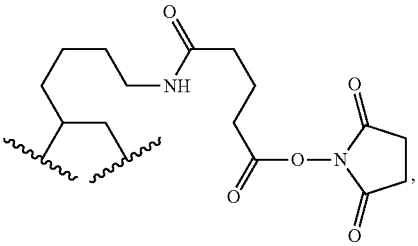,
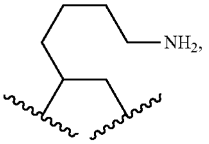
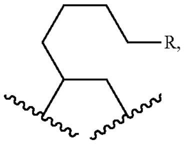 and
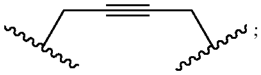;
wherein
n is an integer selected from 0, 1, 2, 3, 4, 5, and 6;
each R and $R^{1a}$ is independently selected from H, substituted or unsubstituted alkyl, substituted or unsubstituted heteroalkyl, a reactive functional group and a modifying moiety; and
X is O, S, or $CH_2$.
3. The compound according to claim 2, wherein $L^{1a}$ has the structure:
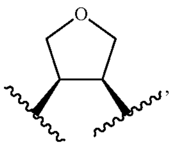,
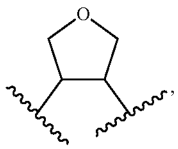,
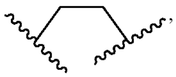, -continued

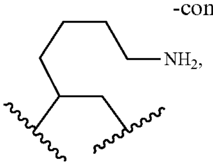

or

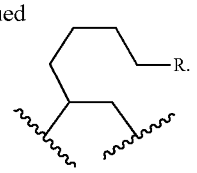

4. The compound according to claim 3, wherein $L^{1a}$ has the structure:

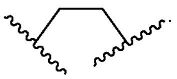 [SMILES: *CC*]

5. The compound according to claim 1, wherein at least one of $L^{x1}$ and $L^{x6}$ is a linker to a reactive functional group, or a linker to a targeting moiety, wherein the linker to the reactive functional group, or the linker to the targeting moiety has the structure:

$$-L^{11}-F^{x},$$

wherein $L^{11}$ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and $F^{x}$ is selected from a reactive functional group, a protected functional group, and a targeting moiety.

6. The compound according to claim 5, wherein the linker to the reactive functional group, or the linker to the targeting moiety has the structure:

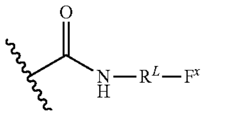

or

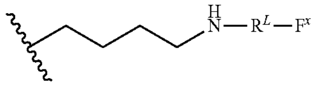

wherein $R^{L}$ is selected from substituted or unsubstituted alkyl, and substituted or unsubstituted heteroalkyl; and $F^{x}$ is selected from a reactive functional group, a protected functional group, and a targeting moiety.

7. The compound according to claim 6, wherein at least one of $L^{x1}$ and $L^{x6}$ is a linker to a reactive functional group, wherein the linker to the reactive functional group has the structure:

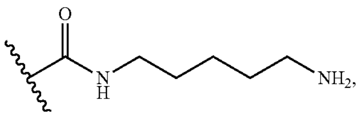

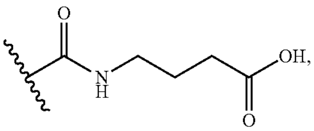

-continued

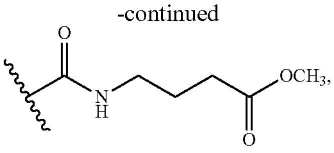

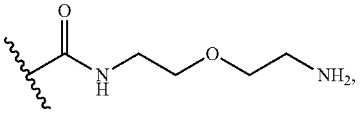

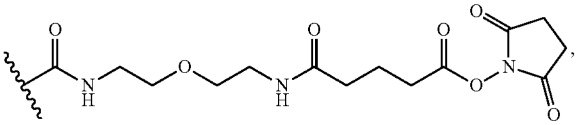

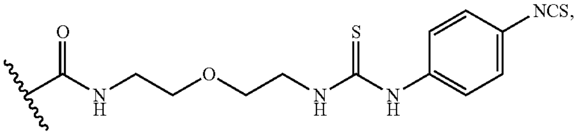

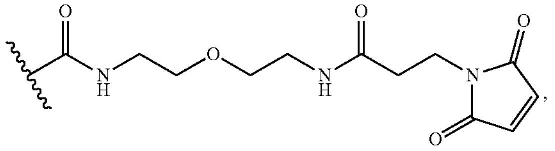

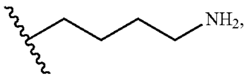

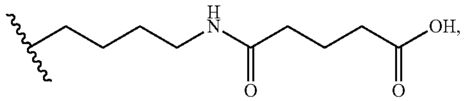

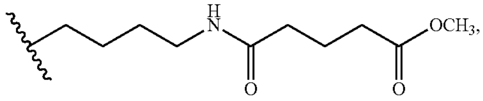

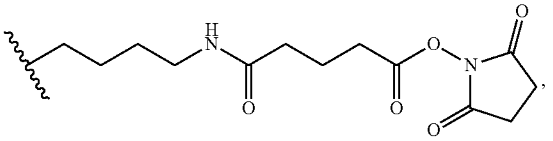

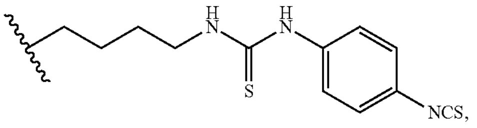

or

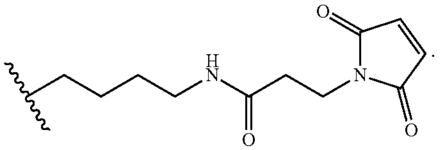

8. The compound according to claim 1, wherein $L^{x1}$ has the structure:

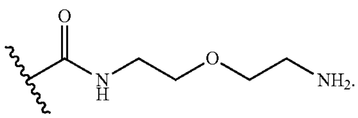 [SMILES: *C(=O)NCCOCCN]

9. The compound according to claim 8, wherein $L^{x6}$ is H.

10. The compound according to claim 1, wherein $L^{x6}$ has the structure:

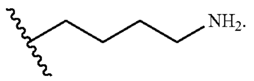 [SMILES: *CCCCN]

11. The compound according to claim 10, wherein $L^{x1}$ is H.

12. The compound according to claim 1, wherein:

$L^{x1}$ is H;

$L^{x6}$ is H; and $L^{1a}$ has the structure:

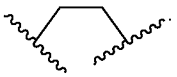 [SMILES: *CC*]

13. The compound according to claim 1, wherein:

$L^{x6}$ is H;

$L^{1a}$ has the structure;

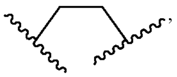 [SMILES: *CC*]

and $L^{x1}$ has the structure:

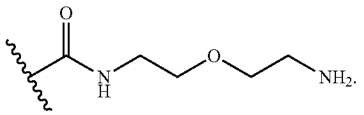 [SMILES: *C(=O)NCCOCCN]

14. The compound according to claim 1, wherein:

$L^{x1}$ is H;

$L^{1a}$ has the structure

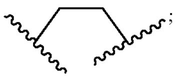

and $L^{x6}$ has the structure

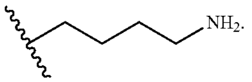 [SMILES: *CCCCN]

15. A complex comprising the compound according to claim 1 and a metal ion complexed therewith.

16. The complex according to claim 15, wherein the metal ion is selected from Zr(IV), Fe(III), Sc(III), In(III), Eu(III), Ho(III), Lu(III), Y(III), Tb(III), Yb(III), Gd(III), Sm(III), Dy(III), Er(III), Th(IV), Ca(II) and Mg(II).

17. The complex according to claim 15, wherein the metal ion is Eu(III).

18. The complex according to claim 15, wherein the metal ion is Ca(II).

19. The complex according to claim 15, wherein the metal ion is Lu(III).

20. The complex according to claim 15, wherein the metal ion is Zr(IV).

* * * * *